US006506906B1

(12) United States Patent
Dervan

(10) Patent No.: US 6,506,906 B1
(45) Date of Patent: Jan. 14, 2003

(54) PREPARATION AND USE OF BIFUNCTIONAL MOLECULES HAVING DNA SEQUENCE BINDING SPECIFICITY

(75) Inventor: Peter B. Dervan, San Marino, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/414,611

(22) Filed: Oct. 8, 1999

Related U.S. Application Data

(63) Continuation of application No. PCT/US98/06997, filed on Apr. 8, 1998, which is a continuation-in-part of application No. PCT/US97/12722, filed on Jul. 21, 1997, and a continuation-in-part of application No. 08/853,522, filed on May 8, 1997, and a continuation-in-part of application No. PCT/US97/03332, filed on Feb. 20, 1997, each is a continuation-in-part of application No. 08/837,524, filed on Apr. 21, 1997, and a continuation-in-part of application No. 08/607,078, filed on Feb. 26, 1996.

(60) Provisional application No. 60/042,002, filed on Apr. 16, 1997, provisional application No. 60/043,446, filed on Apr. 8, 1997, and provisional application No. 60/043,444, filed on Apr. 8, 1997.

(51) Int. Cl.$^7$ .................... C07D 231/00; C07D 233/40; C07D 233/26; C07D 207/10

(52) U.S. Cl. ............................... 548/312.4; 548/314.1; 548/334.5; 548/557

(58) Field of Search ........................ 548/312.4, 214.1

(56) References Cited

U.S. PATENT DOCUMENTS

| 4,795,700 A | 1/1989 | Dervan et al. ................. 435/5 |
| 5,539,083 A | 7/1996 | Cook et al. ................. 530/333 |
| 5,563,250 A | 10/1996 | Hylarides et al. ............. 536/4.1 |
| 5,578,444 A | 11/1996 | Edwards et al. ............... 435/6 |
| 5,693,463 A | 12/1997 | Edwards et al. ............... 435/6 |
| 5,726,014 A | 3/1998 | Edwards et al. ............... 435/6 |
| 5,738,990 A | 4/1998 | Edwards et al. ............... 435/6 |
| 5,801,155 A | 9/1998 | Kutyavin et al. ............. 514/44 |
| 6,090,947 A | 7/2000 | Dervan et al. ........... 548/312.4 |

FOREIGN PATENT DOCUMENTS

| DE | 43 31 012 A1 | 3/1995 |
| EP | 0 246 868 A1 | 11/1987 |
| EP | 0 388 948 A1 | 9/1990 |
| GB | 2 261 661 A | 5/1993 |
| WO | 92/09574 | 6/1992 |
| WO | 92/13838 | 8/1992 |
| WO | 92/14707 | 9/1992 |
| WO | 93/00446 | 1/1993 |
| WO | 94/03434 | 2/1994 |
| WO | 94/14980 | 7/1994 |
| WO | 94/20463 | 9/1994 |
| WO | 94/25436 | 11/1994 |
| WO | 95/04732 | 2/1995 |
| WO | 96/05196 | 2/1996 |
| WO | 96/32496 | 10/1996 |
| WO | 97/30975 | 8/1997 |

OTHER PUBLICATIONS

Arcamone, F., "Design and Synthesis of Anthracycline and Distamycin Derivattives as New, Sequence–Specific, DNA–binding Pharmacological Agents", *Gene* 149:57–61 (1994).

Baguley, B.C., "Nonintercalative DNA–binding Atitumour Compounds," *Molecular and Cellular Biochemistry* 43:167–181 (1982).

Bailer, et al., "A Total Synthesis of Distamycin a, an Antiviral Antibiotic," *Tetrahedron* 34:2389–2391 (1978).

Bailey, et al., "Untitled" *Organic Synthesis* 51:101–102 (1971).

Bailly and Henichart, "DNA Recognition by Intercalator–Minor–Groove Binder Hybrid Molecules," *Bioconjugate. Chemistry* 2:379–393 (1991).

Bailly et al., "Recation of a Biscationic Distamycin–Ellipticine Hybrid Ligand with DNA. Mode and Sequence Specificity of Binding", *Biochemistry* 33:15348–15364 (1994).

Bellon, et al., "Crystal Structure of the RAG1 Dimerization Domain Reveals Multiple Zinc–binding Motifs Including a Novel Zinc Binuclear Cluster," *Nature Struct. Biol.* 4:586–591 (1997).

Boger, et al, "1,2,9,9a–Tetrahydrocyclopropa[c]benz[e]indol–4–one(CBI)Analogs of CC–1065 and the Duocarmycins: Synthesis and Evaluation,," *N. Bioorganic & Medicinal Chemistry* 3:1429–145 (1995).

Bourdouxhe–Housiaux, et al., "Interaction of a DNA–Threading Netropin–Amsacrine Combination with DNA and Chromatin," *Biochemistry* 35:4251–4264 (1996).

Brenowitz, et al., "Quantitative Dnase Footprint Titration: A Method for Studying Protein–DNA Interactions,". *Methods in Enzymology* 130:132–181 (1985).

(List continued on next page.)

Primary Examiner—Deborah C. Lambkin
(74) Attorney, Agent, or Firm—Foley & Lardner

(57) ABSTRACT

Small molecule polyamides that specifically bind with subnanomolar affinity to any predetermined sequence in the human genome with potential use in molecular biology and human medicine are described. Further, the designed compounds which target the minor groove of B-form double helical DNA offer a general approach for the control of gene-expression. Simple rules are disclosed which provide for rational control of the DNA-binding sequence specificity of synthetic polyamides containing N-methylpyrrole and N-methylimidazole amino acids. A series of molecular templates for polyamide design are disclosed which provide for small molecules which recognize predetermined DNA sequences with affinities and specificities comparable to sequence-specific DNA-binding proteins such as transcription factors. These design rule are applied to provide a polyamide for specific targeting of a predetermined 7 base pair sequence from a conserved HIV gene promoter at subnanomolar concentration. The pyrrole-imidazole polyamides described herein represent the only class of designed small molecules to date that can bind any predetermined sequence of double helical DNA.

8 Claims, 46 Drawing Sheets

OTHER PUBLICATIONS

Bresloff and Crothers, "DNA–Ethidium Reaction Kinetics: Demonstration of Direct Ligand Transfer Between. DNA Binding Sites," *Journal of Molecular Biology* 95:103–123 (1975).

Caruthers, M.H., "Chemical Synthesis of DNA and DNA Analogues," *Acc. Chem. Res.* 24:278–284 (1991).

Caruthers, M.H. et al., "Chemical Synthesis of Deoxyoligonucleotides by the Phosphoramidite Method," *Methods in Enzymology* 154:287–313 (1985).

Chen, et al., "Binding of Two Distamycin A Molecules in the Minor Groove of an Alternating B–DNA Duplex," *Structural Biology* 1:169–175 (1994).

Choo, Y. and Klug, "Selection of DNA Binding Sites for Zinc Fingers Using Rationally Randomized DNA Reveals Coded Interactions," A. *Proc. National Academy of Science USA* 91:11168–11172 (1994).

Clemens, et al., "Relative Contributions of the Zinc Fingers of Transcription Facto IIIA to the Energetics of DNA Binding," *Journal of Molecular Biology* 244:23–35 (1994).

Coll, et al., "A Bifurcated Hydrongen–bonded Conformation in the d(A.T) Base Pairs of the DNA Dodecamer d(CG-CAAATTTGCG) and its Complex with Distamycin," *Proc. National. Academy of Science USA* 84:8385–8389 (1987).

Dervan and Becker "Molecular Recognition of DNA by Small Molecules. Synthesis of Bis(methidium)spermine, a DNA Polyintercalating Molecule," *Journal of the American Chemical Society* 100:1968–1970 (1978).

Dickerson, et al., "The Anatomy of A–, B–, and Z–DNA," *Science*, 216:475 (1982).

Duval–Valentin, et al., "Specific Inhibition of Transcription by Triple Helix–forming Oligonucleotides," *Proc. National Academy of Science USA* 89:50–508 (1992).

Edelson, et al., "Treatment of Cutaneous T–cell Lymphoma by Extracorporeal Photochemotherapy," *New England Journal of Medicine* 316:297–303 (1987).

Frech, et al., "Common Modular Structure of Lentivirus LTRs," *Virology* 224:256–267 (1996).

Fujiwara, et al, "Modulation of Sequence Specificity of Duocarmycin–Dependent DNA Alkylation by Pyrrole–Imidazole Triamides," *Journal of American Chemical Society* 121:7706–7707 (1999).

Gao, et al., "Structure Refinement of the Chromomycin Dimer–DNA Oligomer Complex in Solution," *Journal of Molecular Biology* 223:259–279 (1992).

Gerierstanger, et al., "NMR Characterization of a Heterocomplex Formed by Distamycin and its Analog 2–ImD with d(CGCAAGTTGGC0:(GCCAACTTGCG): Preference for the 1:1:1 2–ImD:Dst:DNA Complex over the 2:1 2–ImD:DNA and the 2:1 Dst:DNA Complexes," *Journal of the American Chemical Society* 115:4474–4482 (1993).

Gottesfeld, J.M., et al., "Regulation of Gene Expression by Small Molecules," *Nature* 387:202–205 (1997).

Greisman, H.A. and Pabo, C.O, "A General Strategy of Selecting.High–Affinity Zinc Finger Proteins for Diverse DNA Target Sites," *Science* 275:657–661 (1997).

Gutte, et al., "The Synthesis of Ribonuclease A," *Journal of Biological Chemistry* 246:1922–1941 (1971).

Hansen and Hurley, "Pluramycins. Old Drugs Having Modern Friends in Structural Biology," *American. Chemical Research* 29:249 (1996).

Herman, et al., "Stereochemical Control of the DNA Binding Affinity, Sequence Specificity and Orientation Preference of Chiral Hairpin Polyamides in the Minor Groove," *Journal of American Chemical Society* 1382–1390 (1998).

Hertzberg and Dervan, "Cleavage of Double Helical DNA by (Methidiumpropyl–EDTA) Iron (II)," *Journal of the American Chemical Society* 104:313–314 (1982).

Ho, et al., "Specific Inhibition of Formation of Transcription Complex by a Calicheamicin Oligosaccharide: A Paradigm for the Development of Transcriptional Antagonists," *Proc. National Academy of Science USA* 91:9203–9207 (1994).

Honig and Nicholls, "Classical Electrostatics in Biology and Chemistry," *Science* 268:1144 (1995).

Ito, T., et al., "Sequence–specific DNA Purification by Triplex Affinity Capture," *Proc. National. Academy of Science USA* 89:495–498 (1992).

Jamieson, et al., "In Vitro Selection of Zinc Fingers with Altered DNA–Binding Specificity," *Biochemistry* 33:5689–5695 (1994).

Kopka, et al., "The Molecular Origin of DNA–drug Specificity in Netropin and Distamycin," *Proc. Natl. Acad Sci. USA* 82:1376–1380 (1985).

Krowicki, et al., "Synthesis of Novel Imidazole–Containing DNA Minor Groove Binding Oligopeptides Related to the Antiviral Antibiotic Netropsin," 52:3493–3501 ( 1987).

Jones, et al., "Control of RNA Initiation and Elongation at the HIV–I Promoter," *Annual Review of Biochemistry* 63:717–743 (1994).

Ju, et al., "Fluorescence Energy Transfer Dye–labeled Primers for DNA Sequencing and Analysis," *Proc. National. Academy of Science USA* 92::4347–4351.

Kamitori, et al. "Crystal Structure of the 2:1 Complex Between d(GAAGCTTC) and the Anticancer Drug Actinomycin D," *Journal of Molecular Biology* 225:445–456 (1992).

Keilkopf, et al., "Structural Basis for G.C Recognition in the DNA Minor Groove," *Nature Structural Biology.* 5:104–109 (1998).

Kent, S.B.H. "Chemical Synthesis of Peptides and Proteins," *Annual Review of Biochemistry* 57:957–989 (1988).

Klemn, et al., "Crystal Structure of the Oct–1 POU Domain Bound to an Octamer Site: DNA Recognition with Tethered DNA–Binding Modules," *Cell* 77:21–32 (1994).

Krylov, et al., "Quantiative Estimation of the Contribution of Pyrrolcarboxamide Groups of the Antibiotic Distamycin A into Specificity of its Binding to DNA AT Pairs," *Nucleic Acids Research.* 6:289–304 (1979).

Le Doan, et al., "Sequence–specific, photocrosslinking and Cleavage of the DNA Double Helix by an Oligo[a] Thymidylate Covalently Linked to an Azidoproflavine Derivative," *Nucleic Acids Research* 15:7749 (1987).

Lee, et al., "In Vitro Photoinduced Cytotoxicity and DNA Binding Properties of Psoralen and Coumarin Conjugates of Netropsin Analogues: DNA Sequence–Direct Alkylation and Cross–Link Formation," *Journal of Medical Chemistry* 37:1208 (1994).

Lee, et al., "GC Base Sequence Recognition by Oligo (imidazolecarboxa mide) and C–Terminus–Modified Analogues of Distamycin Deduced from Circular Dichroism, Proton Nuclear Magnetic Resonance, and Methidiumproyl-ethylenediaminetetraacetate–Iron (II) Footprinting Studies," *Biochemistry* 32:4237–4245 (1993).

LePecq and Paoletti, "A Fluorescent Complex between Ethidium Bromide and Nucleic Acids," *Journal of Molecular Biology* 27:87–106 (1967).

Lerman, L.S., "Structural Considerations in the Interactions of DNA and Acridines," *Journal of Molecular Biology* 3:18–30 (1961).

Liu, C., et al., "Sequence–selective Carbohydrate–DNA Interaction: Dimeric and Monomeric Forms of the Calicheamicin Oligosaccharide Interfere with Transcription Factor Function," *Proc. National Academy of Science USA* 93:940–944 (1996).

Lukhtanov, et al., "Rapid and Efficient Hybridization–triggered Crosslinking within a DNA Duplex by an Oligodeoxyribonucleotide Bearing a Conjugated Cyclopropapyrroloindole," *Nucleic Acids Research* 24:683–687 (1996).

Manning, G.S., "The Molecular Theory of Polyelectrolyte Solutions with Applications to the Electrostatic Properties of Polynucleotides," *Quarterly Reviews of Biophysics* 11:179–246 (1978).

Marmorstein, et al., "DNA Recognition by GAL4: Structure of a Protein–DNA Complex," *Nature* 356:408–414 (1992).

Merrifield, "Solid Phase Peptide Synthesis: I. The Synthesis of a Tetrapeptide[1]," *Journal of the American Chemical Society* 85:2149–2154 (1963).

Merrifield, "Solid Phase Synthesis," *Science* 232:341–347.

Mitchell, A. R., et al., "A New Synthesis Route to tert–Butyloxycarbonylaminoacyl–4–(oyymethyl) Phenylacetamidomethy–Resin, an Improved Support for Solid–Phase Peptide Synthesis," *Journal of Organic Chemistry* 43:2845 (1978).

Moser, et al., "Sequence–Specific Cleavage of Double Helical DNA by Triple Helix Formation" *Science* 238:645–650 (1987).

Neidle and Abraham, "Structural and Sequence–Dependent Aspects of Drug Intercalation into Nucleic Acids," *CRC Critical Reviews in Biochemistry*. 17:73–121.

Nie, et al., "Probing Individual Molecules with Confocal Fluorescence Microscopy," *Science* 266:1018–1021 (1994).

Pabo, et al., "Transcription Factors: Structural Families and Principles of DNA Recognition," *Annual Review of Biochemistry* 61:1053–1095 (1992).

Paloma, et al, "Interaction of Calicheamicin with Duplex DNA: Role of the Oligosaccharide Domain and Identification of Multiple Binding Modes," *Journal of the American Chemical Society* 116:3697–3708 ( 1994).

Pelton, J.G. & Wemmer, D.E., "Binding Modes of Distamycin A with d(CGCAAATTTGCG)$_2$ Determined by Two–Dimensional NMR," *Journal of the American Chemical Society* 112:1393–1399 (1990).

Penco, et al., "Distamicina A– Nota II. Sintesi Totale," *Gass. Chim. Ital.* 97:1110 (1967).

Pullman, et al., "Molecular Electrostatic Potential of the Nucleic Acids," *Quarterly Reviews of Biophysics* 14:289–380 (1981).

Pullman, B. "Molecular Mechanisms of Specificity in DNA–Antiumour Drug Interactions," *Advances in Drug Research* 18:1–13 (1989).

Roeder, R.G. "The Role of General Initiation Factors in Transcription by RNA Polymerase II," *TIBS,* 9:327–335 (1996).

Schmidt, et al., "Molecular Recognition by DNA by Small Molecules. Synthesis of Bis(methidium) Spermine, a DNA Polyintercalating Molecule," *Journal of the American Chemical Society* 100:6:1968–1978 (1978).

Schnolzer, et al., "In Situ Neutralizationj in Boc–chemistry Solid Phase Peptide Synthesis," *International Journal of Peptide Protein Res.* 40:180 (1992).

Simon, et al., "Peptoids: A Modular Approach to Drug Discovery," *Proc. National Academy of Science USA* 89:9367–9371 (1992).

Steitz, T.A. "Structural Studies of Protein–Nucleic Acid Interaction: The Sources of Sequence–Specific Binding," *Quarterly Review of Biophysics* 23:205 (1990). *Quaterly Review of Biophysics* 23:205.

Strobel, et al., "Site–Specific Cleavage of Human Chromosome 4 Mediated by Triple–Helix Formation," *Science* 254:1639–1642 (1991).

Subra, et al., "Bis (pyrrolecarboxmide) Linked to Intercalating Chromophore Oxazolopyridocarbazole (OPC): Selective Binding to DNA and Polynucleotides," *Biochemistry* 30:1642–1650 (1991).

Szewczky, et al., "Sequence–Specific Recognition of DNA by a Major and Minor Groove binding Ligand," *Agew. Chemie Int. Ed. Eng.*, 35:1487–1489 (1996).

Tao, et al., "Rational Design of Sequence–Specific DNA Alkylating Agents Based on Duocarmycin A and Pyrrole–Imidazole Hairpin Polyamides," *Journal of American Chemical Society*, 121:4961–4967 ( 1999).

Tao, et al., "Sequence–Specific DNA Alkylation by Hybrid Molecules between Segment A of Duocarmycin A and Pyrrole/Imidazole Diamide," *Angew. Chem. Intl. Ed Engl.* 38:650–653 (1999).

Tagle, D.A., et al., "Magnetic Bead Capture of Expressed Sequence Encoded within Large Genomic Segments," *Nature* 361:751–753.

Thuong, et al. "Sequence–Specific Recognition of Modification of Double–Helical DNA by Oligonucleotides," *Angew. Chem. Int. Ed. Engl.* 32:666–690 (1993).

Tjian, "Molecular Machines that Control Genes," *Scientific America*, 2:54–61 (1995).

Trauger, et al. Extended Hairpin Polyamide Motif for Sequence–Specific Recognition in the Minor Groove of DNA *Chemistry & Biology* 3:369–377 (1996).

Trauger, et al., "Extension of Sequence–Specific Recognition in the Minor Groove of DNA by Pyrrole– Imidazole 1 Polyamides to 9–13 Base Pairs," *Journal of the American Chemical Society* 118:6160–6166 (1996).

Van Dyke and Dervan "Foothprinting with MPE • Fe (II). Complementary–stand Analyses of Distamycin _and Actinomycin–binding sites on Heterogeneous DNA" *Cold Spring Harbor Symposium on Quantum Biology* 47.

Wade, et al., "Binding Affinities of Synthetic Peptides, Pyridrine–2–Carboxamideonetropsin and 1– Methylimidazole–2– Carboxamidonetropsin, That Form 2:1 Complexes in the Minor Groove of Double–Helical DNA," *Biochemistry*. 32:11385–11389 (1993).

Wang. A, et al., "Interactive Drug Binding to DNA, " *Current Opinion in Structural Biology* 2:361–368 ( 1992).

Wang. J.C., et al., "The Degree of Unwinding of the DNA Helix by Ethidium I. Titration of Twisted PM2 DNA Molecules in Alkaline Cesium Density Gradients," *Journal of Molecular Biology* 89:783–801 (1974).

Waring M. "Variation of the Supercoils on Closed Circular DNA by Binding of Antibiotics and Drugs: Evidence for Molecular Models Involving Intercalation," *Journal of Molecular Biology* 54:247–279 (1970).

Watson, J.D. "Double Helix: Recombination DNA: Gene Therapy; Predictive Genetics," *Gene,* 135:309–315 ( 1993).

Weber, P. C., et al., "Structural Origins of High–Affinity Biotin Binding to Streptavidin," *Science* 243:85–88.

Weiss, et al., "The Structure of Antibiotic T–1384. Synthesis of the Degradation Fragments," *Journal of the American Chemical Society* 79:1266 (1957).

White, et al., "Effects of the A•T/T•A Degeneracy of Pyrrole–Imidazole Polyamide Recognition in the Minor Groove of DNA," *Biochemistry* 35:12532–12537 (1996).

White, et al., "One the Pairing Rules for Recognition in the Minor Groove of DNA by Pyrrole–Imidazole Polyamides," *Chemistry & Biology* 4:569–578 (1997).

Zasedatelev, et al., *Dokl. Akad. Nauk. SSSR* 231:1006–1009 (1976).

Zasedatelev, et al., "Binding of Netropsin to DNA and Synthetic Polynucleotides," *Molecular Biology Report* 1:337–342 (1974).

Zimmer, C. "Effects of the Antibiotics Netropsin and Distamycin A on the Structure and Function of Nucleic Acids," *Prog. Nucleic Acid Res. Mol Biol.* 15:285 (1975).

Zimmer and Wanhert, "Nonintercalating DNA Binding Ligands: Specificity of the Interaction and their Use as Tools in Biophysical, Biochemical Investigations of the Genetic Material" *Prog. Biophys. Mol.* 47:31–112 (1986).

Zukermann, et al., "Efficient Method for the Preparation of Peptoids [Oligo (N–substituted glycines)] by Submonomer Solid–Phase Synthesis," *Journal of the American Chemical Society* 114:10646–10647 (1992).

Church, et al., "N– (2–Chloroethyl)–N–nitrosoureas Covalently Bound to Nonionic and Monocationic Lexitropsin Dipeptides. Synthesis, DNA Affinity binding Characteristics, and Reaction with 32 P–End–Labeled DNA," *Biochemistry* 29:6827 (1990).

De Claire, et al., "NMR Characterixation of Hairpin Polyamide Complexes with the Minor Groove of DNA," *Journal of the American Chemical Society* 119:7909–7916 (1997).

He, et al., "Microgonotropens and Their Interactions with DNA. 1.$^1$ Synthesis of the Tripyrrole Peptides Dien–Microgonotropen–a, –b and –c and Characterization of Their Interactions with dsDNA," *Journal of the American Chemical Society* 115:7061 (1993).

Kelly, et al., "Binding site size limit of the 2:1 pyrrole—imidazole polyamide–DNA motif," *Proc. National Academy of Science USA* 93:6981–6985 (1996).

Pelton, J.G. & Wemmer, D.E., "Structural characterization of a 2:1 distamycin A.d (CGCAAATTGGC) complex by two–dimensional NMR," *Proc. National Academy of Science* 86:5723–5727 (1989).

Swalley, et al. I, A Pyrrole—Imidazole Motif for Recognition of Eleven Base Pair Sequences in the Minor Groove of DNA, *Chemical. European. Journal* 3:1600–1607 (1997).

Swalley, et al. II, "Discrimination of 5'–GGGG–3', 5'–GCGC–3' Sequences in the Minor Groove of DNA by Eight–Ring Hairpin Polyamides," *Journal of the American Chemical Society* 119:6953–6961 (1997).

Turner, et al., "Recognition of Seven Base Pair Sequences in the Minor Groove of DNA by Ten–Ring Pyrrole–Imidazole Polyamide Hairpins," *Journal of the American Chemical Society* 119:7636–7644 (1997).

Wade, et al., "Design of Peptides That Bind in the Minor Groove of DNA at 5'–(A, T) G (A, T) C (A, T)–3' Sequences by a Dimeric Side–by–Side Motif," *Journal of the American Chemical Society* 114:8783–8794. (1992).

Abu–Daya et al., "DNA sequence preferences of several AT–selective minor groove binding ligands," *Nucleic Acids Research* 23:3385–3392 (1995).

Abu–Daya et al., "Interaction of minor groove binding ligands with long AT tracts," *Nucleic Acids Research* 25:4962–4969 (1997).

Aleman et al., "Toward an Understanding of the Drug–DNA Recognition Mechanism. Hydrogen–Bond Strength in Netropsin–DNA Complexes," *J. Phys. Chem.* 100:11480–11487 (1996).

Al–Said et al., "A convenient synthesis of cross–linked homodimeric bis–lexitropsins," *Synth. Commun.* 25(7):1059–1070 (1995).

Al–Said et al., "Synthesis of novel cross–linked bis–lexitropsins," *Tetrahedron Lett.* 35(41):7577–7580 (1994).

Andronikashvili et al., "Spectral Manifestations of the Action of $Zn^{2+}$ Ions on DNA Complexes with Distamycin," *Biophysics* 33:824–829 (1988).

Arcamone et al., "Distamicina A. Nota I. Isolamento e struttura dell'agente antivirale distamicina A," pp. 1097–1109 (In Spanish with English Abstract).

Arcamone et al., "Structure and synthesis of Distamycin A," *Nature* 203:1064–1065 (1964).

Arcamone et al., "Synthesis, DNA binding and antiviral activity of distamycin analogues containing different heterocyclic moieties," *Anti–Cancer Drug Design* 1:235–244 (1986).

Bailly et al., "Depsipeptide Analogs of the Antitumor Drug Distamycin Containing Thiazole Amino Acids Residues," *Tetrahedron* 44:5833–5843 (1988).

Bailly et al., "Design, Synthesis, DNA Binding, and Biological Activity of a Series of DNA Minor–Groove–Binding Intercalating Drugs," *Journal of Pharmaceutical Sciences* 78:910–917 (1989).

Bailly et al., "Subcellular Distribution of a Nitroxide Spin–Labeled Netropsin in Living KB Cells," *Biochemical Pharmacology* 38:1625–1630 (1989).

Baird and Dervan, "Solid Phase Synthesis of Polyamdies Containing Imidazole and Pyrrole Amino Acids," *J. Am. Chem .Soc.* 118:6141–6146 (1996).

Baker and Dervan, "70. Sequence Specific Cleavage or Double Helical DNA. N–Bromoacetyldistamycin" (Abstract).

Baker and Dervan, "Sequence–Specific Cleavage of DNA by N–Bromoacetyldistamycin. Product and Kinetic Analyses," *J. Am. Chem. Soc.* 111:2700–2712 (1989).

Baker and Dervan, "Sequence–Specific Cleavage of Double–Helix DNA. N–Bromoacetyldistamycin," *J. Am. Chem. Soc.* 107:8266–8268 (1985).

Baliga et al., "RecA•oligonucleotide filaments bind in the minor groove of double–stranded DNA," *Proc. Natl. Acad. Sci. USA* 92:10393–10397 (1995).

Beal and Dervan, "Recognition of Double Helical DNA by Alternate Strand Triple Helix Formation," *J. Am. Chem. Soc.* 114:4976–4982 (1992).

Best and Dervan, "Energetics of Formation of Sixteen Triple Helical Complexes Which Vary at a Single Position within a Pyrimidine Motif," *J. Am. Chem Soc.* 117:1187–1193 (1995).

Bianchi et al., "Alteration of the Expression of Human Estrogen Receptor Gene by Distamycin," *J. Steroid Biochem. Molec. Biol.* 54:211–215 (1995).

Borodulin et al., "Interaction of Ligand of the bis–Netropsin Type with Poly(dA)•Poly(dT). Optical, Structural, and Energettic Characteristics of AT–Specific Binding," *Institute of Molecular Biology*, Academy of Sciences of USSR, pp. 929–934 (1987) translated from *Molekulyarnaya Biologiya* 20(4):1144–1149 (1986).

Borodulin et al., "New Modes of Ligand Interaction with DNA: A Trimeric bis–Netropsin Complex with Poly-(dA–dT)," *Molecular Biology* 30:661–665 (1996).

Botella and Nieto, "The C–terminal DNA–binding domain of Chironomus BR gene products shows pdeferentially affinity for (dA•dT)–rich sequences," *Mol Gen Genet* 251:422–427 (1996).

Brabec and Balcarova, "459—The Effect of Netropsin on the Electrochemical Oxidation of DNA at a Graphite Electrode," *Bioelectrochemistry & Bioenergetics* 9:245–252 (1982).

Braun et al., "Stereoselective Aldol Reactions with (R)– and (S)–2–Hydroxy–1,2,2–triphyenylethyl Acetate ("HYTRA")" (Abstract).

Broeker et al., "The Mixed Lineage Leukemia (MLL) Protein Involved in 11q23 Translocations Contains a Domain that Binds Cruciform DNA and Scaffold Attachment Region (SAR) DNA," pp. 259–268.

Broggini et al., "Modulations of transcription factor–DNA interactions by anticancer drugs," *Anti–Cancer Drug Design* 9:373–387 (1994).

Bruice et al., "Rational design of substituted tripyrrole peptides that complex with DNA by both selective minor–groove binding and electrostatic interaction with the phosphate backbone," *Proc. Natl. Acad. Sci. USA* 89:1700–1704 (1992).

Bruzik et al., "Specific Activation of Transcription Initiation by the Sequence–Specific DNA–Binding Agents Distamycin A and Netropsin," *Biochemistry* 26:950–956 (1987).

Burckhardt et al., "Reversal of the Z– to B–Conformation of Poly(dA–dT)•Poly(dA–dT) Induced by Netropsin and Distamycin A," *Journal of Biomolecular Structure & Dynamics* 13:671–676 (1996).

Burkhardt et al., "Two Binding Modes of Netropsin are Involved in the Complex Formation with Poly(dA–dT)•Poly(dA–dT) and other Alternating DNA Duplex Polymers," *Journal of Biomolecular Structure and Dynamics* 2:721–736 (1985).

Burckhardt et al., "Variation of DNA sequence specificity of DNA–oligopeptide binding ligands related to netropsin: imidazole–containing lexitropsins," *Biochimica et Biophysica Acta* 1009:11–18 (1989).

Burridge et al., "Electrostatic potential and binding of drugs to the minor groove of DNA," 5(3):165–166 (Sep. 1987).

Cartwright et al., "Cleavage of chromatin with methidiumpropyl–EDTA•iron(II)," *Proc. Natl. Acad. Sci. USA* 80:3213–3217 (1983).

Chai and Alonso, "Distamycin–induced inhibition of formation of a nucleoprotein complex between the terminase small subunit of G1P and the non–encapsidated end (pacL site) of *Bacillus subtilis* bacteriophage SPP1," *Nucleic Acids Research* 24:282–288 (1996).

Chaloupka and Kucerova, "Netropsin increases formation of mRNA coding for a neutral metalloproteinase in *Bacillus megaterium*," *J. Basic Microbiol.* 28:11–16 (1988).

Chandra et al., "Some Structural Requirements for the Antibiotic Action of Distamycins," *FEBS Letters* 16:249–252 (1971).

Chang et al., "On the importance of van der Waals interaction in the groove binding of DNA with ligands: restrained molecular dynamics study," *International Journal of Biological Macromolecules* 19:279–285 (1996).

Chen et al., "Design of Distamicin Analogues to Probe the Physical Origin of the Antiparallel Side by Side Oligopeptide Binding Motif in DNA Minor Groove Recognition," *Biochemical and Biophysical Research Communications* 220:213–218 (1996).

Chen et al., "Only one of the two DNA–bound orientations of AP–1 found in solution cooperates with NFATp," *Current Biology* 5:882–889 (1995).

Chen et al., "Optimization of Cross–Linked Lexitropsins," *Journal of Biomolecular Structure & Dynamics* 14:341–355 (1996).

Chen et al., "Design and synthesis of sequence–specific DNA minor groove recognizing ligands of the cross–linked lexitropsin class," *Heterocycles* 41(8):1691–1707 (1995).

Chen et al., "DNA minor groove binding of cross–linked lexitropsins: Experimental conditions required to observe the covalently linked WPPW (Groove wall peptide–peptide–groove wall)motif," *Biophys. J.* 68(5):2041–2048 (1995).

Chen et al., "A new DNA minor groove binding motif: Cross–linked lexitropsins," *J. Am. Chem. Soc.* 116(16):6995–7005 (1994).

Chen, "Design, synthesis and evaluation of novel bismustard cross–linked lexitropsins," *Bioorg. Med. Chem. Lett.* 5(19):2223–2228 (1995).

Chiang et al., "Effect of DNA–binding Drugs on Early Growth Response Factor–I and TATA Box–binding Protein Complex Formation with the Herpes Simplex Virus Latency Promoter," *J. Biol. Chem.* 271:23999–24004 (1996).

Cho et al., "Cyclic polyamides for recognition in the minor groove of DNA," *Proc. Natl. Acad. Sci. USA* 92:10389–10392 (1995).

Colocci and Dervan, "Cooperative Binding of 8–mer Oligonucleotides Containing 5–(1–Propynyl)–2'–deoxyuridine to Adjacent DNA Sites by Triple–Helix Formation," *J. Am. Chem. Soc.* 116:785–786 (1994).

Colocci and Dervan, "Cooperative Triple–Helix Formation at Adjacent DNA Sites: Sequence Composition Dependence at the Junction," *J. Am. Chem. Soc.* 117:4781–4787 (1995).

Colocci et al., "Cooperative Oligonucleotide–Directed Triple Helix Formation at Adjacent DNA Sites," *J. Am. Chem.Soc.* 115:4468–4473 (1993).

Colson et al., "Electrical linear dichroism as a new tool to study sequence preference in drug binding to DNA," *Biophysical Chemistry* 58:125–140 (1996).

Dasgupta et al., "DNA–Binding Characteristics of a Synthetic Analogue of Distamycin," *Biochemical and Biophysical Research Communications* 140:626–631 (1986).

Dasgupta et al., "Interaction of Synthetic Analogues of Distamycin with Poly(dA–dT): Role of the Conjugated N–Methylpyrrole System," *Biochemistry* 26:6381–6386 (1987).

Debart et al., "Synthesis, DNA Binding, and Biological Evaluation of Synthetic Precursors and Novel Analogues of Netropsin," *J. Med. Chem.* 32:1074–1083 (1989).

Dervan and Baker, "Design of Sequencec–Specific DNA Cleaving Molecules," *Annals of the New York Academy of Sciences* pp. 51–59.

Dervan, "113. A Chemical Approach to the Single Site Cleavage of Human Chromosomes," *Abstracts, Division of Biological Chemistry* 31:2209 (1992).

Dervan, "117. A Chemical Approach to the Single Site Cleavage of Human Chromosomes" (Abstracts).

Dervan, "122. Design of Sequence Specific DNA Binding Molecules" (Abstract).

Dervan, "7. Design of Sequence Specific DNA Cleaving Molecules" (Abstract).

Dervan, "83. Design of Sequence Specific DNA Cleaving Molecules" (Abstract).

Dervan, "83. Synthetic Sequence Specific DNA Binding Molecules" (Abstract).

Dervan, "Synthetic Sequence Specific DNA Binding Molecules," *Abstracts, Division of Biological Chemistry* 26:4171 (1987).

Dervan, "Design of Sequence–Specific DNA–Binding Molecules," *Science* 232:464–471 (1986).

Dervan, "Reagents for the site–specific cleavage of megabase DNA," *Nature* 359:87–88 (1992).

Di Marco et al., "Experimental Studies on Distamycin A—A New Antibiotic with Cytotoxic Activity," *Cancer Chemotherapy Reports* 18:15–19 (1962).

Di Marco et al., "Selective Inhibition of the Multiplication of Phage T1 in *E. coli* K12," *Experientia* 19:134–136 (1963).

Di Marco et al., "The Antimitotic Activity of Antibiotic Distamycin A," pp. 423–426.

Di Pietro et al., "N–Formimidoyl analogues of distamycin," *J. Chem. Soc., Perkin Trans. 1*, pp. 1333–1335 (1996).

D'Incalci et al., "Studies on the Mode of Action of FCE 24517, a New Distamycin A Derivative," *Proceedings of AACR* 29:329 at abstract No. 1310 (1988).

Ding et al., "The preparation of partially protected 3–amino–1–methylpyrazole–5–carboxylic acids to be used as intermediates in the synthesis of analogs of distamycin–A," Acta Chemica Scandivavica 44(1):75–81 (1990).

Ding et al., "Synthesis and antiviral activity of three pyrazole analogues of distamycin A," Acta Chemica Scandinavica 48:498–505 (1994).

Distefano and Dervan, "Energies of cooperative binding olgionucleotides with discrete dimerization domains to DNA by triple helix formation," *Proc. Natl. Acad. Sci. USA* 90:1179–1183 (1993).

Distefano and Dervan, "Ligand–Promoted Dimerization of Oligonucleotides Binding Cooperatively to DNA," *J. Am. Chem. Soc.* 114:11006–11007 (1992).

Dorn et al., "Dystamycin– induced inhibitor of homeodomain DNA complexes," EMBO Journal 11:279–286 (1992).

Dreyer and Dervan, "Sequence–specific cleavage of single-stranded DNA: Oligonucleotide–EDTA•Fe(II)," *Proc. Natl. Acad. Sci. USA* 82:968–970 (1985).

Dunner et al., "Enhancement of a Fra(16)(q22) with Distamycin A: A Family Ascertained Through an Abnormal Proposita," *American Journal of Medical Genetics* 16:277–284 (1983).

Durand and Maurizot, "Distamycin A Complexation with a Nucleic Acid Triple Helix," *Biochemistry* 35:9133–9139 (1986).

Dwyer et al., "Structural Analysis of Covalent Peptide Dimers, Bis(pyridine–2–carboxamidonetropsin)$(CH_2)_{3-6}$, in Complex with 5'–TGACT–3' Sites by Two–Dimensional NMR," *J. Am. Chem. Soc.* 115:9900–9906 (1993).

Eliadis et al., "The Synthesis and DNA Footprinting of Acridine–linked Netropsin and Distamycin Bifunctional Mixed Ligands," *J. Chem. Soc. Chem. Commun.* 1049–1052 (1988).

Feng et al., "Hin recombinase bound to DNA: The origin of specificity in major and minor groove interactions," Science 236:348–355 (1994).

Feng et al., "Crystallization and preliminary X–ray analysis of the DNA binding domain of the Hin recombinase with its DNA binding site," J. Mol. Biol. 232:982–986 (1993).

Fesen and Pommier, "Topoisomerase Inhibition by Anticancer Drugs in Antagonized by Distamycin," *Proceedings of AACR* 29:276 at abstract No. 1095 (1988).

Filipowsky et al., "Linked lexitropsins and the in vitro inhibition of HIV–1 reverse transcriptase RNA–directed DNA polymerization: A novel induced–fit of 3,5 m–pyridyl bisdistamycin to enzyme–associated template primer," Biochemistry 35(48)15397–15410 (1996).

Fish et al., "Determination of Equilibrium Binding Affinity of Distamycin and Netropsin to the Synthetic Deoxyolignucleotide Sequence $d(GGTATACC)_2$ by Quantitative DNase 1 Footprinting," *Biochemistry* 27:6026–6032 (1988).

Fox and Waring, "DNA structural variations produced by actinomycin and distamycin as revealed by DNAse I footprinting," *Nucleic Acids Research* 12:9271–9285 (1984).

Fransson et al., "High–performance liquid chromatography of distamycin A and its primary decomposition products as well as some synthetic analogues," *Journal of Chromatography* 268:347–351 (1983).

Fregeau et al., "Characterization of a CPI–lexitropsin conjugate–oligonucleotide covalent complex by 1H NMR and restrained molecular dynamics simulations," J. Am. Chem. Soc. 117(35):8917–8925.

Frigerio et al., "Determination of FCE 26644, a new polysulphonated derivative of distamycin A, in monkey plasma by reversed–phase ion–pair high–performance liquid chromatography with ultraviolet detection," *Journal of Chromatography A* 729:237–242 (1996).

Gao et al., "Comparative NMR Studies of Oligo–N–Methylpyrrolecarboxamide d[CGAAATTTCG] Complexes" (Abstract).

Geierstanger et al., "Design of a G•C–Specific DNA Minor Groove–Binding Peptide," *Science* 266:646–650 (1994).

Geierstanger et al., "Extending the recognition site of designed minor groove binding molecules," *Nature Structural Biology* 3:321–324 (1996).

Geierstanger et al., "Structural and Dynamic Characterization of the Heterodimeric and Homodimeric Complexes of Distamycin and 1–Methylimidazole–2–carboxamide–Netropsin Bound to the Minor Groove of DNA," *Biochemistry* 33:3055–3062 (1994).

Geierstanger, Bernhard Hubert, PhD Thesis entitled *NMR Studies of Peptides, Distamycin and its Analogs Bound to the Minor Groove of DNA*, University of Berkely (1994).

Genelabs, PCR Newswire—"Genelabs Receives Seven Patent Allowances for Its DNA–Binding Technology" (1987—exact date unknown).

Germann et al., "Relative Stability of Parallel– and Antiparallel–Stranded Duplex DNA," *Biochemistry* 27:8302–8306 (1988).

Giuliani et al., "Distamycin A derivatives: in vitro and in vivo activity of a new class of antitumor agents," *Proceedings of AACR* 29:330 at abstract No. 1311 (1988).

Goodsell et al., "Structure of dicationic monoimidazole lexitropsin bound to DNA," Biochemistry 34(51):16654–16661 (1995).

Greenberg et al., "Energetics of Formation of Sixteen Triple Helical Complexes Which Vary at a Single Position within a Purine Motif," J. Am. Chem. Soc. 117:5016–5022 (1995).

Grehn et al. "Synthesis and Antiviral Activity of Distamycin A Analogues: Substitutions on the Different Pyrrole Nitrogens and in the Amidine Function," J. Med. Chem. 26:1042–1049 (1983).

Grehn et al., "A convenient method for the preparation of 1% Tert–butyloxycarbonyl <Pyrroles," Angewandte Chemie International Edition in English v23(4)296 (1984).

Grehn et al., "Novel efficient total synthesis of antiviral antibiotic distamycin A." Journal of Organic Chemistry 46:3492–3497 (1981).

Grehn et al., "Removal of formyl, acetyl, and benzoyl groups from amides with conversion into the corresponding tert–butyl carbamates," Journal of the Chemical Society Chemical Communications 19(2):1317–1318 (1985).

Grehn et al., "Structure–activity–relationships in distamycin–A analogs–effect of alkyl groups on the pyrrole nitrogen at the non–amidine end of the molecule combined with methylelimination in the following ring," Acta Chemica Scandivavica 40(2):145–151 (1986).

Grehn et al., "The preparation and properties of partially protected 4–amino–1–methylimidazole–2–carboxylic acids to be used as intermediates in the synthesis of analogs of dystamycin–A," Acta Chemica Scandivavica 44(1):67–74 (1990).

Griffin and Dervan, "207. Sequence Specific Recognition of DNA by Chiral (Bis(Netropsin)s" (Abstract).

Griffin and Dervan, "98. Designed, Synthetic, Metalloregulatory DNA Binding Molecules" (Abstract).

Griffin and Dervan, "Recognition of Thymine–Adenine Base Pairs by Guanine in a Pyrimidine Triple Helix Motif," Science 245:967–971 (1989).

Griffin and Dervan, "Sequence–Specific Chiral Recognition of Right–Handed Double–Helical DNA by (2S,3S)– and (2R,3R)–Dihydroxybis(netropsin)succinamide," J. Am. Soc. Chem. 108:5008–5009 (1986).

Griffin, Dreyer and Dervan, "68. Sequence Specific Cleavage of Single Stranded DNA: Oligodeoxynucleotide–EDTA–FE(II)" (Abstract).

Griffin, John Hampton, PhD Thesis entitled Structure–, Stereochemistry–, and Metal–Regulated DNA Binding/ Cleaving Molecules, California Institute of Technology, Pasadena, California (Submitted Jul. 11, 1989).

Grygon and Spiro, "Ultraviolet Resonance Raman Spectroscopy of Distamycin Complexes with Poly(dA)–(dT) and Poly(dA–dT): Role of H–Bonding," Biochemistry 28:4397–4402 (1989).

Guo et al., "DNA sequence–selective binding of head–to–tail linked bis–lexitropsins: relation of phasing to cytotoxic potency," Anti–Cancer Drug Des. 8(5):369–397 (1993).

Gupta et al., "Design, synthesis and topoisomease II inhibition activity of 4'–demethylepipodo– phyllotoxin–lexitropsin conjugates," Anti–Cancer Drug Design 11:325–338 (1996).

Gupta et al., "Novel DNA–directed alkylating agents consisting of naphthalimide, nitrogen mustard and lexitropsin moieties: synthesis, DNA sequence specificity and biological evaluation," Anti–Cancer Drug Des.. 11:581–596 (1996).

Gupta et al., "Hybrid molecules containing propargylic sulfones and DNA minor groove–binding lexitropsins: Synthesis, sequences specificity of reaction with DNA and biological evaluation," Gene 149(1):81–90 (1994).

Hacia et al., "Inhibition of Klenow Fragment DNA Polymerase on Double–Helical Templates by Oligonucleotide–Directed Triple–Helix Formation," Biochemistry 33:6192–6200 (1994).

Hacia et al., "Phosphorothioate Oligonucleotide–Directed Triple Helix Formation," Biochemistry 33:5367–5369 (1994).

Han and Dervan, "Different conformational families of pyrimidine•purine•pyrimidine triple helices depending on backbone composition," Nucleic Acids Research 22:2837–2844 (1994).

Han and Dervan, "Sequence–specific recognition of double helical RNA and RNA•DNA by triple helix formation," Proc. Natl. Acad. Sci. USA 90:3806–3810 (1993).

Han and Dervan, "Visulation of RNA tertiary structure by RNA–EDTA•Fe(II) autocleavage: Analysis of tRNA$^{Phe}$ with uridine–EDTA•Fe(II) at position 47," Proc. Natl. Acad. Sci. USA 91:4955–4959 (1994).

Han et al., "Mapping RNA Regions in Eukaryotic Ribosomes That Are Accessible to Methidiumpropyl–EDTA•Fe(II) and EDTA•Fe(II)," Biochemistry 33:9831–9844 (1994).

Harapanhalli et al., [$^{125}$I/$^{127}$I]IodoHoechst 33342: Synthesis, DNA Binding, and Biodistribution, J. Med. Chem. 39:4804–4809 (1996).

Harshman and Dervan, "Molecular recognition of B–DNA by Hoechst 33258," Nucleic Acids Research 13:4825–4835 (1985).

Hertzberg and Dervan, "Cleavage of DNA with Methidiumpropyl–EDTA–Iron(II): Reaction Conditions and Product Analyses," Biochemistry 23:3934–3945 (1984).

Hinsberg et al., "Direct Studies of 1,1–Diazenes. Syntheses, Infrared and Electronic Spectra, and Kinetics of the Thermal Decomposition of N–(2,2,6,6–Tetramethylpiperidyl)nitrene and N–(2,2,5,5,–Tetramethylpyrrolidyl)nitrene," J. Amer. Chem. Soc. 104:766–773 (1982).

Huang et al., "Synthesis of designed functional models of bleomycin incorporating imidazole– containing lexitropsins as novel DNA recognition sites," Heterocycles 41(6):1181–1196 (1995).

Huang et al., "Design, synthesis, and sequence selective DNA cleavage of functional models of bleomycin. a. Hybrids incorporating a sample metal–complexing moiety of blemycin and lexitropsin carriers," Bioconjugate Chem. 6(1):21–33 (1995).

Huang et al., "Design of DNA–cleaving modecules which incorporate a simplified metal–complexing moiety of bleomycin and lexitropsin carriers," Bioorg. Med. Chem. Lett. 3(8):1751–1756 (1993).

Huntingon's Disease Collaborative Research Group, "A Novel Gene Containing a Trinucleotide Repeat That is Expanded and Unstable on Huntington's Disease Chromsomes," Cell 72:971–983 (1993).

Hunziker et al., "Design of an N$^7$–Glycosylated Purine Nucleoside for Recognition of GC Base Pairs by Triple Helix Formation," J. Am. Chem. Soc. 117:2661–2662 (1995).

Ikeda and Dervan, "Sequence–Selective Inhibition of Restriction Endonucleases by the Polyintercalator Bis(methidium)spermine," J. Am. Chem. Soc. 104:296–297 (1982).

Iverson and Dervan, "69. Cleavage of Complementary Strands of Nucleic Acids with Single Base Specificity. Enzymatic Incorporation of Modified Uridine Triphosphates" (Abstract).

Iverson and Dervan, "Adenine–Specific DNA Chemical Sequencing Reaction," *Methods in Enzymology* 218:222–227 (1993).

Iverson and Dervan, "Piperdine specific DNA chemical sequencing reaction," *Nucleic Acids Research* 14:7823–7830 (1987).

Jensen and Lysek, "Differences in the mycelial growth rhythms in a population of Sclerotinia fructigena (Pers.) Schroter," *Experientia* 39:1401–1402 (1983).

Jotterand–Bellomo, "The effects of distamycin A on cultured amniotic fluid cells," *Ann. Genet.* 26:27–30 (1983) (In French with English Abstract).

Kharatishvili et al., "Formation of the left Helix On Simultaneous Exposure to Poly [d/(GC)] bis–Netropsin and Zn(II) Ions," *Biophysics* 30:764–766 (1985).

Kiessling et al., "Flanking Sequence Effects within the Pyrimidine Triple–Helix Motif Characterized by Affinity Cleaving," *Biochemistry* 31:2829–2834 (1992).

Koh and Dervan, "Design of a Nonnatural Deoxyribonucleoside for Recognition of GC Base Pairs by Oligonucleotice–Directed Triple Helix Formation," *J. Am. Chem. Soc.* 114:1470–1478 (1992).

Koppel et al., "Basicity of 3–Aminopropionamidine Derivatives in Water and Dimethyl Sulphoxide, Implication for a Pivotal Step in the Synthesis of Distamycin A Analogues," *Journal of Physical Organic Chemistry* 9:265–268 (1996).

Koshlap et al., "Nonnatural Deoxyribonucleoside $D_3$ Incorporated in an Intramolecular DNA Triplex Binds Sequence–Specifically by Intercalation," *J. Am. Chem. Soc.* 115:7908–7909 (1993).

Kothekar et al., "Influence of Local Exitations in DNA Conformation on Binding of Nonintercalating Antitumor Antibiotic in the Minor Groove," *International Journal of Quantum Chemistry: Quantum Biology Symposium* 13:175–183 (1986).

Krauch et al., "New Base Pairs for DNA and RNA" (abstract).

Krowicki and Lown, "Synthesis of Novel Imidazole–Containing DNA Minor Groove Binding Oligopeptides Related to the Antiviral Antibiotic Netropsin," *J. Org. Chem.* 52:3493–3501 (1987).

Kucerova et al., "Netropsin stimulates the formation of an extracellular proteinase and suppresses protein turnover in sporulating *Bacillus megaterium*," *FEMS Microbiology Letters* 34:21–26 (1986).

Kumar et al., "Molecular recognition and binding of a GC site–avoiding thiazole–lexitropsin to the decadeoxyribonucleotide d–[CGCAATTCGC]$_2$: An H–NMR evidence for thiazole intercalation," *J. Biomol. Struct. Dyn.* 8(1):99–121 (1990).

Kumar et al., "Structural and dynamic aspects of non–intercalative (1:1) binding of a thiazole–lexitropsin to the decadeoxyribonucleotide d–[CGCAATTCGC]$_2$: An H–NMR and molecular modeling study," *J. Biomol. Struct. Dyn.* 9(1):1–21 (1991).

Kuroda et al., "Intelligent compounds which read DNA base sequences," *Supramolecular Chemistry* 6:95–102 (1995).

Kurrech et al., "Endor spectroscopy—A promising technique for investigating the structure of organic radicals," *Angew. Chem. Int. Ed. Engl.* 23:173–194 (1984).

Lane et al., "Sequence specificity of actinomycin D and Netropsin binding to pBR322 DNA analyzed by protection from Dnase I," *Proc. Natl. Acad. Sci. USA* 80:3260–3264 (1983).

Larsen and Dickerson, "As the Helix Turns, or, Rational Design of Sequence Specific DNA Minor Groove Binding Drugs," *J. Mol. Graphics* 6:211 (1988).

Lee and Walker, "Ch. 3—Sequence–Selective Binding of DNA by Oligopeptides as a Novel Approach to Drug Design," in *Polymeric Drugs and Drug Administration*, American Chemical Society, pp. 29–46 (1994).

Lee et al., "Structural and Dynamic Aspects of the Sequence Specific Binding of Netropsin and its Bis–Imidazole Analogue on the Decadeoxyribonucleotide d–[CGCAA TTGCG]$_2$," *Journal of Biomolecular Structure & Dynanmics* 5:939–949 (1988).

Lee et al., "Sequence specific molecular recognition and binding of a monocationic bis–imidazole lexitropsin to the decadeoxyribonucleotide d–[(GATCCGTATG) (CATACG-GATC)]: structural and dynamic aspects of intermolecular exchange studied by H–NMR," *J. Biomol. Struct. Dyn.* 5(5):1059–1087 (1988).

Lee et al., "Molecular recognition between oligopeptides and nucleic acids. Specificity of binding of a monocationaic bis–furan lexitropsin to DNA deducted from footprinting and H NMR studies," *J. Mol. Recognit.* 2(2):84–93 (1989).

Leinsoo et al., "Attachment of Trivaline to a Netropsin Analog Changes the Specificity of its Binding to DNA," *Institute of Molecular Biology*, Academy of Sciences of USSR, pp. 134–148 (1988) translated from *Molekulyarnaya Biologiya* 22(1):159–175 (1988).

Levina et al., "Conjugates of Minor Groove DNA Binders with Oligodeoxynucleotides: Synthesis and Properties," *Antisense & Nucleic Acid Drug Development* 6:75–85 (1996).

Liquier et al., "FTIR Study of Netropsin Binding to Poly d(A–T) and Poly dA • Poly dT," *J. Biomolecular Structure & Dynamics* 7:119–126 (1989).

Lombardi and Crisanti, "Antimalarial Activity of Synthetic Analogues of Distamycin," *Pharmacol. Ther.* 76:125–133 (1977).

Lown and Krowicki, "Efficient Total Syntheses of the Oligopeptide Antibiotics Netropsin and Distamaycin," *J. Org. Chem.* 50:3774–3779 (1985).

Lown et al., "Molecular Recognition between Oligopeptides and Nucleic Acids: Novel Imidazole–Containing Oligopeptides Related to Netropsin That Exhibit Altered DNA Sequence Specificity," *Biochemistry* 25:7408–7416 (1986).

Lown et al., "Novel Linked Antiviral and Antitumor Agents Related to Netropsin and Distamycin: Synthesis and Biological Evaluation," *J. Med. Chem.* 32:2368–2375 (1989).

Lown et al., "Structure–Activity Relationship of Novel Oligopeptide Antiviral and Antitumor Agents Related to Netropsin and Distamycin," *J. Med. Chem.* 29:1210–1214 (1986).

Lown, "Design and Development of Sequence Selective Lexitropsin DNA Minor Groove Binders," *Drug Development Research* 34:145–183 (1995).

Lown, "Lexitropsins in antiviral drug development," *Antiviral Res.* 17(3):179–196 (1992).

Lown, "DNA recognition by lexitropsins, minor groove binding agents," *J. Mol. Recognit.* 7(2):79–88 (1994).

Lown, "Design of sequence–specific agents: Lexitropsins," *Mol. Aspects Anticancer Drug– DNA Interact* Ch. 11:322–355 (1993).

Lown, "Synthetic chemistry of naturally occurring oligopeptide antibiotics and related lexitropsins," *Org. Prep. Proced. Int.* 21(1):1–46 (1989).

Luebke and Dervan, "Nonenzymatic Ligation of Oligodeoxyribonucleotides on a Duplex DNA Template by Triple–Helix Formation," *J. Am. Chem. Soc.* 111:8733–8735 (1989).

Lythgoe and Ramsden, "4–Unsubstituted, 5–Amino and 5–Unsubstituted, 4–Aminoimidazoles," *Advances in Heterocyclic Chemistry* 61:1–58 (1994).

Mack and Dervan, "Sequence–Specific Oxidative Cleavage of DNA by a Designed Metalloprotein, Ni(II)•GGH(Hin139–190)," *Biochemistry* 31:9399–9405 (1992).

Maner et al., "Analysis of Promoter–Specific Repression by Triple–Helical DNA Complexes in a Eukaryotic Cell–Free Transcription System," *Biochemistry* 31:70–81 (1992).

Maher et al., "Inhibition of DNA Binding Proteins by Oligonucleotide–Directed Triple Helix Formation," *Science* 245:725–730 (1989).

Malcom and Snounou, "Netropsin Increases the Linking Number of DNA," pp. 323–326.

Marck et al., "Specific interaction of netropsin, distamycin–3 and analogs with I.C duplexes: reversion towards the B form of the 2–deoxy–, 2'–deoxy–2'–fluoro– hybrid duplexes upon specific interactions with netropsin, distamycin–3 and analogs," *Nucleic Acids Research* 10:6147–6161 (1982).

Marky et al., "Calorimetric and spectroscopic investigation of drug–DNA interactions. I. The binding of netropsin to poly d(AT)," *Nucleic Acids Research* 11:2857–2871 (1983).

Marky, "Interaction of a Non–Intergalative Drug with DNA: Netropsin," pp. 417–418.

Martello et al., "Specific Activation of Open Complex Formation at an *Escherichia coli* Promoter by Oligo(N–m-ethylpyrrolecarboxamide)s: Effects of Peptide Length and Identification of DNA Target Sites," *Biochemistry* 28:4455–4461 (1989).

Matyasek et al., "Evidence for a sequence–directed conformation perodicity in the genomic highly repetitive DNA detectable with single–strand–specific chemical probe potassium parmangante," *Chromosome Research* 4:340–349 (1996).

Mazurek et al., "The binding of prototype lexitropsins to the minor groove of DNA: Quantum chemical studies," *J. Biomol. Struct. Dyn.* 9(2)299–313 (1991).

Milton et al., "Total chemical synthesis of a D–enzyme: The enatiomers of HIV–1 protease show demonstration of reciprocal chiral substrate specificity," *Science* 256:1445–1448 (1992).

Mitchell and Dervan, "Interhelical DNA–DNA Cross–Linking. Bis(monoazidomethidium)octaoxahexacosanediamine: A Probel of Packaged Nucleic Acid," *J. Am. Chem. Soc.* 104:4265–4266 (1982).

Momose et al., "3–hydroxypyrroles. I. A general synthetic route to 4,5–unsubstituted alkyl 3–hydroxypyrrole–2–carboxylates," *Chemical Pharmacology Bulletin* 26:2224–2232 (1978).

Momose et al., "3–hydroxypyrroles. II. The reaction of 4,5–unsubstituted alkyl 3–hydroxypyrrole–2–carboxylates with some electrophiles," *Chemical Pharmacology Bulletin* 26:3521–3529 (1978).

Moser and Dervan, "Sequence–Specific Cleavage of Double Helical DNA by Triple Helix Formation," *Science* 238:645–650 (1987).

Mosher et al., "Synthesis of N–Methyl–2–trichloroacetylpyrrole—A Key Building Block in Peptides that Bind DNA: Micro–, Semimicro–, and Macro–Scale Organic Lab Experiments," *Journal of Chemical Education* 73:1036–1039 (1996).

Mrksich and Dervan, "Antiparallel Side–by–Side Heterodimer for Sequence–Specific Recognition in the Minor Groove of DNA by a Distamycin/ 1–Methylimidazole–2–carboxamide–netropsin Pair," *J. Am. Chem. Soc.* 115:2572–2576 (1993).

Mrksich and Dervan, "Design of a Covalent Peptide Heterodimer of Sequence–Specific Recognition in the Minor Groove of Double–Helix DNA," *J. Am. Chem. Soc.* 116:3663–3664 (1994).

Mrksich and Dervan, "Enhanced Sequence Specific Recognition in the Minor Groove of DNA by Covalent Peptide Dimers: Bis(pyridine–2–carboxamidonetropsin)($CH_2$)$_{3-6}$," *J. Am. Chem. Soc.* 115:9892–9899 (1993).

Mrksich and Dervan, "Recognition in the Minor Groove of DNA at 5'–(A,T)GCGC(A,T)–3'by a Four Ring Tripetide Dimer. Reversal of the Specificity of the Natural Product Distamycin," *J. Am. Chem. Soc.* 117:3325–3332 (1995).

Mrksich et al., "Antiparallel side–by–side dimeric motif for sequence–specific recognition in the minor groove of DNA by the designed peptide 1–methylimidazole–2–carboxamide netropsin," *Proc. Natl. Acad. Sci. USA* 89:7586–7590 (1992).

Mrksich et al., "Hairpin Peptide Motif. A New Class of Oligopeptides for Sequence–Specific Recognition in the Minor Groove of Double–Helical DNA," *J. Am. Chem. Soc.* 116:7983–7988 (1994).

Mrksich et al., "Design of a covalent peptide heterodimer for sequence–specific recognition in the minor groove of double–helical DNA," *J. Am. Chem. Soc.* 116:3663–1664 (1994).

Mrksuch et al., Abstracts of the American Chemical Society 206 Part 2:413 (1993).

Mrksich, Milan, phD Thesis entitled *Design of Peptides for Sequence–Specific Recognition of the Minor Groove of DNA*, California Institute of Technology, Pasadena, California (submitted Mar. 8, 1994).

Nechipurenko et al., "Cooperative Interactions Between Analogs of Distamycin A, Adsorbed on DNA," *Institute of Molecular Biology*, Academy of Sciences of USSR, pp. 263–272 (1984) translated from *Molekulyarnaya Biologiya* 18(2):332–342 (1984).

Nikolaev et al., "Design of Sequence–Specific DNA Binding Ligands That Use a Two–Stranded Peptide Motif for DNA Sequence Recognition," *Journal of Biomolecular Structure & Dynamics* 14:31–47 (1996).

Nilsson et al., "Structure at restriction endouclease MboI cleavage sites protected by actinomycin D or distamycin A," *FEBS Letters* 145:360–364 (1982).

Nishiwaki et al., "Efficient Synthesis of Oligo–N–Methylpyrrolecarboxamides and Related Compounds," *Heterocycles* 27:1945–1952 (1988).

Oakley et al., "Synthesis of a Hybrid Protein Containing the Iron–Binding Ligand of Bleomycin and the DNA–Binding Domain of Hin," *Bioconjugate Chem.* 5:242–247 (1994).

Oakley et al., "Evidence that a major groove– binding peptide can simultaneously occupy a common site on DNA," *Biochemistry* 31:10969–10975 (1992).

Oakley, thesis entitled "Design, Synthesis and characterization of sequence–specific DNA, cleaning metallophoteths," California Institute of Technology, Pasadena, California Submitted Nov. 8, 1993.

Ochi et al., "New Heritable Fragile Site on Chromosome 8 Induced by Distamycin A," *Jpn. J. Cancer Res.* 79:145–147 (1988).

Parks et al., "Optimization of the Hairpin Polyamide Design for Recognition of the Minor Groove of DNA," *J. Am. Chem. Soc.* 118:6147–6152 (1996).

Parks et al., "Recognition of 5'–(A,T)GG(A,T)$_2$–3' Sequences in the Minor Groove of DNA by Hairpin Polyamides," *J. Am. Chem. Soc.* 118:6153–6159 (1996).

Parrack et al., "Interaction of synthetic analogs of distamycin with DNA: Role of the conjugated N–methylpyrrole system in specificity of binding," *FEBS Letters* 212:297–301 (1987).

Portugal and Waring, "Comparison of binding sites in DNA for berenil, netropsin and distamycin: A footprinting study," *Eur. J. Biochem.* 167:281–289 (1987).

Portugal and Waring, "Hydroxyl radical footprinting of the sequence–selective binding of netropsin and distamycin to DNA," *FEBS Letters* 225:195–200 (1987).

Portugal and Waring, "Interaction of nucleosome core particles with distamycin and echinomycin: analysis of the effect of DNA sequences," *Nucleic Acids Research* 15:885–903 (1987).

Povsic and Dervan, "Triple Helix Formation by Oligonucleotides on DNA Extended to the Physiological pH Range," *J. Am. Chem. Soc.* 111:3059–3061 (1989).

Priestley and Dervan, "Sequence Composition Effects on the Energetics of Triple Helix Formation by Oligonucleotides Containing a Designed Mimic of Protonated Cytosine," *J. Am. Chem. Soc.* 117:4761–4765 (1995).

Radhakrishnan and Patel, "NMR Structural Studies on a Nonnatural Deoxyribonucleoside Which Mediates Recognition of GC Base Pairs in Pyrimidine•Purine•Pyrimidine DNA Triplexes," *Biochemistry* 32:11228–11234 (1993).

Rajagopalan et al., "Interaction of non–intercalative drugs with DNA: Distamycin analogues," *J. Biosci.* 7:27–32(1985).

Rajagopalan et al., "Synthesis of a Distamycin Analogue: Tris(m–benzamido) Compound," *Indian Journal of Chemistry* 26B:1021–1024 (1987).

Rao et al., "Interaction of Synthetic Analogues of Distamycin and Netropsin with Nucleic Acids. Does Curvature of Ligand Play a Role in Distamycin–DNA Interactions?" *Biochemistry* 27:3018–3024 (1988).

Rao et al., "Molecular recognition between ligands and nucleic acids: Sequence preferences and binding of Pyrrolo [3,2–d] and [2,3–d]thiazole–containing lexitropsins deduced from MPE–Fe(II) footprinting," *Actual. Chim. Ther.* 20:159–188 (1993).

Rao et al., "Psoralen–lexitropsin hybrids: DNA sequence selectivity of photoinduced cross–linking from MPE footprinting and exonuclease III stop assay, and mode of binding from electric linear dichroism," *Anti–Cancer Drug Des.* 9(3):221–237 (1994).

Rao et al., "Molecular recognition between oligopeptides and nucleic acids: DNA binding selectivity of a series of 1,2,4–triazole–containing lexitropsins," *Chem. Res. Toxicol.* 4(2):241–252 (1991).

Rao et al., "Sequence–selective DNA binding by linked Bis–N–methylpyrrole dipeptides: an analysis by MPE footprinting and force field calculations," *J. Org. Chem.* 56(2):786–797 (1991).

Reinert et al., "Deformyldistamycin–DNA Interaction; DNA Conformational Changes as Revealed by Titration Rotational Viscometry," *J. Biomolecular Structure & Dynamics* 14(2):245–253 (1996).

Reinert et al., "DNA interaction of the imidazole–containing lexitropsin ImPy: Titration viscometric study in comparison to Netropsin," *J. Biomol. Struct. Dyn.* 12(4):847–855 (1995).

Ronne et al., "The effect of in vitro distamycin A exposure on metaphase chromosome structure," *Hereditas* 96:269–277 (1982).

Royyuru et al., "Theortical Study of Conformational Flexibility of Distamycin–A Analog and its Binding to DNA," *Current Science* 56:581–584 (1987).

Rubin et al., "An unexpected major groove binding of netropsin and distamycin A to tRNA$^{phe}$," *Journal of Biomolecular Structure and Dynamics* 2:165–174 (1984).

Sakaguchi et al., "Effect of netropsin on plasmid DNA cleavage by BAL 31 nuclease," *FEBS Letters* 191:59–62 (1985).

Salmanova et al., "Interaction of DNA with Synthetic Ligands Containing N,4–Disubstituted Mono– and Diphthalimides," *Molecular Biology* 29:491–498 (1995).

Sanfilippo et al., "Activity of the Distamycin A on the Induction of Adaptive Enzymes in *Escherichia coli*," *J. gen. Microbiol.* 43:369–374 (1966).

Sarma et al., "Structure of Poly(dA)•Poly(dT) is not Identical to the AT Rich Regions of the Single Crystal Structure of CGCGAATT$^{Br}$CGCG. The Consequence of this to Netropsin Binding to Poly(dA)•Poly(dT)," *J. Biomolecular Structure & Dynamics* 3(3):433–436 (1985).

Schabel et al., "Observations on Antiviral Activity on Netropsin," *Proceedings of the Society for Experimental Biology and Medicine* 83:1–3 (1953).

Schmid et al., "Characterization of a Y/15 translocation by banding methods, distamycin A treatment of lymphocytes and DNA restriction endonuclease analysis," *Clinical Genetics* 24:234–239 (1983).

Schmid et al., "The use of distamycin A in human lymphocyte cultures," *Human Genet* 65:377–384 (1984).

Schuhmann et al., "Wirkung von Distamycin A und Netropsin auf normale und zellwandlose Zellen von *Escherichia coli* W 1655F$^+$," *Zeitschrift fur Allg. Mikrobiologie* 14:321–327 (1974) (In German with English Abstract).

Schultz and Dervan, "Distamycin and Penta–N–Methylpyrrolecarboxamide Binding Sites on Native DNA—A Comparison of Methidiumpropyl–EDTA–Fe(II) Footprinting and DNA Affinity Cleaving," *J. Biomolecular Structure & Dynamics* 1:1133–1147(1984).

Schultz and Dervan, "Sequence–specific double–strand cleavage of DNA by penta–N–methylpyrrolecarboxamide–EDTA•Fe(II)," *Proc. Natl. Acad. Sci. USA* 80:6834–6837 (1983).

Schultz, "141. Design and Synthesis of Sequence Specific DNA Cleaving Molecules" (Abstract).

Shultz, thesis entitled "I. Ground and Excited state studies of persistent 1,1–diazenes," and "II. Design of sequence specific DNA cleaving molecules," California Institute of Technology, Pasadena, California Submitted Feb. 2, 1989.

Schulz and Dervan, "Sequence–Specific Double–Strand Cleavage of DNA by Bis(EDTA–distamycin–Fe$^{II}$) and EDTA–Bis(distamycin)•Fe$^{II}$," *J. Am. Chem. Soc.* 105:7748–7750 (1983).

Sengupta et al., "A Microgonotropen Pentaaza Pentabutylamine and its Interactions with DNA," *Bioorganic & Medicinal Chemistry* 4:803–813 (1996).

Shabtai et al., "Familial fragile site found at the cancer breakpoint (1)(q32): Inducibility by distamycin A, concomitance with gragile (16)(q22)," *Hum Genet* 73:232–234 (1986).

Shabtai et al., "Familial Fragility on Chromosome 16 (Fra 16q22) Enhanced by Both Interferon and Distamycin A," *Hum Genet* 63:341–344 (1983).

Shin, Sluka, Horvath, Simon and Dervan, "99. Synthetic DNA–Cleaving Proteins" (Abstract).

Shishido et al., "Enhancement of S1 Nuclease–Susceptibility of Negatively Superhelical DNA by Netropsin," *Biochemical & Biophysical Research Communications* 124:388–392 (1984).

Sidorova et al., "Competition between Netropsin and Restriction Nuclease EcoRl for DNA Binding," *J. Biomolecular Structure & Dynamics* 13(2):367–385 (1995).

Singh et al., "Isohelicity and Strand Selectivity in the Minor Groove Binding of Chiral (1R,2R)– and (1S,2S)–Bis(netropsin)–1,2–cyclopropanedicarboxamide Ligands to Duplex DNA," *J. Am. Chem. Soc.* 116:7006–7020 (1994).

Singh et al., "Structural characterization of side–by side binding for a cross–linked lexitropsin dimer designed to target G–C base pairs in the DNA minor groove," *Magn. Reson. Chem.* 34:S55–S66 (1996).

Singh et al., "A H–NMR study of the DNA binding characteristics of thioformyldistamycin an amide isosteric lexitropsin," *Biochemistry* 31(28):6453–6461 (1992).

Singleton and Dervan, "Equilibrium Association Constants for Oligonucleotide–Directed Triple Helix Formation at Single DNA Sites: Linkage to Cation Valence and Concentration," *Biochemistry* 32:13171–13179 (1993).

Singleton and Dervan, "Influence of ph on the Equilibrium Association Constants for Oligodeoxyribonucleotide–Directed Triple Helix Formation at Single DNA Sites," *Biochemistry* 31:10995–11003 (1992).

Singleton and Dervan, "Temperaturee Dependence of the Energetics of Oligonucleotide–Directed Triple–Helix Formation at a Single DNA Site," *J. Am. Chem. Soc.* 116:10376–10382 (1994).

Skamrov et al., "Specific Protection of DNA from the Action of Dnase I by Distamycin A, Netropsin, and Bis–Netropsins," *Institute of Molecular Biology*, Academy of Sciences of USSR, pp. 153–167 (1985) translated from *Molekulyarnaya Biologiya* 19(1):177–195 (1985).

Sluka et al., "Synthesis of a Sequence–Specific DNA–Cleaving Peptide," *Science* 238:1129–1132 (1987).

Snounou and Malcolm, "Production of Positively Supercoiled DNA by Netropsin," *J. Mol. Biol.* 167:211–216 (1983).

Sponar and Votavova, "Selective Binding of Synthetic Polypeptides to DNA of Varying Composition and Sequence: Effect of Minor Groove Binding Drugs," *J. Biomolecular Structure & Dynamics* 13(6):979–987 (1996).

Stanchev et al., "Netropsin, Distamycin A, bis–Netropsins as Selective Inhibitors of the Effect of Restrictase and DNase I," *Institute of Molecular Biology*, Academy of Sciences of USSR, pp. 1324–1333 (1987) translated from *Molekulyarnaya Biologiya* 20(6):1614–1624 (1986).

Staubli and Dervan, "Sequence specificity of the non–natural pyrido[2,3–d]pyrimidine nucleoside in triple helix formation," *Nucleic Acids Research* 22:2637–2642 (1994).

Stilz and Dervan, "Specific Recognition of CG Base Pairs by 2–Deoxynebularine within the Purine•Purine•Pyrimidine Triple–Helix Motif," *Biochemistry* 32:2177–2185 (1993).

Strobel and Dervan, "Cooperative Site Specific Binding of Oligoonucleotides to Duplex DNA," *J. Am. Chem. Soc.* 111:7286–7287 (1989).

Strobel and Dervan, "Triple Helix–Mediated Single–Site Enzymatic Cleavage of Megabase Genomic DNA," *Methods in Enzymology* 216:309–321 (1992).

Surovaya et al., "Construction of Peptide β–Hairpins Recognizing DNA Sequences," *Molecular Biology* 30:818–825 (1996).

Swalley et al., "Recognition of a 5'–(A,T)GGG(A,T)$_2$–3' Sequence in the Minor Groove of DNA by an Eight–Ring Hairpin Polyamide" *J. Am. Chem. Soc.* 118:8198–8206 (1996).

Takahashi et al., "82. Distamycin A–Induced Fragility on Chromosome 16, Fra(16)(q22), in a Japanese Population," *Proc. Japan Acad.* 61(B):299–302 (1985).

Takahashi et al., "A new rare distamycin A–inducible fragile site, fra(11)(p15.1), found in two acute nonlymphocytic leukemia (ANLL) patients with t(7;11)(p15–p13;p15)," *Hum Genet* 80:124–126 (1988).

Taylor et al., "DNA Affinity Cleaving—Sequence Specific Cleavage of DNA by Distamycin–EDTA•Fe(II) and EDTA–Distamycin•Fe(II)," *Tetrahedron* 40:457–465 (1984).

Tenette et al., "Force field development and conformational search strategy in the simulation of biomolecular processes," *Biochemical Society Transactions* 24:268–274 (1996).

Tor and Dervan, "Site–Specific Enzymatic Incorporation of an Unnatural Base, N$^6$–(6–Aminohexyl)isoguanosine, into RNA," *J. Am. Chem. Soc.* 115:4461–4467 (1993).

Trauger et al., "Recognition of DNA by designed ligands at subnanomolar concentrations," *Nature* 382:559–561 (1996).

Turner et al., "The mutagenic properties of DNA minor–groove binding ligands," *Mutation Research* 355:141–169 (1996).

Uchida et al., "High resolution footprinting of EcoRl and distamycin with Rh(phi)$_2$(bpy)$^{3+}$, a new photofootprinting reagent," *Nucleic Acids Research* 17:10259–10279 (1989).

Van Dyke and Dervan, "Chromoycin, Mithramycin, and Olivomycin Binding Sites on Heterogeneous Deoxyribonucleic Acid. Footprinting with (Methidiumpropyl–EDTA) iron (II)," *Biochemistry* 22:2373–2377 (1983).

Van Dyke and Dervan, "Echinomycin Binding Sites on DNA," *Science* 225:1122–1127 (1984).

Van Dyke and Dervan, "Footprinting with MPE•Fe(II). Complementary–strand Analyses of Distamycin– and Actinomycin–binding Sites on Heterogeneous DNA," pp. 347–353.

Van Dyke and Dervan, "Methidiumpropyl–EDTA•Fe(II) and DNase I footprinting report different small molecule binding site sizes on DNA," *Nucleic Acids Research* 11:5555–5567 (1983).

Van Dyke et al., "Map of distamycin, netropsin, and actinomycin binding sites on heterogeneous DNA: DNA cleavage–inhibition patterns with methidiumpropyl–EDTA•Fe(II)," *Proc. Natl. Acad. Sci. USA* 79:5470–5474 (1982).

Vigneswaran et al., "Influence of GC and AT Specific Minor Groove Binding Drugs on Intermolecular Triplex Formation in the Human c–Ki–ras Promoter," *Biochemistry* 35:1106–1114 (1996).

Wade and Dervan, "Alteration of the Sequence Specificity of Distamycin on DNA by Replacement of an N–Methylpyrrolecarboxamide with Pyridine–2–carboxamide," *J. Am. Chem. Soc.* 109:1574–1575 (1987).

Wade et al., "Binding Affinities of Synthetic Peptides, Pyridine–2–carboxamidonetropsin and 1–Methylimidazole–2–carboxamidonestropsin, That Form 2:1 Complexes in the Minor Groove of Double–Helical DNA," *Biochemistry* 32:11385–11389 (1993).

Wade et al., "Design of Peptides That Bind in the Minor Groove of DNA at 5'–(A,T)G(A,T)C(A,T)–3' Sequences by a Dimeric Side–by–Side Motif," *J. Am. Chem. Soc.* 114:8783–8794 (1992).

Wade et al., "Recognition of G,C Base Pairs in the Minor Groove of DNA" (Abstract).

Wade, thesis entitled Sequence specific complexation of BDNA at sites containing G, C Pairs, California Institute of Technology, Pasadena, California Submitted Feb. 2, 1989.

Wang et al., "Interactions Between a Symmetrical Minor Groove Binding Compound and DNA Oligonucleotides: $^1$H and $^{19}$F NMR Studies," *J. Biomolecular Structure & Dynamics* 7:101–117 (1989).

Wang et al., "Design, synthesis, cytotoxic properties and preliminary DNA sequencing evaluation of CPI–N–methylpyrrole hybrids. Enhancing effect of a trans double bond linker and role of the terminal amide functionality on cytotoxic potency," *Anti–Cancer Drug Des.* 11(1):15–34 (1996).

Wang et al., "Anti–HIV–I activity of linked lexitropsins," *J. Med. Chem.* 35(15):2890–2897 (1992).

Wang et al., "Convenient synthesis of pyrroloiminoquinone and its lexitropsin–linked derivative," *Tatrahedron Lett.* 35(24):4085–4086 (1994).

Ward et al., "Determination of Netropsin–DNA Binding Constants from Footprinting Data," *Biochemistry* 27:1198–1205 (1988).

Ward et al., "Quantitative Footprinting Analysis of the Netropsin–DNA Interaction,"*J. Biomolecular Structure & Dynamics* 4(5):685–695 (1987).

Wemmer et al., Abstracts of the American Chemical Soceity 208 Part 2:9 (1994).

Wiederholt et al., "DNA–Tethered Hoechst Groove–Binding Agents: Duplex Stabilization and Fluorescence Characteristics," *J. Amer. Chem. Soc.* 118:7055–7062 (1996).

Wilkins, "Selective binding of actinomycin D and distamycin D and distamycin A to DNA," *Nucleic Acids Research* 10:7273–7282 (1982).

Williamson et al., "Phase–Sensitive Heteronuclear Multiple– Bond Correlation in the Presence of Modest Homonuclear Coupling. Application to Distamycin A," *Journal of Magnetic Resonance* 82:605–612 (1989).

Wong and Bateman, "TBP–DNA interactions in the minor groove discriminate between A:T and T:A base pairs," *Nucleic Acids Research* 22:1890–51896 (1994).

Woynarowski et al., "DNA Minor–Groove Binding Agents Interfere with Topoisomerase II–Medidated Effects of VM–26 and m–AMSA," *Proceedings of AACR* 29:274 at abstract No. 1089 (1988).

Xie et al., "Synthesis and DNA cleaving properties of hybrid molecules containing propargylic sulfones and minor groove binding lexitropsins," *Bioorg. Med. Chem. Lett.* 3(8):1565–1570 (1993).

Yamamoto et al., "Synthesis and DNA Binding Properties of Amide Bond–Modified Analogues Related to Distamycin," *Tetrahedron Letters* 37:7801–7804 (1996).

Yang et al., "Studies on Cooperative Binding of an Extended Distamycin A Analogue in the Minor Groove of DNA by NMR Spectroscopy," *Biochemical and Biophysical Research Communications* 222:764–769 (1996).

Youngquist and Dervan, "Sequence–specific recognition of B–DNA by oligo(N–methylpyrrolecarboxamide)s," *Proc. Natl. Acad. Sci. USA* 82:2565–2569 (1985).

Youngquist and Dervan, "Sequence–specific recognition of B–DNA by Bis(EDTA–distamycin)fumaramide," *J. Am. Chem. Soc.* 107:5528–5529 (1985).

Zakrzewska and Pullman, "Theoretical Study of the Sequence Selectivity of Isolexins, Isohelical DNA Groove Binding Ligands. Proposal for the GC Minor Groove Specific Compounds," *Journal of Biomolecular Structure & Development* 5(5):1043–1058 (1988).

Zakrzewska et al., "Drug Recognition of DNA. Proposal for GC Minor Groove Specific Ligands: Vinylexins," *Journal of Biomolecular Structure & Development* 6(2):331–344 (1988).

Zasedatelev et al., "Mono–, di– and trimeric binding of a bis–netropsin to DNA," *FEBS Letters* 375:304–306 (1995).

Zimmer and Wahnert, "Nonintercalating DNA–Binding Ligands: Specificity of the Interaction and Their Use as Tools in Biophysical, Biochemical and Biological Investigations of the Genetic Material," *Prog. Biophys. molec.Biol.* 47:31–112 (1986).

Zimmer et al., "Binding of Analogues of the Antibiotics Distamycin A and Netropsin to Native DNA," *Eur. J. Biochem.* 26:81–89 (1972).

Zimmer et al., "Chain Length–Dependent Association of Distamycin–Type Oligopeptides with A•T and G•C Pairs in Polydeoxynucleotide Duplexes," *Biochimica et Biophysica Acta* 741:15–22 (1983).

Zimmer et al., "Differential stabilization by netropsin of inducible B–like conformations in deoxyribo–, ribo– and 2'–deoxy–2'–fluororibo–adenosine containing duplexes of $(dA)_n$•$(dT)_n$ and $(dA)_n$•$(dU)_{n^a}$," *Nucleic Acids Research* 10:1721–1732 (1982).

Zimmer et al., "Effects of the Antibiotics Netropsin and Distamycin A on the Structure and Function of Nucleic Acids," pp. 285–318.

Zimmer et al., "Z–DNA and other non–B–DNA structures are reversed to B–DNA by interaction with netropsin," *FEBS Letters* 154:156–160 (1983).

FIG. 9

Y = N, Z = N; ImImImPy-β-PyPyPyPy-β-Dp
Y = N, Z = CH; ImImPyPy-β-PyPyPyPy-β-Dp
Y = CH, Z = CH; ImPyPyPy-β-PyPyPyPy-β-Dp (+)- CC-1065

(+)- Duocarmycin A (+)- Duocarmycin SA

ImPyPyPy-γ-PyPyPyPy-β-Dp-NBD

ImPyPyPy-γ-PyPyPyPy-β-Dp-Dansyl

ImPyPyPy-β-ImPyPyPy-β-ED-TO

Pyrene-PyPyPy-β-ImPyPyPy-γ-ImPyPy-β-Dp

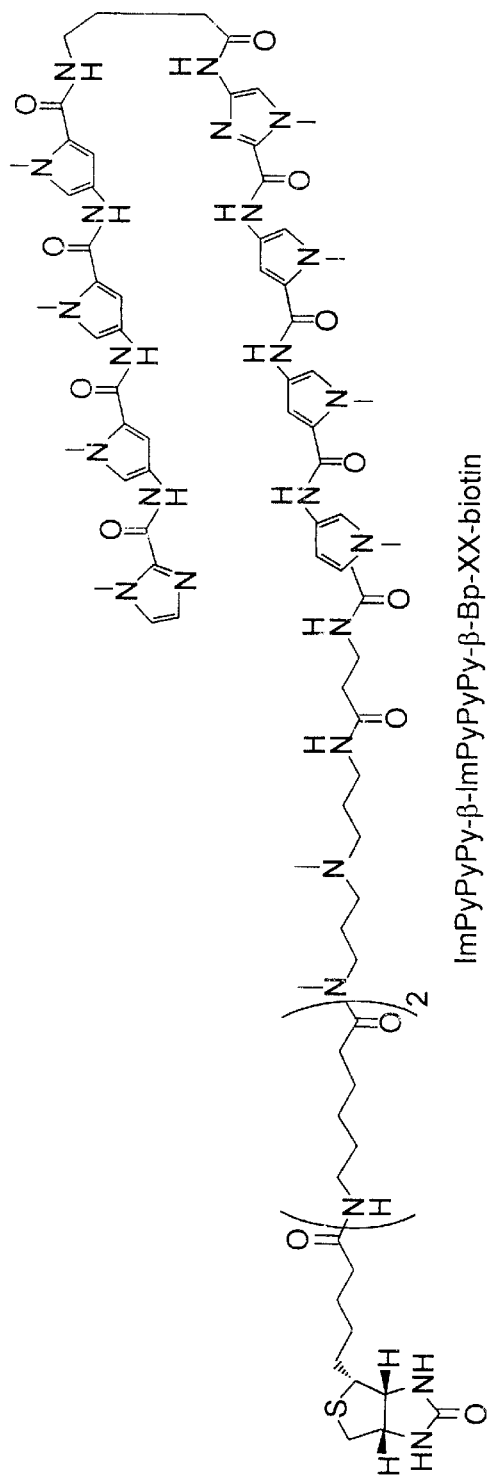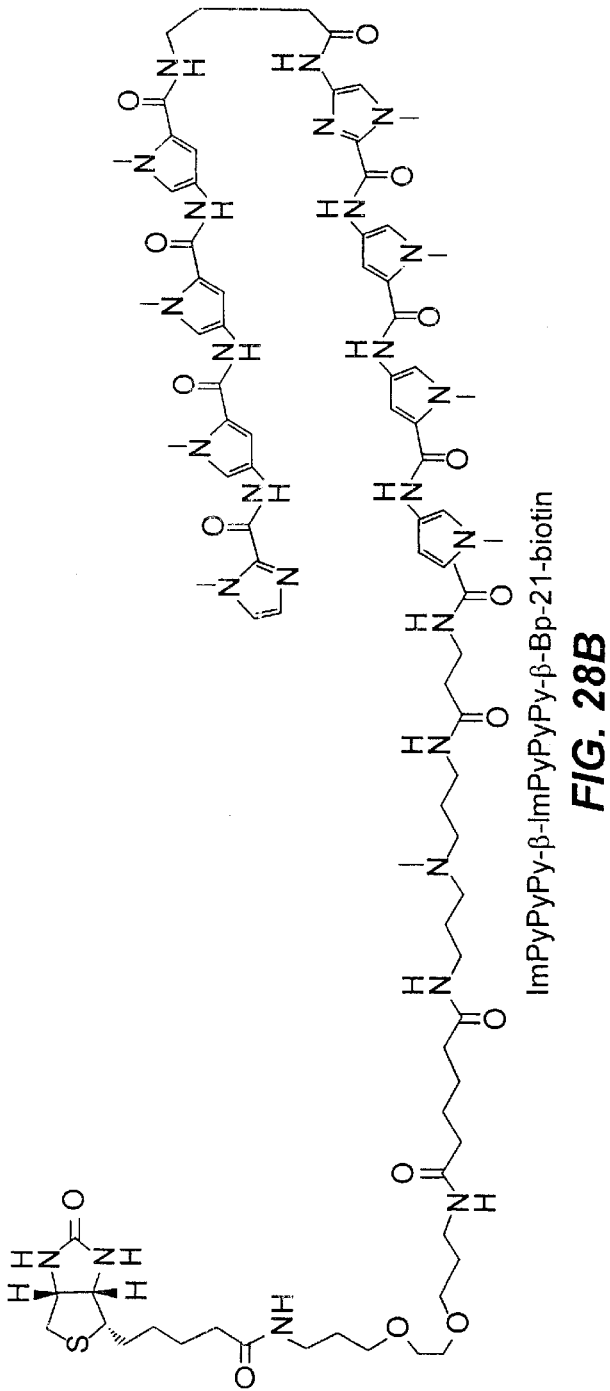
FIG. 28A  ImPyPyPy-β-ImPyPyPy-β-Bp-XX-biotin
FIG. 28B  ImPyPyPy-β-ImPyPyPy-β-Bp-21-biotin ImPyPyPy-β-ImPyPyPy-β-Bp-X-biotin ImPyPyPy-β-ImPyPyPy-β-15-biotin $Ka < 10^8 M^{-1}$ $Ka = 2 \times 10^9 M^{-1}$ ImPyPy-X-ImImPy-γ-PyPyPy-β-Dp

| X | Affinityy | Specificity |
|---|---|---|
| γ | $1\times10^7$ | none |
| C5 | $4\times10^8$ | 10-20-fold |
| C6 | $2\times10^8$ | 10-15-fold |
| C7 | $2\times10^8$ | 2-fold |
| C8 | $2\times10^8$ | 10-fold |
| β–β | $3\times10^8$ | 2-fold |
| β–C5 | $1\times10^8$ | 2-fold |

FIG. 39A
FIG. 39B
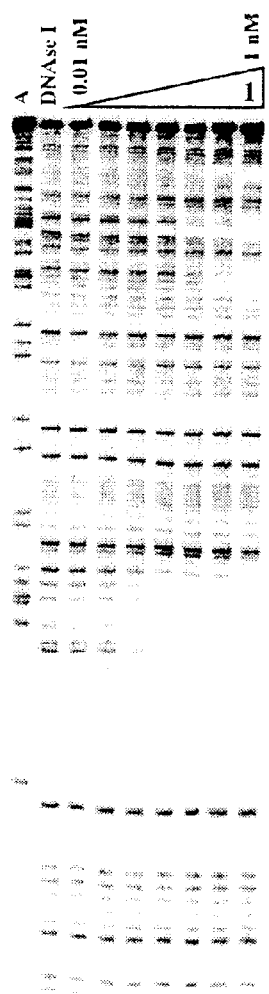
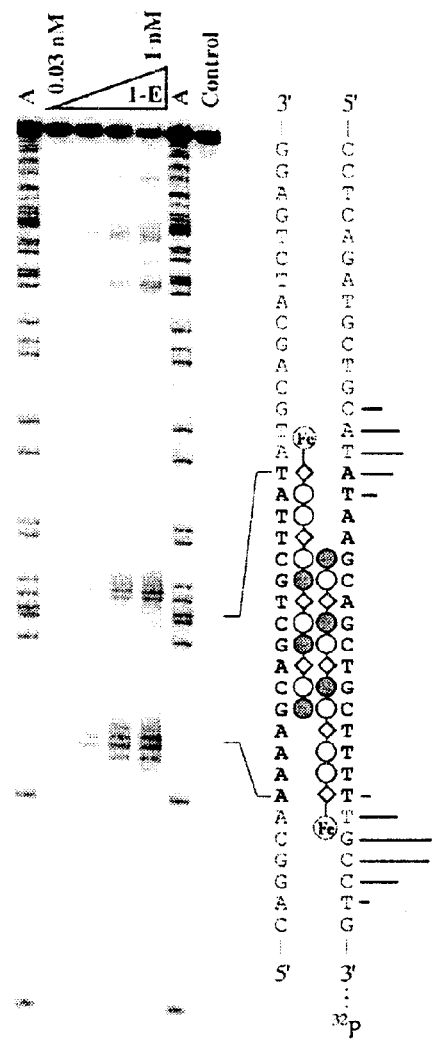
FIG. 39C
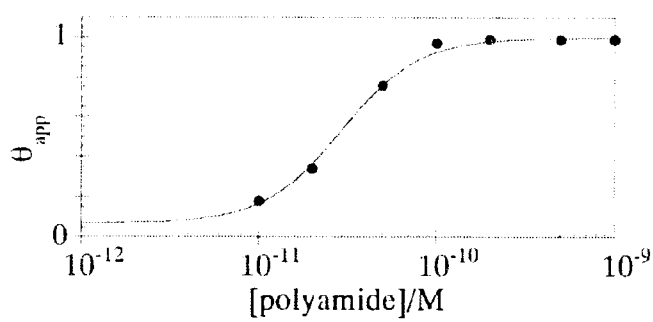
FIG. 39D
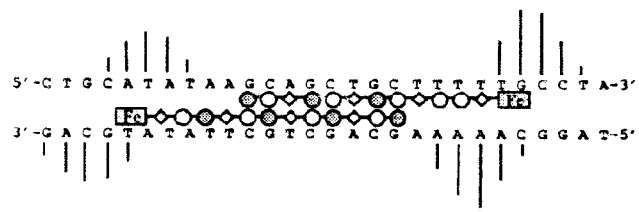

PREPARATION AND USE OF BIFUNCTIONAL MOLECULES HAVING DNA SEQUENCE BINDING SPECIFICITY

CROSS REFERENCE TO RELATED APPLICATIONS

This application is a continuation of International Application Number: PCT/US98/06997, filed on Apr. 8, 1998, entitled DNA-BINDING PYRROLE AND IMIDAZOLE POLYAMIDE DERIVATIVES, which is a continuation-in-part of PCT/US97/03332 filed Feb. 20, 1997, Ser. No. 08/853,522 filed May 8, 1997 and PCT/US 97/12722 filed Jul. 21, 1997 which are continuation-in-part applications of Ser. No. 08/837,524 filed Apr. 21, 1997 and Ser. No. 08/607,078 filed Feb. 26, 1996, U.S. provisional application 60/043,444 filed Apr. 8, 1997, U.S. provisional application 60/043,446 filed Apr. 8, 1997 and U.S. Provisional application 60/042,002 filed Apr. 16, 1997.

This work was supported in part by a grant from the National Institutes of Health (GM-27681). The United States Government may have certain rights to this invention.

FIELD OF THE INVENTION

This invention relates to the fields of molecular biology, biochemistry, and drug design. More particularly, the present invention provides synthetic polyamides containing pyrrole and imidazole amino acids which bind specific base pair sequences of double helical DNA with affinities and specificities comparable to DNA binding proteins such as the transcription factors. A series of molecular templates are described which allow for rational targeting of any predetermined DNA sequence of therapeutic potential. This non-biological approach to DNA recognition provides an underpinning for the design of synthetic cell-permeable ligands for the control of gene-expression.

BACKGROUND OF THE INVENTION

In every human cell, genetic information is stored on a string-like DNA polymer which is approximately 1 meter in length and contains $3 \times 10^9$ units of information in the form of base pairs, within which is encoded approximately 80,000 to 100,000 genes or sets of instructions. (Watson, J. D. *Gene*, 135, 309–315 (1993).) The specific interaction of proteins such as transcription factors with DNA controls the regulation of genes and hence cellular processes. (Roeder, R. G. *TIBS*, 9, 327–335 (1996).) A wide variety of human conditions ranging from cancer to viral infection arise from malfunctions in the biochemical machinery that regulates gene-expression (R. Tijan, *Sci. Am.*, 2, 54–61 (1995).) Designed small molecules which target specific DNA sequences offer a potentially general approach for gene-specific regulation. (Gottesfeld, et al. *Nature Accepted.* (1997). Such molecules could be powerful therapeutics for combating life threatening diseases which result from mis-regulation in transcription.

Designed bifunctional small molecules which target specific DNA sequences offer a potentially general approach for gene-specific, sequence-specific, or organism specific modification, detection or capture of plasmids, genes, cDNA, cosmids, or chromosomes. More specifically, a life threatening disease may result from a single error within the $3 \times 10^9$ units of information stored within the double helix. Sequence-specific polyamides may discriminate such small errors, hence bifunctional polyamides could have broad diagnostic applications which range from determining the molecular basis of life threatening diseases to sequence-specific visualization of disease genes in living organisms.

The genetic information is in fact, stored on two stands of DNA (in antiparallel orientation) in a structure termed the double helix. The DNA double helix consists of A,T and G,C base pairs held together by specific Watson-Crick hydrogen bonds like rungs on a twisted ladder. (Dickerson, et al. *Science*, 216, 475 (1982). The common B-form of DNA is characterized by a wide (12 Å) and shallow major groove and a deep and narrow (4–6 Å) minor. Individual sequences may be distinguished by the pattern of hydrogen bond donors and acceptors displayed on the edges of the base pairs. (*Principles of Nucleic Acid Structure* Sanger, W.; Springer-Verlag, New York, 1984.) In the minor groove, the A,T base pair presents two symmetrically placed hydrogen bond acceptors in the minor groove, the purine N3 and the pyrimidine O2 atoms. The G,C base pair presents these two acceptors, but in addition presents a hydrogen bond donor, the 2-amino group of guanine (Steitz, T. A. *Quart. Rev. Biophys.* 23, 205).

Small molecules isolated from natural sources which bind DNA are found to be a structurally diverse class, as evidenced by consideration of four representative molecules, chromomycin, distamycin, actinomycin D, and calicheamicin. (Gao, et al. *J. Mol. Biol.* 223, 259–279. (1992); Kamitori, et al. *J. Mol. Biol.* 225, 445–456 (1992); Paloma et al. *J. Am. Chem. Soc.* 116, 3697–3708 (1994); Coll, et al. *Proc. Natl. Acad. Sci. U.S.A.* 84, 8385–8389 (1987)). There is no simple natural recognition code for the readout of specific sequences of DNA.

The structures of four small molecules isolated from natural sources are shown in FIG. 1. Among these DNA-binding molecules, distamycin is distinguished by its structural simplicity, having no chiral centers and an oligopyrrolecarboxamide core structure. (Zimmer, C. *Prog. Nucleic Acid Res. Mol. Biol.* (1975) 15, 285; Baguley, B. C. *Molecular and Cellular Biochemistry* (1982) 43, 167–181; Zimmer, et al., *Prog. Biophy. Mol. Biol.* 47, 31 (1986)). Structural studies of distamycin-DNA complexes reveal modular complexes in which adjacent pyrrolecarboxamides makes similar contacts with adjacent DNA base pairs. The relative simplicity of distamycin, with respect both to its chemical structure and its complexes with DNA, guided the initial decision to use distamycin as a basis for designed polyamides having novel DNA-binding sequences specificity. (Dervan, P. B. *Science* 232, 464–471 (1986).)

A schematic representation of recognition of A,T rich sequences in the minor groove by Distamycin is shown below:

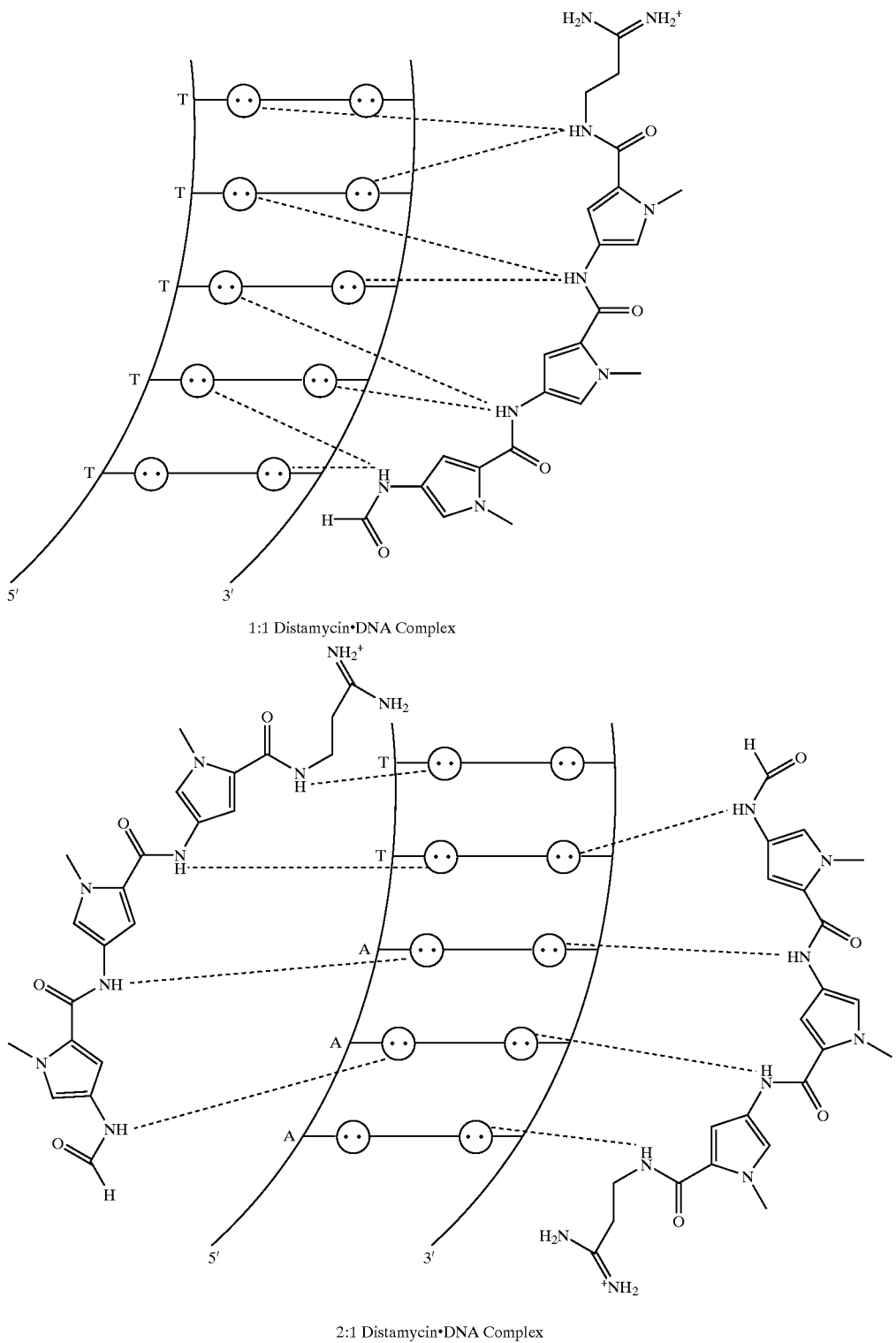

1:1 Distamycin•DNA Complex

2:1 Distamycin•DNA Complex

Two distinct DNA binding modes exist for Distamycin A. In the first binding mode, a single molecule of Distamycin binds in the middle of the minor groove of a 5 base pair of A,T rich sequence. The amine hydrogens of the N-methylpyrrole-carboxamides form bifurcated hydrogen bonds with Adenine N3 and thymine O2 atoms on the floor of the minor groove.[10] In the second binding mode, 2 distamycin ligands form an antiparallel side-by-side dimer in the minor groove of a 5 base pair A,T rich site. (Pelton, J. G. & Wemmer, D. E. (1989) *Proc. Natl. Acad. Sci.* 86, 5723–5727; Pelton, J. G. & Wemmer, D. E. (1990) *J. Am. Chem. Soc.* 112, 1393–1399; Chen, et al. (1994). *Nature Struct. Biol.* 1, 169–175.) In the 2:1 model each polyamide subunit forms hydrogen bonds to a unique DNA strand in the minor groove.

Polyamides containing N-methylpyrrole (Py) and N-methylimidazole (Im) amino acids provide a model for the design of artificial molecules for recognition of double helical DNA. For side-by-side complexes of Py/Im-polyamides in the minor groove of DNA, the DNA binding sequence specificity depends on the sequence of side-by-side amino acid pairings. (Wade, et al. (1992). *J. Am. Chem. Soc.* 114, 8783–8794; Mrksich, et al. (1992). *Proc. Natl. Acad. Sci. U.S.A.* 89, 7586–7590; Wade, W. S., Mrksich, M. & Dervan, P. B. (1993); *Biochemistry* 32, 11385–11389 (1993)). A pairing of Im opposite Py targets a G•C base pair while a pairing of Py opposite Im targets a C•G base pair. A Py/Py combination is degenerate targeting both A•T and T•A base pairs. Specificity for G,C base pairs results from the formation of a putative hydrogen bond between the imidazole N3 and the exocyclic amine group of guanine. Validity of the pairing rules is supported by a variety of footprinting and NMR structure studies. (Mrksich, et al., *J. Am. Chem. Soc.*, 115, 2572 (1993); Geierstanger, et al. *Science,* 266, 646 (1994); Mrksich et al., *J. Am. Chem. Soc.*, 117, 3325 (1995).)

A schematic representation of the polyamide pairing rules is shown below:

imidazole polyamides by covalently linking polyamide subunits. (Mrksich, M. & Dervan, P. B. (1993). *J. Am. Chem. Soc.* 115, 9892–9899; Dwyer, et al. (1993). *J. Am. Chem. Soc.* 115, 9900–9906; Mrksich, M. & Dervan, P. B. (1994). *J. Am. Chem. Soc.* 116, 3663–3664; Chen, Y. H. and Lown, J. W. (1994) *J. Am. Chem. Soc.* 116, 6995–7005. Chen, Y. H. and Lown, J. W. *Heterocycles* 41, 1691–1707 (1995). Geierstanger, et al., *Nature Structural Biology,* 3, 321 (1996). Chen, et al. *J. Biomol. Struct. Dyn.* 14, 341–355 (1996); Cho, et al. *Proc. Natl. Acad. Sci. USA,* 92, 10389 (1995)). A simple hairpin polyamide motif with γ-aminobutyric acid (γ) serving as a turn-specific internal-guide-residue provides a synthetically accessible method of linking polyamide subunits within the 2:1 motif. The head-to-tail linked polyamide ImPyPy-γ-PyPyPy-dimethylaminopropylamide (Dp) was shown to specifically bind the designated target site 5'-TGTTA-3' with an equilibrium association constant of $K_a=8\times10^7$ $M^{-1}$, an increase of 300-fold relative to the unlinked three-ring polyamide pair ImPyPy and PyPyPy. (Mrksich, et al. *J. Am. Chem. Soc.* 116, 7983–7988). The hairpin polyamide model is supported by footprinting, affinity cleaving and NMR structure studies. (Church, et al. *Biochemistry* 1990, 29, 6827; He, et al. *J. Am. Chem. Soc.* 1993, 115, 7061; de Clairac, et al. *J. Am. Chem. Soc.* submitted).

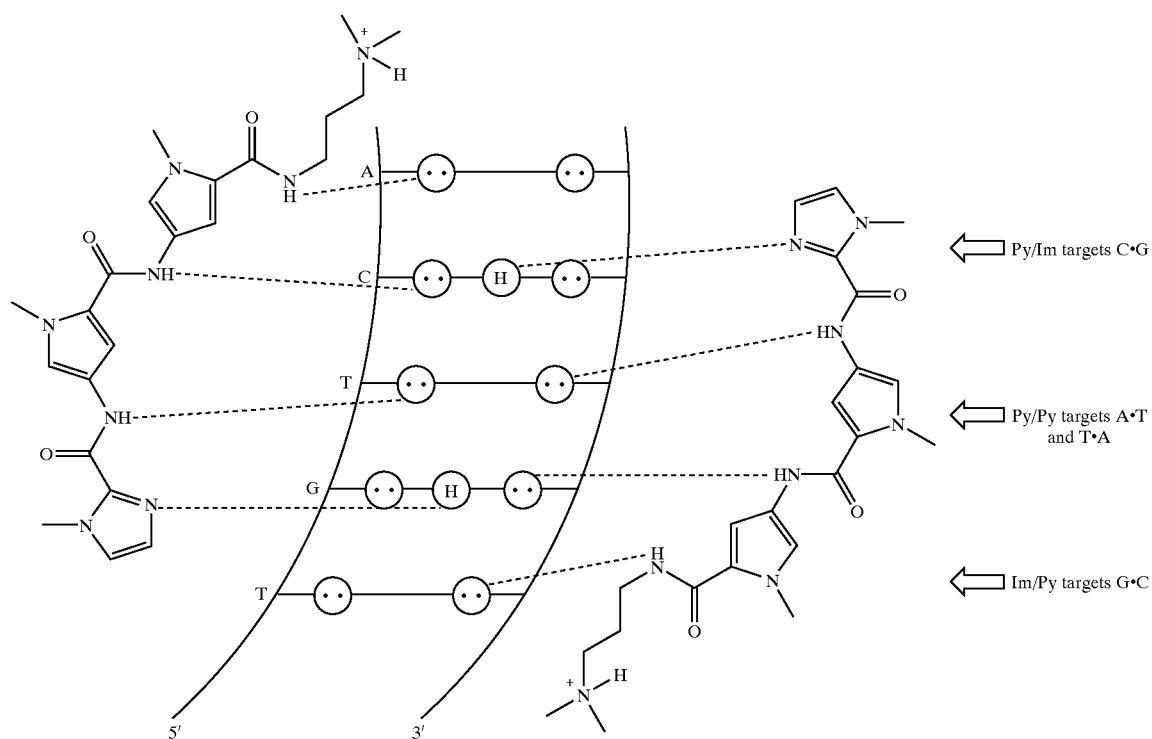

In parallel with the elucidation of the scope and limitations of the pairing rules, efforts have been made to increase the DNA-binding affinity and specificity of pyrrole- A schematic representation of recognition of a 5'-TGTTA-3' sequence by unlinked subunits (left) and γ-aminobutyric acid linked subunits (right) is shown below:

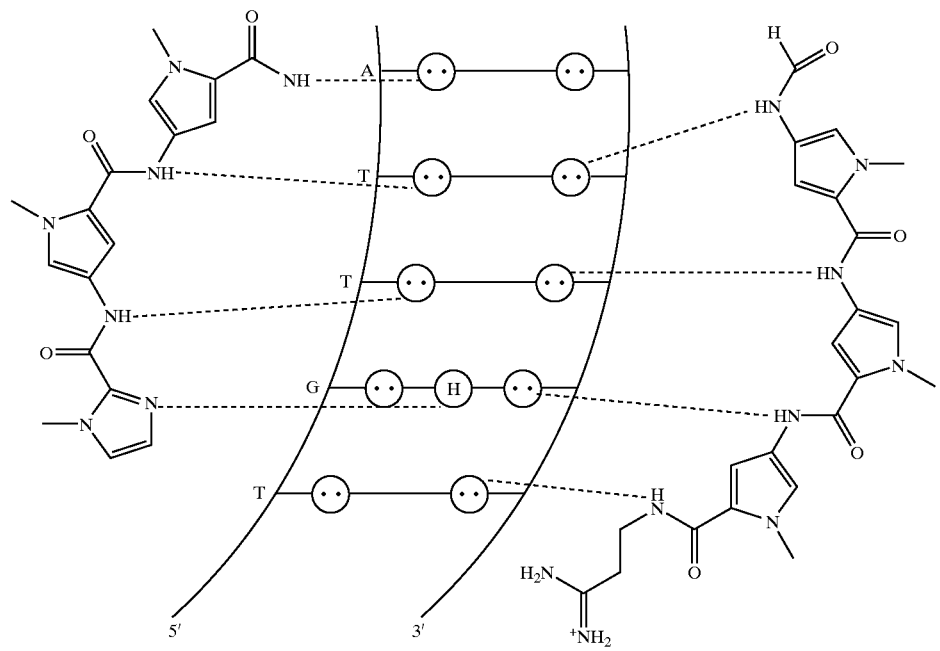
ImPyPy-Dp/PyPyPy•TGTTA
$K_a \sim 2 \times 10^5 M^{-1}$
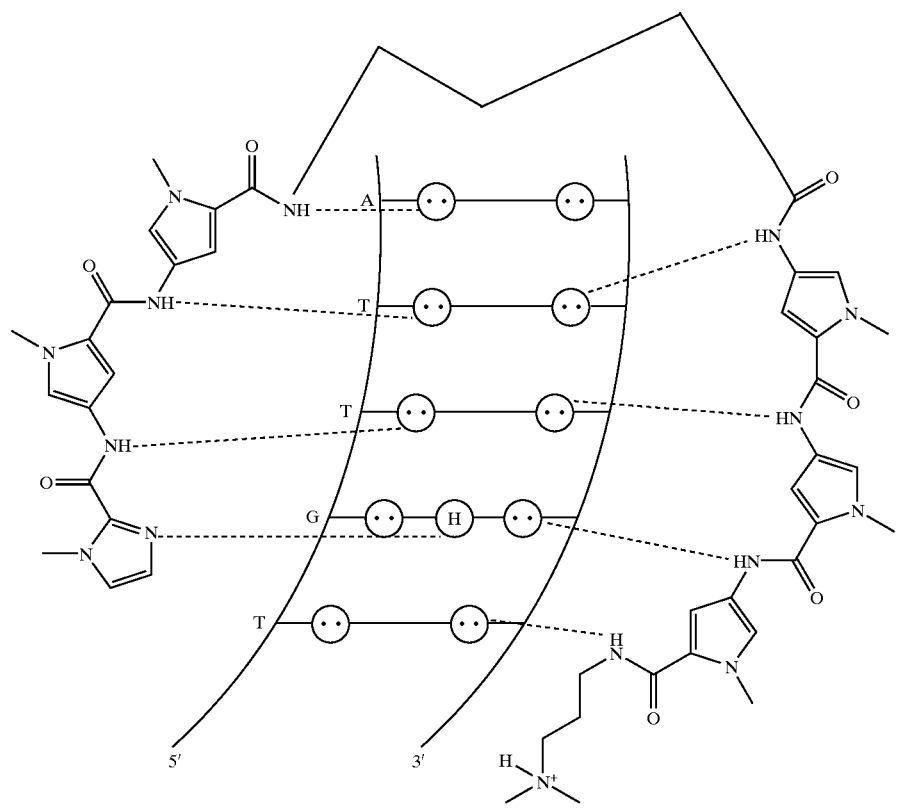
ImPyPy-γ-PyPyPy-Dp•TGTTA
$K_a = 8 \times 10^7 M^{-1}$ Closing the ends of the hairpin to form a cyclic polyamide increases the overall energetics for DNA-binding presumably by restricting conformational space for the molecule. (Lown, J. W. and Krowicki, K. *J. Org. Chem.* 1985, 50, 3774.) A cyclic polyamide cyclo-(ImPyPy-γ-PyPyPy-γ-) was shown to specifically bind the designated target site 5'-TGTTA-3' with an equilibrium association constant of $K_a = 2.9 \times 10^9$ M$^{-1}$, an increase of 40-fold relative to the corresponding hairpin polyamide of sequence composition ImPyPy-γ-PyPyPy. The sequence-specificity versus single base pair mismatch sites drops from 30-fold for the hairpin polyamide to 2-fold for the cyclic polyamide.

A schematic representation of a cyclic polyamide recognizing the minor groove is shown below:

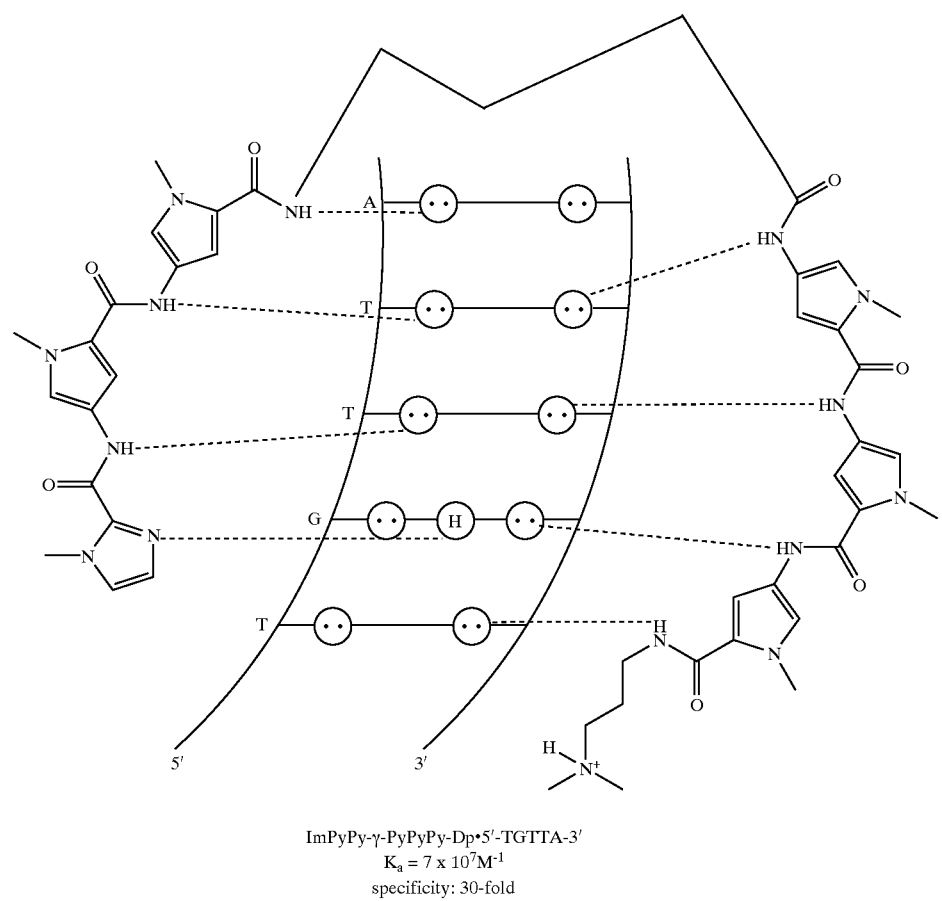

ImPyPy-γ-PyPyPy-Dp•5'-TGTTA-3'
$K_a = 7 \times 10^7 M^{-1}$
specificity: 30-fold -continued

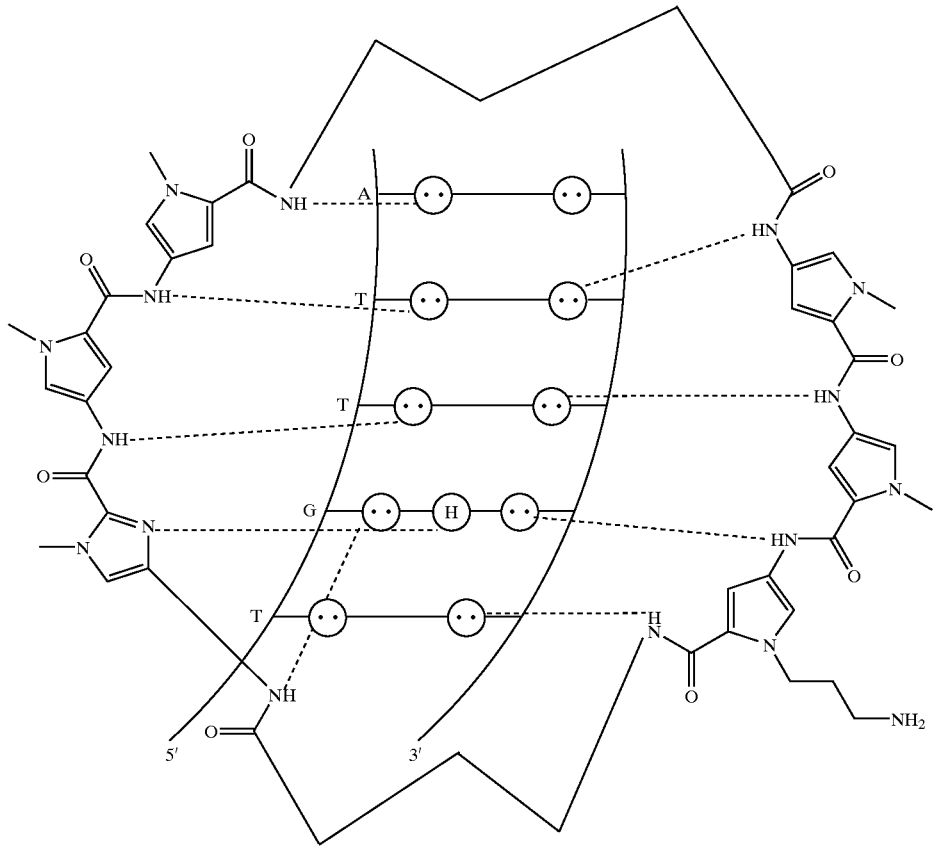

cyclo-(ImPyPy-γ-PyPyPy-γ-)•5'-TGTTA-3'
$K_a = 2 \times 10^9 M^{-1}$
specificity: 2-fold Despite the design breakthrough in molecular recognition of DNA, the binding affinities of linked and unlinked polyamide dimers of the prior art are modest when compared to those found with natural DNA binding proteins. (Clemens, et al. *J. Mol. Biol.* 244, 23–25 (1994)). For example DNA-binding transcription factors recognize their cognate sites at subnanomolar concentrations. (Jamieson, et al. *Biochemistry* 33, 5689–5695 (1994); Choo, Y. and Klug, A. *Proc.Natl. Acad. Sci. U.S.A.* 91, 11168–11172 (1994); Greisman, H. A. and Pabo, C. O. *Science* 275, 657–661 (1997)). Six-ring hairpin polyamides require concentrations greater than 10 nM to occupy their target sites. The only class of polyamides described in the prior art with affinities similar to DNA-binding proteins are the 6-ring cyclic polyamides; however, this class of molecules lacks the sequence-specificity of proteins (i.e. an energetic penalty for binding a single base pair mismatch site) and therefore currently has no potential for therapeutic applications.

Two prior approaches for the development of synthetic transcriptional antagonists have been reported. Oligodeoxynucleotides which recognize the major groove of double helical DNA via triple helix formation bind a broad sequence repertoire with high affinity and specificity (Moser, H. E. & Dervan, P. B. *Science* 238, 645–650 (1987); Thuong, et al. *Agnew. Chem. Int. Ed. Engl.* 32, 666–690 (1993)). Although oligonucleotides and their analogs have been shown to interfere with gene expression (Maher, et al. *Biochemistry* 31, 70–81 (1992); Duvalvalentin, et al. *Proc.* *Natl. Acad. Sci. U.S.A.* 89, 504–508 (1992)). The triple helix approach is limited to purine tracks and suffers from poor cellular uptake. There are a few examples of cell-permeable carbohydrate based ligands that interfere with transcription factor function. (Ho, et al. *Proc. Natl. Acad. Sci. USA* 91, 9203–9207 (1994); Liu, C. et al. *Proc. Natl. Acad. Sci. USA* 93, 940–944 (1996)). However oligosaccharides are not yet amenable to recognition of a broad range of predetermined DNA sequences.

Because of the small size and hydrophobic nature of polyamides (MW≈1200) and because the parent ligand Distamycin is itself cell-permeable these ligands have the potential to underpin a new field of small molecule regulation of gene expression. It remained to be determined if low molecular weight (MW≈1200) pyrrole-imidazole polyamides could be constructed which recognize predetermined DNA sites at subnanomolar concentrations without compromising sequence-selectivity.

SUMMARY OF THE INVENTION

This invention provides improved polyamides for selectively binding a DNA molecule. Compounds of the present invention comprise a polyamide of the formula:

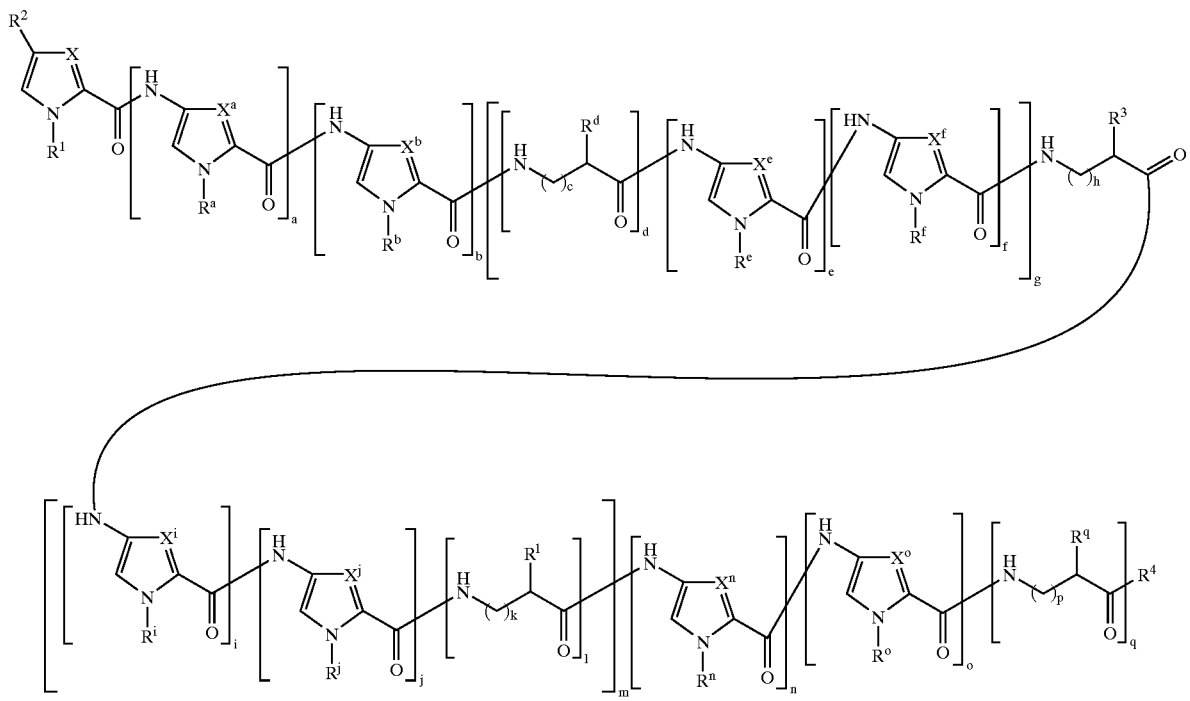

where $R^1$, $R^a$, $R^b$, $R^e$, $R^f$, $R^i$, $R^j$, $R^n$, and $R^o$ are chosen independently from H, Cl, NO, N-acetyl, benzyl, $C_{1-6}$ alkyl, $C_{1-6}$ alkylamine, $C_{1-6}$ alkyldiamine, $C_{1-6}$ alkylcarboxylate, $C_{1-6}$ alkenyl, and $C_{1-6}$ alkynyl;

$R^2$ is selected from the group consisting of H, $NH_2$, SH, Cl, Br, F, N-acetyl, and N-formyl;

$R^3$, $R^d$, $R^l$ and $R^q$ are selected independently from the group consisting of H, $NH_2$, OH, SH, Br, Cl, F, OMe, $CH_2OH$, $CH_2SH$, $CH_2NH_2$;

X, $X^a$, $X^b$, $X^e$, $X^f$, $X^i$, $X^j$, $X^n$, $X^o$ are chosen independently from the group consisting of N, CH, COH, $CCH_3$, $CNH_2$, CCl, CF; and a, b, c, d, e, f, i, j, k, and m are integers chosen independently, having values ranging from 0 to 5;

or a pharmaceutically acceptable salt thereof.

The invention further comprises a polyamide having the formula:

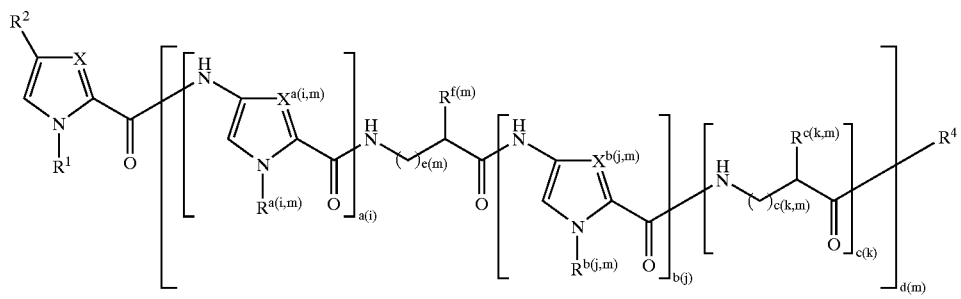

$R^4$ is $-NH(CH_2)_{0-6}NR^5R^6$ or $NH(CH_2)_rCO\ NH(CH_2)_{0-6}NR^5R^6$ or $NHR^5$ or $NH(CH_2)_rCONHR^5$, where $R^5$ and $R^6$ are independently chosen from H, Cl, NO, N-acetyl, benzyl, $C_{1-6}$ alkyl, $C_{1-6}$ alkylamine, $C_{1-6}$ alkyldiamine, $C_{1-6}$ alkylcarboxylate, $C_{1-6}$ alkenyl, $C_{1-6}$L, where L groups are independently chosen from biotin, oligodeoxynucleotide, N-ethylnitrosourea, fluorescein, bromoacetamide, iodoacetamide, DL-α-lipoic acid, acridine, ethyl red, 4-(psoralen-8-xyloxy)-butyrate, tartaric acid, (+)-α-tocopheral, and $C_{1-6}$ alkynyl, where r is an integer having a value ranging from 0 to 6;

where $R^1$, $R^{a(i,m)}$ and $R^{b(j,m)}$ are chosen independently from H, Cl, NO, N-acetyl, benzyl, $C_{1-6}$ alkyl, $C_{1-6}$ alkylamine, $C_{1-6}$ akyldiamine, $C_{1-6}$ alkylcarboxylate, $C_{1-6}$ alkenyl, and $C_{1-6}$ alkynyl;

$R^2$ is selected from the group consisting of H, $NH_2$, SH, Cl, Br, F, N-acetyl, and N-formyl;

$R^{f(m)}$ and $R^{c(k,m)}$ are selected independently from the group consisting of H, $NH_2$, OH, SH, Br, Cl, F, OMe, $CH_2OH$, $CH_2SH$, $CH_2NH_2$;

$R^4$ is $-NH(CH_2)_{0-6}NR^5R^6$ or $NH(CH_2)_rCO\ NH(CH_2)_{0-6}NR^5R^6$ or $NHR^5$ or $NH(CH_2)_rCONHR^5$, where $R^5$ and $R^6$ are independently chosen from H, Cl, NO, N-acetyl, benzyl, $C_{1-6}$ alkenyl, $C_{1-6}$ alkylamine, $C_{1-6}$ alkyldiamine, $C_{1-6}$ alkylcarboxylate, $C_{1-6}$ alkenyl, $C_{1-6}$L, where L groups are independently chosen from biotin, oligodeoxynucleotide, N-ethylnitrosourea, fluorescein, bromoacetamide, iodoacetamide, DL-α-lipoic acid, acridine, ethyl red, 4-(psoralen-8-yloxy)-butyrate, tartaric acid, (+)-α-tocopheral, and $C_{1-6}$ alkynyl, where r is an integer having a value ranging from 0 to 6;

X, $X^{a(i,m)}$ and $X^{b(j,m)}$ are chosen independently from the group consisting of N, CH, COH, $CCH_3$, $CNH_2$, CCl, CF; and a, b, c, d, e, f, g, h, i, j, k, l, m, n, o and p are integers chosen independently, having values ranging from 0 to 5;

or a pharmaceutically acceptable salt thereof.

By "alkyl" or "lower alkyl" in the present invention is meant $C_1$–$C_6$ alkyl, i.e., straight or branched chain alkyl groups having 1–6 carbon atoms, such as, for example, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Preferred $C_1$–$C_6$ alkyl groups are methyl, ethyl, propyl, butyl, cyclopropyl or cyploroyl-methyl. Particularly preferred are $C_1$–C alkyl groups such as methyl, ethyl, and propyl.

BRIEF DESCRIPTION OF THE FIGURES

FIG. 9. Eight-residue hairpin polyamides.

FIG. 39. Determination of 16 base pair sequence.

DETAILED DESCRIPTION OF THE PREFERRED EMBODIMENTS

Figure 1:
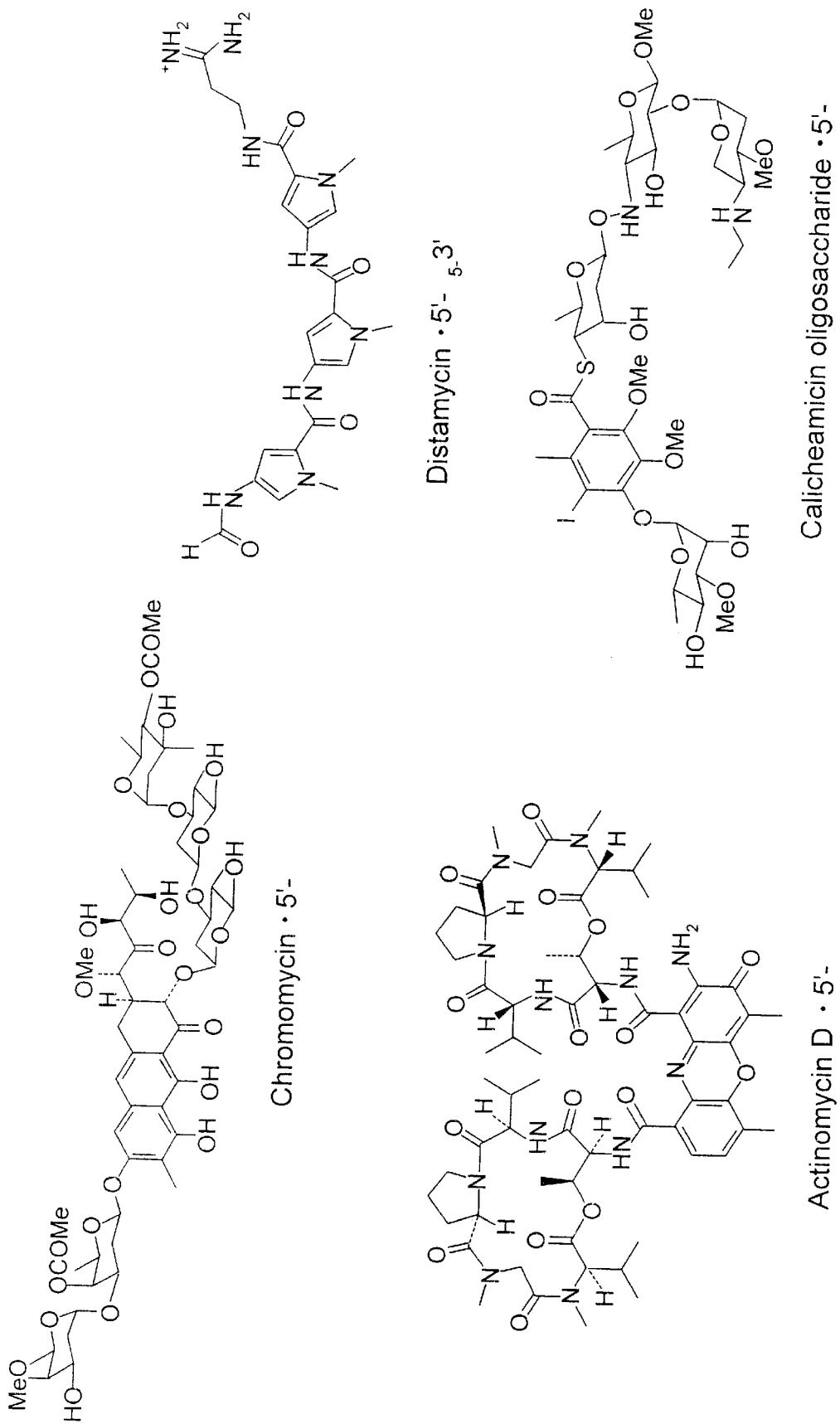
FIG. 1. Small molecules isolated from natural sources.

Within this application, unless otherwise stated, definitions of the terms and illustration of the techniques of this application may be found in any of several well-known references such as: Sambrook, J., et al., *Molecular Cloning: A Laboratory Manual*, Cold Spring Harbor Laboratory Press (1989); Goeddel, D., ed., *Gene Expression Technology, Methods in Enzymology*, 185, Academic Press, San Diego, Calif. (1991); "Guide to Protein Purification" in Deutshcer, M. P., ed., *Methods in Enzymology*, Academic Press, San Diego, Calif. (1989); Innis, et al., *PCR Protocols: A Guide to Methods and Applications*, Academic Press, San Diego, Calif. (1990); Freshney, R. I., *Culture of Animal Cells: A Manual of Basic Technique*, $2^{nd}$ Ed., Alan Liss, Inc. New York, N.Y. (1987); Murray, E. J., ed., *Gene Transfer and Expression Protocols*, pp. 109–128, The Human Press Inc., Clifton, N.J. and Lewin, B., *Genes VI*, Oxford University Press, New York (1987).

For the purposes of this application, a promoter is a regulatory sequence of DNA that is involved in the binding of RNA polymerase to initiated transcription of a gene. A gene is a segment of DNA involved in producing a peptide, polypeptide or protein, including the coding region, non-coding regions preceding ("leader") and following ("trailer") the coding region, as well as intervening non-coding sequences ("introns") between individual coding segments ("exons"). Coding refers to the representation of amino acids, start and stop signals in a three base "triplet" code. Promoters are often upstream ("'5 to") the transcription initiation site of the corresponding gene. Other regulatory sequences of DNA in addition to promoters are known, including sequences involved with the binding of transcription factors, including response elements that are the DNA sequences bound by inducible factors. Enhancers comprise yet another group of regulatory sequences of DNA that can increase the utilization of promoters, and can function in either orientation (5'-3' or 3'-5') and in any location (upstream or downstream) relative to the promoter. Preferably, the regulatory sequence has a positive activity, i.e., binding of an endogenous ligand (e.g. a transcription factor) to the regulatory sequence increases transcription, thereby resulting in increased expression of the corresponding target gene. In such a case, interference with transcription by binding a polyamide to a regulatory sequence would reduce or abolish expression of a gene.

The promoter may also include or be adjacent to a regulatory sequence known in the art as a silencer. A silencer sequence generally has a negative regulatory effect on expression of the gene. In such a case, expression of a gene may be increased directly by using a polyamide to prevent binding of a factor to a silencer regulatory sequence or indirectly, by using a polyamide to block transcription of a factor to a silencer regulatory sequence.

It is to be understood that the polyamides of this invention bind to double stranded DNA in a sequence specific manner. The function of a segment of DNA of a given sequence, such as 5'-TATAAA-3', depends on its position relative to other functional regions in the DNA sequence. In this case, if the sequence 5'-TATAAA-3' on the coding strand of DNA is positioned about 30 base pairs upstream of the transcription start site, the sequence forms part of the promoter region (Lewin, *Genes VI*, pp. 831–835). On the other hand, if the sequence 5'-TATAAA-3' is downstream of the transcription start site in a coding region and in proper register with the reading frame, the sequence encodes the tyrosyl and lysyl amino acid residues (Lewin, *Genes VI*, pp. 213–215).

While not being held to one hypothesis, it is believed that the binding of the polyamides of this invention modulate gene expression by altering the binding of DNA binding proteins, such as RNA polymerase, transcription factors, TBF, TFIIIB and other proteins. The effect on gene expression of polyamide binding to a segment of double stranded DNA is believed to be related to the function, e.g., promoter, of that segment of DNA.

It is to be understood by one skilled in the art that the improved polyamides of the present invention may bind to any of the above-described DNA sequences or any other sequence having a desired effect upon expression of a gene. In addition, U.S. Pat. No. 5,578,444 describes numerous promoter targeting sequences from which base pair sequences for targeting an improved polyamide of the present invention may be identified.

It is generally understood by those skilled in the art that the basic structure of DNA in a living cell includes both major and a minor groove. For the purposes of describing the present invention, the minor groove is the narrow groove of DNA as illustrated in common molecular biology reference such as Lewin, B., *Genes VI*, Oxford University Press, New York (1997).

To affect gene expression in a cell, which may include causing an increase or a decrease in gene expression, a effective quantity of one or more polyamide is contacted with the cell and internalized by the cell. The cell may be contacted in vivo or in vitro. Effective extracellular concentrations of polyamides that can modulate gene expression range from about 10 nanomolar to about 1 micromolar. Gottesfeld, J. M., et al., *Nature* 387 202–205 (1997). To determine effective amounts and concentrations of polyamides in vitro, a suitable number of cells is plated on tissue culture plates and various quantities of one or more polyamide are added to separate wells. Gene expression following exposure to a polyamide can be monitored in the cells or medium by detecting the amount of the protein gene product present as determined by various techniques utilizing specific antibodies, including ELISA and wester blot. Alternatively, gene expression following exposure to a polyamide can be monitored by detecting the amount of messenger RNA present as determined by various techniques, including northern blot and RT-PCR.

Similarly, to determine effective amounts and concentrations of polyamides for in vivo administration, a sample of body tissue or fluid, such as plasma, blood, urine, cerebrospinal fluid, saliva, or biopsy of skin, muscle, liver, brain or other appropriate tissue source is analyzed. Gene expression following exposure to a polyamide can be monitored by detecting the amount of the protein gene product present as determined by various techniques utilizing specific antibodies, including ELISA and wester blot. Alternatively, gene expression following exposure to a polyamide can be monitored by the detecting the amount of messenger RNA present as determined by various techniques, including northern blot and RT-PCR.

The polyamides of this invention may be formulated into diagnostic and therapeutic compositions for in vivo or in vitro use. Representative methods of formulation may be found in *Remington: The Science and Practice of Pharmacy*, 19th ed., Mack Publishing Co., Easton, Pa. (1995).

For in vivo use, the polyamides may be incorporated into a physiologically acceptable pharmaceutical composition that is administered to a patient in need of treatment or an animal for medical or research purposes. The polyamide composition comprises pharmaceutically acceptable carriers, excipients, adjuvants, stabilizers, and vehicles. The composition may be in solid, liquid, gel, or aerosol form. The polyamide composition of the present invention may be administered in various dosage forms orally, parentally, by inhalation spray, rectally, or topically. The term parenteral as used herein includes, subcutaneous, intravenous, intramuscular, intrasternal, infusion techniques or intraperitoneally.

The selection of the precise concentration, composition, and delivery regimen is influenced by, inter alia, the specific pharmacological properties of the particular selected compound, the intended use, the nature and severity of the condition being treated or diagnosed, the age, weight, gender, physical condition and mental acuity of the intended recipient as well as the route of administration. Such considerations are within the purview of the skilled artisan. Thus, the dosage regimen may vary widely, but can be determined routinely using standard methods.

Polyamides of the present invention are also useful for detecting the presence of double stranded DNA of a specific sequence for diagnostic or preparative purposes. The sample containing the double stranded DNA can be contacted by polyamide linked to a solid substrate, thereby isolating DNA comprising a desired sequence. Alternatively, polyamides linked to a suitable detectable marker, such as biotin, a hapten, a radioisotope or a dye molecule, can be contacted by a sample containing double stranded DNA.

The design of bifunctional sequence specific DNA binding molecules requires the integration of two separate entities: recognition and functional activity. Polyamides that specifically bind with subnanomolar affinity to the minor groove of a predetermined sequence of double stranded DNA are linked to a functional molecule, providing the corresponding bifunctional conjugates useful in molecular biology, genomic sequencing, and human medicine. Polyamides of this invention can be conjugated to a variety of functional molecules, which can be independently chosen from but is not limited to arylboronic acids, biotins, polyhistidines comprised from about 2 to 8 amino acids, haptens to which an antibody binds, solid phase supports, oligodeoxynucleotides, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)- butyrate, tartaric acid, (+)-α-tocopheral, psoralen, EDTA, methidium, acridine, Ni(II)•Gly-Gly-His, TO, Dansyl, pyrene, N-bromoacetamide, and gold particles. Such bifunctional polyamides are useful for DNA affinity capture, covalent DNA modification, oxidative DNA cleavage, DNA photocleavage. Such bifunctional polyamides are useful for DNA detection by providing a polyamide linked to a detectable label. DNA complexed to a labeled polyamide can then be determined using the appropriate detection system as is well known to one skilled in the art. For example, DNA associated with a polyamide linked to biotin can be detected by a streptavidin/alkaline phosphatase system.

The present invention also describes a diagnostic system, preferably in kit form, for assaying for the presence of the double stranded DNA sequence bound by the polyamide of this invention in a body sample, such brain tissue, cell suspensions or tissue sections, or body fluid samples such as CSF, blood, plasma or serum, where it is desirable to detect the presence, and preferably the amount, of the double stranded DNA sequence bound by the polyamide in the sample according to the diagnostic methods described herein.

The diagnostic system includes, in an amount sufficient to perform at least one assay, a specific polyamide as a separately packaged reagent. Instructions for use of the packaged reagent(s) are also typically included. As used herein, the term "package" refers to a solid matrix or material such as glass, plastic (e.g., polyethylene, polypropylene or polycarbonate), paper, foil and the like capable of holding within fixed limits a polyamide of the present invention. Thus, for example, a package can be a glass vial used to contain milligram quantities of a contemplated polyamide or it can be a microliter plate well to which microgram quantities of a contemplated polyamide have been operatively affixed, i.e., linked so as to be capable of being bound by the target DNA sequence. "Instructions for use" typically include a tangible expression describing the reagent concentration or at least one assay method parameter such as the relative amounts of reagent and sample to be admixed, maintenance time periods for reagent or sample admixtures, temperature, buffer conditions and the like. A diagnostic system of the present invention preferably also includes a detectable label and a detecting or indicating means capable of signaling the binding of the contemplated polyamide of the present invention to the target DNA sequence. As noted above, numerous detectable labels, such as biotin, and detecting or indicating means, such as enzyme-linked (direct or indirect) streptavidin, are well known in the art.

Trauger, et al. (Nature, 382: 559–561) and Swalley, et al. (J. Am. Chem. Soc. 119: 6953–6961) have described recognition of DNA by certain polyamides at subnanomolar concentrations. Pairing specific carboxyamide groups allows for recognition of specific DNA sequences (Swalley, et al. supra). Polyamides comprising Hp, Im, and Py provide for coded targeting of pre-determined DNA sequences with high affinity and specificity. Im and Py polyamides may be combined to form Im/Py, Py/Im, Py/Py binding pairs which complement the four Watson-Crick base pairs A, C, G, and T. Table 1 illustrates such pairings.

TABLE 1

Pairing Codes for Base Pair Recognition*

| Pair | G · C | C · G | T · A | A · T |
|---|---|---|---|---|
| Im/Py | + | − | − | − |
| Py/Im | − | + | − | − |
| Im/β | + | − | − | − |
| β/Im | − | + | − | − |
| Py/Py | − | − | + | + |

*favored (+), disfavored (−)

The basic polyamide pairing rules of the prior art are insufficient for design of ligands recognizing target sites having subnanomolar binding affinities. Additional second generation rules for polyamide design are provided herein. Each additional rule alone may not be sufficient for design of polyamides with subnanomolar affinity. However, simultaneous application of the second generation design rules provided herein allows for the construction of a number of versatile molecular templates for polyamide design.

It has been found that a hairpin polyamide synthesized from Boc-β-alanine-Pam-Resin, ImPyPy-γ-PyPyPy-β-Dp binds with both enhanced affinity and specificity relative to the parent compound, ImPyPy-γ-PyPyPy-Dp, which lacks the C-terminal β-alanine residue. (Optimization of the Hairpin Polyamide Design for Recognition of the Minor Groove of DNA. M. E. Parks, E. E. Baird and P. B. Dervan, J. Am. Chem. Soc., 118, 6147 (1996).) More specifically ImPyPy-γ-PyPyPy-β-Dp binds with an apparent first order association constant, $K_a = 3 \times 10^8$ $M^{-1}$, a factor of four greater than the parent polyamide, ImPyPy-γ-PyPyPy-Dp, $K_a = 8 \times 10^7$ $M^{-1}$. Furthermore, ImPyPy-γ-PyPyPy-β-Dp binds the target 5'-TGTTA-3' match site with 60-fold specificity relative to a single base pair 5'-TGACA-3' mismatch site. This can be compared with the parent polyamide ImPyPy-γ-PyPyPy-Dp which has a 24-fold specific binding relative to the same two DNA sites. The modest increased binding affinity of the C-terminal β-alanine polyamide, may result from an additional hydrogen bond between the β-alanine carboxamide and a 'sixth' base pair of the binding site.

Three or four-ring improved polyamides of the present invention are covalently coupled to form six or eight-ring structures, respectively, that bind specifically to four or six base pair targets, respectively, at subnanomolar concentrations. As such, the improved polyamides of the present invention may be directed to any DNA sequence comprised of A, C, G, or T.

In one embodiment, the present invention comprises improved polyamides having three or four-ring polyamide structures covalently coupled to form six or eight-ring hairpin structures, respectively, of the general structures I–XXVIII:

$X_1X_2X_3X_4\gamma X_5X_6X_7X_8$
I
$X_1X_2X_3\beta X_4X_5X_6$
III
$X_1X_2X_3X_4X_5\beta X_6X_7X_8$
V
$X_1X_2X_3\beta X_4X_5X_6X_7X_8$
VII
$X_1X_2X_3X_4X_5\beta X_6X_7X_8X_9X_{10}$
IX $X_1X_2X_3X_4X_5\gamma X_6X_7X_8X_9X_{10}$
II
$X_1X_2X_3X_4\beta X_5X_6X_7X_8$
IV
$X_1X_2X_3X_4\beta X_5X_6X_7$
VI
$X_1X_2X_3X_4\beta X_5X_6X_7X_8$
VIII
$X_1X_2X_3X_4X_5X_6\gamma X_7X_8X_9X_{10}X_{11}X_{12}$
X -continued $$X_1X_2X_3X_4X_5\beta\gamma X_6X_7X_8X_9X_{10}$$
XI
$$X_1X_2\beta X_3X_4\gamma X_5X_6\beta X_7X_8$$
XII
$$X_1X_2X_3\beta X_4X_5\gamma X_6X_7X_8\beta X_9X_{10}$$
XV
$$X_1\beta X_2X_3X_4X_5\gamma X_6\beta X_7X_8X_9X_{10}$$
XVII
$$X_1X_2X_3\beta X_4X_5\gamma X_6X_7\beta X_8X_9X_{10}$$
XIX
$$X_1\beta X_2X_3X_4X_5\gamma X_6X_7\beta X_8X_9\beta X_{10}$$
XXI
$$X_1X_2X_3\beta X_4X_5X_6\beta X_7X_8X_9$$
XXIII
$$X_1X_2X_3\gamma X_4X_5X_6\beta X_7X_8X_9$$
XXV
$$X_1X_2X_3\gamma X_4X_5X_6GX_7X_8X_9$$
XXVII $$X_1\beta X_2X_3\gamma X_4\beta X_5X_6$$
XIII
$$X_1X_2\beta X_3X_4X_5\gamma X_6X_7X_8\beta X_9X_{10}$$
XIV
$$X_1X_2X_3X_4\beta X_5\gamma X_6\beta X_7X_8X_9X_{10}$$
XVI
$$X_1X_2X_3X_4\beta X_5\gamma X_6X_7X_8X_9\beta X_{10}$$
XVIII
$$X_1X_2\beta X_3X_4X_5\gamma X_6X_7\beta X_8X_9X_{10}$$
XX
$$X_1X_2\beta X_3X_4\beta X_5X_6\beta X_7X_8$$
XXII
$$X_1X_2X_3X_4\beta X_5\beta X_6X_7X_8X_9$$
XXIV
$$X_1X_2X_3\gamma X_4X_5X_6\beta X_7X_8X_9\beta X_{10}X_{11}X_{12}$$
XXVI
$$X_1X_2X_3X_4\gamma X_5X_6X_7X_8\beta X_9X_{10}X_{11}X_{12}$$
XXVIII where $X_{1-12}$ is a substituted imidazole such as N-methylimidazolecarboxamide (Im), or a substituted pyrrole such as N-methylpyrrolecarboxamide (Py). An improved polyamide of the present invention may also include a C-terminal aliphatic amino acid such as a β-alanine residue (β) joined to an amide group such as dimethylaminopropylamide (Dp). In addition, an improved polyamide of the present invention may further include a aliphatic amino acid such as β-alanine residue (β) or glycine (G), an amide group such as dimethylaminopropylamide (Dp), an alcohol such as EtOH, an acid such as ethylenediaminetetraacetic acid (EDTA), or any derivative thereof joined to the γ-aminobutyric acid (γ) residue.

The use of β-alanine in the synthetic methods provides aromatic/aliphatic pairing (Im/β, β/Im, Py/β, and β/Py) and aliphatic/aliphatic pairing (β/β) substitution. The use of γ-aminobutyric acid, or a substituted γ-aminobutyric acid such as (R)-2,4 diaminobutyric acid, provides for preferred hairpin turns. Many other groups suitable for the purposes of practicing this invention are well known and widely available to one skilled in the art.

The polyamide subunit structures I–XXVIII above, and XXIX below may be covalently coupled through the γ residue which represents a —NH—CH$_2$—CH$_2$—CH$_2$—CONH— hairpin linkage derived from γ-aminobutyric acid or a chiral hairpin linkage derived from R-2,4-diaminobutyric acid. The present invention provides the reagents and methodologies for substituting the γ-residue of certain polyamides with a moiety such as (R)-2,4,-diaminobutyric acid ((R)$^{H_2N}$γ). The NMR structure of a hairpin polyamide of sequence composition ImPyPy-γ-PyPyPy complexed with a 5'-TGTTA-3' target site indicated that it was possible to substitute the α-position of the γ-aminobutyric acid residue within the hairpin-DNA complex (de Claire, et al. J. Am. Chem. Soc. 1997, 119, 7909). Modeling indicated that replacing the α-H of γ with an amino group that may confer an R-configuration at the α-carbon and could be accommodated within the floor and walls of the minor groove.

A polyamide of Formulas I–XXIX may also be conjugated to a bifunctional group including but not limited to arylboronic acid, biotins, polyhistidine of 2 to 8 amino acids, hapten to which an antibody binds, solid phase support, oligodeoxynucleotide, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoraen-8-yloxy)-butyrate, tartaric acid, or (+)-α-tocopheral. Many other groups suitable for the purposes of practicing this invention are well known and widely available to one skilled in the art.

As used herein "polyamide" refers to a polymer comprising the subunits listed below:

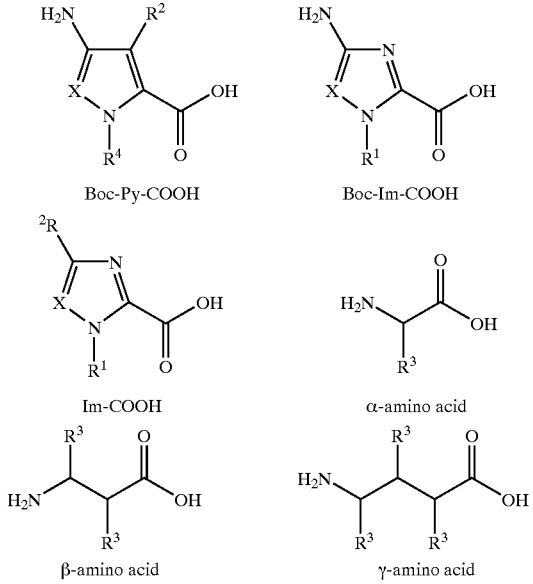

Boc-Py-COOH   Boc-Im-COOH

Im-COOH   α-amino acid

β-amino acid   γ-amino acid where $R^1$ is $C_{1-100}$ alkyl (preferably $C_{1-10}$ alkyl such as methyl, ethyl, isopropyl), $C_{1-100}$ alkylamine (preferably $C_{1-10}$ alkylamine such as ethylamine), $C_{1-100}$ alkyldiamine (preferably $C_{1-10}$ alkyldiamine such as N,N-dimethylpropylamine), $C_{1-100}$ alkylcarboxylate (preferably a $C_{1-10}$ alkylcarboxylate such as —CH$_2$COOH), $C_{1-100}$ alkenyl (preferably $C_{1-10}$ alkenyl such as CH$_2$CH═CH$_2$), $C_{1-100}$ alkynyl (preferably $C_{1-10}$ alkynyl such as CH$_2$C≡CH$_3$), or $C_{1-100}$L;

L includes but is not limited to an arylboronic acid, biotin, polyhistidine comprising from 2 to 8 amino acids, hapten to which an antibody binds, solid phase support, oligodeoxynucleotide, N-ethylnitrosourea, fluorescein, bromoacetamide, iodoacetamide, DL-α-lipoic acid, acridine, captothesin, pyrene, mitomycin, texas red, anthracene, anthrinilic acid, avidin, DAPI, isosulfan blue, malachite green, psoralen, ethyl red, 4-(psoralen-8-yloxy)-butyrate, tartaric acid, and (+)-α-tocopheral;

m is an integer value ranging from 0 to 12;

$R^2$ is H, NH$_2$, SH, Cl, Br, F, N-acetyl, or N-formyl;

R3 is H, NH$_2$, OH, SH, Br, Cl, F, OMe, CH$_2$OH, CH$_2$SH, or CH$_2$NH$_2$; and, X is N, CH, COH, CCH$_3$, CNH$_3$, CCl, or CF.

In a preferred embodiment, $R^5$ and $R^6$ are H.

The compounds of the present invention may comprise a compound of Formula XXIX or XXX:

XXIX

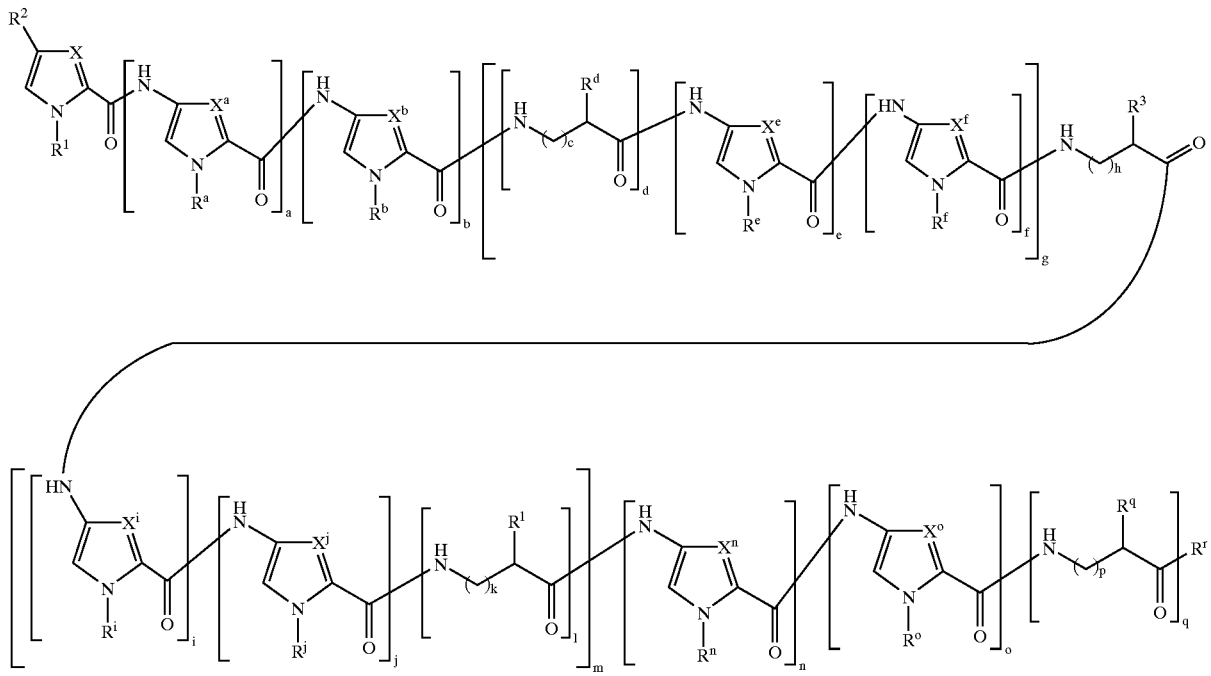

where

- $R^1$, $R^a$, $R^b$, $R^e$, $R^f$, $R^i$, $R^j$, $R^n$, and $R^o$ are chosen independently from H, Cl, NO, N-acetyl, benzyl, $C_{1-6}$ alkyl, $C_{1-6}$ alkylamine, $C_{1-6}$ alkyldiamine, $C_{1-6}$ alkylcarboxylate, $C_{1-6}$ alkenyl, and $C_{1-6}$ alkynyl;
- $R^2$ is selected from the group consisting of H, $NH_2$, SH, Cl, Br, F, N-acetyl, and N-formyl;
- $R^3$, $R^d$, $R^l$ and $R^q$ are selected independently from the group consisting of H, $NH_2$, OH, SH, Br, Cl, F, OMe, $CH_2OH$, $CH_2SH$, $CH_2NH_2$;

X, $X^a$, $X^b$, $X^e$, $X^f$, $X^i$, $X^j$, $X^n$, $X^o$ are chosen independently from the group consisting of N, CH, COH, $CCH_3$, $CNH_2$, CCl, CF; and a, b, c, d, e, f, i, j, k, and m are integers chosen independently, having values ranging from 0 to 5;

or a pharmaceutically acceptable salt thereof.

The invention further comprises a polyamide having the formula:

XXX

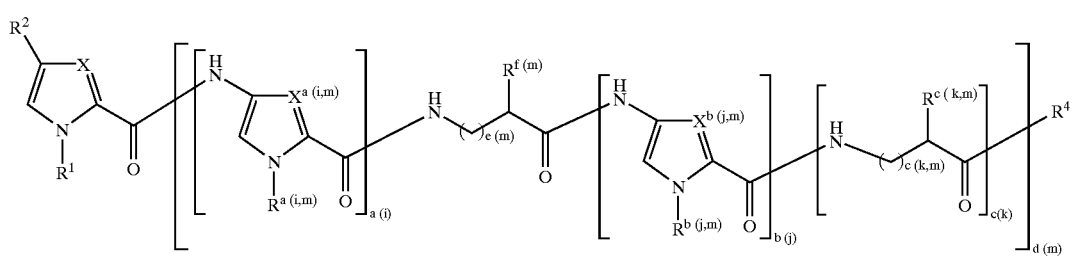

$R^4$ is —$NH(CH_2)_{0-6}NR^5R^6$ or $NH(CH_2)_rCO$ $NH(CH_2)_{0-6}$ $NR^5R^6$ or $NHR^5$ or $NH(CH_2)_rCONHR^5$, where $R^5$ and $R^6$ are independently chosen from H, Cl, NO, N-acetyl, benzyl, $C_{1-6}$ alkyl, $C_{1-6}$ alkylamine, $C_{1-6}$ alkyldiamine, $C_{1-6}$ alkylcarboxylate, $C_{1-6}$ alkenyl, $C_{1-6}$L, where L groups are independently chosen from biotin, oligodeoxynucleotide, N-ethylnitrosourea, fluorescein, bromoacetamide, iodoacetamide, DL-α-lipoic acid, acridine, ethyl red, 4-(psoralen-8-yloxy)-butyrate, tartaric acid, (+)-α-tocopheral, and $C_{1-6}$ alkynyl, where r is an integer having a value ranging from 0 to 6;

where $R^1$, $R^{a(i,m)}$ and $R^{b(j,m)}$ are chosen independently from H, Cl, NO, N-acetyl, benzyl, $C_{1-6}$ alkyl, $C_{1-6}$ alkylamine, $C_{1-6}$ alkyldiamine, $C_{1-6}$ alkylcarboxylate, $C_{1-6}$ alkenyl, and $C_{1-6}$ alkynyl;

$R^2$ is selected from the group consisting of H, $NH_2$, SH, Cl, Br, F, N-acetyl, and N-formyl;

$R^{f(m)}$ and $R^{c(k,m)}$ are selected independently from the group consisting of H, $NH_2$, OH, SH, Br, Cl, F, OMe, $CH_2OH$, $CH_2SH$, $CH_2NH_2$;

$R^4$ is —$NH(CH_2)_{0-6}NR^5R^6$ or $NH(CH_2)_rCO$ $NH(CH_2)_{0-6}$ $NR^5R^6$ or $NHR^5$ or $NH(CH_2)_rCONHR^5$, where $R^5$ and $R^6$ are independently chosen from H, Cl, NO, N-acetyl, benzyl, $C_{1-6}$ alkyl, $C_{1-6}$ alkylamine, $C_{1-6}$ alkyldiamine, $C_{1-6}$ alkylcarboxylate, $C_{1-6}$ alkenyl, $C_{1-6}$L, where L groups are independently chosen from biotin, oligodeoxynucleotide, N-ethylnitrosourea, fluorescein, bromoacetamide, iodoacetamide, DL-α-lipoic acid, acridine, ethyl red, 4-(psoralen-8-yloxy)-butyrate, tartaric acid, (+)-α-tocopheral, and $C_{1-6}$ alkynyl, where r is an integer having a value ranging from 0 to 6;

X, $X^{a(i,m)}$ and $X^{b(j,m)}$ are chosen independently from the group consisting of N, CH, COH, $CCH_3$, $CNH_2$, CCl, CF; and a, b, c, d, e, f, g, h, i, j, k, l, m, n, o and p are integers chosen independently, having values ranging from 0 to 5;

or a pharmaceutically acceptable salt thereof.

Baird, et al. (*J. Am. Chem. Soc.* 118: 6141–6146) and PCT/US97/003332 describe methods for synthesis of polyamides which are suitable for preparing polyamides of this invention. Polyamides of the present invention may be synthesized by solid phase methods using compounds such as Boc-protected 3-methoxypyrrole, imidazole, and pyrrole aromatic amino acids, which are cleaved from the support by aminolysis, deprotected with sodium thiophenoxide, and purified by reverse-phase HPLC. The identity and purity of the polyamides may be verified using any of a variety of analytical techniques available to one skilled in the art such as 1H-NMR, analytical HPLC, and/or matrix-assisted laser-desorption ionization time-of-flight mass spectrometry (MALDI-TOF MS-monoisotropic).

In addition, the above polyamide subunits can be synthesized in small scale by methods known in the art. The synthesis of Boc-Py-OBt ester 7 (Grehn, L. and Ragnarsson, U. *J. Org. Chem.* 1981, 46, 3492.) and Boc-Im acid 11 (Grehn, et al. *Acta. Chim. Scand.* 1990, 44, 67.) has been previously described. Available procedures provide only milligram to gram quantities of monomer (*J. Org. Chem.* 52, 3493–3500 (1987); Bailey, et al. *Org. Synth.* 51, 101 (1971); Nishsiwaki, et al. *Heterocycles* 27, 1945 (1988). Bailey, et al. *J. Pharm. Sci.* 78, 910, (1989)), while requiring difficult column chromatography and the use of toxic chlorofluorophosgene for introduction of the Boc group. An optimized synthesis, using inexpensive starting materials, has been developed by the present inventor allowing Boc-Py-OBt ester and Boc-Im acid monomers to be prepared on 50 g scale without the use of column chromatography. Two dimeric building blocks have also been prepared, Boc-Py-Im acid and Boc-γ-Im acid.

A general method for preparation of these compounds is as follows:

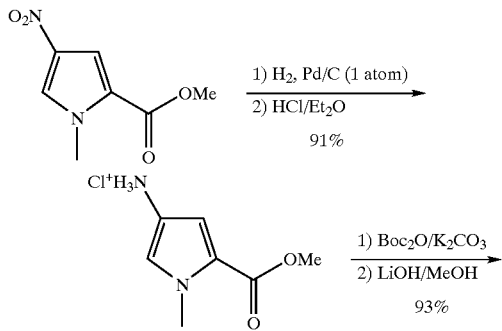

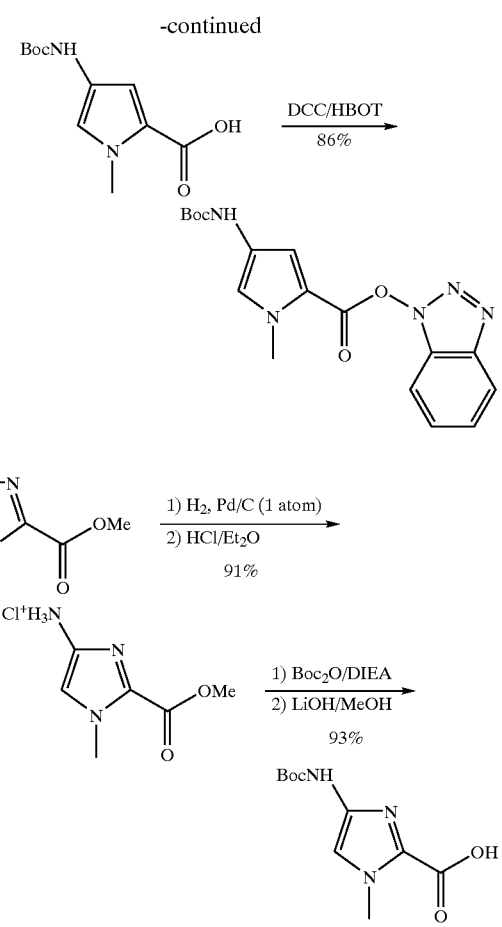

The polyamide polymer can be a homopolymer of Py and Im subunits or a copolymer with strategically placed aliphatic amino acid monomers such as α-amino acids (including but not limited to the naturally occurring amino acids and preferably being glycine); amino acids of the formula —NH—(CH)$_n$—CO—, where n is an integer from 1–12 (preferably n being 1 as in β-alanine or 2 as in γ-aminobutyric acid).

The carboxy terminus of the polyamide may comprise —NH(CH$_2$)$_{0-6}$, NR$^1$R$^2$ or NH(CH$_2$)$_b$CO NH(CH$_2$)$_{0-6}$ NR$^1$R$^2$, NHR$^1$ or NH(CH$_2$)$_b$CO NHR$^1$ where b is an integer from 1–6 (preferably 1) and R$^1$ and R$^2$ are independently chosen from $C_{1-6}$ alkyl (preferably $C_{1-3}$ alkyl such as methyl, ethyl, isopropyl), $C_{1-6}$ alkylamine (preferably $C_{1-3}$ alkylamine such as ethylamine), $C_{1-6}$ alkyldiamine (preferably $C_{1-3}$ alkyldiamine such as N,N-dimethylpropylamine), $C_{1-6}$ alkylcarboxylate (preferably a $C_{1-3}$ alkylcarboxylate such as —CH$_2$COOH), $C_{1-6}$ alkenyl (preferably $C_{1-3}$ alkenyl such as CH$_2$CH=CH$_2$), $C_{1-6}$ alkynyl (preferably $C_{1-3}$ alkynyl such as —CH$_2$C≡CH$_3$), or a $C_{1-6}$L where L includes but is not limited to biotin, oligodeoxynucleotide, N-ethylnitrosourea, fluorescein, bromoacetamide, iodoacetamide, DL-α-lipoic acid, acridine, ethyl red, 4-(psoraen-8-yloxy)-butyrate, tartaric acid, (+)-α-tocopheral.

Most preferred compounds of the instant invention are polyamides core sequence composition: ImPyPyPy-γ-PyPyPyPy, PyPyImPy-γ-PyPyPyPy, ImPyPyPy-γ-ImPyPyPy, PyImPyPy-γ-PyImPyPy, ImPyImPy-γ-PyPyPyPy, ImImPyPy-γ-PyPyPyPy, ImImImPy-γ-PyPyPyPy, ImImPyPy-γ-ImPyPyPy, ImPyPyPy-γ-ImImPyPy, ImImPyPy-γ-ImImPyPy, ImPyImPy-γ-ImPyImPy, ImImImPy-γ-ImPyPyPyPy, ImImImIm-γ-PyPyPyPy, Im-β-PyPy-γ-Im-β-PyPy, Im-β-ImIm-γ-Py-β-PyPy, Im-β-ImPy-γ-Im-β-ImPy, ImPyPyPyPy-γ-ImPyPyPyPy, ImImPyPyPy-γ-ImPyPyPyPy, ImPyImPyPy- γImPyPyPyPy, ImImPyImIm-γ-PyPyPyPyPy, ImPyPyImPy-γ-ImPyPyImPy, ImPy-β-PyPy-γ-ImPy-β-PyPy, ImIm-β-ImIm-γ-PyPy-β-PyPy, ImPy-β-ImPy-γ-ImPy-β-ImPy ImPy-β-PyPyPy-γ-ImPyPy-β-PyPy, ImIm-β-PyPyPy-γ-PyPyPy-β-PyPy, ImPy-β-ImPyPy-γ-ImPyPy-β-PyPy, ImIm-β-PyPyPy-γ-ImImPy-β-PyPy, ImPy-β-PyPyPy-γ-PyPyPy-β-ImPy, ImPyPyPyPyPy-γ-ImPyPyPyPyPy, ImPyPy-β-PyPy-γ-ImPyPy-β-PyPy, ImPyPyPy-β-Py-γ-Im-β-PyPyPyPy, ImImPyPyPyPy-γ-ImImPyPyPyPy, Im-β-PyPyPyPy-γ-Im-β-PyPyPyPy, ImPyPyPy-β-Py-γ-ImPyPyPy-β-Py, ImPyImPyPyPy-γ-ImPyPyPyPyPy, ImPyPy-β-PyPy-γ-ImPy-β-PyPyPy, ImPyPyPyPy-β-γ-ImPyPyPyPy-β, ImPy-β-ImPyPy-γ-ImPy-β-ImPyPy, Im-β-PyPyPyPy-γ-ImPyPyPy-β-Py, Im-β-ImPyPyPy-γ-ImPyPyPy-β-Py, ImPyPy-β-PyPyPy, ImImPy-β-PyPyPy, ImImIm-β-PyPyPy, ImPyPyPyPy-β-PyPyPy, ImPyPyPy-β-PyPyPy, ImPyPy-β-PyPyPyPyPy, ImPyPyPy-β-PyPyPyPy, ImImPyPy-β-PyPyPyPy, ImImImPy-β-PyPyPyPy, ImPyPyPy-β-ImPyPyPy, ImImPyPy-β-ImPyPyPy, ImImPyPyPy-β-PyPyPyPyPy, ImImImPyPy-β-PyPyPyPyPy, ImIm-β-PyPy-β-PyPy-β-PyPy, ImImPy-β-PyPyPy-β-PyPyPy, ImImPyPy-β-Py-β-PyPyPyPy, ImPyPy-γ-ImPyPy-β-PyPyPy, ImPyPy-γ-PyPyPy-β-PyPyPy, PyImPy-γ-ImPyPy-β-PyPyPy, PyImPy-γ-ImPyPy-β-PyPyPy-β-PyPyPy, ImImPy-γ-ImPyPy-β-PyPyPy, ImPyPy-γ-ImPyPy-G-PyPyPy, ImPyPyPy-γ-ImImImPy-β-PyPyPyPy, ImImPyPy-γ-ImImPyPy-β-PyPyPyPy, and ImImPyPy-γ-PyPyPyPy-β-PyPyPyPy.

The compounds of the following invention may be synthesized by any of several well-known and widely available techniques. Distamycin and its analogs can be produced by traditional multi-step synthetic organic chemistry (Weiss, et al. *J. Am. Chem. Soc.* 1957, 79, 1266; Arcamone, et al. *Gazz. Chim. Ital.* 1967, 97, 1097; Penco, et al *Gazz. Chim. Ital.* 1967, 97, 1110; Bailer, et al. *Tetrahedron* 1978, 34, 2389.) The repeating amide of distamycin is formed from an aromatic carboxylic acid and an aromatic amine, both of which have proven problematic for solution phase coupling reactions. The aromatic acid is often unstable to decarboxylation and the aromatic amines have been found to be air and light sensitive. (Lown, et al. *J. Org. Chem.* 1985, 50, 3774.) Variable coupling yields, long reaction times (often>24 h); numerous side products, and reactive intermediates (acid chlorides and trichloroketones) are characteristic of the traditional solution phase coupling reactions. (Church, et al. *Biochemistry* 1990, 29, 6827. He, et al. *J. Am. Chem. Soc.* 1993, 115, 7061.)

The process of expanding the 2:1 polyamide-DNA motif to include longer sequences recognized by increasingly complex polyamides is demanding. For example, using previously described multi-step solution phase chemistry, the total synthesis of the hairpin polyamides ImPyPy-γ-PyPyPy-Dp required more than a month's effort.

The chemical structures of the polyamide of the prior art ImPyPy-γ-PyPyPy-Dp, and the optimized hairpin polyamide ImPyPy-γ-PyPyPy-β-Dp provided by the instant invention are shown below:

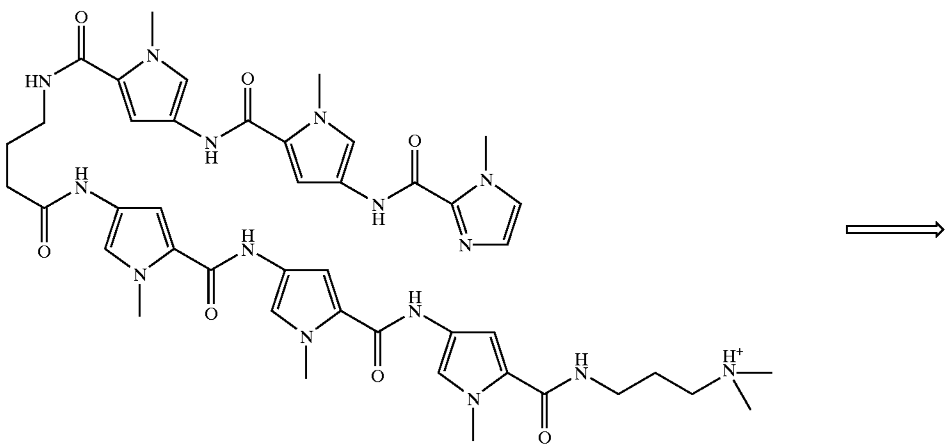

ImPyPy-γ-PyPyPy-β-Dp
$K_a = 7 \times 10^7\ M^{-1}$
specificty: 24-fold

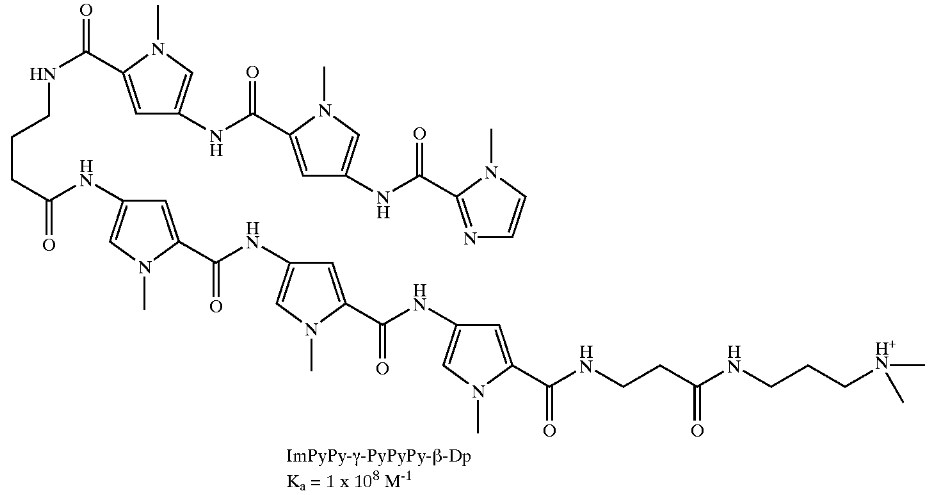

ImPyPy-γ-PyPyPy-β-Dp
$K_a = 1 \times 10^8\ M^{-1}$
specificty: 60-fold

Hereinafter hairpins may be shown as chemical structures binding to a schematic representation of the minor groove. An abbreviated representation may alternatively be used wherein, imidazole rings are represented as filled circles, pyrrole rings are represented as unfilled circles, β-alanine is represented as a diamond, Glycine is represented as a triangle, amide bonds are represented as lines, γ-aminobutyric acid is represented as a curved line, and the positively charged dimthylaminopropylamide is represented with a (+). An example of both notations is shown below for the optimized 6-ring hairpin polyamide ImPyPy-γ-PyPyPy-β-Dp binding to a cognate 5'-TGTTA-3' site:

generality with regard to targeting sequences of mixed A•T/T•A composition. (White, et al. *Biochemistry* 35, 12532–12537 (1996)). To test the extent of this degeneracy, the affinity of the hairpin polyamide ImPyPy-γ-PyPyPy-β-Dp was measured for eight possible five base pair 5'-TG(A,T)$_3$-3' match sites. Quantitative DNase I footprint titration experiments reveal that ImPyPy-γ-PyPyPy-β-Dp binds all eight 5'-TG(A,T)$_3$-3' target sites with only a 12-fold difference in the equilibrium association constants between the strongest site, 5'-TGTTT-3' ($K_a$=2.1×10$^8$ M$^{-1}$) and the weakest site, 5'-TGAAT-3' ($K_a$=1.8×10$^7$ M$^{-1}$) (10 mM Tris•HCl, 10 mM KCl, 10 mM MgCl$_2$, 5 mM CaCl$_2$, pH 7.0, 22° C.).

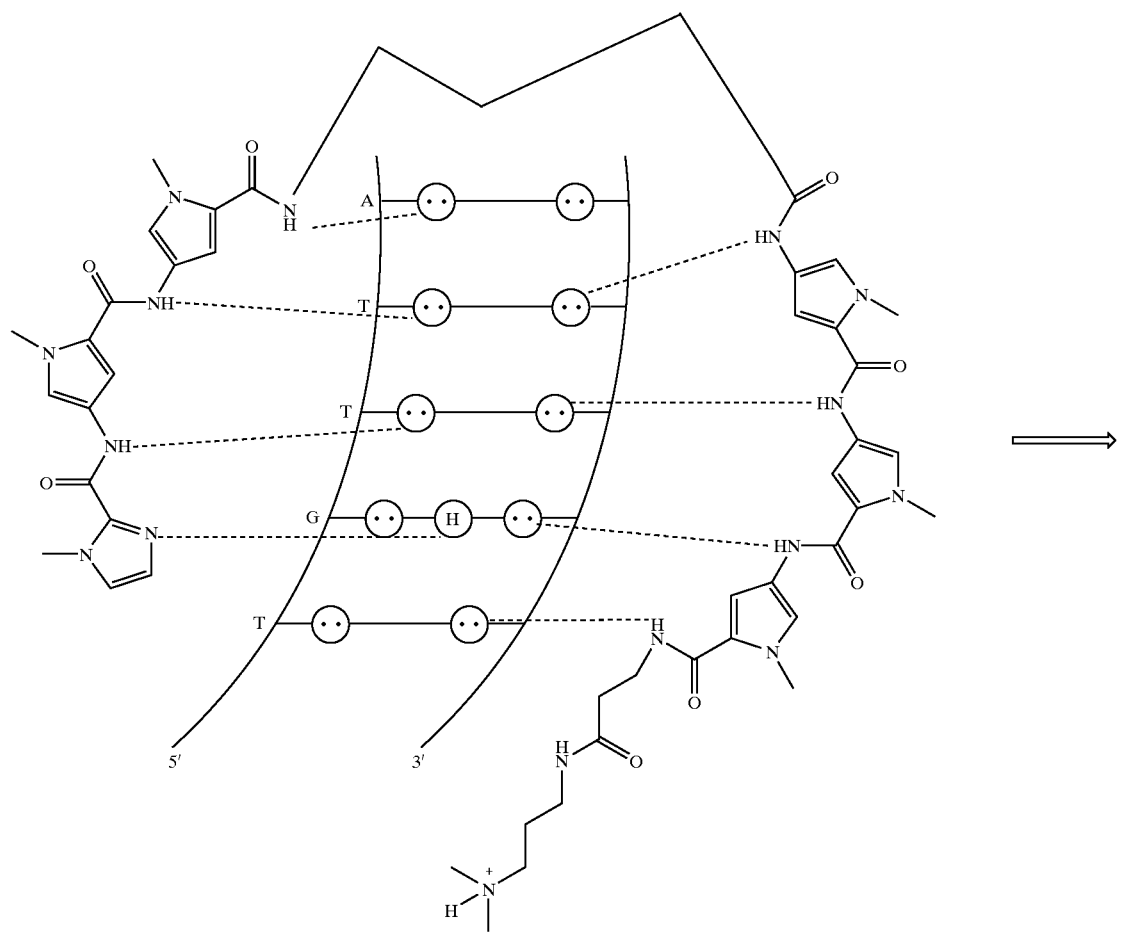

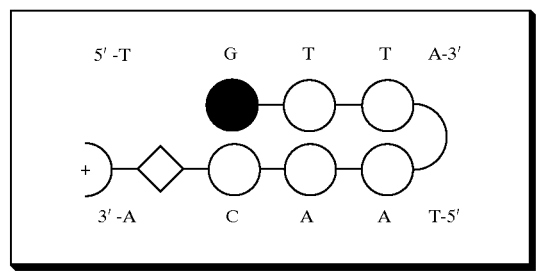

ImPyPy-γ-PyPyPy-β-Dp•5'-TGTTA-3'

It has been shown that the Py/Py pair is approximately degenerate for recognition of A,T base pairs, affording Sites are recognized with decreasing affinity: 5'-TGTTT-3'>5'-TGTTA-3'>5'-TGTAA-3'>5'-TGTAT-3'>5'-TGATT- 3'>5'-TGATA-3'>5'-TGAAA-3'>5'-TGAAT-3' as shown in schematic form below:

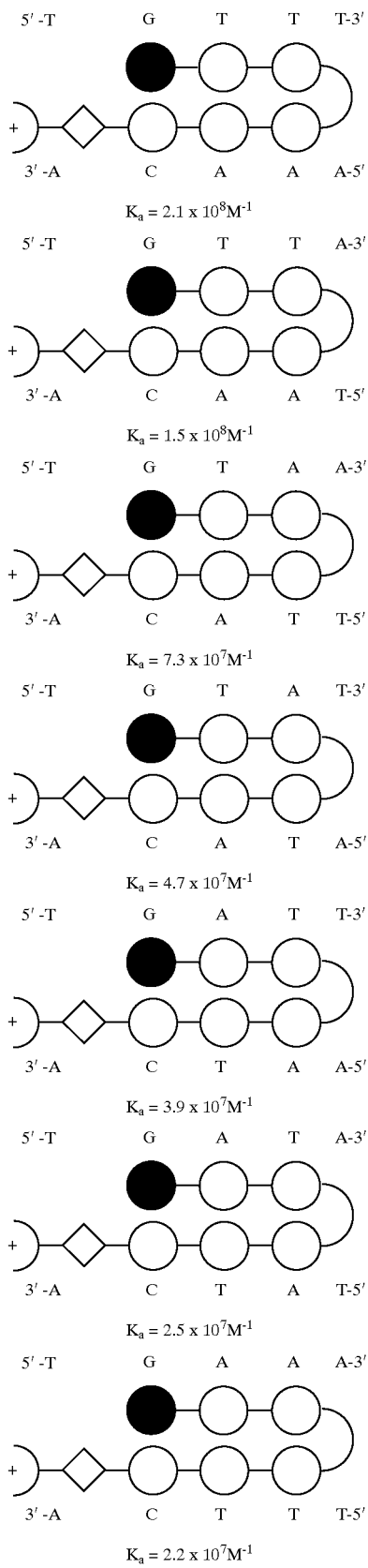

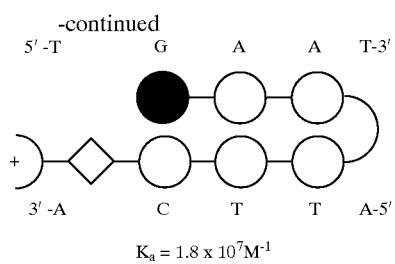

$K_a = 1.8 \times 10^7 M^{-1}$

These results indicate that all sites of the form 5'-TG(A, T)$_3$-3' are structurally compatible with polyamide-DNA complex formation. However, the affinities of ImPyPy-γ-PyPyPy-β-Dp for 5'-TG(A,T)$_3$-3' binding sites may be grouped into two sets according to sequence composition: 5'-TGT(A,T)$_2$-3' and 5'-TGA(A,T)$_2$-3'. ImPyPy-γ-PyPyPy-β-Dp binds 5'-TGT(A,T)$_2$-3' sites with between 2-fold and 12-fold higher affinity than 5'-TGA(A,T)$_2$-3' sites. Therefore binding sites containing 5'-GT-3' steps may be preferred over those containing 5'-GA-3' steps for therapeutic targets.

These results indicate that at least a 10-fold range of binding affinities and sequence specificities will be observed for a polyamide binding to a designated set of match sites containing A•T base pairs. This relatively small range indicates that, in contrast to the Im/Py pair which may distinguish G•C from C•G and both of these from A•T/T•A base pairs, the Py/Py pair appears not to distinguish A•T from T•A base pairs. The similarity of the polyamide binding affinities for the eight 5'-TG(A,T)$_3$-3' match sites reflects a limit to the specificity of the hairpin polyamide binding motif. Because G•C is distinct from C•G, the most specific recognition will be observed for G•C rich sequences.

In principle, individual polyamide subunits can recognize DNA with two possible binding orientations. Recognition of 5'-TGTTA-3' by a polyamide of core sequence composition ImPyPy-γ-PyPyPy places the N-terminus of each polyamide subunit at the 5'-side of each recognized DNA strand. Placement of the polyamide N-terminus at the 3' side of each recognized strand would result in targeting of a 5'-TCTTA-3' sequence. Each binding orientation represents a unique and distinguishable hairpin fold. Subunit orientation preference was not defined by the prior art, however, in order to successfully apply the pairing rules towards polyamide design, a single predictable subunit binding orientation must be preferred.

A schematic model of two possible hairpin polyamide DNA-binding orientations is shown below:

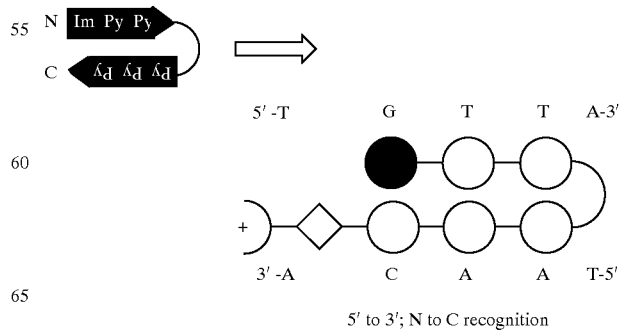

5' to 3'; N to C recognition

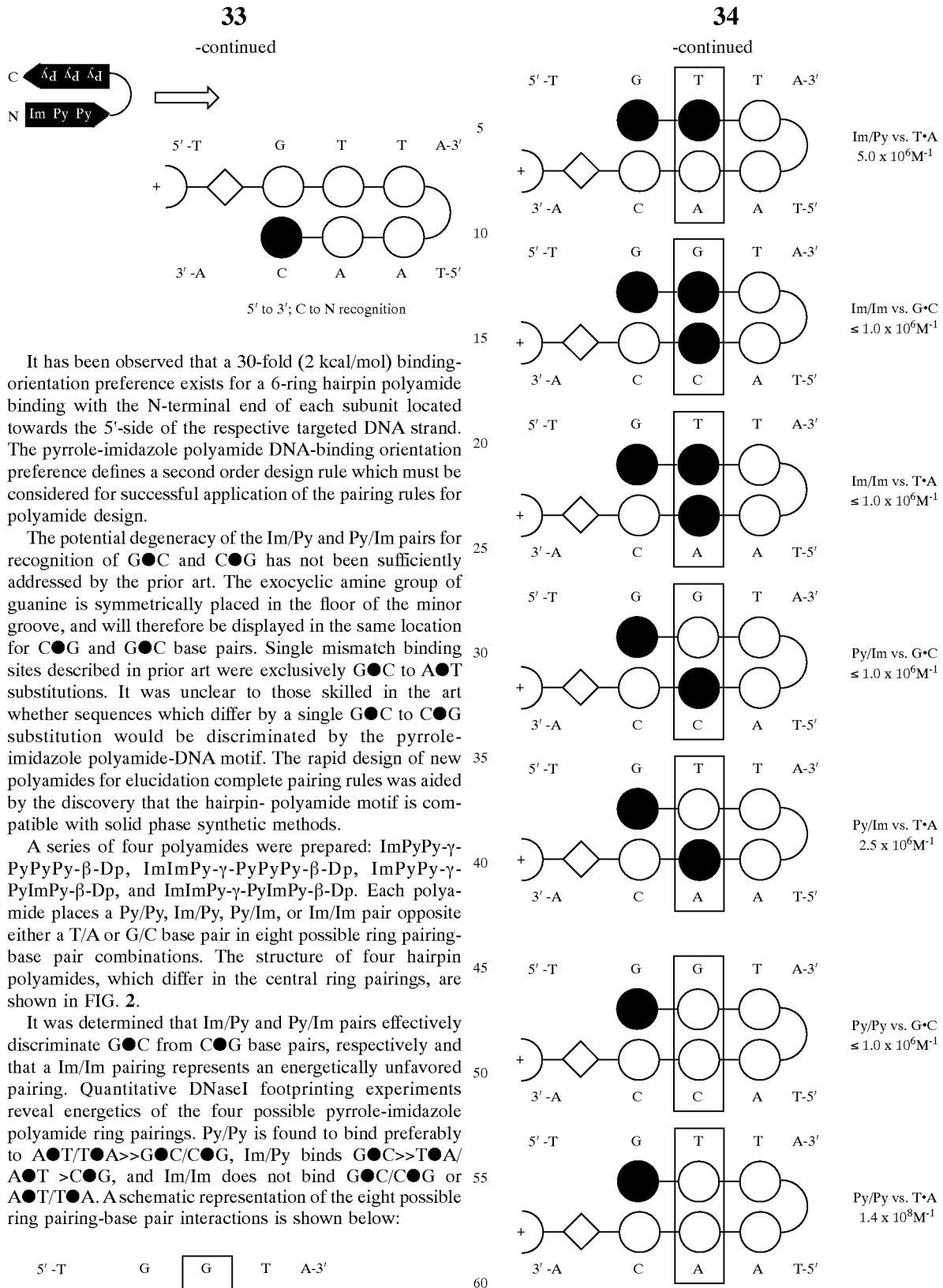

It has been observed that a 30-fold (2 kcal/mol) binding-orientation preference exists for a 6-ring hairpin polyamide binding with the N-terminal end of each subunit located towards the 5'-side of the respective targeted DNA strand. The pyrrole-imidazole polyamide DNA-binding orientation preference defines a second order design rule which must be considered for successful application of the pairing rules for polyamide design.

The potential degeneracy of the Im/Py and Py/Im pairs for recognition of G●C and C●G has not been sufficiently addressed by the prior art. The exocyclic amine group of guanine is symmetrically placed in the floor of the minor groove, and will therefore be displayed in the same location for C●G and G●C base pairs. Single mismatch binding sites described in prior art were exclusively G●C to A●T substitutions. It was unclear to those skilled in the art whether sequences which differ by a single G●C to C●G substitution would be discriminated by the pyrrole-imidazole polyamide-DNA motif. The rapid design of new polyamides for elucidation complete pairing rules was aided by the discovery that the hairpin- polyamide motif is compatible with solid phase synthetic methods.

Figure 2:
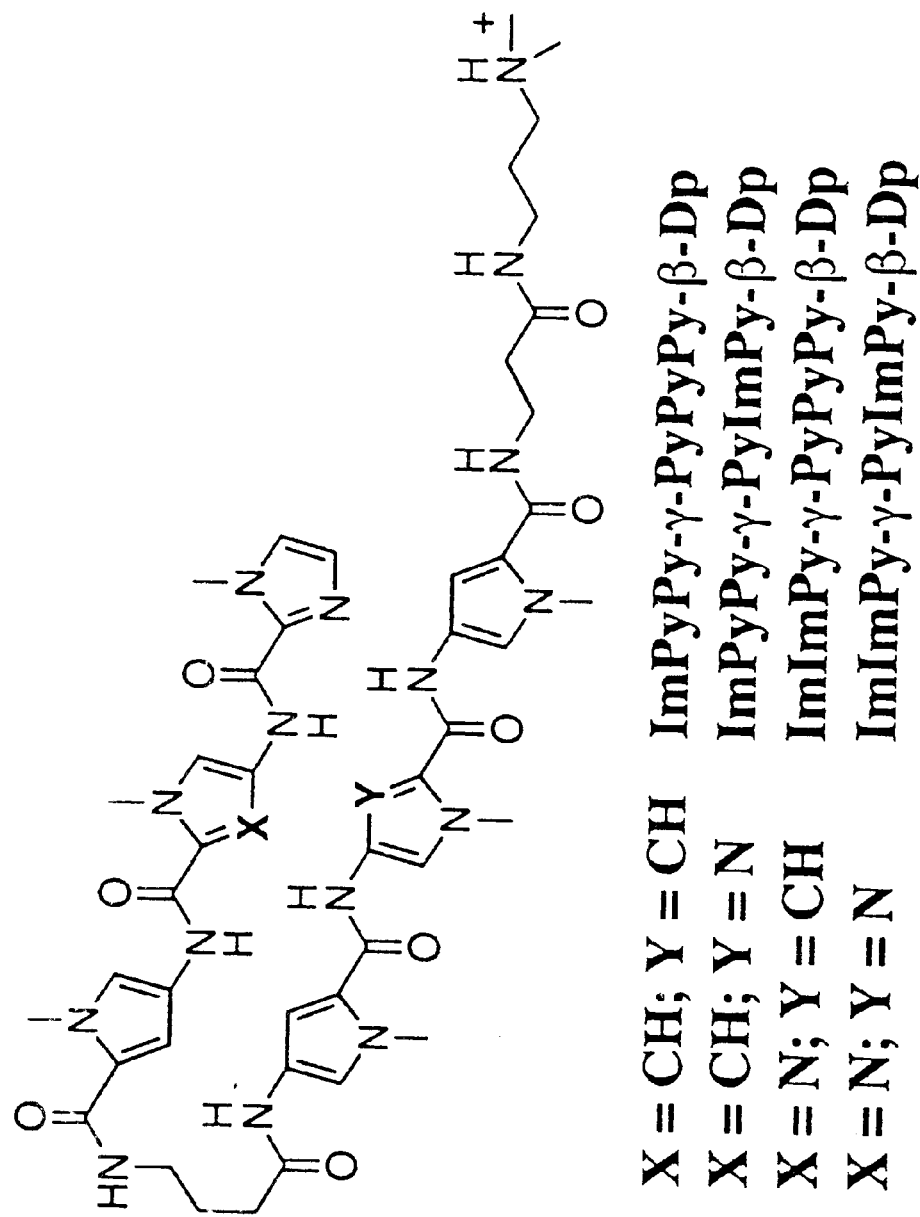
FIG. 2. Hairpin polyamides.

A series of four polyamides were prepared: ImPyPy-γ-PyPyPy-β-Dp, ImImPy-γ-PyPyPy-β-Dp, ImPyPy-γ-PyImPy-β-Dp, and ImImPy-γ-PyImPy-β-Dp. Each polyamide places a Py/Py, Im/Py, Py/Im, or Im/Im pair opposite either a T/A or G/C base pair in eight possible ring pairing-base pair combinations. The structure of four hairpin polyamides, which differ in the central ring pairings, are shown in FIG. 2.

It was determined that Im/Py and Py/Im pairs effectively discriminate G●C from C●G base pairs, respectively and that a Im/Im pairing represents an energetically unfavored pairing. Quantitative DNaseI footprinting experiments reveal energetics of the four possible pyrrole-imidazole polyamide ring pairings. Py/Py is found to bind preferably to A●T/T●A>>G●C/C●G, Im/Py binds G●C>>T●A/A●T >C●G, and Im/Im does not bind G●C/C●G or A●T/T●A. A schematic representation of the eight possible ring pairing-base pair interactions is shown below:

These results shown that G●C and C●G base pairs may be distinguished in the minor groove, while the energetic penalty for formation of an Im/Im pairing provides a basis for design of specific unlinked overlapped polyamide complexes as will become evident below.

It has been determined that the 6-ring hairpin polyamide motif provides a versatile template for recognition of a wide variety of sequences in the DNA minor groove. (Parks, et al. *J. Am. Chem. Soc.,* 118, 6153 (1996); Szewczyk, et al. *Angew. Chemie,* 35, 1487–1489 (1996); Swalley, et al. *J. Am. Chem. Soc.* 118, 8198–8206(1996)). Six-ring hairpin polyamides recognize their cognate sites with affinities ranging from $1 \times 10^7$ $M^{-1}$ to $1 \times 10^8$ $M^{-1}$ and specificity against single base pair mismatch sites ranging from 2-fold to 60-fold.

A schematic of nine 6-ring hairpin polyamides recognizing cognate 5 base pair sites is shown below:

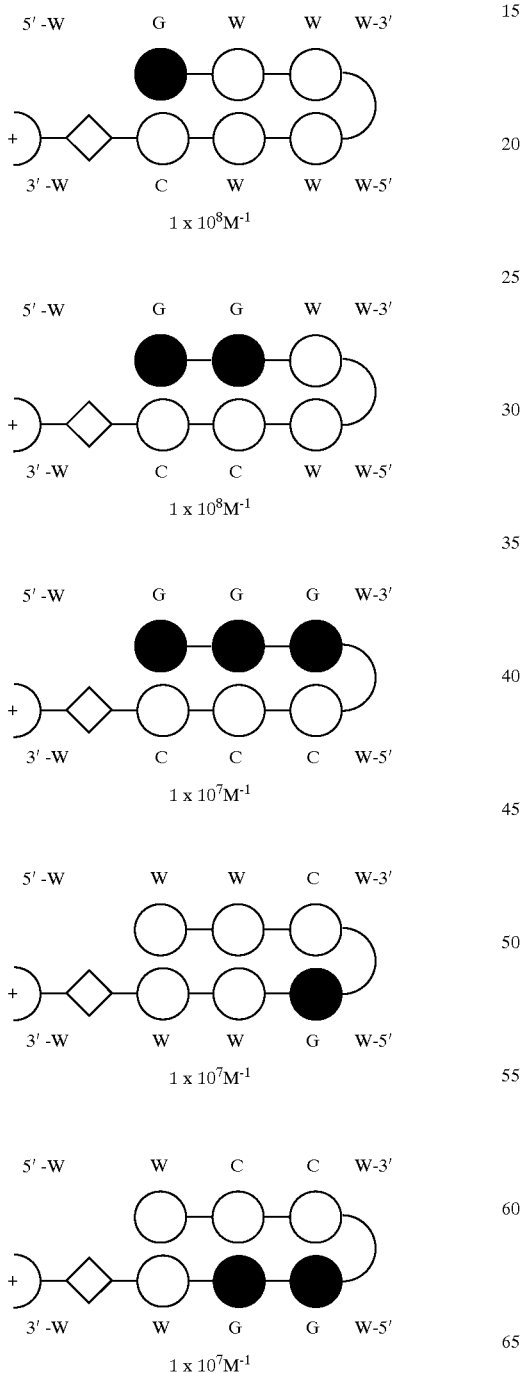

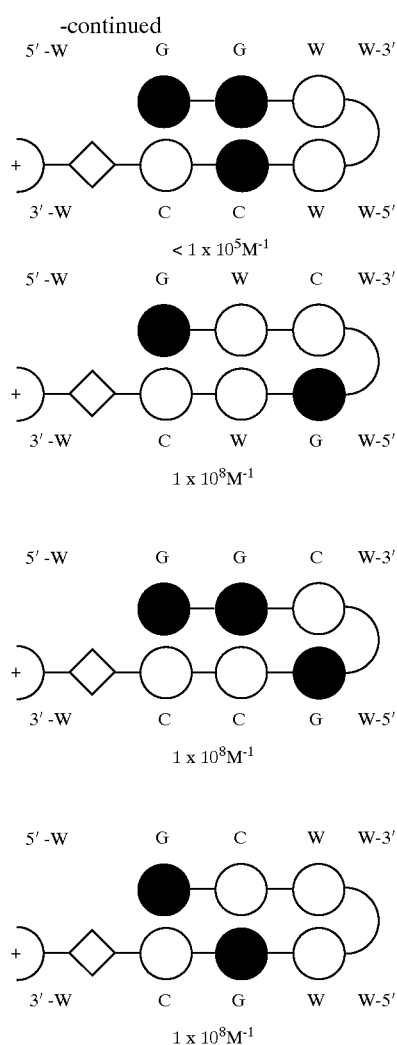

The broad sequence repertoire recognized by the 6-ring hairpin motif represents a significant advance in ligand design. However, no 6-ring hairpin polyamide has been identified which recognizes a target site with subnanomolar affinity.

Figure 3:
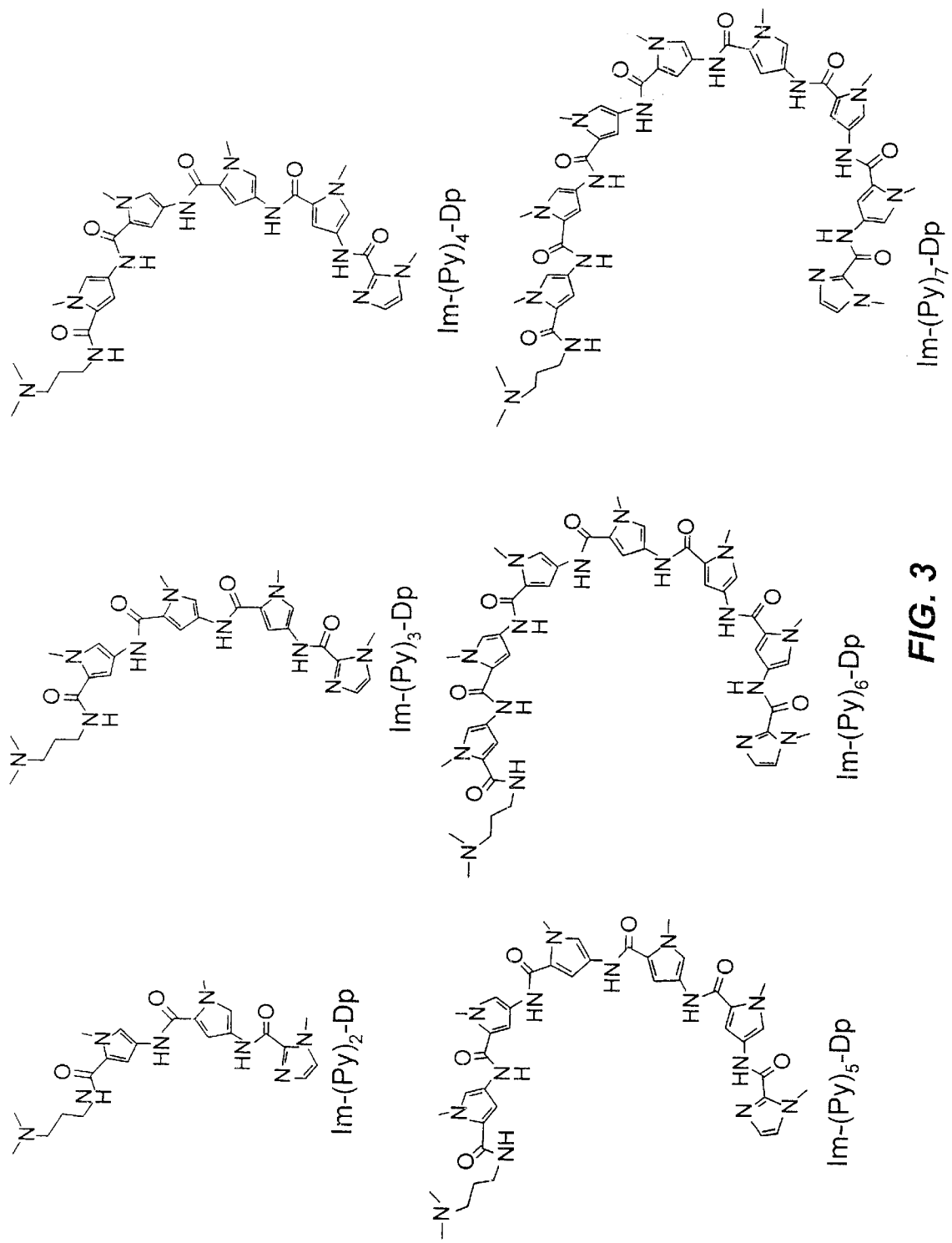
FIG. 3. Chemical structures of polyamides.

To determine the effect of polyamide length on binding site size, binding affinity, and sequence specificity, a series of six polyamides containing three to eight rings was synthesized. (Kelly, et al. *Proc. Natl. Acad. Sci. U.S.A.* 93, 6981–6985 (1996).) The series is based on ImPyPy-Dp with pyrrolecarboxamide moieties added sequentially to the C-termini to afford ImPyPyPy-Dp, ImPyPyPyPy-Dp, ImPyPyPyPyPy-Dp, ImPyPyPyPyPyPy-Dp, and ImPyPyPyPyPyPyPy-Dp which are designed to bind 5 to 10 base pair sites, respectively as side-by-side antiparallel dimers. DNA binding sites are based on a 5'-TGACA-3' core sequence and contain sequential A,T inserts in the center of the binding site that will be recognized by the additional pyrrole carboxamides. Chemical structures of the polyamides are shown in FIG. 3.

It was determined that polyamides based on 4 or 5-ring subunits are optimal, and that subunits must not contain more than 5 consecutive rings. Binding affinity reaches a maximum value for the five ring polyamide ImPyPyPyPy-Dp and addition of up to two additional pyrrolecarboxamides has no effect on the observed association constant (Table 2). Furthermore, sequence specificity decreases as the length of the polyamides increases beyond five rings.

TABLE 2

Table 1*

| polyamide-DNA complex | association constant | specificity‡ |
|---|---|---|
| 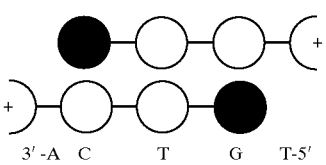 | $1.3 \times 10^5 \text{ M}^{-1}$ | 6.5-fold |
| 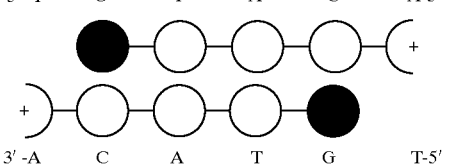 | $8.5 \times 10^6 \text{ M}^{-1}$ | 5.3-fold |
| 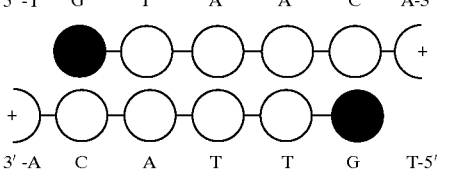 | $4.5 \times 10^7 \text{ M}^{-1}$ | 5.7-fold |
| 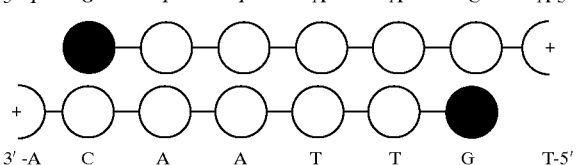 | $5.3 \times 10^7 \text{ M}^{-1}$ | 2.7-fold |
| 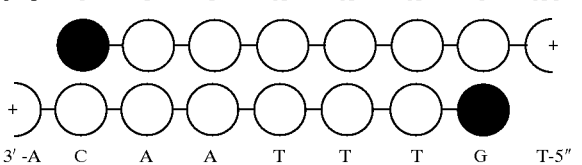 | $4.7 \times 10^7 \text{ M}^{-1}$ | 2.8-fold |
| 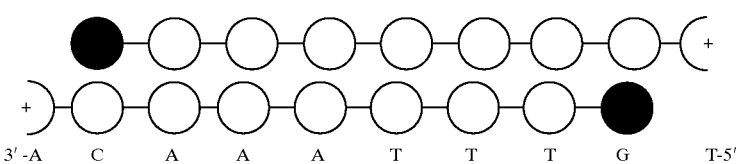 | $<2 \times 10^7 \text{ M}^{-1}$ | 1-fold |

*Values reported are the mean values from at least three footprint titration experiments. The assays were performed at 22° C., pH 7.0, in the presence of 10 mM TrisHCl, 10 mM KCl, 10 mM $MgCl_2$ and 5 mM $CaCl_2$.

‡Defined as the ratio of the match site affinity to the affinity of the single base pair mismatch site.

These results, specifically the failure of an eight-ring polyamide to recognize a 10-base pair target site suggested that a new class of polyamides was needed was needed for extension of the 2:1 polyamide-DNA motif to sequences longer than 9 base pairs. The present invention provides for the replacement of a central pyrrole or imidazole amino acid with a more flexible amino acid subunit, thus allowing the antiparallel dimer to reset the register for continued gain in affinity and specificity.

To identify a flexible linker amino acid, four polyamides of the formula ImPyPy-X-PyPyPy-Dp where X=Py, G (glycine), β, or γ, respectively, were synthesized and their equilibrium association constants determined for 5'-TGTTAAACA-3' (9 base pair) sites. (Trauger, et al. *J. Am. Chem. Soc.*, 118, 6160 (1996).)

The structure of polyamides based on ImPyPy and PyPyPy-Dp subunits linked by pyrrole or flexible glycine or β-alanine linkers are shown below:

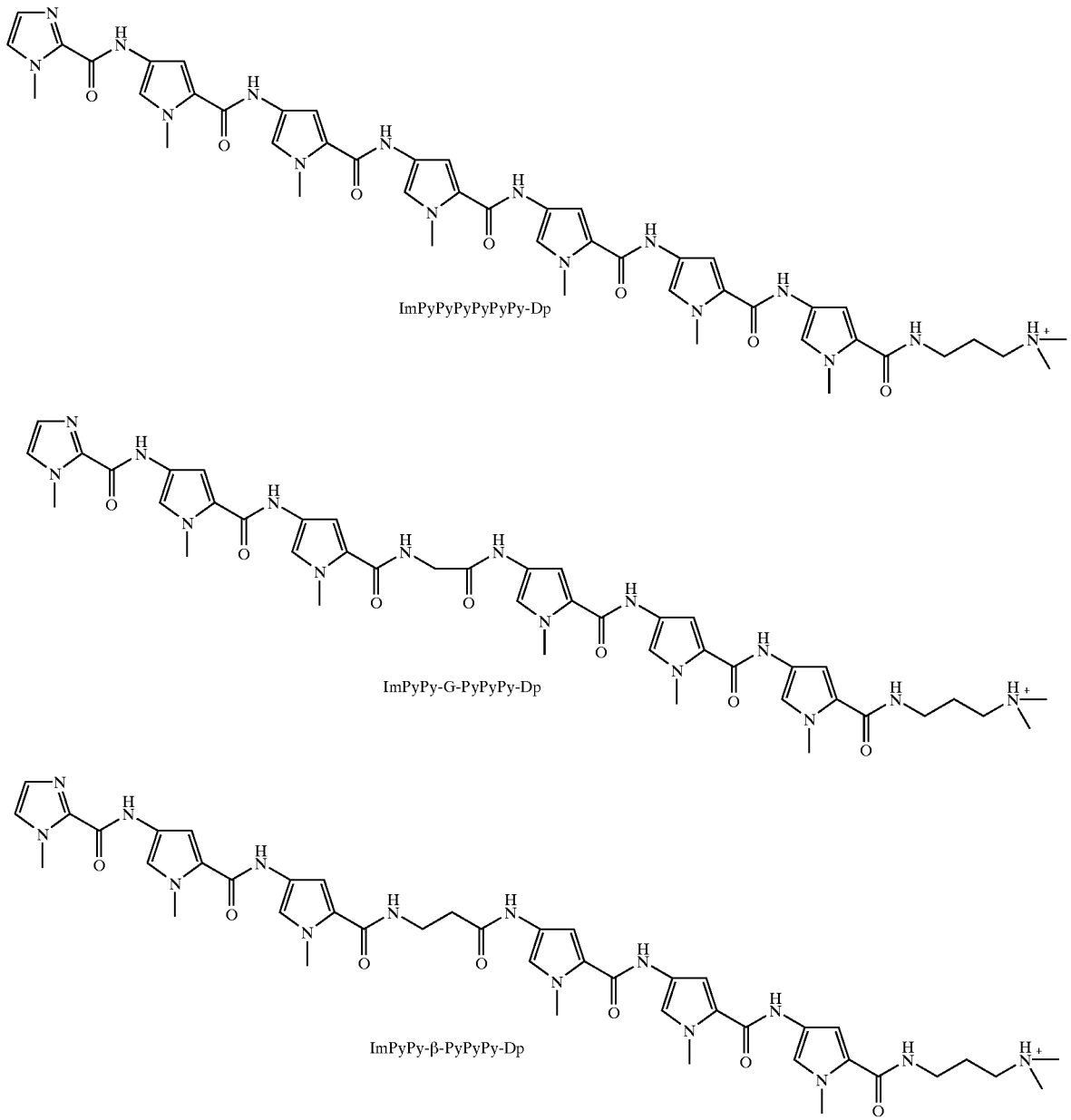

It was determined that β-alanine is an optimal linker for joining polyamide subunits in an extended conformation, providing a useful structural motif for the design of new polyamides targeted to sequences longer than 7 base pairs. The β-alanine-linked compound ImPyPy-β-PyPyPy-Dp has the highest binding affinity of the four polyamides, binding the 9 bp site 5'-TGTTAAACA-3'($K_a$=8×10$^8$ M$^{-1}$) with affinities higher than the formally N-methylpyrrole-linked polyamide ImPyPy-Py-PyPyPy-Dp by a factor of –10.

Solid phase synthesis involves the stepwise assembly of a molecule while one end is covalently anchored to an insoluble matrix at all stages of the synthesis. (Merrifield, *J. Am. Chem. Soc.* 85, 2149–2154 (1963); Merrifield, *Science* 232, 341–347.) The solid phase approach has been successfully developed for a variety of proteins' (Gutte, et al. 246, 1922–1941 (1971)), oligonucleotides (Ként, S. B. H. *Ann. Rev. Biochem.* 57, 957–989 (1988); Caruthers, et al. *Methods In Enzymology* 154, 287–313 (1987); Caruthers, M. H. *Acc. Chem. Res.* 24, 278–284 (1991)) peptoids, (Simon, et al. *Proc. Natl Acad. Sci. U.S.A.*, 89, 9367–9371 (1992); Zuckermann, et al. *J. Am. Chem. Soc.* 114 10646–10647 (1992)), oligosacharides (*Science* 269, 202–204 (1995); *Science* 260, 1307–1309 (1993)), and small non-polymeric molecules (Ellman, J. A. *Acc. Chem. Res.* 29, 132–143.) General protocols have been developed for manual and machine-assisted Boc-chemistry solid phase synthesis of pyrrole- imidazole polyamides. (Baird and Dervan, *J. Am. Chem. Soc.*, 118, 6141 (1996)). More specifically, the following components were developed: (1) a synthesis which provides large quantities of appropriately protected monomer or dimer building blocks in high purity, (2) optimized protocols for forming an amide in high yield from a support bound aromatic amine and an aromatic carboxylic acid, (3) methods for monitoring reactions on the solid support, (4) a stable resin linkage agent that can be cleaved in high yield upon completion of the synthesis. Solid phase synthesis protocols for pyrrole- imidazole polyamides reduce the synthetic investment from months to days.

Figure 4:
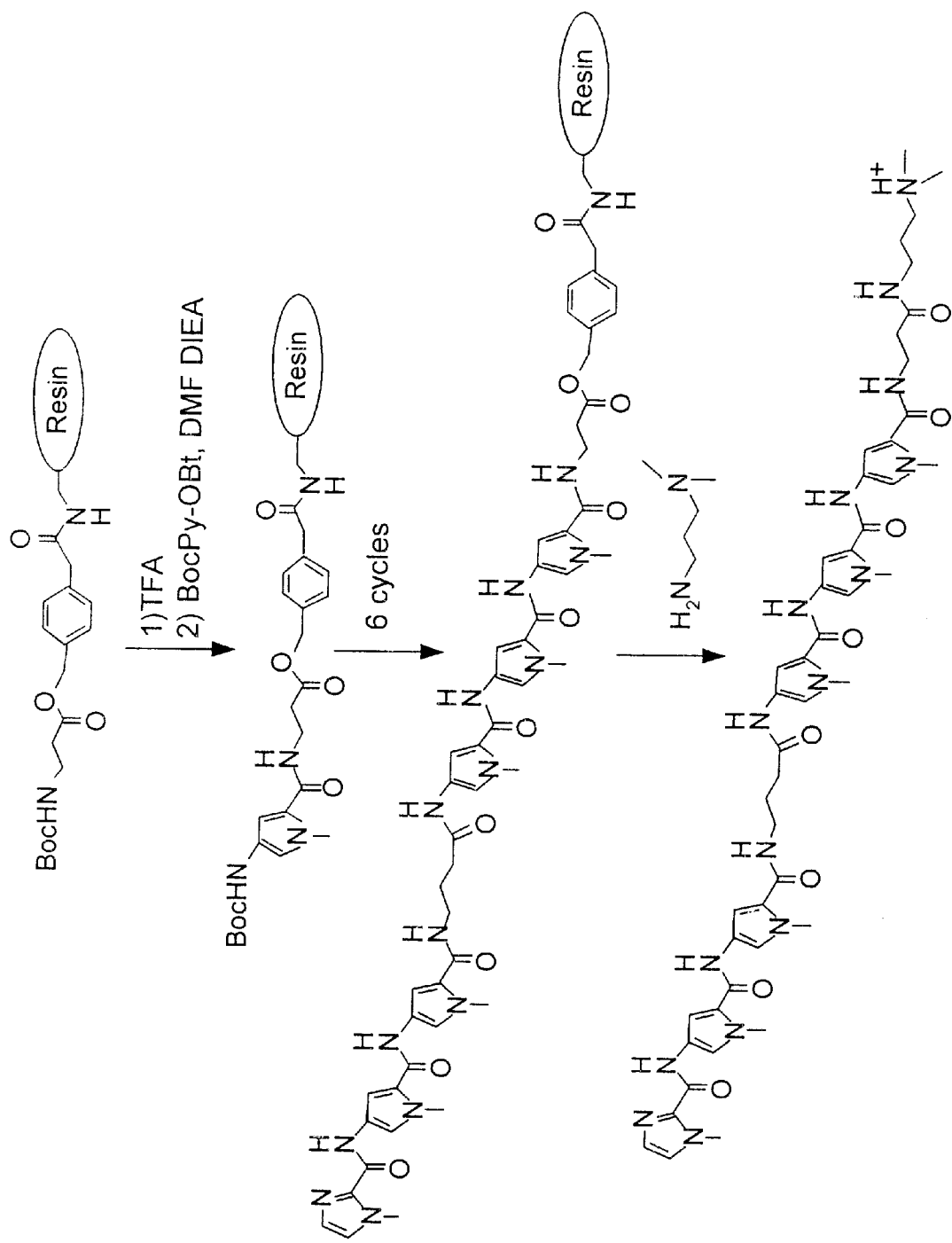
FIG. 4. Solid phase synthesis of polyamides.

A representative solid phase synthesis of a polyamide is shown in FIG. 4. Polyamides containing more than 4 residues are preferably prepared by solid phase methodology. For solid phase synthesis, the polyamide is attached to an insoluble matrix by a linkage which is cleaved by a single step process which introduces a positive charge into the polyamide. The addition of an aliphatic amino acid at the C-terminus of the pyrrole- imidazole polyamides allows the use of Boc-β-alanine-Pam-Resin resin which is commercially available in appropriate substitution levels (0.2 mmol/gram) (Mitchell, et al. *J. Org. Chem.* 1978, 43, 2845.) Aminolysis of the resin ester linkage provides a simple and efficient method for cleaving the polyamide from the support.

Solid phase polyamide synthesis protocols were modified from the in situ neutralization Boc-chemistry protocols recently reported by Kent and coworkers. (Schnolzer, et al. *Int. J. Peptide. Protein. Res.* 1992, 40, 180: Milton, et al. *Science* 1992, 256,1445.) Coupling cycles are rapid, 72 min per residue for manual synthesis or 180 min per residue for machine-assisted synthesis, and require no special precautions beyond those used for ordinary solid phase peptide synthesis. The manual solid phase protocol for synthesis of pyrrole-imidazole polyamides has been adapted for use on a ABI 430A peptide synthesizer. Stepwise cleavage of a sample of resin and analysis by HPLC indicates that high stepwise yields (>99%) are routinely achieved.

The large number of polyamides made available by solid phase synthetic methodology makes possible the elucidation of the rules necessary for development of polyamides which bind DNA with subnanomolar affinities. Cleavage of the polyamide from the resin with a primary diamine provides a polyamide having an unmodified primary amine group. The amine group may then be modified with an activated carboxylic acid or by nucleophilic aromatic substitution to provide a bifunctional polyamide.

Standard techniques available to one skilled in the art may be used to determine the DNA binding properties of novel pyrrole-imidazole polyamides. Affinity cleaving titration experiments ((25 mM Tris-Acetate, 20 mM NaCl, 100 mM bp calf thymus DNA, pH 7, 22° C., 10 mM DTT, 10 mM Fe(II)) using polyamides modified with EDTA●Fe(II) at the C-terminus are used to determine oriented binding. MPE●Fe(II) footprinting experiments (Hertzberg and Dervan, *J. Am. Chem. Soc.*, 104, 313 (1982); Van Dyke and Dervan, *Biochemistry*, 22, 2373 (1983); Van Dyke and Dervan, *Nucleic Acids Res.*, 11, 5555 (1983); Hertzberg and Dervan, *Biochemistry*, 23, 3934 (1984)) (25 mM Tris-acetate, 10 mM NaCl, 100 µM calf thymus DNA, 5 mM DTT, pH 7.0 and 22° C.) are used to determine binding site size. Quantitative DNaseI footprinting (Brenowitz, et al. (1986). *Methods Enzymol.* 130, 132–181.; Fox and Waring (1984). *Nucleic Acids Res.* 12, 9271–9285 Brenowitz, M., Senear, D. F., Shea, M. A. & Ackers, G. K. (1986); *Proc. Natl. Acad. Sci. U.S.A.* 83, 8462–8466.) (10 mM Tris-HCl, 10 mM KCl, 10 mM $MgCl_2$, and 5 mM $CaCl_2$, pH 7.0, 22° C.) reveals the equilibrium association constants for binding to match and mismatch sites. All footprinting experiments are performed on 3' and 5'$^{32}$P end restriction fragments derived from plasmids. 3'-shifted cleavage patterns are consistent with location of the polyamide in the minor groove.

Tert-butoxycarbonylaminoacyl-4-(oxymethyl)phenylacetamidomethyl-resin (PAM resin) is commercially available and cleaved in high yield by aminolysis with primary amines. (Mitchell, A. R.; Kent, S. B. H., Engelhard, M.; Merifield, R. B., *J. Org. Chem.* 43, 2845.) Insertion of a C-terminal aliphatic amino acid residue makes the hairpin-polyamide motif compatible with solid phase synthetic methods, allowing the rapid design of new polyamides. This result sets the stage for the elucidation of the limits of hairpin motif with regards to binding site size, binding affinity, and sequence specificity.

A schematic representation of the recognition of a nine base pair target site, by a polyamide containing a β-spring is shown below:

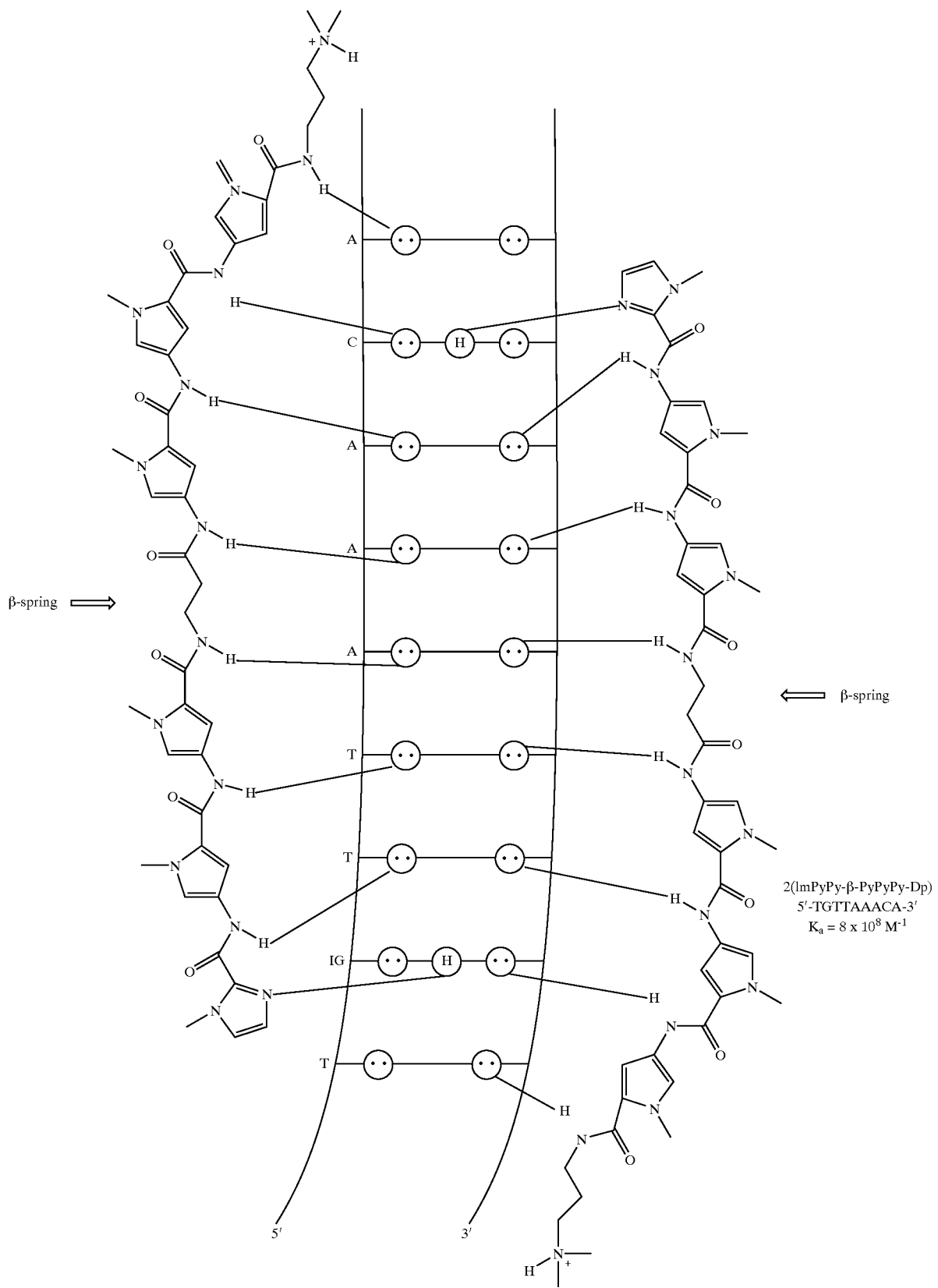

The binding data for ImPyPy-γ-PyPyPy-Dp, which was shown previously to bind DNA in a "hairpin" conformation, indicates that γ-aminobutyric acid does not effectively link polyamide subunits in an extended conformation. The discovery of β-alanine as an effective linker for joining polyamide subunits in an extended conformation, provides a useful structural motif for the design of new polyamides based on subunits <5-rings targeted to sites longer than 7 bp.

At least two distinct binding modes are expected to form for the ImPyPy-X-PyPyPy-Dp polyamides described above that bind in an extended conformation. These binding modes as "slipped" and "overlapped". In the overlapped (9 base pair) binding mode, two ImPyPy-X-PyPyPy-Dp polyamides bind directly opposite one another. The "slipped" (13 base pair) binding mode integrates the 2:1 and 1:1 polyamide-DNA binding motifs at a single site. In this binding mode, the ImPyPy moieties of two ImPyPy-X-PyPyPy-Dp polyamides bind the central 5'-AGACA-3' sequence in a 2:1 manner as in the ImPyPy homodimer, and the PyPyPy moieties of the polyamides bind to A,T flanking sequences as in the 1:1 complexes of distamycin.

A schematic model of the "slipped" and "overlapped" binding modes is shown below.

higher than the formally N-methylpyrrole-linked polyamide ImPyPy-Py-PyPyPy-Dp by a factor of ~85.

As described above, γ-aminobutyric acid, and preferably β-alanine, effectively link polyamides in hairpin and extended conformations, respectively. It has also been demonstrated that γ-aminobutyric does not optimally link polyamide subunits in extended conformations, and that β-alanine does not optimally link polyamide subunits in hairpin conformations. These results suggested that γ-aminobutyric acid and β-alanine could be combined within a single polyamide with predictable results. (Trauger, et al, *Chem. & Biol.*, 3, 369 (1996)).

It has been determined that the nine-ring "extended hairpin" polyamide ImPyPy-γ-ImPyPy-β-PyPyPy-G-Dp binds a 9-bp target site 5'-AAAAAGACA-3' at 0.05 nM concentration, an increase in affinity relative to the six-ring hairpin polyamide ImPyPy-γ-ImPyPy-β-Dp of ~400-fold. These results provide a strategy for increasing the DNA-binding affinity of hairpin polyamides into the subnanomolar range. Furthermore, as will become evident below, many important DNA binding transcription factors such as TBP

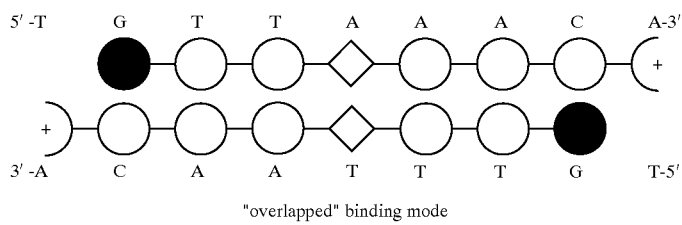

"overlapped" binding mode

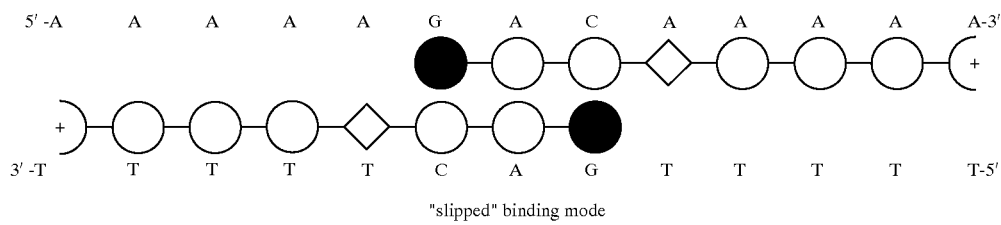

"slipped" binding mode

The present invention provides β-alanine as an optimal linker for joining polyamide subunits in a "slipped" extended conformation, providing a structural motif whereby a MW≈900 polyamide recognizes a 13 base-pair DNA sequence. The β-alanine-linked compound ImPyPy-β-PyPyPy-Dp binds to a 13 bp 5'-AAAAAGACAAAAA-3' site with an association constant. $K_a = 5 \times 10^9$ M$^{-1}$, that is and homeodomain proteins have A,T rich consensus sequences. Extended hairpin polyamides provide a general method by which a polyamide may interfere with protein-DNA interactions by recognizing a unique sequence adjacent to certain protein binding sites. A schematic binding model of extended hairpin polyamide recognition of a 9 base pair sequence is shown below:

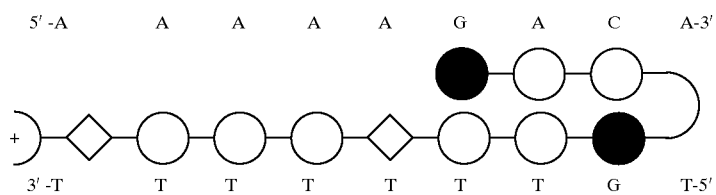

Figure 5:
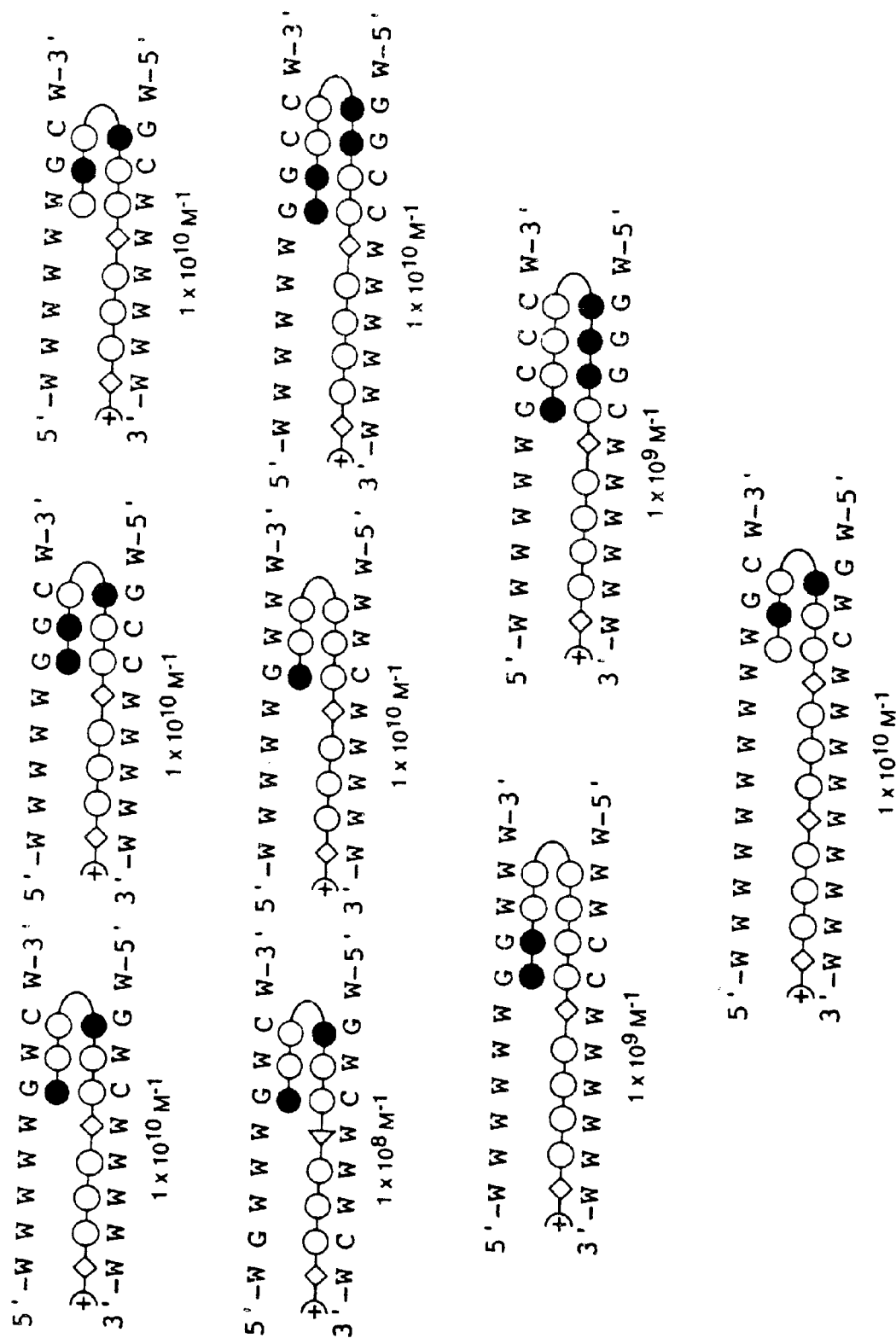
FIG. 5. Extended hairpin polyamides.

-continued
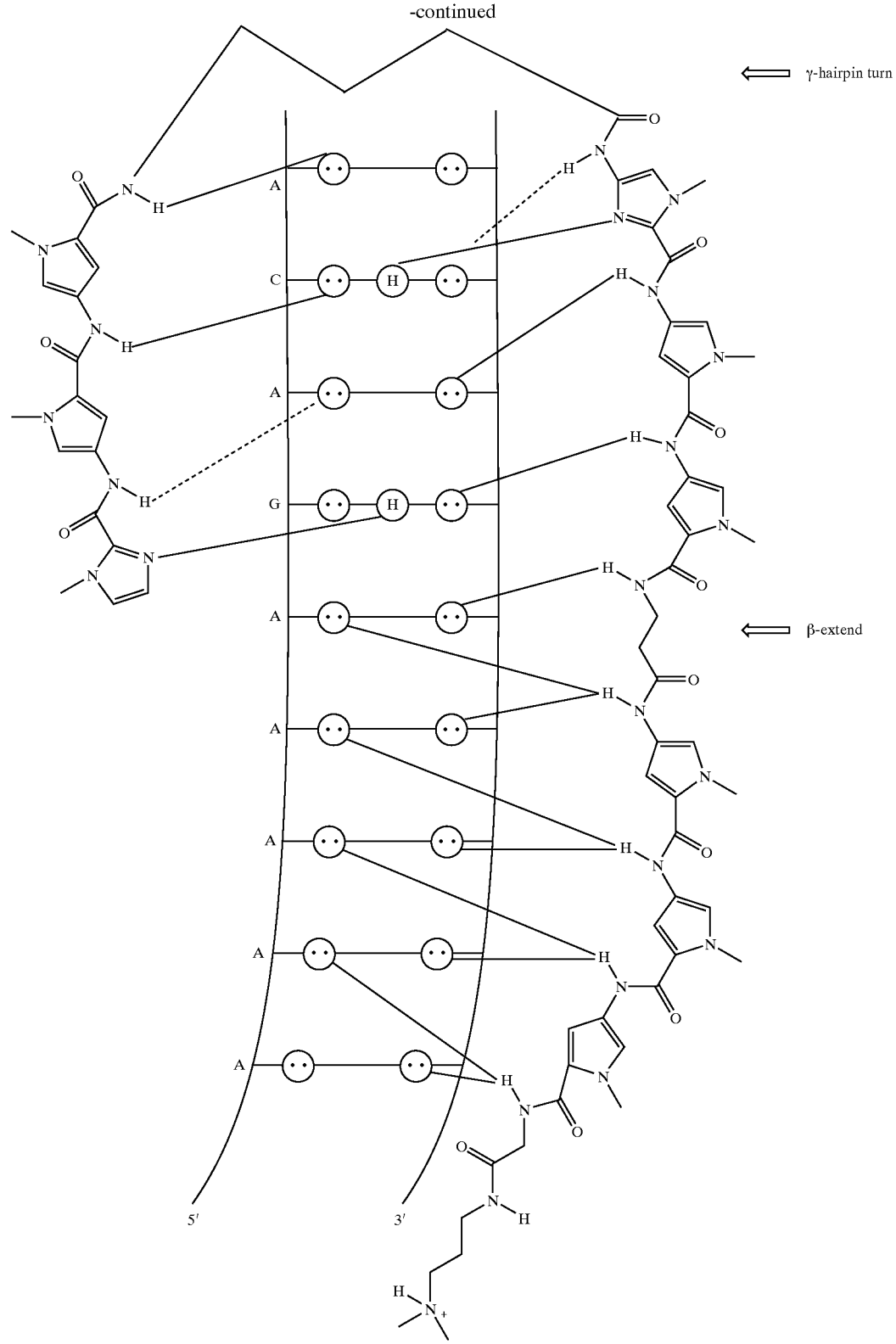
ImPyPy-γ-ImPyPy-β-PyPyPy-G-Dp
$K_a = 2 \times 10^{10} \text{ M}^{-1}$
Provided herein are extended hairpin polyamide motifs that provide versatile templates for recognition of a wide variety of sequences in the DNA minor groove. Extended hairpin polyamides recognize their 9 to 13 base pair sites target site with affinities ranging from 1×10$^8$ M$^{-1}$ to >5×10$^{10}$ M$^{-1}$ and specificity against single base pair mismatch sites ranging from 5-fold to 60-fold. A schematic of nine extended hairpin polyamides containing 9 to 12 rings and recognizing 9 to 13 base pair target sites is shown in FIG. 5.

Provided herein is an endonuclease protection assay to measure the rate of polyamide-DNA complex formation. Such an assay may comprise a labeled restriction fragment comprising a polyamide binding site that overlaps a restriction endonuclease cleavage site. Cleavage by the cognate is prevented when the overlapping polyamide binding site is occupied by the polyamide. As a control, a second labeled DNA fragment may be that contains the restriction site, but lacks the overlapping polyamide binding site. The rate of polyamide association with its target binding site may be assessed by incubating the solutions of the polyamide with the labeled target and reference fragments for a sufficient timer period. Using the experimental conditions provided herein, the reference site is nearly completely digested, but protection at the target site is observed and can be correlated with polyamide concentration and the time of equilibration. Similarly, the dissociation rate is analyzed by adding an excess of unlabeled competitor DNA to an equilibrated solution of the labeled DNA fragments and polyamide. Addition of the competitor reduces the concentration of free polyamide to zero. The rate at with polyamide dissociation occurs from the target site on the labeled fragment can be followed by the rate of loss of protection from restriction enzyme digestion as the re-equilibration time is increased.

First generation six-ring hairpin polyamides bind DNA with association constants of approximately 1×10$^8$ M$^{-1}$ (FIG. 6) The observation that unlinked four-ring polyamides form 2:1 complexes with 70-fold-higher affinity relative to three-ring polyamides suggested an eight-ring hairpin polyamide motif for recognition of DNA at subnanomolar concentration. The present inventor has shown that two eight-ring pyrrole-imidazole polyamides differing in sequence by a single amino acid bind specifically to respective six base pair target sites which differ in sequence by a single base pair. (Trauger, et al. *Nature,* 382, 559–561 (1996)). Binding is observed at subnanomolar concentrations of ligand.

Figure 7:
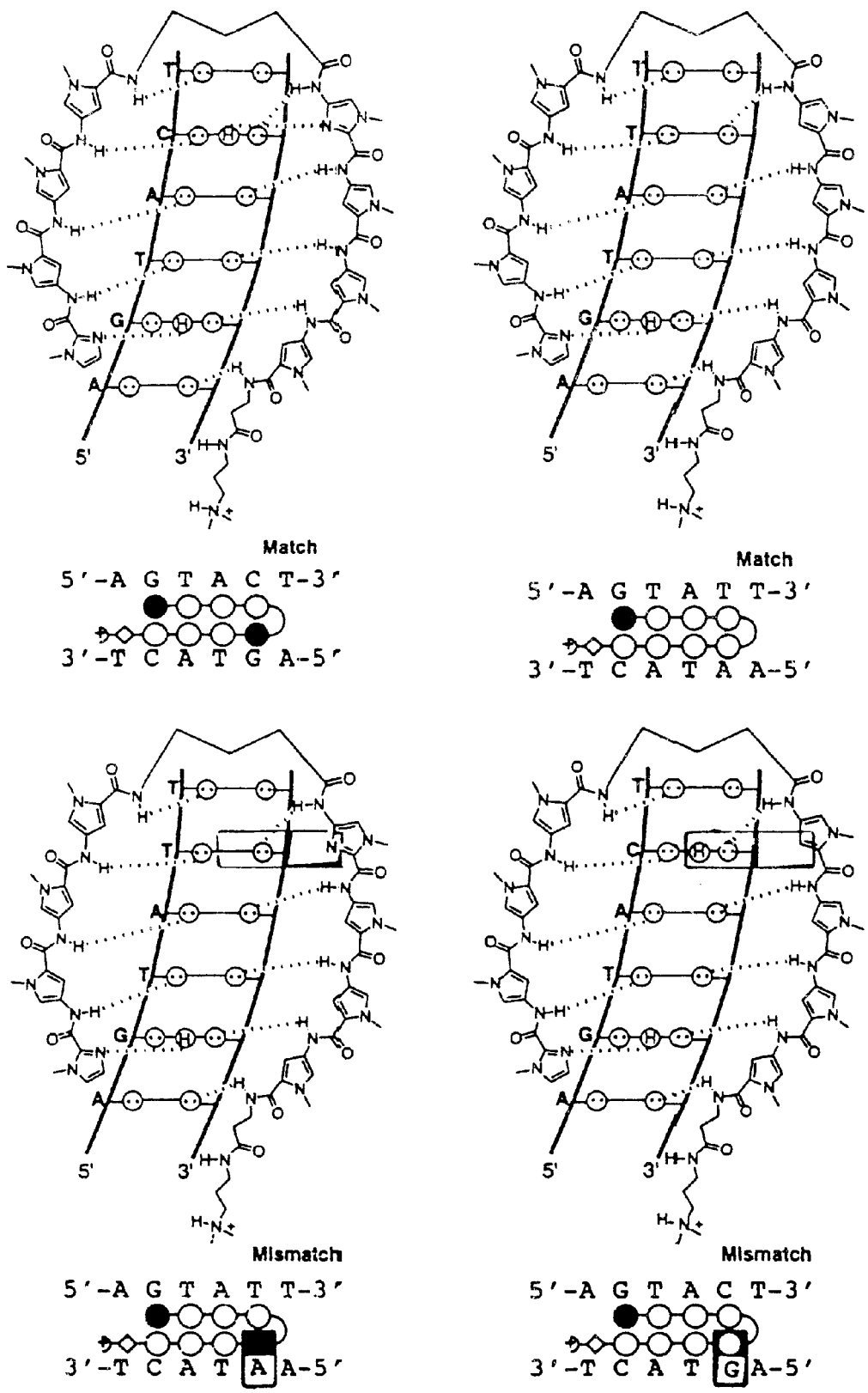
FIG. 7. Binding models for polyamides.

DNA-binding affinities were determined for two eight-ring hairpin polyamides. ImPyPyPy-γ-ImPyPyPy-β-Dp and ImPyPyPy-γ-PyPyPyPy-β-Dp, which differ by a single amino acid, for two 6 base pair (bp) target sites, 5'-AGTACT-3' and 5'-AGTATT-3', which differ by a single base pair. Based on the pairing rules for polyamide-DNA complexes, the sites 5'-AGTACA-3' and 5'-AGTATT-3' are for ImPyPyPy-γ-ImPyPyPy-β-Dp "match" and "single base pair mismatch" sites, respectively, and for polyamide ImPyPyPy-γ-PyPyPyPy-β-Dp "single base pair mismatch" and "match" sites, respectively. Binding models for 5'-AGTACT-3' and 5'-AGTATT-3' in complex with ImPyPyPy-γ-ImPyPyPy-β-Dp and ImPyPyPy-γ-PyPyPyPy-β-Dp are shown in FIG. 7.

ImPyPyPy-γ-ImPyPyPy-β-Dp and ImPyPyPy-γ-PyPyPyPy-0β-Dp were synthesized by solid phase methods and purified by reversed phase HPLC. Equilibrium association constants for match and mismatch six base pair binding sites on a 3'-$^{32}$P-labeled 229 bp restriction fragment were determined by quantitative DNase I footprint titration experiments. ImPyPyPy-γ-ImPyPyPy-β-Dp binds its match site 5'-AGTACT-3' at 0.03 nM concentration and its single base pair mismatch site 5'-AGTA<u>T</u>T-3' with nearly 100-fold lower affinity. ImPyPyPy-γ-PyPyPyPy-β-Dp binds its designated match site 5'-AGTATT-3' at 0.3 nM concentration and its single base pair mismatch site 5'-AGTA<u>C</u>T-3' with nearly 10-fold lower affinity. The specificity of ImPyPyPy-γ-ImPyPyPy-β-Dp and ImPyPyPy-γ-PyPyPyPy-β-Dp for their respective match sites results from very small structural changes. Replacing a single nitrogen atom in ImPyPyPy-γ-ImPyPyPy-β-Dp with C—H reduces the affinity of the polyamide●5'-AGTACT-3' complex by ~75-fold representing a free energy difference of −2.5 kcal/mole. Similarly, replacing a C—H in ImPyPyPy-γ-PyPyPyPy-β-Dp with N reduces the affinity of the polyamide●5'-AGTATT-3' complex ~10-fold, a loss in binding energy of −1.3 kcal/mol.

These results show that using a simple molecular shape and a two letter aromatic amino acid code, pyrrole-imidazole polyamides can achieve affinities and specificities comparable to DNA-binding proteins. It remained to be determined if additional motifs could be discovered to provide polyamides with subnanomolar binding affinities.

It has been suggested that pyrrole-imidazole polyamides would bind G/C rich sequences with low binding affinity due to steric hindrance with the exocyclic amines of the guanine bases. It has also been noted that the lower negative electrostatic potential of a G/C rich minor groove relative to an A, T rich minor groove might prohibit high affinity binding. (Pullman, et al. Quarterly Reviews of Biophysics. (1981) 14, 289–380; Pullman, B. Advances in Drug Research. (1989) 18, 1–113. Manning, G. S. Q. Rev. of Biophysics. (1978) 11, 179–246; Honig and Nicholls. Science (1995) 268, 1144.) It has been found that an 8-ring hairpin polyamide can recognize a G/C rich target sequence with subnanomolar affinity.

Schematic binding models of eight-ring hairpin polyamides designed for recognition of 5'-(A/T) (G/C)$_4$ (A/T)-3' sequences.

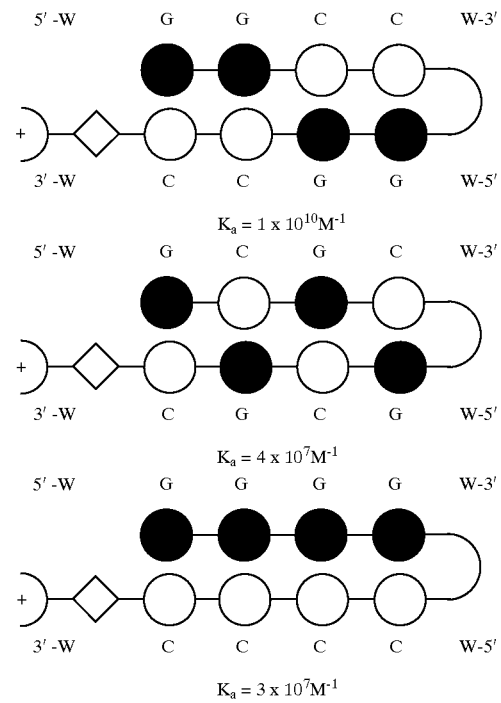

To examine whether a core sequence of purely G,C base pairs could be recognized with high affinity and specificity, three eight-ring hairpin polyamides which differ only by the arrangement of pyrrole and imidazole amino acids. ImImPyPy-γ-ImImPyPy-β-Dp, ImPyImPy-γ-ImPyImPy-β-Dp, and ImImImIm-γ-PyPyPyPy-β-Dp were designed for recognition of three core sequences consisting of solely G,C base pairs. DNase I footprint titrations allow the determination of equilibrium association constants ($K_a$) for each polyamide. ImImPyPy-γ-ImImPyPy-β-Dp binds the match site 5'-TGGCCA-3' with an equilibrium association constants of $K_a=1\times10^{10}$ M$^{-1}$ (10 mM Tris•HCl, 10 mM KCl, 10 mM MgCl$_2$ and 5 mM CaCl$_2$, pH 7.0 and 22° C.). The two designed double base pair mismatch sequences, 5'-TGCGCA-3' and 5'-TGGGGA-3', are bound with at least 200-fold reduced affinity. ImPyImPy-γ-ImPyImPy-β-Dp binds the site 5'-TGCGCA-3' with a $K_a=4\times10^7$ M$^{-1}$ with 4-fold specificity, and ImImImIm-γ-PyPyPyPy-β-Dp binds the site 5'-TGGGGA-3' with a $K_a=3\times10^7$ M$^{-1}$ with 6-fold specificity.

These results indicate that the positioning of the Im amino acids have a profound effect on the binding affinities of pyrrole-imidazole polyamides. More specifically these results indicate that binding affinity could be restored by the design of hairpin polyamides where a pyrrole ring has been substituted by more flexible spacer amino acid such as β-alanine.

It has been found that replacement of a pyrrole residue with a β-alanine spacer residue in each subunit of ImPyImPy-γ-ImPyImPy-β-Dp provides an eight residue hairpin polyamide, Im-β-ImPy-γ-Im-β-ImPy-β-Dp, which recognizes 5'-TGCGCA-3' sequences with subnanomolar affinities.

Figure 8:
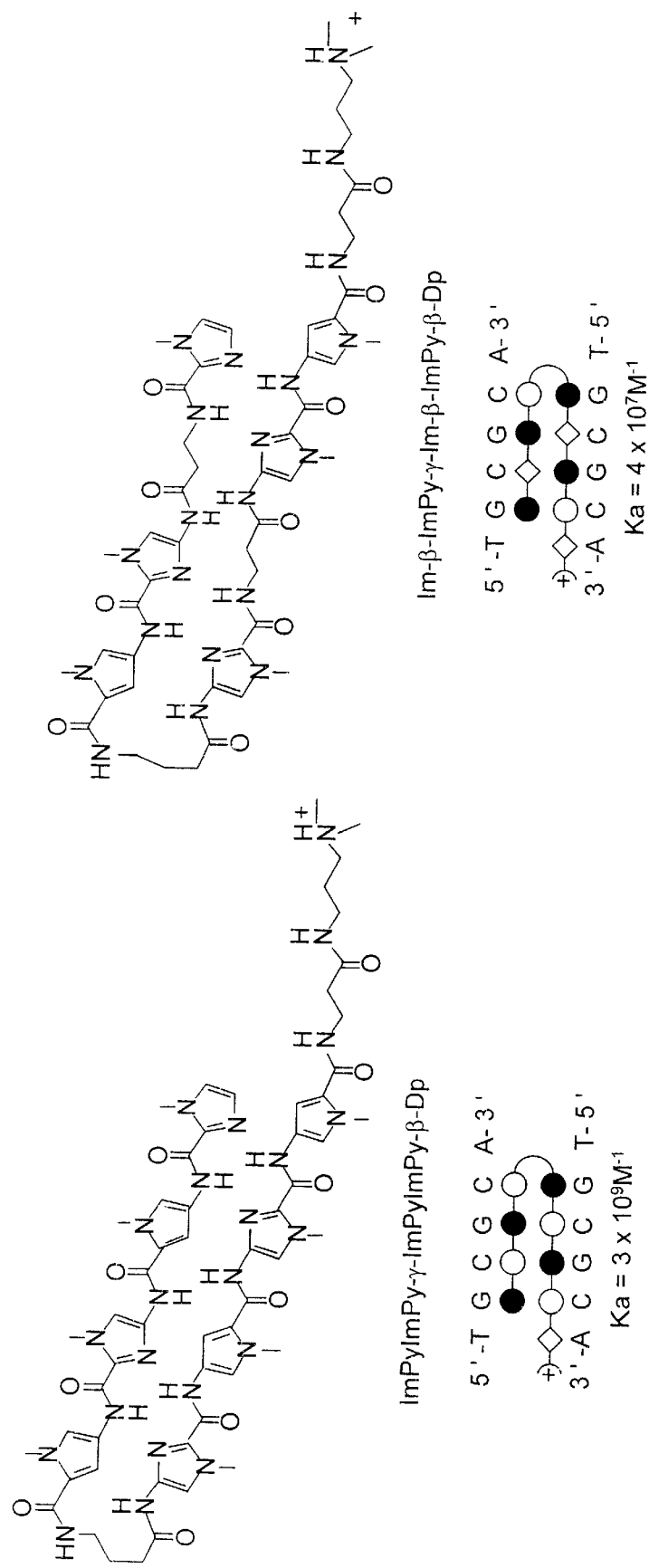
FIG. 8. Schematic binding models for eight ring hairpin polyamide.

Structures and schematic binding models for the eight ring hairpin polyamide ImPyImPy-γ-ImPyImPy-β-Dp and the eight residue hairpin polyamide Im-β-ImPy-γ-Im-0β-ImPy-β-Dp are shown in FIG. 8.

Figure 9:
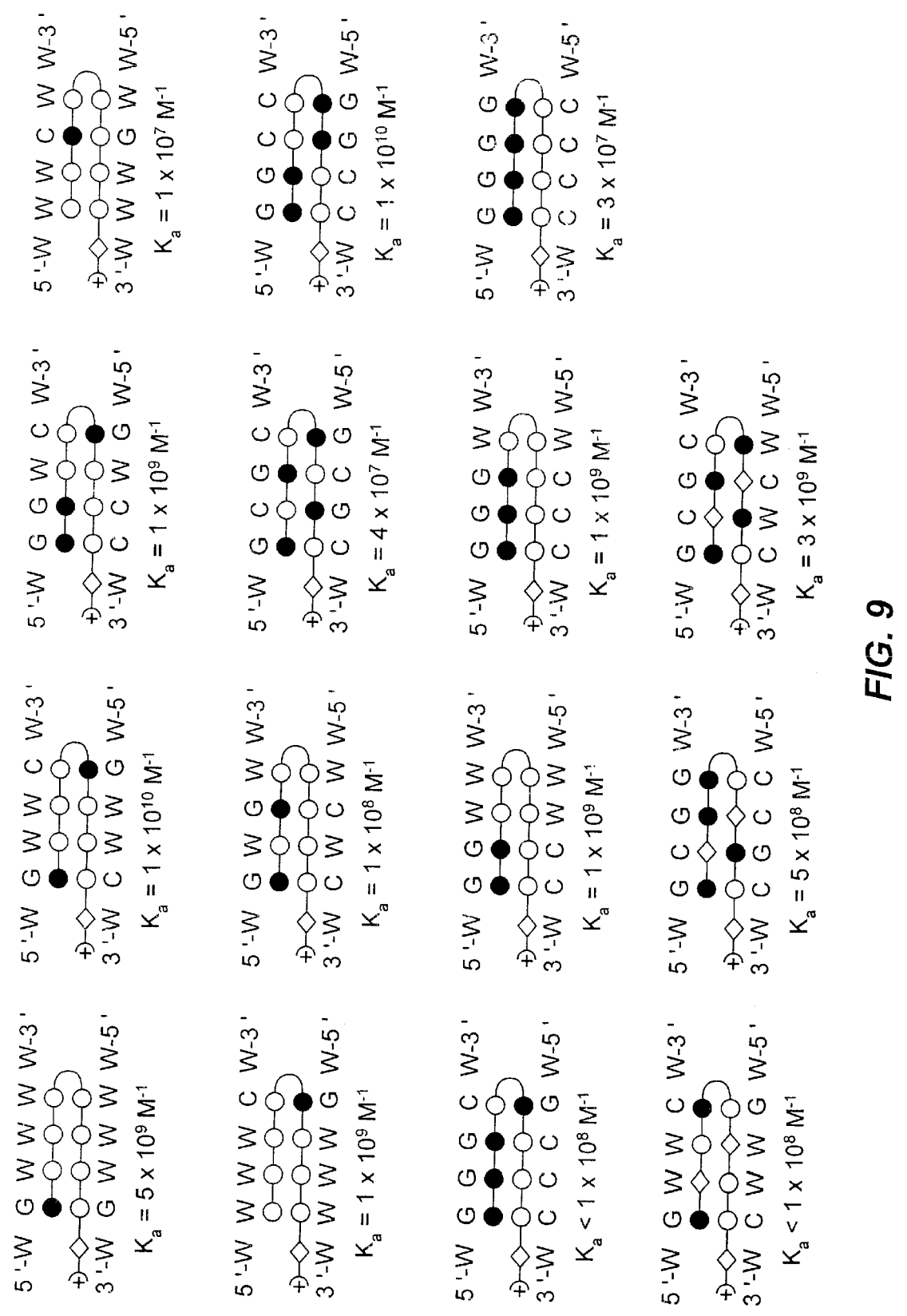

It has been found that the four ring hairpin polyamide motif provides a versatile template for recognition of a wide variety of sequences in the DNA minor groove. Eight ring and residue hairpin polyamides recognize 6 base pair target sites with affinities ranging from $1\times10^7$ M$^{-1}$ to $>1\times10^{10}$ M$^{-1}$ and specificity against single base pair mismatch sites ranging from 2-fold to >100-fold. A schematic of fifteen 8-residue hairpin polyamides recognizing 6 base pair target sites is shown in FIG. 9.

Figure 10:
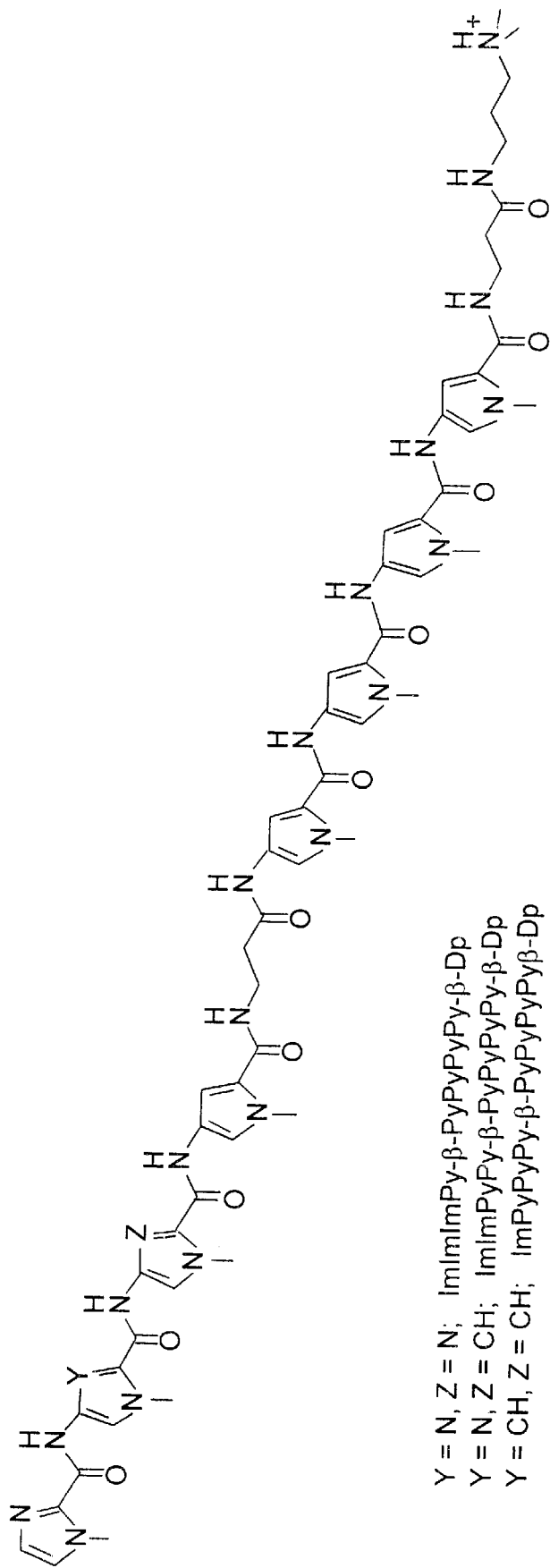
FIG. 10. Structure of 4-β-4 polyamides.

First generation fully overlapped β-linked polyamides based on three ring subunits bind DNA with association constants of approximately $8\times10^8$ M$^{-1}$. The observation that unlinked four-ring polyamides form 2:1 complexes with 70-fold-higher affinity relative to three-ring polyamides suggested a fully overlapped 8-ring 4-β-4 polyamide motif for recognition of 11 base pairs of DNA at subnanomolar concentration. The chemical structures of three 4β-4 polyamides are shown in FIG. 10.

It has been found that three eight ring 4β-4 pyrrole-imidazole polyamide, ImImImPy-β-PyPyPyPy-β-Dp, ImImPyPy-β-PyPyPyPy-β-Dp and ImPyPyPy-β-PyPyPyPy-β-Dp specifically recognize targeted 5'-AGGGATTCCCT-3', 5'-AGGTATTATCCT-3' and 5'-AGTAATTTACT-3' sites, respectively. DNase I footprint titrations reveal that each polyamide binds its respective target site at subnanomolar conentrations with equilibrium association constants ranging from $K_a=7\times10^9$ M$^{-1}$ to $K_a$ $5\times10^{10}$ M$^{-1}$, and with 7 to 30-fold specificity over double base pair mismatch sites.

Figure 11:
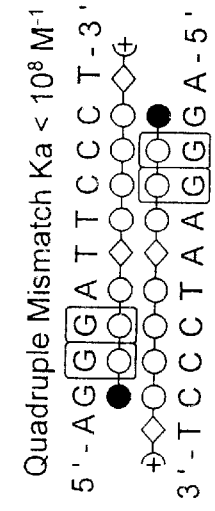
FIG. 11. Recognition of DNA by 4-β-4 polyamides
Figure 11:
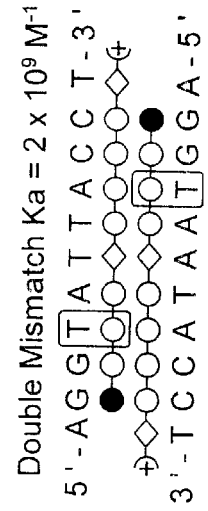
Figure 11:
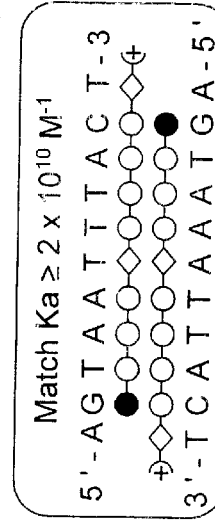
Figure 11:
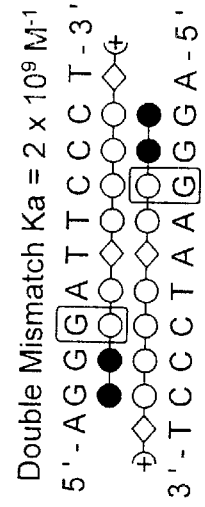
Figure 11:
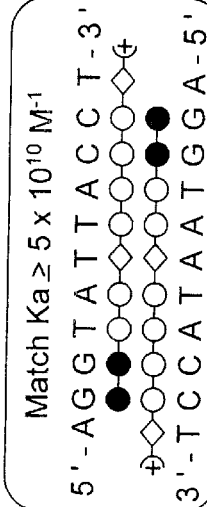
Figure 11:
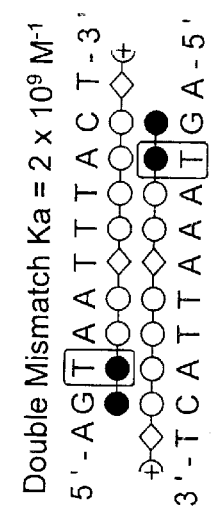
Figure 11:
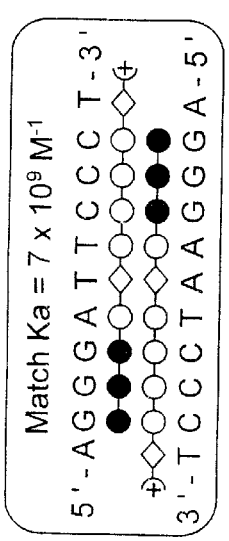
Figure 11:
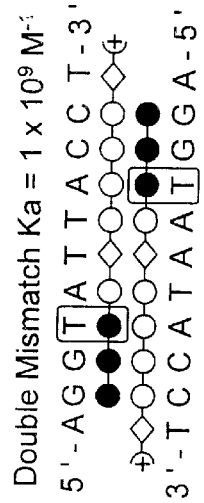
Figure 11:
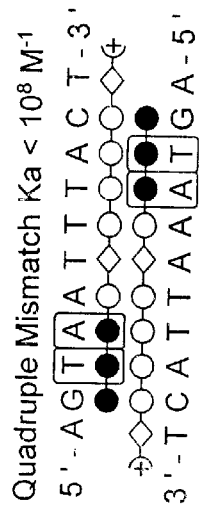

The ability of 3β-3 and 4β-4 polyamides to recognize both "slipped" and "overlapped" complexes for recognition of two separate classes of target sites represents a limit to the sequence specificity of the β-extended polyamide motif. The discovery that a Im/Im polyamide pairing is disfavored, suggests that the 4β-4 polyamide ImImImPy-β-PyPyPyPy-β-Dp should bind preferentially in the fully overlapped polyamide motif. A schematic representation of the recognition of three targeted DNA sites by three 4β-4 polyamides is shown in FIG. 11.

The 4γ-4 polyamide ImImImPy-γ-PyPyPyPy-β-Dp binds a 5'-AGGGAA-3' target site in a hairpin conformation with an association constant of $K_a=4\times10^8$. The 4γ-4 polyamide ImImImPy-γ-PyPyPyPy-β-Dp is related to the 4-β-4 polyamide ImImImPy-β-PyPyPyPy-β-Dp by deletion of a single methylene unit (MW=14) from the linker region. The γ and β linkers specificity turn and extended binding respectively and enlarge targeted binding site size from 6 to 11 base pairs, resulting in a 2.1 kcal/mol enhancement in binding energy. These results, the specific recognition of a G,C-rich 11 base pair sequence, represent a significant advance in the development of general DNA-binding that can recognize a single site in the human genome.

Figure 12:
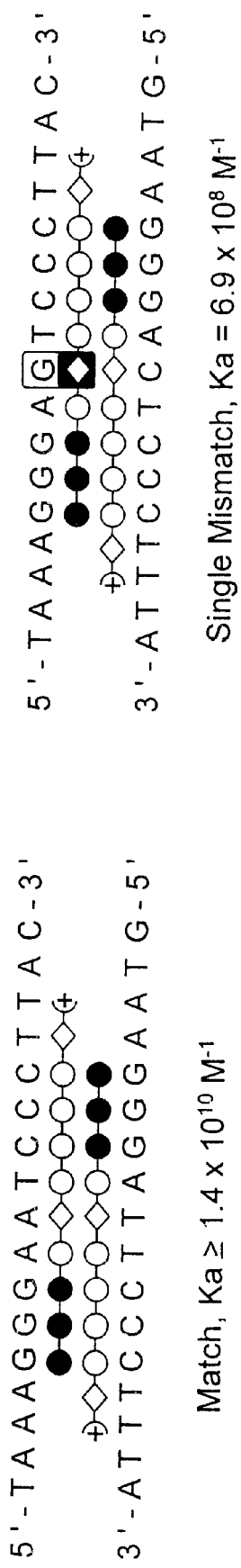
FIG. 12. Placement of β/β pairs.

It has been determined that there exists at least a 20-fold preference for placement of a β/β pair opposite an A•T or T•A base pair relative to a G•C or C•G base pair. Quantitative DNase I footprint titration experiments reveal that ImImImPy-β-PyPyPyPy-β-Dp binds the designed match site 5'-AGGGAATCCCT-3' with an equilibrium association constant of $K_a$ $1.4\times10^{10}$ M$^{-1}$ and the single base pair β/β mismatch sequence 5'-AGGGAGTCCCT-3' with at least 20-fold lower affinity ($K_a=6.9\times10^8$ M$^{-1}$). These results implicate the β/β combination as both a flexible spacer unit and a sequence-specific DNA binding element. The specificity of the β/β pairing reveals an additional pairing rule pivotal to the design of polyamides for recognition of longer binding sites. A schematic model of placement of the β/β pair opposite, G,C or A,T base pairs is shown in FIG. 12.

Figure 13:
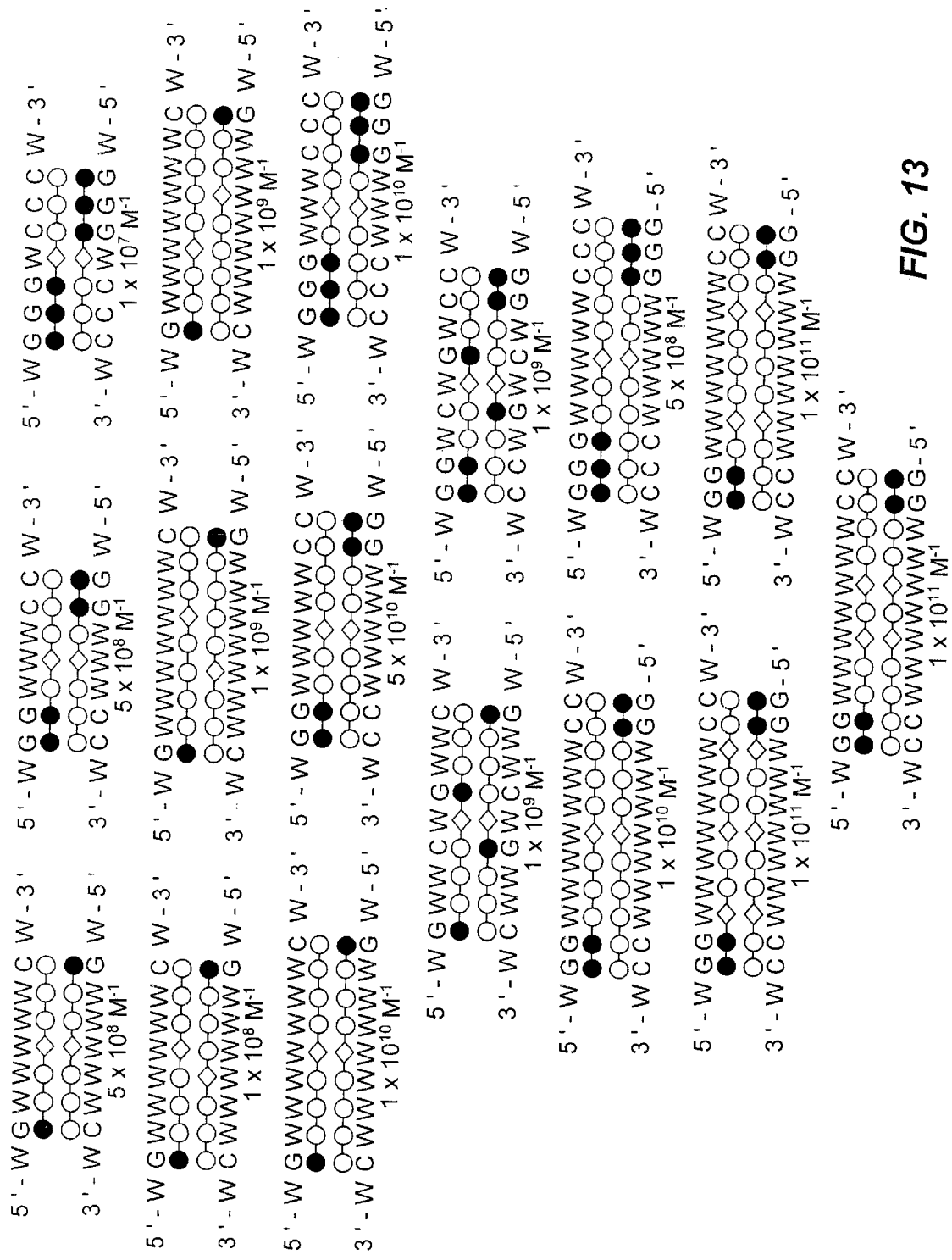
FIG. 13. β-linked fully overlapped polyamide complexes.

It has been found that the extended, fully overlapped polyamide-DNA motif, provides a versatile template for recognition of symmetric sequences containing from 9 to 13 base pairs in the minor groove. Equilibrium association constants for cooperative complex formation range from $K_a=1\times10^7$ M$^{-1}$ to $K_a>1\times10^{11}$ M$_{-1}$. Specificities have been found to range from 2-fold to >20-fold for discrimination of single base pair mismatch sites. A schematic representation of several β-linked fully overlapped polyamide complexes is shown in FIG. 13.

Figure 14:
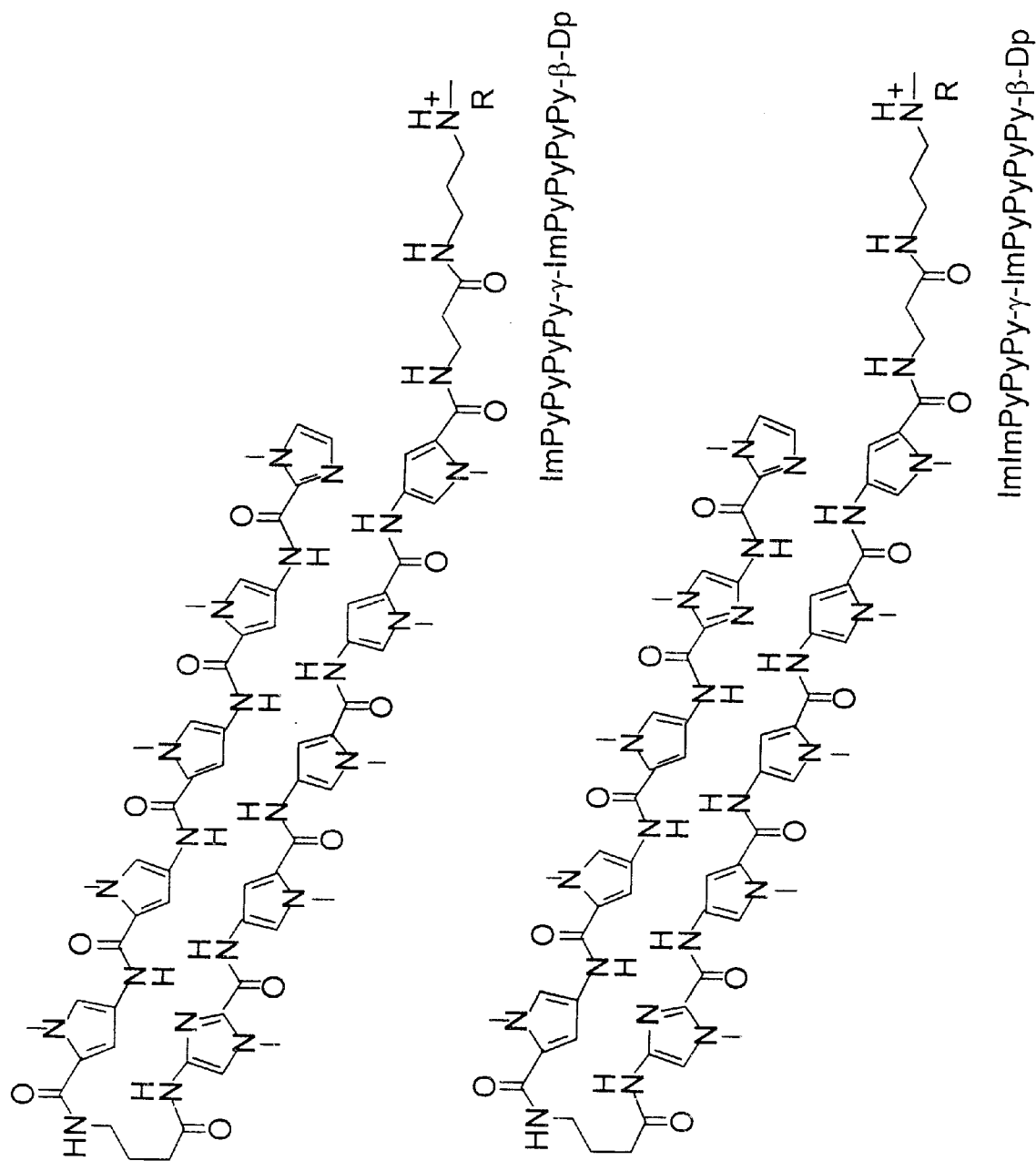
FIG. 14. 10-ring hairpin polyamides.

To further expand the targetable binding site size and sequence repertoire available to the hairpin polyamide motif, two polyamides containing either two or three Im amino acid residues, ImPyPyPyPy-γ-ImPyPyPyPy-β-Dp and ImImPyPyPy-γ-ImPyPyPyPy-β-Dp, were prepared by solid phase synthetic methodology and their DNA binding properties analyzed. The structures of two 10-ring hairpin polyamides are shown in FIG. 14.

It has been shown that that ImPyPyPyPy-γ-ImPyPyPyPy-β-Dp binds the formal 7 bp match sequence 5'-TGTAACA-3' with an equilibrium association constant ($K_a$) of $K_a$ $1.2\times10^{10}$ M$^{-1}$ and the single base pair mismatch sequence 5'-TGGACA-3' with $K_a=6.8\times10^8$ M$^{-1}$. (10 mM Tris.Hcl, 10 mM KCl, 10 mM MgCl$_2$, 5 mM CaCl$_2$, pH 7.0, 22° C.). ImImPyPyPy-γ-ImPyPyPyPy-β-Dp, which differs from ImPyPyPyPy-γ-ImPyPyPyPy-β-Dp by a single amino acid substitution binds its formal match sequence 5'-TGGAACA-3' with an equilibrium association constant of $K_a=3.6\times10^9$ M$^{-1}$ and its corresponding single base pair mismatch sequence 5'-TGTAACA-3' with $K_a<1\times10^7$ M$^{-1}$. The replacement of a single electron lone-pair with a hydrogen atom within a ~1500 MW polyamide is found to modulate affinity and specificity by more than an order of magnitude. Sequence-specific recognition of a 7 bp target site by a ten-ring hairpin polyamide at subnanomolar concentration expands the effective targetable sequence repertoire of the pyrrole-imidazole polyamide-DNA motif.

A schematic model of two 10-ring hairpin polyamides recognizing match and mismatch 7 base pair sequences is shown below:

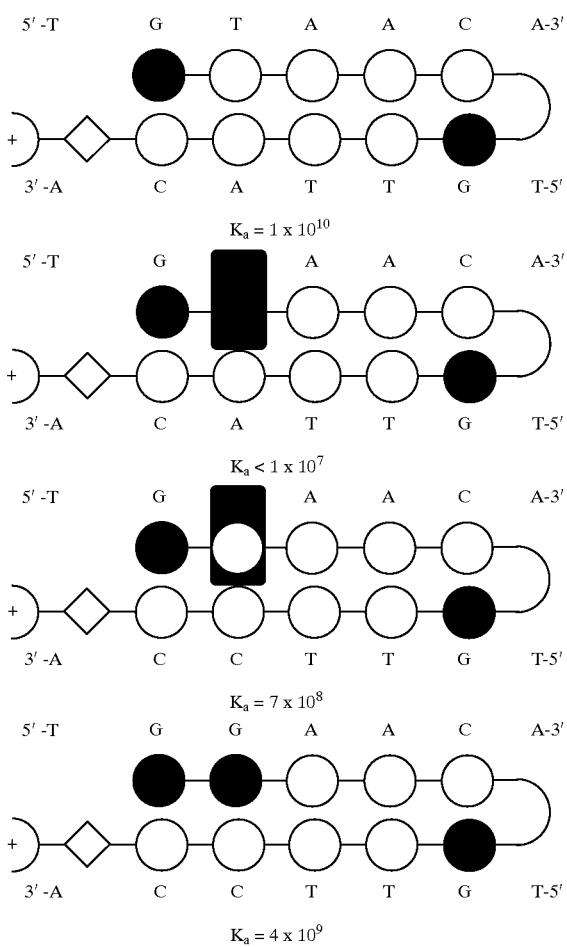

of the ImPyPyPyPy-γ-ImPyPyPyPy-β-Dp.5'-TGGAACA-3' complex relative to the ImImPyPyPy-γ-ImPyPyPyPy-β-Dp.5'-TGGAACA-3' complex by a factor of 5-fold, a loss in binding energy of −1 kcal/mol. The reduced overall specificity and binding affinity of that ImImPyPyPy-γ-ImPyPyPy-β-Dp relative to that ImPyPyPyPy-γ-ImPyPyPyPy-β-Dp most likely results from the presence of a 5'-GA-3' step in the designated target site.

Figure 15:
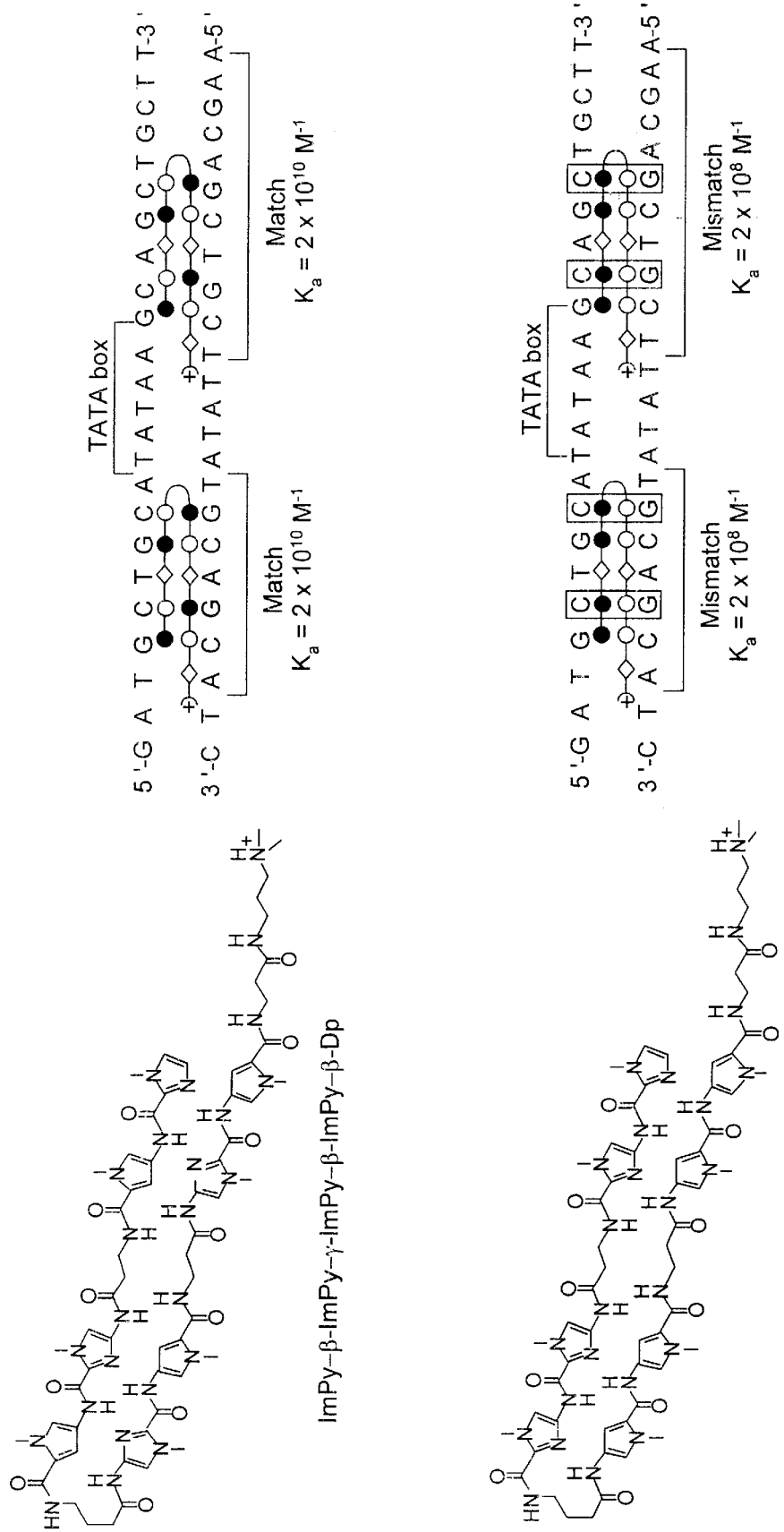
FIG. 15. Discrimination of seven base pair sequence by polyamides.

A polyamide, ImPy-β-ImPy-γ-ImPy-β-ImPy-β-Dp, based on β-alanine linked 2-ring subunits was prepared to target a seven basepair region adjacent to a binding site for the transcription factor TBP in a conserved HIV gene-promoter sequence. The polyamide was designed based on the pairing rules described herein, and was found to recognize its designated 5'-TGCTGCA-3' target sequence with a binding affinity of $K_a=3.6\times10^9$ $M^{-1}$. An isomeric mismatched polyamide, ImPy-β-ImPy-γ-ImPy-β-ImPy-β-Dp, which differs only by the position of the Py and Im amino acids within the 2-β-2-γ-2-β-2 molecular template binds the targeted 5-TGCTGCA-3' sequence with 100-fold reduced affinity. A schematic representation of a polyamide and a control polyamide which are molecular isomers, yet discriminate a 7-base pair sequence of an HIV gene promoter with a 100-fold specificity is shown in FIG. 15.

Figure 16:
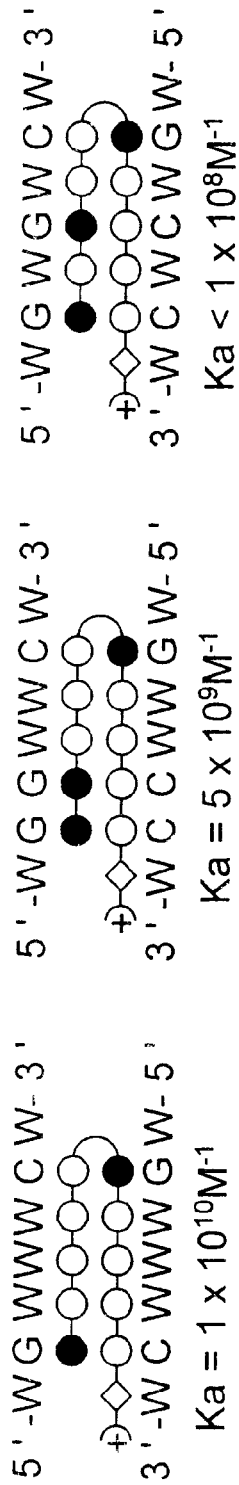
FIG. 16. Hairpin polyamides that recognize seven base pair sequence.
Figure 16:
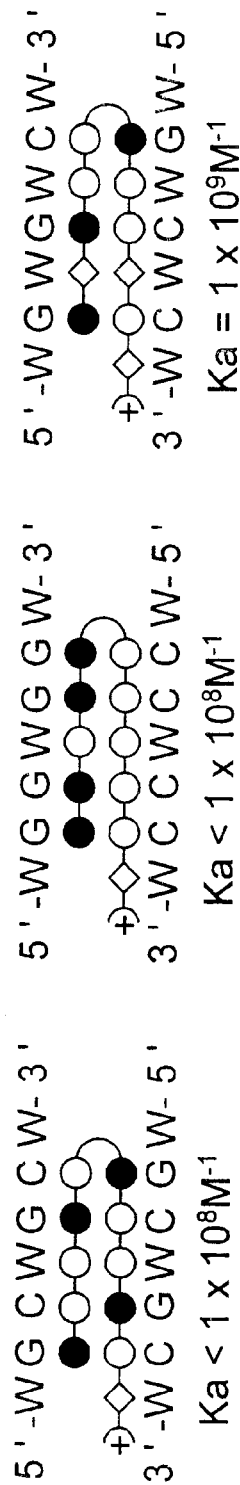
Figure 16:
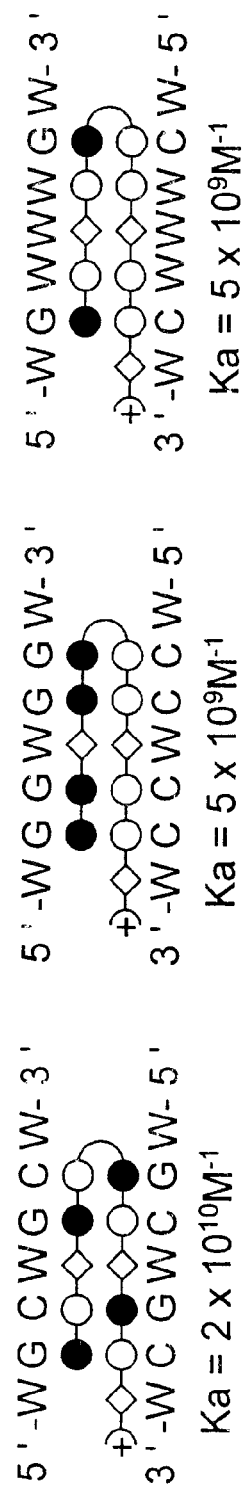

These results reveal that hairpin polyamides based on 5-ring subunits provide a useful structural motif for the recognition of 7 bp binding sites at sunanomolar concentrations. For targeting 5'-WGWWWCW-3' sequence a 5-γ-5 polyamide, ImPyPyPyPy-γ-ImPyPyPyPy-β-Dp based on 2 γ-aminobutyric acid linked 5-ring subunits is preferred over the corresponding β-substituted, 2-β-2-γ-2-β-2 polyamide ImPy-β-PyPy-γ-ImPy-β-PyPy-β-Dp. For targeting 5'-WGCWGCW-3' and 5'-WGGWGGW-3' sequences the respective β-substituted, 2-β-2-γ-2-β-2 polyamides ImPy-β-ImPy-γ-ImPy-β-ImPy-β-Dp and ImIm-β-ImIm-γ-PyPy-β-PyPy-β-Dp are preferred over the respective 5-β-5 polyamides, ImPyPyImPy-γ-ImPyPyImPy-β-Dp and ImImPyImIm-γ-PyPyPyPyPy-β-Dp based on γ-aminobutyric acid linked 5-ring subunits. A series of hairpin polyamides which recognize 7 base pair target sites are shown in FIG. 16.

The present inventor has discovered that a β/β pairing is preferred to a Py/β pairing for extension of the targetable binding site size of the hairpin polyamide motif. Three "12-ring hairpin" polyamides, ImPyPyPyPyPy-γ-ImPyPyPyPyPy-β-Dp, ImPyPy-β-PyPy-γ-ImPyPy-β-PyPy-β-Dp and ImPy-β-PyPyPy-γ-ImPyPy-β-PyPy-β-Dp were synthesized by solid phase synthetic methodology.

The specificity of that ImPyPyPyPy-γ-ImPyPyPyPy-β-Dp and that ImImPyPyPy-γ-ImPyPyPyPy-β-Dp for their respective match sites results from very small structural changes. Replacing a single C—H in that ImPyPyPyPy-γ-ImPyPyPyPy-β-Dp, with a nitrogen atom as in that ImImPyPyPy-γ-ImPyPyPyPy-β-Dp reduces the affinity of the ImImPyPyPy-γ-ImPyPyPyPy-β-Dp.5'-TGTAACA-3' complex relative to the ImPyPyPyPy-γ-ImPyPyPyPy-β-Dp.5'-TGTAACA-3' complex by >300-fold, a free energy difference of at least 4 kcal/mol. Similarly, replacing a N in that ImImPyPyPy-γ-ImPyPyPyPy-β-Dp with a C—H as in that ImPyPyPyPy-γ-ImPyPyPyPy-β-Dp, reduces the affinity

TABLE 3

TABLE 3-continued

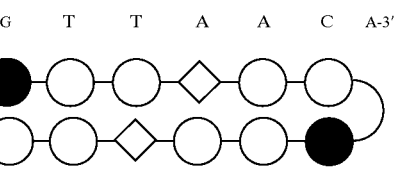

DNase I footprint titrations reveal that the hairpin polyamide based on 6-ring subunits, ImPyPyPyPyPy-γ-ImPyPyPyPyPy-β-Dp, binds the formal 8 bp match sequence 5'-TGTTAACA-3' with an equilibrium association constant ($K_a$) of $K_a=4\times10^9$ M$^{-1}$ and the single base pair mismatch sequence 5'-TGT<u>G</u>AACA-3' with $K_a=2\times10^8$ M$^{-1}$. ImPyPy-β-PyPy-γ-ImPyPy-β-PyPy-β-Dp which differs from ImPyPyPyPyPy-γ-ImPyPyPyPyPy-β-Dp by substitution of two flexible aliphatic amino acid residues for two pyrrole rings, binds a 5'-TGTTAACA-3' match site $K_a=2\times10^{10}$ M$^{-1}$ and a 5'-TGT<u>G</u>AACA-3' mismatch with $K_a=1\times10^9$ M$^{-1}$. ImPy-β-PyPyPy-γ-ImPyPy-β-PyPy-β-Dp binds a 5'-TGTTAACA-3' match site with an equilibrium association constant of $K_a$ $1\times10^{11}$ and a single base pair mismatch sequence 5'-TGT<u>G</u>AACA-3' with $K_a<1\times10^9$. (Table II). These results expand the targetable binding site size accessible to the hairpin polyamide motif to 8 base pairs.

β/β pairing within the hairpin polyamide motif as shown below completely abolishes DNA-binding:

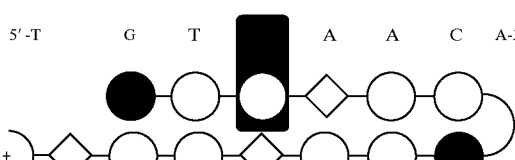

No Specific Binding

The present inventor has found that a paired β/β substituted hairpin motif allows specific targeting of sequences of the form 5'-WGWGWWCW-3'. Substitution of a β/β pair for the second pyrrole pairing of a 12-ring hairpin polyamide, provides polyamides which target a wide variety of 8 base pair sequences of mixed sequence composition. Sequences are bound with subnanomolar affinity and 50–100 fold specificity versus single base pair mismatch sites as shown in Table 4.

TABLE 4

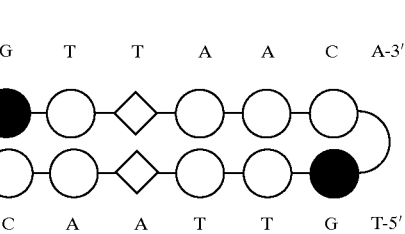
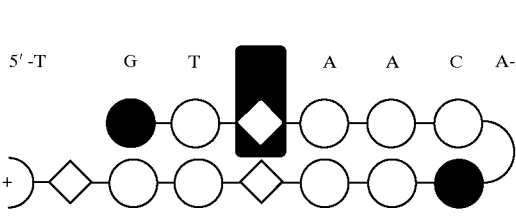

TABLE 4-continued

| Match | Mismatch | Specificity |
|---|---|---|
| $K_a = 3 \times 10^9$ | $K_a = 4 \times 10^8$ | 8-fold |
| $K_a = 5 \times 10^9$ | $K_a < 1 \times 10^8$ | >50-fold |
| $K_a = 1 \times 10^{10}$ | $K_a < 1 \times 10^8$ | >100-fold |

The following examples illustrate particular embodiments of the present invention and are not limiting of the specification and claims in any way.

EXAMPLES

Synthesis of Polyamides

A. Materials

Boc-β-alanine-(-4-carboxamidomethyl)-benzyl-ester-copoly(styrene-divinylbenzene) resin (Boc-β-Pam-Resin), dicyclohexylcarbodiimide (DCC), hydroxybenzotriazole (HOBt), 2-(1H-benzotriazole-1-yl)-1,1,3,3-tetramethyluronium hexa-fluorophosphate (HBTU), Boc-glycine, and Boc-β-alanine were purchased from Peptides International. N,N-diisopropylethylamine (DIEA), N,N-dimethylformamide (DMF), N-methylpyrrolidone (NMP), and DMSO/NMP were purchased from Applied Biosystems. Boc-γ-aminobutyric acid was from NOVA Biochem, dichloromethane (DCM) and triethylamine (TEA) was reagent grade from EM, thiophenol (PhSH), dimethylaminopropylamine, trichloroacetyl chloride, N-methylpyrrole, and N-methylimidazole from Aldrich, and trifluoroacetic acid (TFA) from Halocarbon. All reagents were used without further purification.

$^1$H NMR were recorded on a GE300 instrument operating at 300 MHz. Chemical shifts are reported in ppm relative to the solvent residual signal. UV spectra were measured on a Hewlett-Packard Model 8452A diode array spectrophotometer. IR spectra were recorded on a Perkin-Elmer FTIR spectrometer. High- resolution FAB mass spectra were recorded at the Mass Spectroscopy Laboratory at the University of California, Riverside. Matrix- assisted, laser desorption/ionization time of flight mass spectrometry was carried out at the Protein and Peptide Microanalytical Facility at the California Institute of Technology. HPLC analysis was performed either on a HP 1090M analytical HPLC or a Beckman Gold system using a RAINEN $C_1$. Microsorb MV, 5 μm, 300×4.6 mm reversed phase column in 0.1% (wt/v) TFA with acetonitrile as eluent and a flow rate of 1.0 mL/min, gradient elution 1.25% acetonitrile/min. Preparatory HPLC was carried out on a Beckman HPLC using a Waters DeltaPak 25×100 mm, 100 μm, $C_{18}$ column equipped with a guard, 0.1% (wt/v) TFA, 0.25% acetonitrile/min. 18MΩ water was obtained from a Millipore MilliQ water purification system, and all buffers were 0.2 μm filtered. Thin- layer chromatography (TLC) was performed on silica gel 60 $F_{254}$ precoated plates. Reagent-grade chemicals were used unless otherwise stated.

B. Synthesis of Boc-Protected Pyrrole and Imidazole Monomer 1. 4-Nitro-2-trichloroacetyl-1-methylpyrrole:

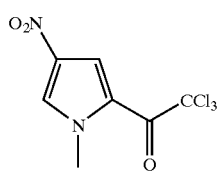

To a well stirred solution of trichloroacetyl chloride (1 kg, 5.5 mole) in 1.5 liter ethyl ether in a 12 liter flask was added dropwise over a period of 3 h a solution of N-methylpyrrole (0.45 kg, 5.5 mole) in 1.5 liter anhydrous ethyl ether. The reaction was stirred for an additional 3 hours and quenched by the dropwise addition of a solution of 400 g potassium carbonate in 1.5 liters water. The layers were separated and the ether layer concentrated in vacuo to provide 2-(trichloroacetyl)pyrrole (1.2 kg, 5.1 mol) as a yellow crystalline solid sufficiently pure to be used without further purification. To a cooled (−40° C.) solution of 2-(trichloroacetyl) pyrrole (1.2 kg, 5.1 mol) in acetic anhydride (6 L) in a 12 L flask equipped with a mechanical stirrer was added 440 mL fuming nitric acid over a period of 1 hour while maintaining a temperature of (−40° C.). The reaction was carefully allowed to warm to room temperature and stir an additional 4 h. The mixture was cooled to −30° C., and isopropyl alcohol (6 L) added. The solution was stirred at −20° C. for 30 min during which time a white precipitate forms. The solution was allowed to stand for 15 min and the resulting precipitate collected by vacuum filtration to provide 4-Nitro-2-trichloroacetyl-1-methylpyrrole. (0.8 kg, 54% yield) TLC (7:2 benzene/ethyl acetate) Rf 0.7; $^1$H NMR (DMSO-$d_6$) δ 8.55 (d, 1H, J=1.7 Hz), 7.77 (d, 1H, J=1.7 Hz), 3.98 (S, 3 H); $^{13}$C NMR (DMSO-$d_6$) δ 173.3, 134.7, 133.2, 121.1, 116.9, 95.0, 51.5; IR (KBr) 1694, 1516, 1423, 1314, 1183, 1113, 998, 750. FABMS m/e 269.936 (M+H 269.937 calc. for $C_7H_5N_2O_3Cl_3$).

2. Methyl 4-nitropyrrole-2-carboxylate:

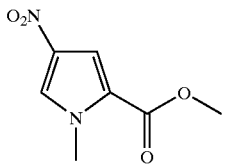

To a solution of 4-Nitro-2-trichloroacetyl-1-methylpyrrole (800 g, 2.9 mol) in 2.5 L methanol in a 4 L Erlenmeyer flask equipped with a mechanical stirrer was added dropwise a solution of NaH (60% dispersion in oil) (10 g, 0.25 mol) in 500 mL methanol. The reaction was stirred 2 h. at room temperature, and quenched by the addition of conc. sulfuric acid (25 mL). The reaction was then heated to reflux, allowed to slowly cool to room temperature as methyl 4-nitropyrrole-2-carboxylate crystallizes as white needles which were collected by vacuum filtration and dried in vacuo. (450 g, 47% yield). TLC (ethyl acetate) Rf 0.8; $^1$H NMR (DMSO-$d_6$) δ 8.22 (d, 1H, J=1.7 Hz), 7.22 (d, 1H, J=1.6 Hz), 3.88 (s, 3 H), 3.75 (s, 3 H), $^{13}$C NMR (DMSO-$d_6$) δ 37.8, 52.2, 112.0, 123.0, 129.9, 134.6, 160.3; IR (KBr) 3148, 1718, 1541, 1425, 1317, 1226, 1195, 1116, 753. FABMS m/e 184.048 (M+H 184.048 calc. for $C_7H_8N_2O_4$).

3. Methyl 4-amino-1-methyl-pyrrole-2-carboxylate hydrochloride:

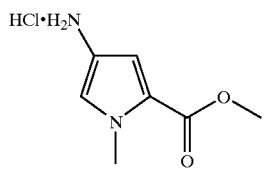

Methyl-4-nitropyrrole-2-carboxylate (450 g, 2.8 mol) was dissolved in ethyl acetate (8 L). A slurry of 40 g of 10% Pd/C in 800 mL ethyl acetate was then added and the mixture stirred under a slight positive pressure of hydrogen (c.a. 1.1 atm) for 48 h. Pd/C was removed by filtration through Celite, washed 1×50 mL ethyl acetate, and the volume of the mixture reduced to c.a. 500 mL. 7 L of cold ethyl ether was added and HCl gas gently bubbled through the mixture. The precipitated amine hydrochloride was then collected by vacuum filtration to yield (380 g, 81.6%) of Methyl 4-amino-1-methyl-pyrrole-2-carboxylate hydrochloride as a white powder. TLC (ethyl acetate) Rf(amine) 0.6, Rf salt (0.0), $^1$H NMR (DMSO-$d_6$) δ 10.23 (br s, 3H), 7.24 (d, 1H J=1.9), 6.79 (d, 1H, J=2.0), 3.83 (s, 3H), 3.72 (s, 3H) $^{13}$C NMR (DMSO-$d_6$) δ 160.8, 124.3, 121.2, 113.4, 112.0, 51.8, 37.1; IR (KBr) 3095, 2693, 1709, 1548, 1448, 1266, 1102, 802, 751. FABMS m/e 154.075 (154.074 calc. for $C_7H_{10}N_2O_2$).

4. 4-[(tert-Butoxycarbonyl)amino]-1-methylpyrrole-2-carboxylic acid:

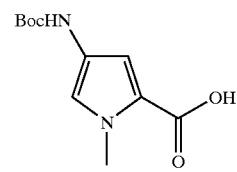

The hydrochloride salt of the pyrrole amine Methyl 4-amino-1-methyl-pyrrole-2-carboxylate hydrochloride (340 g, 1.8 mol) was dissolved in 1 L of 10% aqueous sodium carbonate in a 3 L flask equipped with a mechanical stirrer, di-t-butyldicarbonate (400 g, 2.0 mmol) slurried in 500 mL of dioxane was added over a period of thirty min maintaining a temperature of 20° C. The reaction was allowed to proceed for three h and was determined complete by TLC, cooled to 5° C. for 2 h and the resulting white precipitate collected by vacuum filtration. The Boc-pyrrole ester contamination with Boc-anhydride was dissolved in 700 mL MeOH, 700 mL of 2M NaOH was added and the solution heated at 60° C. for 6 h. The reaction was cooled to room temperature, washed with ethyl ether (4×1000 mL), the pH of the aqueous layer reduced to c.a. 3 with 10% (v/v) $H_2SO_4$, and extracted with ethyl acetate (4×2000 mL). The combined ethyl acetate extracts were dried (sodium sulfate) and concentrated in vacuo to provide a tan foam. The foam was dissolved in 500 mL of DCM and 2 L petroleum ether added, the resulting slurry was concentrated in vacuo. The reaction was redissolved and concentrated three additional times to provide (320 g, 78% yield) of 4-[(tert-Butoxycarbonyl)amino]-1-methylpyrrole-2-carboxylic acid as a fine white powder. TLC (7:2 benzene/ethyl acetate v/v) Rf (ester) 0.8, Rf (acid) 0.1. (ethyl acetate), Rf (acid) 0.6, $^1$H NMR (DMSO-$d_6$) δ 12.10 (s, 1H), 9.05 (s, 1H), 7.02 (s, 1H), 6.55 (s, 1H), 3.75 (s, 3H), 1.41 (s, 9H) $^{13}$C NMR (DMSO-$d_6$) δ 162.4, 153.2, 123.3, 120.1, 119.2, 107.9, 78.9, 36.6, 28.7.; IR (KBr) 3350, 2978, 1700, 1670, 1586, 1458, 1368, 1247, 1112, 887, 779. FABMS m/e 241.119 (M+H 241.119 calc. for $C_{11}H_{17}N_2O_4$).

5. 1,2,3-Benzotriazol-1-yl 4-[(tert-butoxycarbonyl)-amino]-1-methylpyrrole-2-carboxylate:

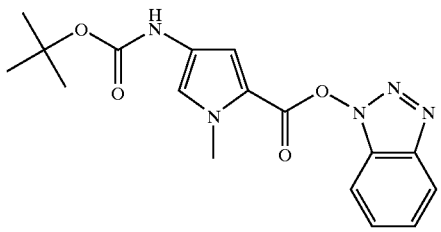

Boc-Py-acid, 4-[(tert-Butoxycarbonyl)amino]-1-methylpyrrole-2-carboxylic acid (31 g, 129 mmol) was dissolved in 500 mL DMF, HOBt (17.4 g, 129 mmol) was added followed by DCC (34 g, 129 mmol). The reaction was stirred for 24 h and then filtered dropwise into a well stirred solution of 5 L of ice water. The precipitate was allowed to sit for 15 min at 0° C. and then collected by filtration. The wet cake was dissolved in 500 mL DCM, and the organic layer added slowly to a stirred solution of cold petroleum ether (4° C.). The mixture was allowed to stand at −20° C. for 4 h and then collected by vacuum filtration and dried in vacuo to provide (39 g, 85% yield) of 1,2,3-Benzotriazol-1-yl 4-[(tert-butoxycarbonyl)-amino]-1-methylpyrrole-2-carboxylate as a finely divided white powder. TLC (7:2 benzene/ethyl acetate v/v) Rf 0.6 $^1$H NMR (DMSO-d$_6$) δ 9.43 (s, 1H), 8.12 (d, 1H, J=8.4 Hz), 7.80 (d, 1H, J=8.2 Hz), 7.64 (t, 1H, J=7.0 Hz), 7.51 (m, 2H), 7.18 (s, 1H), 3.83 (s, 3H), 1.45 (s, 9H), $^{13}$C NMR (DMSO-d$_6$) δ 156.5, 153.3, 143.2, 129.6, 129.2, 125.7, 125.2, 124.6, 120.3, 112.8, 110.3, 109.8, 79.5, 36.8, 28.6.; IR (KBr) 3246, 3095, 2979, 1764, 1711, 1588, 1389, 1365, 1274, 1227, 1160, 1101, 999, 824, 748.; FABMS m/e 358.152 (M+H 358.151 calc. for $C_{17}H_{20}N_5O_4$).

6. Ethyl 1-methylimidazole-2-carboxylate:

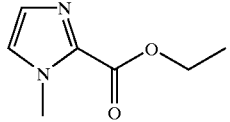

N-methylimidazole (320 g, 3.9 mol) was combined with 2 L acetonitrile and 1 L triethylamine in a 12 L flask equipped with a mechanical stirrer and the solution cooled to −20° C. Ethyl chloroformate (1000 g, 9.2 mol) was added with stirring, keeping the temperature between −20° C. and −25° C. The reaction was allowed to slowly warm to room temperature and stir for 36 h. Precipitated triethylamine hydrochloride was removed by filtration and the solution concentrated in vacuo. at 65° C. The resulting oil was purified by distillation under reduced pressure (2 torr, 102° C.) to provide Ethyl 1-methylimidazole-2-carboxylate as a white solid (360 g, 82% yield). TLC (7:2 benzene/ethyl acetate v/v) Rf 0.2 $^1$H NMR (DMSO-d$_6$) δ 7.44 (d, 1H, J=2.8 Hz), 7.04 (d, 1H, J=2.8 Hz), 4.2 (q, 2 H, J=3.5 Hz), 3.91 (s, 3 H), 1.26 (t, 3 H, J=3.5 Hz); $^{13}$C NMR (DMSO-d$_6$) δ 159.3, 129.1, 127.7, 61.0, 36.0, 14.5; IR(KBr) 3403, 3111, 2983, 1713, 1480, 1422, 1262, 1134, 1052, 922, 782, 666; FABMS m/e 155.083 (M+H 155.083 calc. for $C_7H_{11}N_2O_2$).

7. Ethyl 1-methyl-4-nitroimidazole-2-carboxylate:

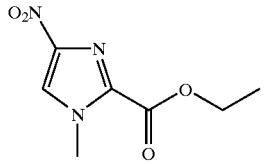

Ethyl 1-methylimidazole-2-carboxylate was carefully dissolved in 1000 mL of concentrated sulfuric acid cooled to 0° C. 90% nitric acid (1 L) was slowly added maintaining a temperature of 0° C. The reaction was then refluxed with an efficient condenser (−20° C.) in a well ventilated hood for 50 min. The reaction was cooled with an ice bath, and quenched by pouring onto 10 L ice. The resulting blue solution was then extracted with 20 L DCM, the combined extracts dried (sodium sulfate) and concentrated in vacuo to yield a tan solid which was recrystallized from 22 L of 21:1 carbon tetrachloride/ethanol. The resulting white crystals are collected by vacuum filtration to provide pure Ethyl 1-methyl-4-nitroimidazole-2-carboxylate. (103 g, 22% yield). TLC (7:2 benzene/ethyl acetate v/v) Rf 0.5, $^1$H NMR (DMSO-d$_6$) δ 8.61 (s, 1H), 4.33 (q, 2 H, J=6.4 Hz), 3.97 (s, 3 H), 1.29 (t, 3 H, J=6.0 Hz), $^{13}$C NMR (DMSO-d$_6$) δ 158.2, 145.4, 135.3, 127.4, 62.2, 37.3, 14.5; IR (KBr) 3139, 1719, 1541, 1498, 1381, 1310, 1260, 1122, 995, 860, 656.; FABMS m/e 200.066 (M+H 200.067 calc. for $C_7H_{10}N_3O_4$).

8. Ethyl 4-amino-1-methylimidazole-2-carboxylate hydrochloride:

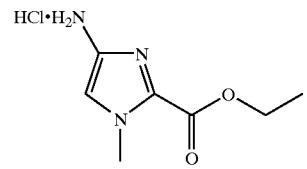

The nitro imidazole ethyl ester Ethyl 1-methyl-4-nitroimidazole-2-carboxylate (103 g, 520 mmol) was dissolved in 5 L of 1:1 ethanol/ethyl acetate, 20 g 10% Pd/C slurried in 500 mL ethyl acetate was added and the mixture stirred under a slight positive pressure of hydrogen (c.a. 1.1 atm) for 48 h. The reaction mixture was filtered, concentrated in vacuo to a volume of 500 mL and 5 L of cold anhydrous ethyl ether added. Addition of HCl gas provided a white precipitate. The solution was cooled at −20° C. for 4 h and the precipitate collected by vacuum filtration and dried in vacuo to provide (75 g, 78% yield) of ethyl 4-amino-1-methylimidazole-2-carboxylate hydrochloride as a fine white powder. TLC (7:2 benzene: ethyl acetate) R$_f$ (amine) 0.3, R$_f$ (salt) 0.0. $^1$H NMR (DMSO-d$_6$) δ 10.11 (br, s, 3H), 7.43 (s, 1H), 4.28 (q, 2H, J=7.1 Hz), 3.92 (s, 1H), 1.28 (t, 3H, J=7.1 Hz) $^{13}$C NMR (DMSO-d$_6$) δ 157.6, 132.6, 117.4, 117.3, 61.8, 36.6, 14.5; IR (KBr) 3138, 2883, 1707, 1655, 1492, 1420, 1314, 1255, 1152, 1057, 837, 776.; FABMS m/e 169.085 (169.084 calc. for $C_7H_{11}N_3O_2$).

9. 4-[(tert-butoxycarbonyl)amino]-1-methylimidazole-2-carboxylic acid:

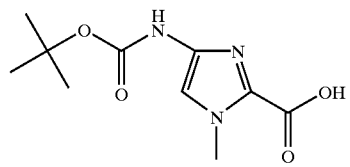

The imidazole amine ethyl 4-amino-1-methylimidazole-2-carboxylate hydrochloride (75 g, 395 mmol) was dissolved in 200 mL DMF. DIEA (45 L, 491 mmol) was added followed by di-t-butyldicarbonate (99 g, 491 mmol). The mixture was shaken at 60° C. for 18 h, allowed to assume room temperature, and partitioned between 500 mL brine, 500 mL ethyl ether. The ether layer was extracted (2×200 mL each) 10% citric acid, brine, satd. sodium bicarbonate, brine, dried over sodium sulfate and concentrated in vacuo to yield the Boc-ester contaminated with 20% Boc-anhydride as indicated by $^1$H NMR. The Boc-ester, used without further purification, was dissolved in 200 mL 1 M NaOH. The reaction mixture was allowed to stand for 3 h at 60° C. with occasional agitation. The reaction mixture was cooled to 0° C., and carefully neutralized with 1 M HCl to pH 2, at which time a white gel forms. The gel was collected by vacuum filtration, frozen before drying, and remaining water lyophilized to yield 4-[(tert-butoxycarbonyl)amino]-1-methylimidazole-2-carboxylic acid as a white powder. (51 g, 54% yield). $^1$H NMR (DMSO-d$_6$) δ 9.47 (s, 1H), 7.13 (s, 1H), 3.85 (s, 3H), 1.41 (s, 9H). $^{13}$C NMR (DMSO-d$_6$) δ 160.9, 152.9, 137.5, 134.5, 112.4, 79.5, 35.7, 28.6; IR(KBr) 3448, 2982, 1734, 1654, 1638, 1578, 1357, 1321, 1249, 1163, 799.; FABMS m/e 241.105 (241.106 calc. for $C_{10}H_{15}N_3O_4$).

10. γ-[(tert-butoxycarbonyl)amino]-butyric acid -(4-carboxamido-1-methyl-imidazole)-2-carboxylic acid:

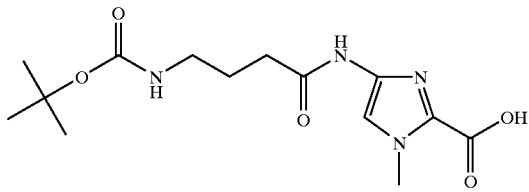

To a solution of Boc-γ-aminobutyric acid (10 g, 49 mmol) in 40 mL DMF was added 1.2 eq HOBt (7.9 g, 59 mmol) followed by 1.2 eg DCC (11.9 g, 59 mmol). The solution was stirred for 24 h, and the DCU removed by filtration. Separately, to a solution of ethyl 4-nitro-1-methylimidazole-2-carboxylate (9.8 g, 49 mmol) in 20 mL DMF was added Pd/C catalyst (10%, 1 g), and the mixture was hydrogenated in a Parr bom apparatus (500 psi H$_2$) for 2 h. The catalyst was removed by filtration through celite and filtrate immediately added to the –OBt ester solution. An excess of DIEA (15 mL) was then added and the reaction stirred at 37° C. for 48 h. The reaction mixture was then added dropwise to a stirred solution of ice water and the resulting precipitate collected by vacuum filtration to provide crude ethyl γ-[[(tert-butoxy)carbonyl]amino]-butyric acid -(4-carboxamido-1-methyl-pyrrole)-2-carboxylate (5 g, 14.1 mmol). To the crude ester dissolved in 50 mL methanol was added 50 mL 1M KOH and the resulting mixture allowed to stir for 6 h at 37° C. Excess methanol was removed in vacuo and the resulting solution acidified by the addition of 1 m HCl. The resulting precipitate was collected by vacuum filtration and dried in vacuo to yield γ-[(tert-butoxycarbonyl) amino]butyric acid -(4-carboxamido-1-methyl-imidazole)-2-carboxylic acid as a brown powder. (4.4 g, 89% yield), $^1$H NMR (DMSO-d$_6$) δ 10.50 (s, 1H), 7.45 (s, 1H), 6.82 (t, 1H, J=3.6 Hz), 3.86 (s, 3 H), 2.86 (q, 2 H, J=4.6 Hz), 2.22 (t, 2 H, J=7.4 Hz), 1.57 (qunitet, 2 H, J=5.9 Hz), 1.29 (s, 9 H); IR 3416, 2950, 2841, 1650,1538 1449, 1392, 1250, 1165, 1108; FABMS m/e 326.160 (326.159 calc. for $C_{14}H_{22}N_4O_5$).

11. 4-[(tert-butoxycarbonyl)amino]-1-methylpyrrole-2-(4-carboxamido-1-methyl imidazole)-2-carboxylic acid:

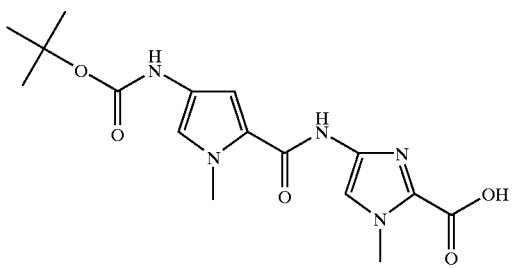

4-[(tert-butoxycarbonyl)amino]-1-methylpyrrole-2-(4-carboxamido-1-methyl imidazole)-2-carboxylic acid was prepared as described below for γ-[(tert-butoxycarbonyl)-amino]-butyric acid -(4-carboxamido-1-methyl-imidazole)-2-caroboxylic acid substituting Boc-Pyrrole acid for Boc-γ-aminobutyric acid. (4.1 g, 91% yield). $^1$H NMR (DMSO-d$_6$) δ 10.58 (s, 1H), 9.08 (S, 1H), 7.57 (s, 1H), 6.97 (s, 1 H), 6.89 (S, 1H), 3.89 (s, 3 H), 3.75 (s, 3 H), 1.35 (s, 9 H); $^{13}$C NMR (DMSO-d$_6$) δ 160.36, 159.1, 153.4, 137.9, 132.3, 122.8, 122.3, 118.5, 115.5, 105.5, 105.4, 78.8, 28.7, 24.9; IR 3346, 2929, 1685, 1618, 1529, 1342, 1274, 1179, 997, 761. FABMS m/e 364.161 (364.162 calc. for $C_{16}H_{22}N_5O_5$).

C. Solution Phase Synthesis of Polyamides Using Boc-Protected Pyrrole and Imidazole Building Blocks.

1. Aminohexa-(N-methylpyrrolecarboxamide) ditrifluoracetate:

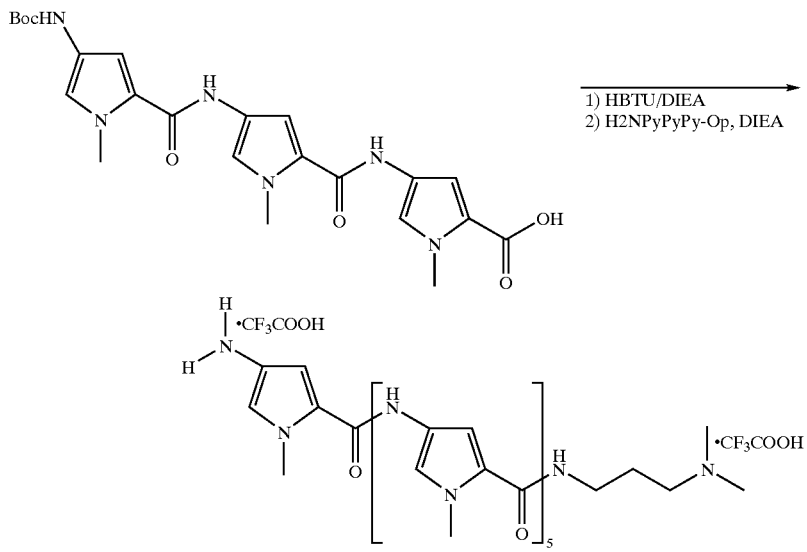

To a solution of N-(tert-butoxycarbonyl)-tris (N-methylpyrrolecarboxamide) (20 mg, 41 μmol) in DMF (100 μl) was added HBTU (26 mg, 69 μmol) followed by DIEA (50 μl, 288 μmol). The reaction was allowed to stand for 5 minutes, agitated, and allowed to stand for an additional five minutes. Aminotris-(N-methylpyrrolecarboxamide) (24 mg, 41 μmol) was then added followed by DIEA (50 μl, 288 μmol) and the reaction agitated for 2 hours. The reaction mixture was concentrated in vacuo and TFA (10 ml) added. After 2 minutes the TFA was removed in vacuo. Purification of the resulting brown oil by reversed phase HPLC afforded the diamine aminohexa-(N-methylpyrrolecarboxamide) ditrifluoroacetate as a white powder. Yield: 26 mg (58%); $^1$H NMR (DMSOd$_6$) δ 10.06 (s, 1 H), 9.95 (m, 2 H), 9.91 (s, 1 H), 9.84 (s, 1 H), 9.44 (br s, 1 H), 8.16 (t, 1 H, J=4.0 Hz), 7.22 (m, 4 H), 7.16 (d, 1 H, J=1.7 Hz), 7.10 (s, 1 H, J=1.7 Hz), 7.07 (m, 3 H), 6.98 (s, 1 H, J=1.7 Hz), 6.93 (s, 1 H J=1.8 Hz), 3.88 (m, 6 H), 3.84 (m, 12 H), 3.79 (m, 6 H), 3.21 (m, 2 H), 3.04 (m, 2 H), 2.77 (d, 6 H, J=4.8 Hz), 1.80 (m, 2 H); FABMS m/e 835.412 (M+H, 835.416 calc. for $C_{41}H_{51}N_{14}O_6$).

2. ImPyPyPyPyPyPy-Dp:

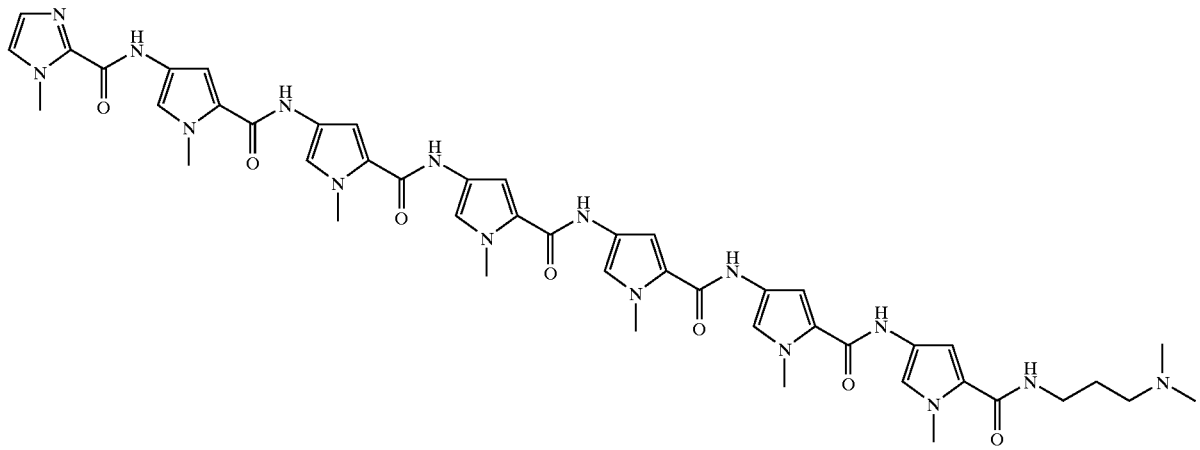

N-methyl-Imidazole-2-carboxylic acid (100 mg, 741 μmol) and HOBt (72 mg, 500 μmol) were suspended in 500 μl DMF. Upon addition of DCC (100 mg, 500 μmol) the reaction mixture become a homogeneous solution. The activation was allowed to stand for 12 hours, precipitated dicyclohexylurea removed by filtration and Aminohexa-(N-methylpyrrolecarboxamide) ditrifluoroacetate (10 mg, 9.4 μmol) added followed by DIEA (100 μl, 576 μmol), and the reaction allowed to stand for 2 hours. Reversed phase HPLC purification of the reaction mixture afforded ImPyPyPyPyPyPy-Dp as a white powder. Yield: 6.3 mg (62%); HPLC, r.t. 27.4 min; UV λ$_{max}$ (ε), 246 (34,100), 304 (56,600) nm; $^1$H NMR (DMSO-d$_6$) δ 10.46 (s, 1 H), 9.55 (s, 1 H), 9.94 (m, 3 H), 9.90 (s, 1 H), 9.20 (br s, 1 H), 8.14 (t, 1 H, J=7.2 Hz), 7.38 (s, 1 H), 7.28 (d, 1 H, J=1.4 Hz), 7.26 (d, 1 H, J=1.4 Hz), 7.23 (m, 4 H), 7.08 (m, 5 H), 7.04 (s, 1 H, J=1.2 Hz), 6.93 (d, 1 H, J=1.6 Hz), 3.98 (s, 3 H), 3.84 (m, 15 H), 3.83 (s, 1 H), 3.30 (q, 2 H, J=7.4 Hz), 3.21 (t, 2 H, J=7.1 Hz), 2.77 (d, 6H, J=4.1 Hz), 1.74 (m, 2 H); MALDI-TOF MS 944.21 (M+H 944.04 calc.); FABMS m/e 965.430 (M+Na, 965.426 calc. for $C_{46}H_{54}N_{16}O_7Na$).

D. Solid Phase Syntheses

1. Activation of Imidazole-2-carboxylic acid, Boc-γ-aminobutyric acid, Boc-glycine, and Boc-β-alanine The appropriate amino acid or acid (2 mmol) was dissolved in 2 mL DMF. HBTU (720 mg, 1.9 mmol) was added followed by DIEA (1 mL) and the solution lightly shaken for at least 5 min.

2. Activation of Boc-Imidazole acid

Boc imidazole acid (257 mg, 1 mmol) and HOBt (135 mg, 1 mmol) were dissolved in 2 mL DMF, DCC (202 mg, 1 mmol) is then added and the solution allowed to stand for at least 5 min.

3. Activation of Boc-γ-Imidazole acid and Boc-Pyrrole-Imidazole acid:

The appropriate dimer (1 mmol) and HBTU (378 mg, 1 mmol) are combined in 2 mL DMF. DIEA (1 mL) is then added and the reaction mixture allowed to stand for 5 min.

4. Activation of Boc-Pyrrole acid. (for coupling to Imidazole amine)

Boc-Pyrrole acid (514 mg, 2 mmol) was dissolved in 2 mL dichloromethane, DCC (420 mg, 2 mmol) added, and the solution allowed to stand for 10 min. DMAP (101 mg, 1 mmol) was added and the solution allowed to stand for 1 min.

5. Acetylation Mix:

2 mL DMF, DIEA (710 μL, 4.0 mmol), and acetic anhydride (380 μL, 4.0 mmol) were combined immediately before use.

6. Manual Synthesis Protocol:

Bocβ-alanine-Pam-Resin (1.25 g, 0.25 mmol) is placed in a 20 mL glass reaction vessel, shaken in DMF for 5 min and the reaction vessel drained. The resin was washed with DCM (2=30 s.) and the Boc group removed with 80% TFA/DCM/0.5M PhSH, 1=30s., 1=20 min The resin was washed washed with DCM (2=30 s.) followed by DMF (1=30 s.) A resin sample (5–10 mg) was taken for analysis. The vessel was drained completely and activated monomer added, followed by DIEA if necessary. The reaction vessel was shaken vigorously to amke a slurry. The coupling was allowed to proceed for 45 min, and a resin sample taken. The reaction vessel was then washed with DCM, followed by DMF.

7. Machine-Assisted Protocols:

Machine-assisted synthesis was performed on a ABI 430A synthesizer on a 0.18 mmol scale (900 mg resin; 0.2 mmol/gram). Each cycle of amino acid addition involved: deprotection with approximately 80% TFA/DCM/0.4M PhSH for 3 minutes, draining the reaction vessel, and then deprotection for 17 minutes; 2 dichloromethane flow washes; an NMP flow wash; draining the reaction vessel; coupling for 1 hour with in situ neutralization, addition of dimethyl sulfoxide (DMSO)/NMP, coupling for 30 minutes, addition of DIEA, coupling for 30 minutes; draining the reaction vessel; washing with DCM, taking a resin sample for evaluation of the progress of the synthesis by HPLC analysis; capping with acetic anhydride/DIEA in DCM for 6 minutes; and washing with DCM. A double couple cycle is employed when coupling aliphatic amino acids to imidazole, all other couplings are performed with single couple cycles.

The ABI 430A synthesizer was left in the standard hardware configuration for NMP-HOBt protocols. Reagent positions 1 and 7 were DIEA, reagent position 2 was TFA/0.5M thiophenol, reagent position 3 was 70% ethanolamine/methanol, regent position 4 was acetic anhydride, reagent position 5 was DMSO/NMP, reagent position 6 was methanol, and reagent position 8 was DMF. New activator functions were written, one for direct transfer of the cartridge contents to the concentrator (switch list 21, 25, 26, 35, 37, 44), and a second for transfer of reagent position 8 directly to the cartridge (switch list 37, 39, 45, 46).

Boc-Py-OBt ester (357 mg, 1 mmol) was dissolved in 2 ml DMF and filtered into a synthesis cartridge. Boc-Im acid monomer was activated (DCC/HOBt), filtered, and placed in a synthesis cartridge. Imidazole-2-carboxylic acid was added manually. At the initiation of the coupling cycle the synthesis was interrupted, the reaction vessel vented and the activated monomer added directly to the reaction vessel through the resin sampling loop via syringe. When manual addition was necessary an empty synthesis cartridge was used. Aliphatic amino acids (2 mmol) and HBTU (1.9 mmol) were placed in a synthesis cartridge. 3 ml of DMF was added using a calibrated delivery loop from reagent bottle 8, followed by calibrated delivery of 1 ml DIEA from reagent bottle 7, and a 3 minute mixing of the cartridge.

The activator cycle was written to transfer activated monomer directly from the cartridge to the concentrator vessel, bypassing the activator vessel. After transfer, 1 ml of DIEA was measured into the cartridge using a calibrated delivery loop, and the DIEA solution combined with the activated monomer solution in the concentrator vessel. The activated ester in 2:1 DMF/DIEA was then transferred to the reaction vessel. All lines were emptied with argon before and after solution transfers.

8. Stepwise HPLC analysis:

A resin sample (c.a. 4 mg) was placed in a 4 mL glass test tube, 200 µL of N,N-dimethylaminopropylamine was added and the mixture heated at 100° C. for 5 min. The cleavage mixture was filtered and a 25 µL sample analyzed by analytical HPLC at 254 nm.

9. Typical Manual Synthesis Protocol: PyPyPy-γ-ImImPy-β-Dp:

Boc-β-Pam-resin (1.25 g, 0.25 mmol amine) was shaken in DMF for 30 min and drained. The N-Boc group removed by washing with DCM for 2=30 s. followed by a 1 min shake in 80% TFA/DCM/0.5M PhSH, draining the reaction vessel and a brief 80% TFA/DCM/0.5 M PhSH wash, and 20 min shaking in 80% TFA/DCM/0.5M PhSH solution. The resin was washed 1 min with DCM and 30 s with DMF. A resin sample (8–10 mg) was taken for analysis. The resin was drained completely and Boc-pyrrole-Obt monomer (357 mg, 1 mmol) dissolved in 2 ml DMF added followed by DIEA (1 ml) and the resin shaken vigorously to make a slurry. The coupling was allowed to proceed for 45 min. A resin sample (8–10 mg) was taken after 40 min to check reaction progress. The reaction vessel was washed with DMF for 30 s and dichloromethane for 1 min to complete a single reaction cycle. Six additional cycles were performed adding, BocIm-OH (DCC/HOBt), BocIm-OH (DCC/HOBt), Boc-γ-aminobutyric acid (HBTU/DIEA) and allowed to couple for 2 hours, BocPy-OBt, BocPy-OBt, and pyrrole-2-carboxylic acid (HBTU/DIEA). The resin was washed with DMF, DCM, MeOH, and ethyl ether and then dried in vacuo. PyPyPy-γ-ImImPy-β-Pam-Resin (180 mg, 29 µmol)[12] was weighed into a glass scintillation vial, 1.5 ml of N,N-dimethylaminopropylamine added, and the mixture heated at 55° C. for 18 hours. The resin was removed by filtration through a disposable polyproplene filter and washed with 5 ml of water, the amine solution and the water washes combined, and the solution loaded on a $C_{18}$ preparatory HPLC column, the column allowed to wash for 4 min in 0.1% TFA at 8 ml/min, the polyamide was then eluted in 100 min. as a well defined peak with a gradient of 0.25% acetonitrile per min. The polyamide was collected in four separate 8 ml fractions, the purity of the individual fractions verified by HPLC and $^1$H NMR, to provide purified PyPyPy-γ-ImImPy-β-Dp: (11.2 mg, 39% recovery), UV $\lambda_{max}$, 246 (31,100), 312 (51,200) HPLC, r.t. 23.6, $^1$H NMR (DMSO-$d_6$) δ 10.30 (s, 1 H), 10.26 (s, 1 H), 9.88 (s, 1 H), 9.80 (s, 1 H), 9.30 (s, 1 H), 9.2 (br s, 1 H), 8.01 (m, 3 H), 7.82 (br s 1 H), 7.54 (s, 1 H), 7.52 (s, 1 H), 7.20 (d, 1 H, J=1.3 Hz), 7.18 (d, 1 H, J=1.2 Hz), 7.15 (d, 1 H, J=1.3 Hz), 7.01 (d, 1 H, J=1.4 Hz), 6.96 (d, 1 H, J=1.4 Hz), 6.92 (d, 1 H, J=1.8 Hz), 6.89 (m, 2 H), 6.03 (t, 1 H, J=2.4 Hz), 3.97 (s, 3 H), 3.96 (s, 3 H), 3.85 (s, 3 H), 3.82 (s, 3 H), 3.78 (m, 6 H), 3.37 (m, 2 H), 3.20 (q, 2 H J=5.7 Hz), 3.08 (q, 2 H J=6.6 Hz), 2.94 (q, 2 H J=5.3 Hz), 2.71 (d, 6 H J=5.8 Hz), 2.32 (m, 4 H), 1.83 (m, 4 H); MALDI-TOF-MS, 978.7 (979.1 calc. for M+H).

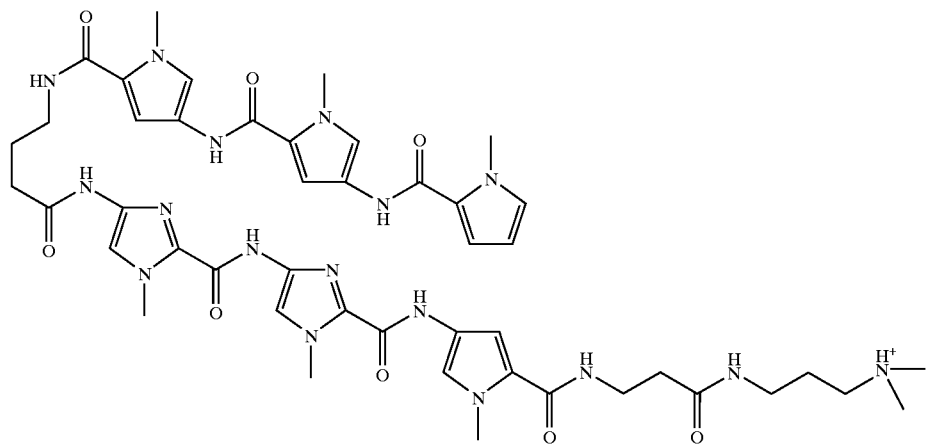

9. ImImPy-γ-PyPyPy-β-Dp:

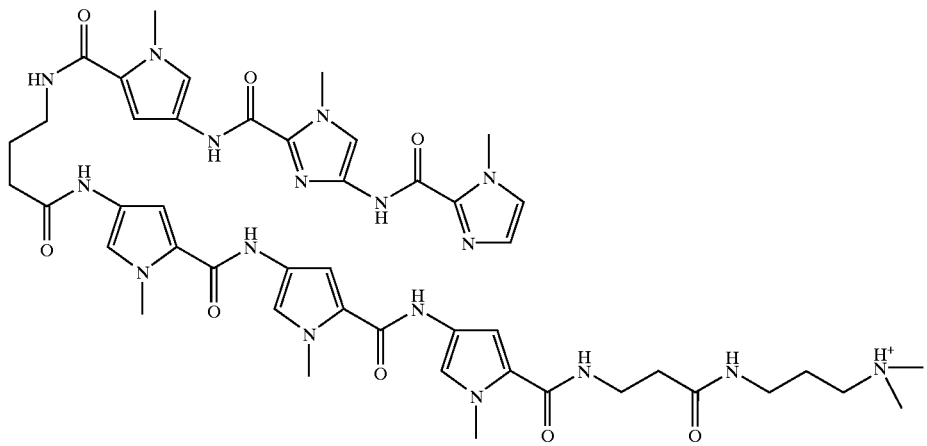

Polyamide was prepared by machine assisted solid phase synthesis protocols and 900 mg resin cleaved and purifed to provide ImImPy-γ-PyPyPy-β-Dp as a white powder. (69 mg, 48% recovery), UV $\lambda_{max}$, 246 (43,300), 308 (54,200) HPLC, r.t. 23.9, $^1$H NMR (DMSO-d$_6$) δ 10.31 (s, 1 H), 9.91 (s, 1 H), 9.90 (s, 1 H), 9.85 (s, 1 H), 9.75 (s, 1 H), 9.34 (br s, 1 H), 8.03 (m, 3 H), 7.56 (s, 1 H), 7.46 (s, 1 H), 7.21 (m, 2 H), 7.15 (m, 2 H), 7.07 (d, 1 H J=1.2 Hz), 7.03 (d, 1 H, J=1.3 Hz), 6.98 (d, 1 H, J=1.2 Hz), 6.87 (m, 2 H), 4.02 (m, 6 H), 3.96 (m, 6 H), 3.87 (m, 6 H), 3.75 (q, 2 H, J=4.9 Hz), 3.36 (q, 2 H, J=4.0 Hz), 3.20 (q, 2 H, J=4.7 Hz), 3.01 (q, 2 H J=5.1 Hz), 2.71 (d, 6H, J=4.8 Hz), 2.42 (m, 4 H), 1.80 (m, 4 H) MALDI-TOF-MS 978.8, (979.1 calc. for M+H)

10. AcImImPy-γ-PyPyPy-β-Dp:

Polyamide was prepared by manual solid phase protocols and isolated as a white powder. (8 mg, 28% recovery), UV $\lambda_{max}$, 246 (43,400), 312 (50,200) HPLC, r.t. 24.8, $^1$H NMR (DMSO-d$_6$) δ 10.35 (s, 1 H), 10.30 (s, 1 H), 9.97 (s, 1 H), 9.90 (s, 1 H), 9.82 (s, 1 H), 9.30 (s, 1 H), 9.2 (br s, 1H), 8.02 (m, 3 H), 7.52 (s, 1 H). 7.48 (s, 1 H), 7.21 (m, 2H), 7.16 (d, 1 H, J=1.1 Hz), 7.11 (d, 1 H, J=1.2 Hz), 7.04 (d, 1 H, J=1.1 Hz), 6.97 (d, 1 H, J=1.3 Hz), 6.92 (d, 1 H, J=1.4 Hz), 6.87 (d, 1 H, J=1.2 Hz), 3.99 (s, 3 H), 3.97 (s, 3 H), 3.83 (s, 3 H), 3.82 (s, 3 H), 3.80 (s, 3 H), 3.79 (s, 3 H), 3.47 (q, 2 H, J=4.7 Hz), 3.30 (q, 2 H, J=4.6 Hz), 3.20 (q, 2 H, J=5.0 Hz), 3.05 (q, 2 H, J=5.1 Hz), 2.75 (d, 6 H, J=4.1 Hz), 2.27 (m, 4 H), 2.03 (s, 3 H), 1.74 (m, 4 H) MALDI-TOF-MS, 1036.4 (1036.1 calc. for M+H).

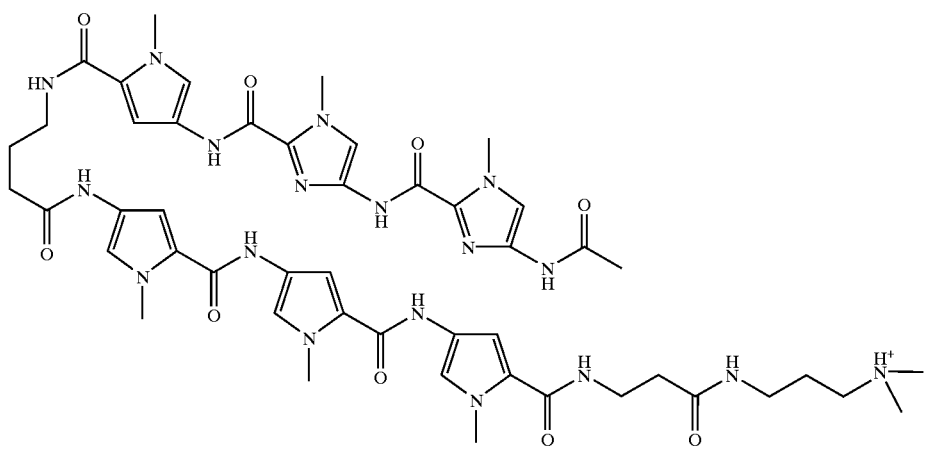

11. AcPyPyPy-γ-ImImPy-β-Dp:

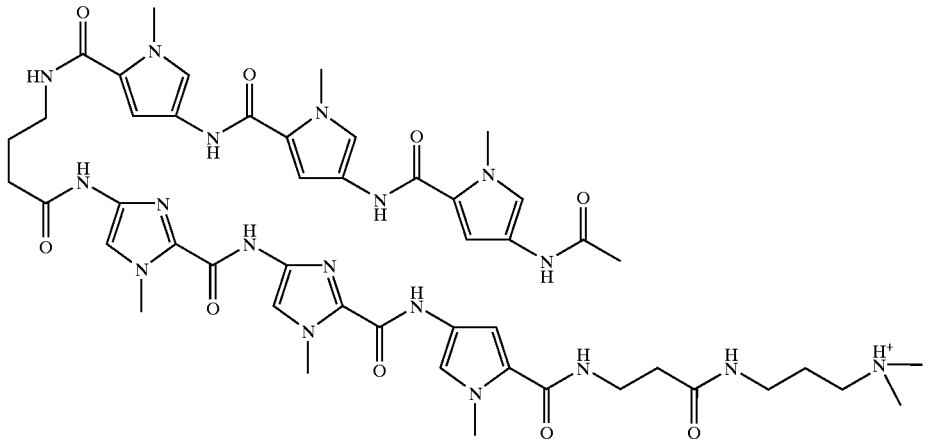

Polyamide was prepared by machine assisted solid phase methods protocols as a white powder. (14 mg, 48% recovery), UV $\lambda_{max}$, 246 (44,400), 312 (52,300) HPLC, r.t. 23.8, $^1$H NMR (DMSO-$d_6$) 10.32 (s, 1 H), 10.28 (s, 1 H), 9.89 (m, 2 H), 9.82 (s, 1 H), 9.18 (s, 1 H), 9.10 (br s, 1 H), 8.03 (m, 3 H), 7.55 (s, 1 H), 7.52 (s, 1 H), 7.21 (d, 1 H, J=1.1 Hz), 7.18 (d, 1 H, J=7.16 ), 7.15 (d, 1 H, J=1.0 Hz), 7.12 (d, 1 H, J=1.0 Hz), 7.02 (d, 1 H, J=1.0 Hz), 6.92 (d, 1 H, J=1.1 Hz), 6.87 (d, 1H, J=1.1 Hz), 6.84 (d, 1H, J=1.0 Hz), 3.97 (s, 3 H), 3.93 (s, 3 H), 3.87 (s, 3 H), 3.80 (s, 3 H), 3.78 (m, 6 H), 3.35 (q, 2 H, J=5.6 Hz), 3.19 (q, 2 H, J=5.3 Hz), 3.08 (q, 2 H, J=5.7 Hz), 2.87 (q, 2 H, J=5.8 Hz), 2.71 (d, 6 H, J=4.0 Hz), 2.33 (m, 4 H), 1.99 (s, 3 H), 1.74 (m, 4 H). MALDI-TOF-MS, 1036.2 (1036.1 calc. for M+H).

12. ImPyPy-γ-PyPyPy-β-Dp:

heated at 55° C. for 18 h. Resin substitution is calculated as $L_{new}(mmol/g)=L_{old}/(1+L_{old}$ $(W_{new}-W_{old})=10^{-3})$; L is the loading, and W is the molecular weight of the polyamide attached to the resin. (Barlos, et al. Int. J. Peptide Protein Res. 1991, 37, 513.) Resin is removed by filtration through a disposable proplyene filter and 16 mL of water added. The polyamide/amine mixture was purified directly by preparatory HPLC and the appropriate fractions lyophylized to yield a white powder. (103 mg, 61% recovery) HPLC r.t. 24.1, UV $\lambda_{max}(H_2O)$ (ε), 234 nm (39,300), 304 nm (52,000); $^1$H NMR (DMSO-$d_6$); 10.47 (s, 1 H), 9.91 (s, 1 H), 9.89 (s, 1 H), 9.87 (s, 1 H), 9.84 (s, 1 H), 9.2 (br s, 1 H), 8.08 (m, 3 H), 7.38 (s, 1 H), 7.26 (d, 1 H, J=1.0 Hz), 7.20 (d, 1 H, J=1.0 Hz), 7.14 (m, 4 H), 7.04 (d, 1 H, J=1.1 Hz), 7.02 (d, 1 H, J=1.1 Hz), 6.89 (d, 1 H, J=1.0 Hz), 6.85 (m, 2 H), 3.97 (s, 3 H), 3.82 (m, 6 H), 3.81 (s, 3 H), 3.77 (m, 6 H), 3.34 (m, 2 H,

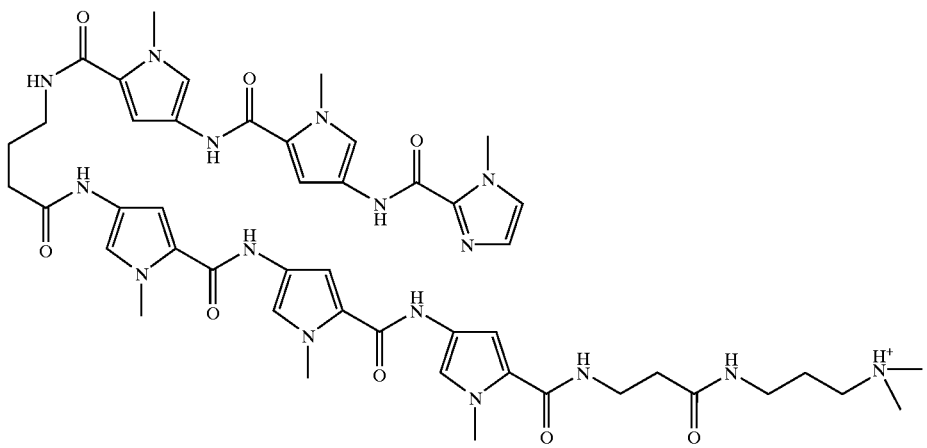

ImPyPy-γ-PyPyPy-β-Pam-Resin was prepared by machine-assisted synthesis protocols. A sample of resin (1 g, 0.17 mmol was placed in a 20 mL glass scintillation vial, 4 mL of dimethylaminopropylamine added, and the solution J=3.9 Hz), 3.18 (m, 2 H, J=5.5 Hz), 3.06 (m, 2 H, J=5.7 Hz), 2.95 (m, 2 H, J=4.9 Hz), 2.71 (d, 6 H, J=4.6 Hz), 2.30 (m, 6 H), 1.75 (m, 4 H); MALDI-TOF MS 978.0 (978.1 calc. for M+H).

13. ImPyPy-γ-PyPyPy-G-Dp:

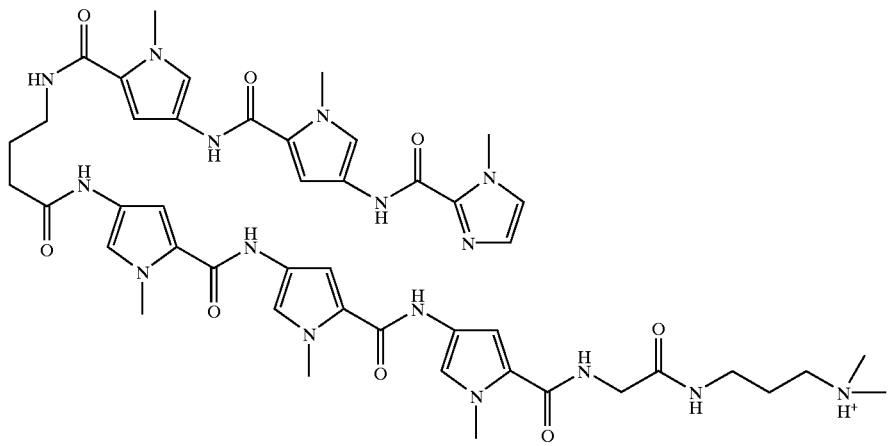

ImPyPy-γ-PyPyPy-G-Dp was prepared as described for ImPyPy-γ-PyPyPy-γ-Dp. (12 mg, 40% recovery). HPLC, r.t. 26.9, UV $\lambda_{max}$ (H$_2$O), 246 (41,100), 306 (51,300) $^1$H NMR (DMSO-d$_6$) δ 10.50 (s, 1 H), 9.95 (s, 1 H), 9.93 (s, 1 H), 9.92 (s, 1 H), 9.86 (s, 1 H), 9.2 (br s, 1H), 8.29 (t, 1 H, J=4.4 Hz), 8.07 (t, 1 H, J=5.2 Hz), 8.03 (t, 1 H, J=5.4 Hz), 7.39 (s, 1 H), 7.27, (d, 1 H, J=1.6 Hz), 7.22 (m, 2 H), 7.16 (m, 2 H), 7.04 (m, 2 H), 6.92 (d, 1 H, J=1.6 Hz), 6.89 (d, 1 H, J=1.7 Hz), 6.86 (d, 1 H, J=1.6 Hz), 3.97 (s, 3 H), 3.82 (m, 6 H), 3.81 (s, 3 H), 3.78 (m, 6 H), 3.70 (d, 2 H, J=5.7 Hz), 3.20 (q, 2 H, J=5.7), 3.11 (q, 2 H, J=4.2 Hz), 3.00 (q, 2 H, J=4.4 Hz), 2.76 (d, 6 H, J=4.7 Hz), 2.24 (t, 2 H, J=4.8 Hz), 1.77 (m, 4 H); MALDI-TOF-MS, 964.3 (964.1 calc. for M+H).

14. AcImPyPy-γ-PyPyPy-G-Dp:

AcImPyPy-γ-PyPyPy-G-Dp was prepared as described for ImPyPy-γ-PyPyPy-β-Dp. (13.1 mg, 30% yield) HPLC, r.t. 24.0, UV $\lambda_{max}$ (H$_2$O), 246 (35,900), 312 (48,800) $^1$H NMR (DMSO-d$_6$) δ 10.23 (s, 1 H), 9.98 (s, 1 H), 9.32 (s, 1 H), 9.90 (m, 2 H), 9.84 (s, 1 H), 9.2 (br s, 1 H), 8.27 (t, 1 H, J=5.0), 8.05 (m, 2 H), 7.41 (s, 1 H), 7.25 (d, 1 H, J=1.4 Hz), 7.22 (m, 2 H), 7.16 (m, 2 H), 7.12 (d, 1 H, J=1.7 Hz), 7.05 (d, 1 H, J=1.5 Hz), 6.94 (d, 1 H, J=1.6 Hz), 6.89 (d, 1 H, J=1.7 Hz) 6.87 (d, 1 H, J=1.6 Hz), 3.93 (s, 3 H), 3.83 (s, 3 H), 3.82 (m, 6 H), 3.81 (s, 3 H), 3.79 (s, 3 H), 3.71 (d, 2 H, J=5.1 Hz), 3.19 (q, 2 H, J=5.8 Hz), 3.12 (q, 2 H, J=5.0 Hz), 3.01 (q, 2 H, J=4.2 Hz), 2.74 (d, 6 H, J=4.6 Hz), 2.26 (t 2 H, J=4.6 Hz), 2.00 (s, 3 H), 1.75 (m, 4 H); MALDI-TOF-MS, 1021.6 (1021.1 calc. for M+H).

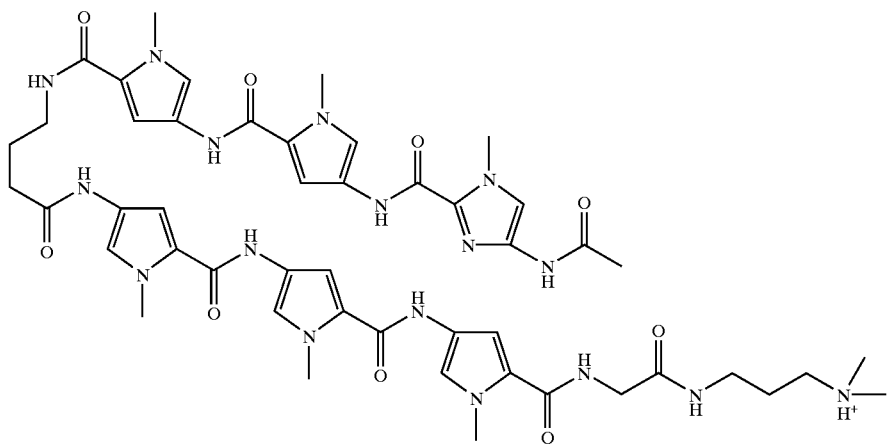

15. AcImPyPy-γ-PyPyPy-β-Dp:

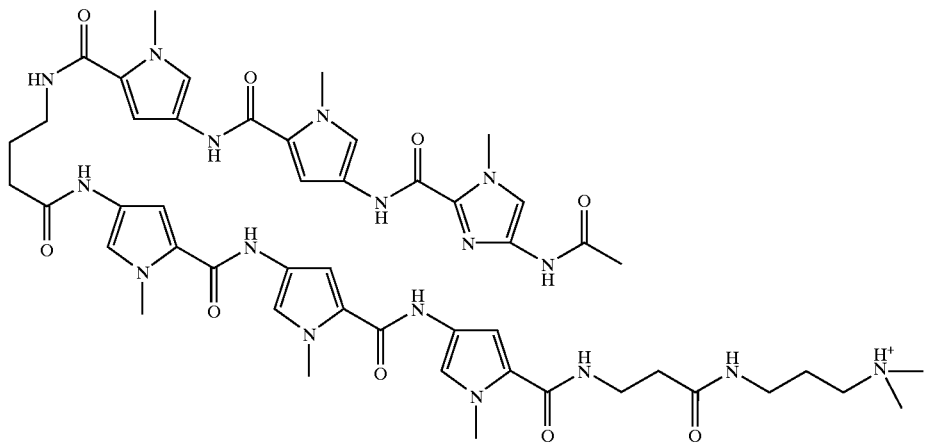

AcImPyPy-γ-PyPyPy-β-Dp was prepared as described for ImPyPy-γ-PyPyPy-β-Dp. (9.2 mg, 31% yield) UV $\lambda_{max}$ (H$_2$O), 246 (42,800), 312 (50,400) HPLC, r.t. 24.9, $^1$H NMR (DMSO-d$_6$) δ 10.25 (s, 1 H), 10.01 (s, 1 H, 9.92 (m, 3 H), 9.86 (s, 1 H), 9.3 (br s, 1 H), 8.10 (m, 3 H), 7.42 (s, 1 H), 7.25 (d, 1 H, J=1.5 Hz), 7.20 (d, 1 H, J=1.6 Hz), 7.16 (m, 3 H), 7.12 (d, 1 H, J=1.4 Hz), 7.03 (d, 1 H, J=1.7), 6.89 (d, 1 H, J=1.6 Hz), 6.86 (m, 2 H), 3.92 (s, 3 H), 3.83 (s, 3 H), 3.82 (s, 3 H), 3.80 (s, 6H), 3.78 (s, 3 H), 3.35 (q, 2 H, J=5.5 Hz), 3.20 (q, 2 H, J=3.8 Hz), 3.08 (q, 2 H, J=3.3 Hz), 2.97 (q, 2 H, J=3.8 Hz), 2.75 (d, 6 H, J=4.8 Hz), 2.34 (t, 2 H, J=5.0 Hz), 2.24 (t, 2 H, J=4.4 Hz), 2.00 (s, 3 H), 1.71 (m, 4 H); MALDI-TOF-MS, 1035.4 (1035.1 calc. for M+H).

16. ImImIm-γ-PyPyPy-β-Dp.

The product was synthesized by manual solid phase protocols and recovered as a white powder (2.4 mg, 4% recovery). UV $\lambda_{max}$ 312 (48,500); $^1$H NMR (DMSO-d$_6$) d 10.09 (s, 1 H), 9.89 (s, 1 H), 9.88 (s, 1 H), 9.83 (s,1 H), 9.57 (s, 1 H), 9.19 (br s, 1 H), 8.36 (t, 1 H, J=5.6 Hz), 8.03 (m, 2 H), 7.64 (s, 1 H), 7.51 (s, 1 H), 7.45 (s, 1 H), 7.20 (d, 1 H, J=1.0 Hz), 7.15 (d, 1 H, J=2.0 Hz), 7.14 (s, 1 H), 7.08 (s, 1 H), 7.0 (s, 1 H), 6.87 (d, 2 H, J=2.2 Hz), 4.01 (s, 3 H), 3.99 (s, 3 H), 3.95 (s, 3 H), 3.82 (s, 3 H), 3.82 (s, 3 H), 3.79 (s, 3 H), 3.37 (q, 2 H, J=5.8 Hz), 3.26 (q, 2 H, J=6.1 Hz), 3.10 (q, 2 H, J=6.1 Hz), 2.99 (m, 2 H), 2.73 (d, 6 H, J=4.8 Hz), 2.34 (t, 2 H, J=7.2 Hz), 2.27 (t, 2 H, J=7.3 Hz), 1.79 (m, 4 H); MALDI-TOF-MS, 980.1 (980.1 calc. for M+H).

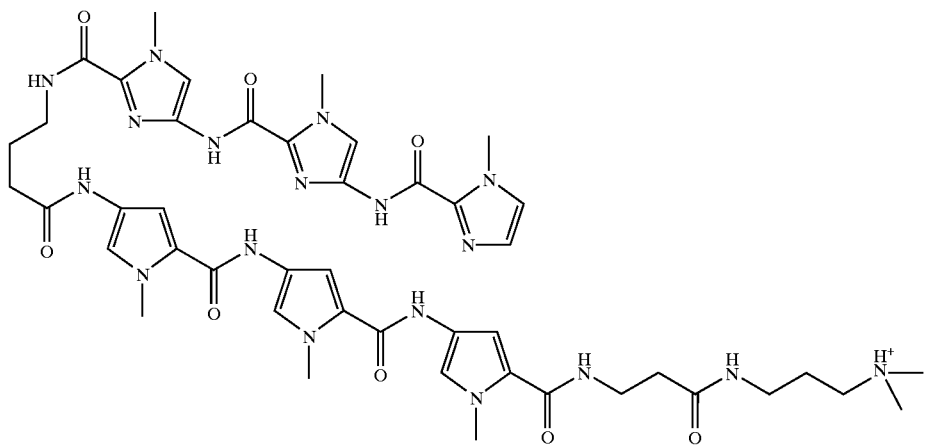

17. ImImIm-γ-PyPyPy-β-Dp-NH₂:

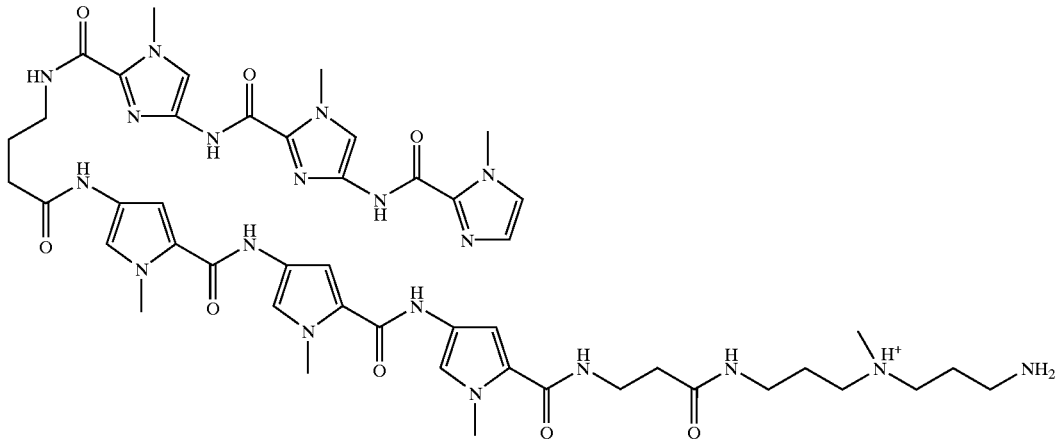

A sample of machine-synthesized resin (350 mg, 0.17 mmol/gram¹) was placed in a 20 mL glass scintillation vial, and treated with 2 mL 3,3'-diamino-N-methyldipropylamine at 55° C. for 18 hours.

The resin was removed by filtration through a disposable propylene filter, and the resulting solution dissolved with water to a total volume of 8 mL, and purified directly by preparatory reversed phase HPLC to provide ImImIm-γ-PyPyPy-β-Dp-NH₂ (28 mg, 41% recovery) as a white powder. $^1$H NMR (DMSO-$d_6$) δ 10.14 (s, 1 H), 9.89 (s, 1 H), 9.88 (s, 1 H), 9.83 (s, 1 H), 9.6 (br s, 1 H), 9.59 (s, 1 H), 8.36 (t, 1 H, J=5.5 Hz), 8.09 (t, 1 H, J=5.0 Hz), 8.03 (t, 1 H, J=5.0 Hz), 7.9 (br s, 3 H), 7.63 (s, 1 H), 7.50 (s, 1 H), 7.44 (s, 1 H), 7.19 (d, 1 H, J=1.2 Hz), 7.13 (m, 2 H), 7.08 (d, 1 H, J=1.3 Hz), 7.02 (d, 1 H, J=1.2 Hz), 6.85 (m, 2 H), 4.01 (s, 3 H), 3.99 (s, 3 H), 3.97 (m, 6 H), 3.80 (s, 3 H), 3.77 (s, 3 H), 3.44 (q, 2 H, J=5.3 Hz), 3.23 (q, 2 H, J=6.0 Hz), 3.05 (m, 6 H), 2.83 (q, 2 H, J=5.0 Hz), 2.70 (d, 3 H, J=4.0 Hz), 2.32 (t, 2 H, J=6.9 Hz), 2.25 (t, 2 H, J=6.9 Hz), 1.90 (m, 2 H), 1.77 (m, 4 H). MALDI-TOF-MS, 1022.8 (1023.1 calc. for M+H).

18. ImPyPy-G-PyPyPy-G-Dp-NH₂:

Polyamide was prepared by manual solid phase methods as a white powder upon cleavage of 240 mg resin with N-methyl-bis(aminopropyl)amine (2 ml, 55° C.) (19.0 mg, 44% recovery after HPLC purification). $^1$H NMR (DMSO-$d_6$) δ 10.49 (s, 1 H), 9.97 (s, 1 H), 9.93 (s, 1 H), 9.91 (s, 1 H), 9.89 (s, 1 H), 9.7 (br s, 1 H), 8.27 (m, 2 H), 8.04 (t, 1 H, J=5.1 Hz), 7.88 (br s, 3 H), 7.39 (s, 1 H), 7.27 (d, 1 H, J=1.6 Hz), 7.21 (m, 3 H), 7.15 (m, 2 H), 7.05 (m, 2 H), 6.93 (m, 3 H), 3.97 (s, 3 H), 3.96 (m, 6 H), 3.92 (m, 9 H), 3.72 (m, 4 H), 3.14 (m, 6 H), 3.05 (q, 2 H, J=5.4 Hz), 2.73 (d, 3 H, J=3.3 Hz), 1.88 (quintet, 2 H, J=4.6 Hz), 1.75 (quintet, 2 H, J=6.3 Hz). MALDI-TOF-MS, 979.0 (979.1 calc for M+H).

19. ImPyPy-G-PyPyPy-β-Dp-NH₂:

Polyamide was prepared by manual solid phase methods as a white powder upon cleavage of 240 mg resin with N-methyl-bis(aminopropyl)amine (2 ml, 55° C.) (25 mg, 55% recovery). HPLC r.t. 22.0; $^1$H NMR (DMSO-$d_6$) δ 10.53 (s, 1 H), 10.00 (s, 1 H), 9.98 (s, 1 H), 9.93 (s, 1 H), 9.92 (s, 1 H), 9.7 (br s, 1 H), 8.31 (t, 1 H, J=5.7 Hz), 8.12 (t, 1 H, J=5.5 Hz), 8.04 (t, 1 H, J=5.6 Hz), 7.9 (br s, 3 H), 7.41 (s, 1 H), 7.29 (d, 1 H, J=1.7 Hz), 7.23 (d, 1 H, J=1.5 Hz), 7.22 (d, 1 H, J=1.4 Hz), 7.16 (m, 3 H), 7.07 (d, 1 H, J=1.2 Hz), 7.03 (d, 1 H, J=1.3 Hz), 6.94 (d, 1 H, J=1.6 Hz), 6.93 (d, 1 H, J=1.5 Hz), 6.86 (d, 1 H, J=1.4 Hz), 3.98 (s, 3 H), 3.88 (d, 2 H, J=5.6 Hz), 3.83 (s, 3 H), 3.82 (m, 6 H), 3.80 (s, 3 H), 3.78 (s, 3 H), 3.37 (q, 2 H, J=6.4 Hz), 3.11 (m, 6 H), 2.86 (q, 2 H, J=6.1 Hz), 2.70 (d, 3 H, J=4.6 Hz),2.32 (t, 2 H, J=7.2 Hz), 1.87 (quintet, 2 H, J=7.4 Hz), 1.75 (quintet, 2 H, J=6.0 Hz), MALDI-TOF-MS, 993.3 (993.1 calc for M+H).

20. ImPyPy-β-PyPyPy-G-Dp-NH₂:

Polyamide was prepared by automated solid phase methods as a white powder upon cleavage of 240 mg resin with N-methyl-bis(aminopropyl)amine (2 ml, 55° C.) (23.0 mg, 53% recovery). HPLC, r.t. 20.6; $^1$H NMR (DMSO-$d_6$) δ 10.45 (s, 1 H), 9.95 (s, 1 H), 9.92 (m, 3 H), 9.6 (br s, 1 H), 8.27 (t, 1 H, J=4.7 Hz), 8.11 (m, 2 H), 7.9 (s, 3 H), 7.38 (s, 1 H), 7.26 (d, 1 H, J=1.7 Hz), 7.21 (m, 2 H), 7.17 (m, 2 H), 7.13 (d, 1 H, J=1.8 Hz), 7.05 (m, 2 H), 6.93 (d, 1 H, J=1.6 Hz), 6.88 (d, 1 H, J=1.6 Hz), 6.83 (d, 1 H, J=1.7 Hz), 3.97 (s, 3 H), 3.82 (s, 9 H), 3.81 (s, 3 H), 3.79 (s, 3 H), 3.73 (m, 2 H), 3.44 (q, 2 H, J=5.5 Hz), 3.2 (m, 6 H), 2.85 (q, 2 H, J=5.8 Hz), 2.73 (d, 3 H, J=4.5 Hz), 1.89 (quintet, 2 H, J=6.4 Hz), 1.77 (quintet, 2 H, J=6.9 Hz), MALDI-TOF-MS, 992.9 (993.1 calc for M+H).

21. ImPyPy-γ-ImPyPy-β-PyPyPy-G-Dp-NH$_2$:

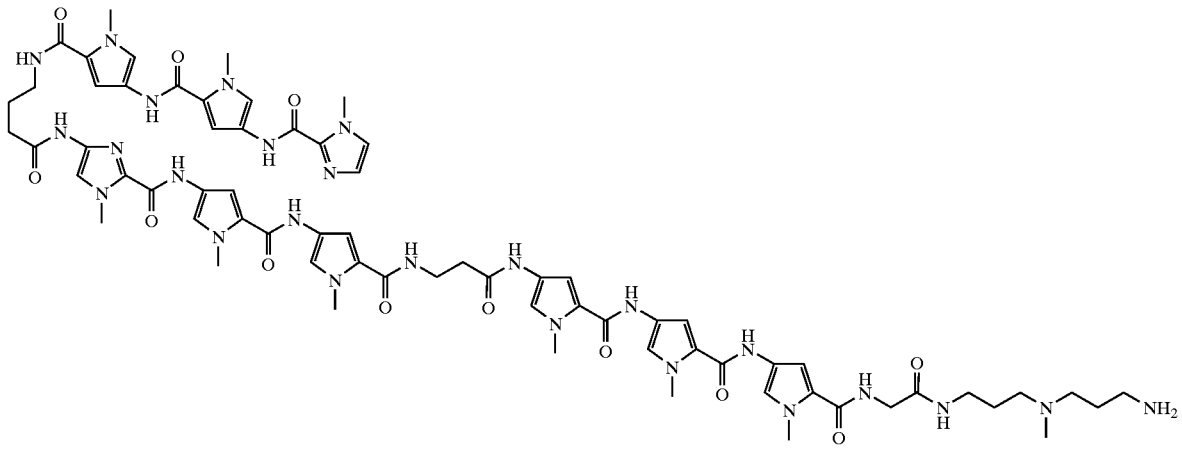

The polyamide was prepared by machine-assisted solid phase methods as a white powder. (29 mg 59% recovery). HPLC r.t. 21.5, $^1$H NMR (DMSO-d$_6$); δ 10.50 (s, 1 H), 10.27 (s, 1 H), 9.96 (s, 1 H), 9.93 (m, 5 H), 9.2 (br s, 1 H), 8.27 (t, 1 H), J=5.1 Hz), 8.03 (m, 3 H), 7.90 (s, 3 H), 7.45 (s, 1 H), 7.40 (s, 1 H), 7.27 (d, 1 H, J=1.3 Hz), 7.25 (d, 1 H, J=1.4 Hz), 7.22 (m, 2 H), 7.18 (m, 2 H), 7.17 (d, 1 H, J=1.4 Hz), 7.14 (d, 1 H, J=1.3 Hz), 7.11 (m, 2 H), 7.06 (d, 1 H, J=1.5 Hz), 6.94 (d, 1 H, J=1.3 Hz), 6.88 (m, 2 H), 6.84 (d, 1 H, J=1.4 Hz), 3.97 (s, 3 H), 3.93 (s, 3 H), 3.83 (m, 9 H), 3.80 (m, 6 H), 3.76 (m, 6 H), 3.72 (d, 2 H, J=5.2 Hz), 3.43 (q, 2 H, J=5.0 Hz), 3.17 (m, 6 H), 3.11 (q, 2 H, J=5.3 Hz), 2.85 (q, 2 H, J=5.2 Hz), 2.73 (d, 3 H, J=3.9 Hz), 2.51 (t, 2 H, J=6.5 Hz), 2.35 (t, 2 H, J=6.7 Hz), 1.92 (quintet, 2 H, J=6.8 Hz), 1.78 (m, 4 H). MALDI-TOF MS 1445.6 (1445.6 calc for M+H).

22. ImImImPy-γ-PyPyPyPy-β-Dp-NH$_2$:

A sample of machine-synthesized resin (350 mg, 0.16 mmol/gram) was placed in a 20 mL glass scintillation vial, and treated with 2 mL 3,3'-diamino-N-methyldipropylamine at 55° C. for 18 hours. The resin was removed by filtration through a disposable propylene filter, and the resulting solution dissolved with water to a total volume of 8 mL, and purified directly by preparatory reversed phase HPLC to provide ImImImPy-γ-PyPyPyPy-β-Dp-NH$_2$ (31 mg, 40% recovery) as a white powder. $^1$H NMR (DMSO-d$_6$) δ 10.37 (s, 1 H), 10.16 (s, 1 H), 9.95 (s, 1 H), 9.93 (s, 1 H), 9.91 (s, 1 H), 9.86 (s, 1 H); 9.49 (br s, 1 H), 9.47 (s, 1 H), 8.12 (m, 3 H), 8.0 (br s, 3 H), 7.65 (s, 1 H), 7.57 (s, 1 H), 7.46 (s, 1 H), 7.20 (m, 3 H), 7.16 (m, 2 H), 7.09 (d, 1 H, J=1.5 Hz), 7.05 (m, 2 H), 7.00 (d, 1 H, J=1.6 Hz), 6.88 (m, 2 H), 4.01 (s, 3 H), 3.99 (s, 3 H), 3.98 (s, 3 H), 3.83 (s, 3 H), 3.82 (s, 3 H), 3.81 (s, 3 H), 3.79 (s, 3 H), 3.78 (s, 3 H), 3.36 (q, 2 H, J=5.3 Hz), 3.21–3.05 (m, 8 H), 2.85 (q, 2 H, J=4.9 Hz), 2.71 (d, 3 H, J=4.4 Hz), 2.34 (t, 2 H, J=5.9 Hz), 2.26 (t, 2 H, J=5.9 Hz), 1.85 (quintet, J=5.7 Hz), 1.72 (m, 4 H). MALDI-TOF-MS, 1267.1 (1267.4 calc. for M+H).

23. ImPyPyPyPy-γ-ImPyPyPyPy-β-Dp-NH$_2$:

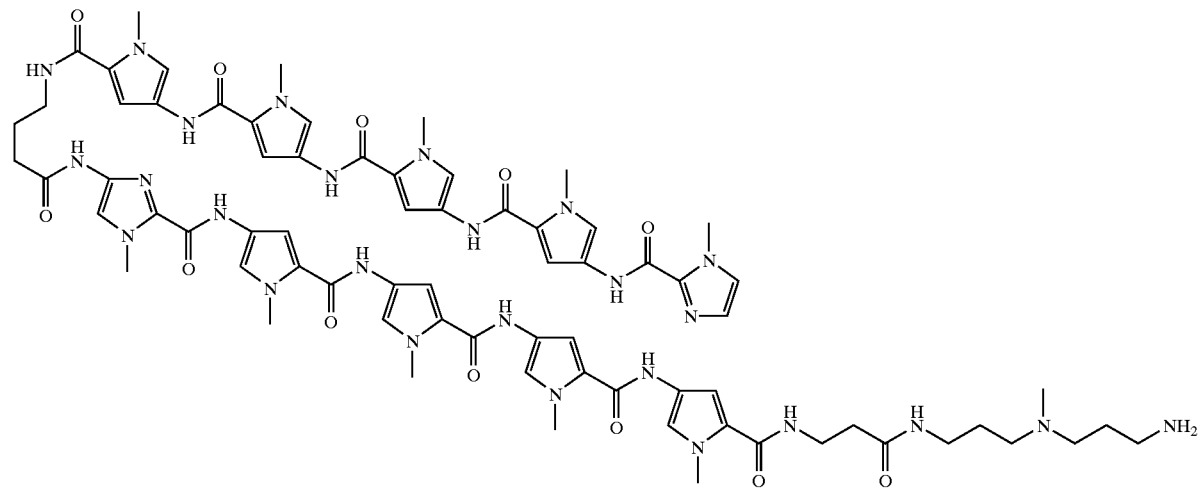

A sample of ImPyPyPyPy-γ-ImPyPyPyPy-β-resin prepared by machine-assisted solid phase synthesis (240 mg, 0.16 mmol/gram) was placed in a 20 mL glass scintillation vial, and treated with 3,3-diamino-N-methyldipropylamine (2 mL) at 55° C. for 18 hours. Resin was removed by filtration, and the filtrate diluted to a total volume of 8 mL with 0.1% (wt/v) aqueous TFA. The resulting crude polyamide/amine solution was purified directly by reversed phase HPLC to provide the trifluoroacetate salt of ImPyPyPyPy-γ-ImPyPyPyPy-β-NH$_2$ (31 mg, 40% recovery) as a white powder. UV λ$_{max}$ 241, 316 (ε) 83300 (calculated based on ε=8,333/ring[5]); $^1$H NMR (DMSO-d$_6$) δ 10.53 (s, 1 H), 10.28 (s, 1 H), 10.03 (s, 1 H), 10.00 (s, 1 H), 9.96 (m, 2 H), 9.92 (m, 2 H), 9.6 (br s, 1 H), 8.07 (m, 4 H), 7.89 (s, 3 H), 7.45 (s, 1 H), 7.41 (s, 1 H), 7.27 (d, 2 H, J=8.5 Hz), 7.23 (m, 4 H), 7.16 (m, 4 H), 7.06 (m, 4 H), 6.87 (m, 2 H), 3.98, (s, 3 H), 3.94 (s, 3 H), 3.84, (m, 6 H), 3.79 (s, 3 H), 3.35 (q, 2 H, J=5.7 Hz), 3.16 (m, 8 H), 2.85 (q, 2 H, J=5.6 Hz), 2.72 (d, 2 H, J=4.2 Hz), 2.34 (m, 2 H), 1.91 (m, 4 H), 1.78 (m, 4 H). MALDI-TOF MS, 1510.4 (1510.7 calc. for M+H).

24. ImImPyPyPy-γ-ImPyPyPyPy-β-Dp-NH$_2$:

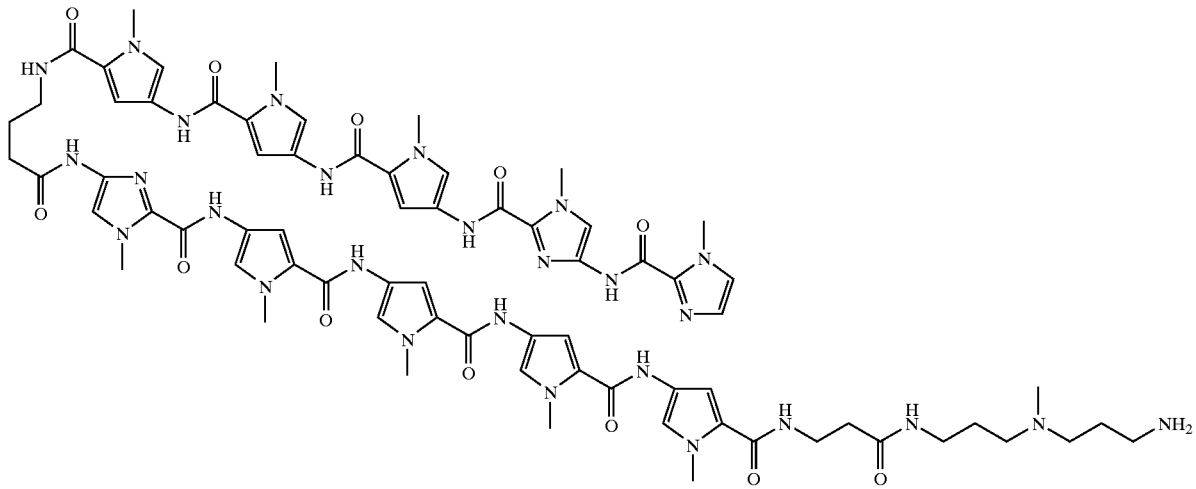

The polyamide was prepared as a white powder as described for ImPyPyPyPy-γ-ImPyPyPyPy-β-NH$_2$. $^1$H NMR (DMSO-d$_6$) δ 10.39 (s, 1 H), 10.28 (s, 1 H), 10.03 (s, 1 H), 10.00 (s, 1 H), 9.92 (m, 2 H), 9.82 (s, 1 H), 9.66 (br s, 1 H), 8.11 (m, 4 H), 7.89 (s, 3 H), 7.57 (s, 1 H), 7.46 (d, 2 H, J=2.4 Hz), 7.27 (dd, 2 H, J=1.0 Hz) 7.32 (m, 4 H), 7.16 (m, 4 H), 7.08 (m, 4 H), 6.88 (m, 1 H), 4.00 (s, 3 H), 3.94 (s, 3 H), 3.78 (s, 3 H), 3.19 (q, 2 H, J=5.1 Hz), 3.05 (m, 8 H), 2.86 (q, 2 H, J=4.8 Hz), 2.72 (d, 2 H, J=4.4 Hz), 2.34 (m, 4 H), 1.90 (m, 4 H), 1.78 (m, 4 H). MALDI-TOF-MS, 1510.4 (1511.7 calc. for M+H).

25. ImImIm-γ-PyPyPy-β-Dp-EDTA:

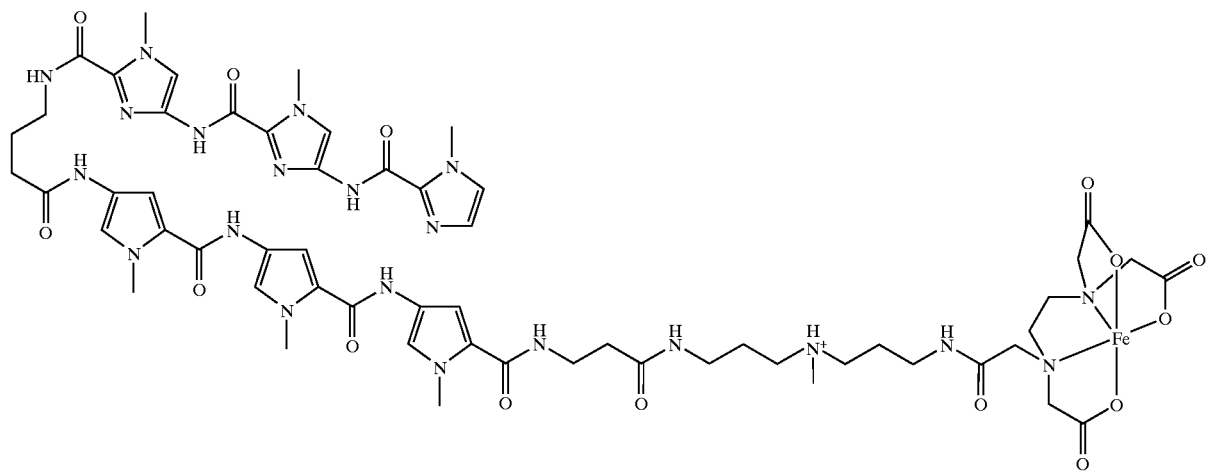

EDTA-dianhydride (50 mg) was dissolved in 1 mL DMSO/NMP solution and 1 mL DIEA by heating at 55° C. for 5 min. The dianhydride solution was added to ImImIm-γ-PyPyPy-β-Dp-NH$_2$ (8.0 mg, 7 μmol) dissolved in 750 μL DMSO. The mixture was heated at 55° C. for 25 minutes, and treated with 3 mL 0.1M NaOH, and heated at 55° C. for 10 minutes. 0.1% TFA was added to adjust the total volume to 8 mL and the solution purified directly by preparatory HPLC chromatography to provide ImImIm-γ-PyPyPy-β-Dp-EDTA as a white powder. (3.3 mg, 30% recovery) $^1$H NMR (DMSO-d$_6$) d 10.14 (s, 1 H), 9.90 (s, 1 H), 9.89 (s, 1 H), 9.85 (s, 1 H), 9.58 (s, 1 H), 9.3 (br s, 1 H), 8.40 (m, 2 H), 8.02 (m, 2 H), 7.65 (s, 1 H), 7.51 (s, 1 H), 7.45 (s, 1 H), 7.20 (d, 1 H, J=1.5 Hz), 7.15 (m, 2 H), 7.08 (d, 1 H, J=1.1 Hz), 7.04 (d, 1 H, J=1.5 Hz), 6.86 (m, 2 H), 4.00 (s, 3 H), 3.98 (s, 3 H), 3.94 (s, 3 H), 3.87 (m, 4 H), 3.82 (s, 3 H), 3.81 (s, 3 H), 3.78 (s, 3 H), 3.72 (m, 4 H), 3.4–3.0 (m, 16 H), 2.71 (d, 3 H, J=4.2 Hz), 2.33 (t, 2 H, J=5.1 Hz), 2.25 (t, 2 H, J=5.9 Hz), 1.75 (m, 6 H). MALDI-TOF-MS, 1298.4 (1298.3 calc. for M+H). The polyamide was loaded with Fe(II) by standard methods.

26. ImPyPy-γ-ImPyPy-β-Dp:

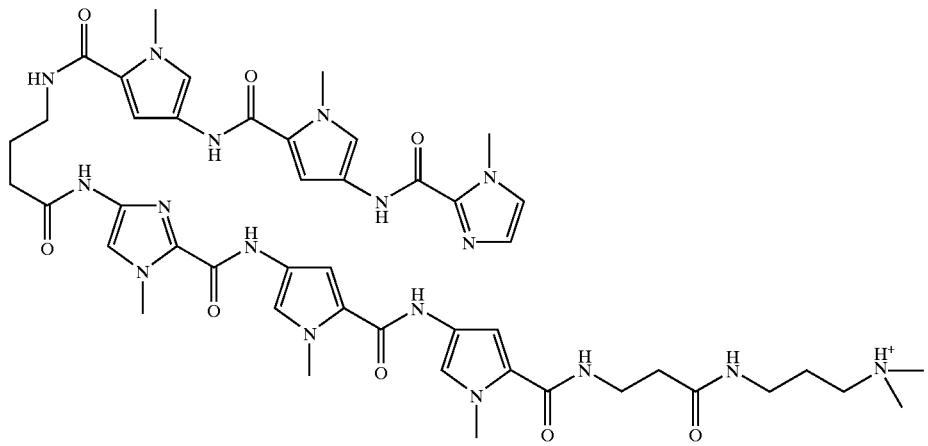

The polyamide was prepared by machine-assisted solid phase methods as a white powder. (17 mg, 56% recovery). HPLC r.t. 26.1, UV λ$_{max}$ (ε), 234 (39,300), 312 (53,200) nm; $^1$H NMR (DMSO-d$_6$); d 10.53 (s, 1 H), 10.27 (s, 1 H), 10.04 (s, 1 H), 9.96 (s, 1 H), 9.94 (s, 1 H), 9.2 (br s, 1 H), 8.08 (m, 3 H), 7.49 (s, 2 H), 7.44 (s, 1 H), 7.31 (d, 1 H, J=1.0 Hz), 7.23 (d, 1 H, J=1.1 Hz), 7.19 (m, 3 H), 7.10 (s, 1 H), 6.92 (d, 1 H, J=1.1 Hz), 6.90 (d, 1 H, J=1.1 Hz). 4.01 (s, 3 H), 3.97 (s, 3 H), 3.86 (m, 6 H), 3.82 (m, 6 H), 3.41 (q, 2 H, J=6.0 Hz), 3.22 (q, 2 H, J=5.9 Hz), 3.13 (q, 2 H, J=5.9 Hz), 3.0 (q, 2 H, J=5.6 Hz), 2.76 (d, 6 H, J=4.8 Hz), 2.37 (m, 4 H), 1.78 (m, 4 H); MALDI-TOF MS 979.3 (979.1 calc. for M+H).

27. ImPyPy-G-PyPyPy-G-Dp:

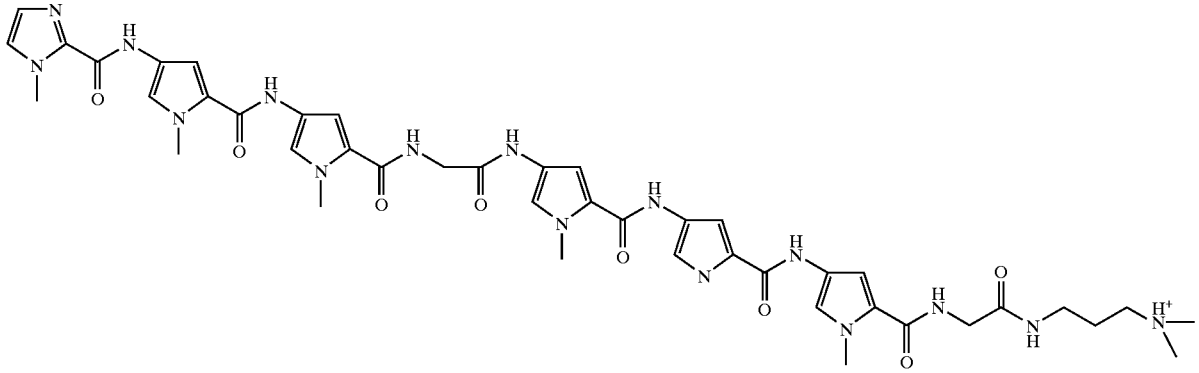

Polyamide was prepared by manual solid phase methods and obtained as a white powder upon cleavage of 240 mg resin. (initial subsitution of 0.2 mmol Boc-Glycine/gram) with dimethylaminopropylamine (11.9 mg, 29% recovery). HPLC, r.t. 26.9 min.; UV $\lambda_{max}$ ($\epsilon$), 246 (41,000), 312 (48,400) nm; $^1$HNMR (DMSO-d$_6$) δ 10.49 (s, 1 H), 9.98 (s, 1 H), 9.95 (s, 1 H), 9.92 (s, 1 H), 9.89 (s, 1 H), 9.2 (br s, 1 H), 8.30 (m, 2 H), 8.06 (t, 1 H, J=5.8 Hz), 7.40 (s, 1 H), 7.24, (d, 1 H, J=1.7 Hz), 7.23 (m, 3 H), 7.17 (m, 2 H), 7.06 (m, 2 H), 6.94 (m, 3 H), 3.99 (s, 3 H), 3.89 (d, 2 H, J=5.8 Hz), 3.84 (s, 3 H), 3.84 (s, 3 H), 3.83 (s, 3 H), 3.81 (s, 3 H), 3.80 (s, 3 H), 3.72 (d, 2 H, J=4.3 Hz), 3.13 (q, 2 H, J=5.7 Hz), 3.01 (q, 2 H, J=5.2 Hz), 2.76 (d, 6 H, J=4.3 Hz), 1.77 (quintet, 2 H, J=7.4 Hz); MALDI-TOF MS 935.7 (M+H 936.0 calc for $C_{44}H_{55}N_{16}O_8$); FABMS m/e 935.433 (M+H 935.439 calcd. for $C_{44}H_{55}N_{16}O_8$).

28. ImPyPy-G-PyPyPy-β-Dp:

for M+H); FABMS m/e 949.458 (M+H 949.455 calc. for $C_{45}H_{57}N_{16}O_8$).

30. ImPyPy-β-PyPyPy-β-Dp:

Polyamide was prepared by automated solid phase methods as a white powder upon cleavage of 240 mg resin (initial subsitution of 0.2 mmol Boc-β-alanine/gram) with dimethylaminopropylamine (2 ml, 55° C.). (19.0 mg, 43% recovery after HPLC purification). HPLC, r.t. 26.8; UV $\lambda_{max}$ ($\epsilon$), 246 (42,100), 312 (53,900) nm; $^1$H NMR (DMSO-d$_6$) δ 10.56 (s, 1 H), 9.90 (s, 1 H), 9.89 (m, 2 H), 9.87 (s, 1 H), 9.21 (br s, 1 H), 8.24 (t, 1 H, J=5.2 Hz), 8.04 (t, 1 H, J=6.1 Hz), 8.01 (t, 1 H, J=6.0 Hz), 7.35 (s, 1 H), 7.26 (d, 1 H, J=1.6 Hz), 7.23 (m, 3 H), 7.16 (m, 3 H), 7.12 (m, 1 H), 7.02 (d, 1 H, J=1.5 Hz), 6.85 (d, 1 H, J=1.9 Hz), 6.80 (d, 1 H, J=1.8 Hz), 3.96 (s, 3 H), 3.79 (s, 3 H), 3.78 (s, 3 H), 3.36 (q, 2 H, J=5.3 Hz), 3.09 (q, 2 H, J=6.0 Hz), 2.75 (q, 2 H, J=5.0 Hz), 2.72 (d, 6 H, J=4.7 Hz), 2.30 (t, 2 H, J=6.1 Hz), 1.72 (quintet, 2 H, J=5.5 Hz); MALDI-TOF MS 964.2 (964.1 calc. for M+H)

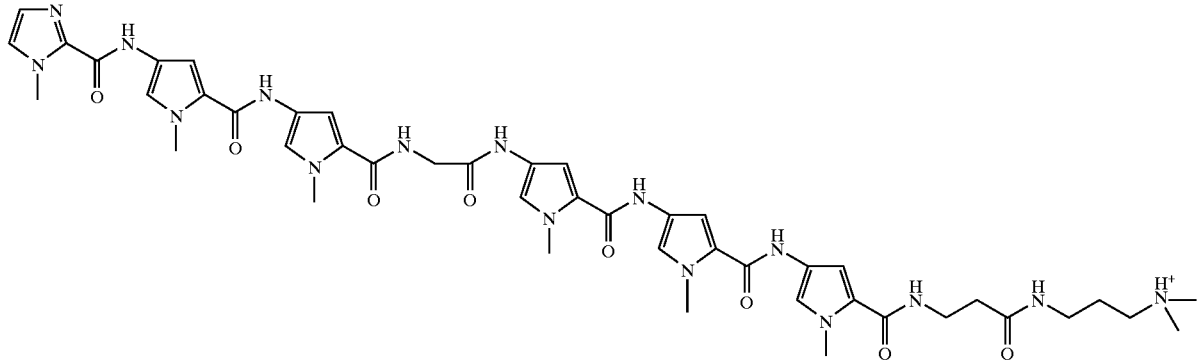

Polyamide was prepared by manual solid phase methods as a white powder upon cleavage of 180 mg resin (initial subsitution of 0.2 mmol Boc-β-alanine/gram) with dimethylaminopropylamine (2 mL, 55° C.). (12.3 mg, 38% recovery after HPLC purification). HPLC, r.t. 25.5, UV $\lambda_{max}$ ($\epsilon$), 246 (39,500), 312 (52,000) nm; $^1$H NMR (DMSO-d$_6$); 10.46 (s, 1 H), 9.96 (s, 1 H), 9.90 (s, 1 H), 9.88 (m, 2 H), 9.21 (br s, 1 H), 8.27 (t, 1 H, J=4.2 Hz), 8.06 (m, 2 H), 7.39 (s, 1 H), 7.28 (d, 1 H, J=1.6 Hz), 7.23 (d, 1 H, J=1.7 Hz), 7.20 (d, 1 H, J=1.5 Hz), 7.15 (m, 3 H), 7.04 (m, 2 H), 7.03 (d, 1 H, J=1.6 Hz), 6.94 (d, 1 H, J=1.7 Hz), 6.92 (d, 1 H, J=1.4 Hz), 3.98 (s, 3 H), 3.88 (d, 2 H, J=5.6 Hz), 3.83 (s, 3 H), 3.82 (m, 6 H), 3.79 (s, 3 H), 3.78 (s, 3 H), 3.36 (q, 2 H, J=5.3 Hz), 3.09 (q, 2 H, J=6.0 Hz), 2.75 (q, 2 H, J=5.2 Hz), 2.72 (d, 6 H, J=4.8 Hz), 2.30 (t, 2 H, J=6.3 Hz), 1.72 (quintet, 2 H, J=5.7 Hz) MALDI-TOF MS 950.1 (950.0 calc for M+H); FABMS m/e 949.462 (M+H 949.455 calc. for $C_{45}H_{57}N_{16}O_8$).

29. ImPyPy-γ-PyPyPy-G-Dp:

Polyamide was prepared by automated solid phase methods as a white powder upon cleavage of 180 mg resin (initial subsitution of 0.2 mmol Boc-Glycine/gram) with dimethylaminopropylamine (2 ml, 55° C.) (17.2 mg, 57% recovery after HPLC purification). HPLC, r.t. 26.5; UV $\lambda_{max}$ ($\epsilon$), 246 (46,500), 312 (54,800) nm; $^1$H NMR (DMSO-d$_6$) δ 10.54 (s, 1 H), 9.92 (s, 1 H), 9.90 (m, 3 H), 9.23 (br s, 1 H), 8.27 (t, 1 H, J=5.5 Hz), 8.06 (t, 1 H, J=6.3 Hz), 8.03 (t, 1 H, J=6.2 Hz), 7.39 (s, 1 H), 7.26 (d, 1 H, J=1.7 Hz), 7.20 (m, 2 H), 7.17 (m, 3 H), 7.13 (m, 2 H), 7.04 (d, 1 H, J=1.5 Hz), 6.87 (d, 1 H, J=1.8 Hz), 6.83 (d, 1 H, J=1.8 Hz), 3.97 (s, 3 H), 3.82 (m, 15 H), 3.78 (d, 2 H, J=3.4 Hz), 3.27 (m, 4 H), 3.15 (m, 2 H), 3.79 (m, 2 H), 2.76 (d, 6 H, J=4.9 Hz), 1.78 (quintet, 2 H, J=6.6 Hz) MALDI-TOF MS 950.2 (950.0 calc.

31. ImPyPy-Py-PyPyPy-G-Dp:

Polyamide was prepared by manual solid phase methods. Recovery is based on cleavage of 180 mg resin (initial subsitution of 0.2 mmol Boc-Glycine/gram) with dimethylaminopropylamine (2 ml, 55° C.). (8 mg, 24% recovery after HPLC purification). A small quantity of the failure heptamide AcPyPyPyPyPyPy-Dp was found in the initial preparation and was removed by a second preparatory HPLC purification to afford pure ImPyPy-Py-PyPyPy-G-Dp as a white powder (1.2 mg). HPLC, r.t. 28.5, UV $\lambda_{max}$ ($\epsilon$), 246 (34,600), 312 (55,300); $^1$H NMR (DMSO-d$_6$) δ 10.55 (s, 1 H), 10.02 (s, 1 H), 10.00 (m, 4 H), 9.3 (br s, 1 H), 8.32 (t, 1 H, J=6.2 Hz), 8.06 (t, 1 H, J=5.9 Hz), 7.44 (s, 1 H), 7.31 (d, 1 H, J=1.7 Hz), 7.26 (m, 5 H), 7.19 (d, 1 H, J=1.8 Hz), 7.10 (m, 5 H), 6.97 (d, 1 H, J=1.7 Hz), 4.01 (s, 3 H), 3.87 (m, 15 H), 3.82 (s, 3 H), 3.73 (d, 2 H, J=5.5 Hz), 3.16 (q, 2 H, J=6.2 Hz), 3.03 (q, 2 H, J=5.2 Hz), 2.74 (d, 6 H, J=4.9 Hz), 1.77 (quintet, 2 H, J=6.7 Hz); MALDI-TOF MS 1000.5; FABMS m/e 1001.471 (M+H 1001.473 calcd. for $C_{48}H_{59}N_{17}O_8$).

32. ImPyPy-Py-PyPyPy-β-Dp:

Polyamide was prepared by machine assisted solid phase synthesis to afford a white powder upon cleavage of 800 mg resin (initial subsitution of 0.2 mmol Boc-β-alanine/gram) with dimethylaminopropylamine (2 ml, 55° C.). (56 mg, 36% recovery after HPLC purification) ($\epsilon$) 246 (34,800), 308 (57,000); HPLC r.t. 27.9 min.; $^1$H NMR (DMSO-d$_6$) δ 10.47 (s, 1 H), 9.95 (m, 4 H), 9.89 (s, 1 H), 9.2 (br s, 1 H), 8.03 (m, 2 H), 7.39 (s, 1 H), 7.27 (d, 1 H, J=1.3 Hz), 7.22 (m, 4 H), 7.15 (m, 2 H), 7.07 (m, 4 H), 7.03 (d, 1 H, J=1.4 Hz), 6.86 (d, 1 H, J=1.0 Hz), 3.97 (s, 3 H), 3.84 (m, 12 H), 3.82 (s, 3 H), 3.77 (s, 3 H), (β-ala quartet covered by water.), 3.11 (q, 2 H, J=5.1 Hz), 3.08 (q, 2 H, J=6.0 Hz), 2.72 (d, 6 H, J=4.8 Hz), 2.34 (t, 2 H, J=4.4 Hz), 1.7 (m, 2 H); MALDI-TOF-MS, 1014.7 (1015.1 calc for M+H).

33. ImPyPy-G-PyPyPy-G-Dp:

Polyamide was prepared by manual solid phase methods as a white powder upon cleavage of 240 mg resin with N-methyl-bis(aminopropyl)amine (2 ml, 55° C.) (19.0 mg, 44% recovery after HPLC purification). $^1$H NMR (DMSO-$d_6$) δ 10.49 (s, 1 H), 9.97 (s, 1 H), 9.93 (s, 1 H), 9.91 (s, 1 H), 9.89 (s, 1 H), 9.7 (br s, 1 H), 8.27 (m, 2 H), 8.04 (t, 1 H, J=5.1 Hz), 7.88 (br s, 3 H), 7.39 (s, 1 H), 7.27 (d, 1 H, J=1.6 Hz), 7.21 (m, 3 H), 7.15 (m, 2 H), 7.05 (m, 2 H), 6.93 (m, 3 H), 3.97 (s, 3 H), 3.96 (m, 6 H), 3.92 (m, 9 H), 3.72 (m, 4 H), 3.14 (m, 6 H), 3.05 (q, 2 H, J=5.4 Hz), 2.73 (d, 3 H, J=3.3 Hz), 1.88 (quintet, 2 H, J=4.6 Hz), 1.75 (quintet, 2 H, J=6.3 Hz). MALDI-TOF-MS, 979.0 (979.1 calc for M+H).

34. ImPyPy-G-PyPyPy-β-Bp:

Polyamide was prepared by manual solid phase methods as a white powder upon cleavage of 240 mg resin with N-methyl-bis(aminopropyl)amine (2 ml, 55° C.) (25 mg, 55% recovery). HPLC, r.t. 22.0; $^1$H NMR (DMSO-$d_6$) δ 10.53 (s, 1 H), 10.00 (s, 1 H), 9.98 (s, 1 H), 9.93 (s, 1 H), 9.92 (s, 1 H), 9.7 (br s, 1 H), 8.31 (t, 1 H, J=5.7 Hz), 8.12 (t, 1 H, J=5.5 Hz), 8.04 (t, 1 H, J=5.6 Hz), 7.9 (br s, 3 H), 7.41 (s, 1 H), 7.29 (d, 1 H, J=1.7 Hz), 7.23 (d, 1 H, J=1.5 Hz), 7.22 (d, 1 H, J=1.4 Hz), 7.16 (m, 3 H), 7.07 (d, 1 H, J=1.2 Hz), 7.03 (d, 1 H, J=1.3 Hz), 6.94 (d, 1 H, J=1.6 Hz), 6.93 (d, 1 H, J=1.5 Hz), 6.86 (d, 1 H, J=1.4 Hz), 3.98 (s, 3 H), 3.88 (d, 2 H, J=5.6 Hz), 3.83 (s, 3 H), 3.82 (m, 6 H), 3.80 (s, 3 H), 3.78 (s, 3 H), 3.37 (q, 2 H, J=6.4 Hz), 3.11 (m, 6 H), 2.86 (q, 2 H, J=6.1 Hz), 2.70 (d, 3 H, J=4.6 Hz), 2.32 (t, 2 H, J=7.2 Hz), 1.87 (quintet, 2 H, J=7.4 Hz), 1.75 (quintet, 2 H, J=6.0 Hz), MALDI-TOF-MS, 993.3 (993.1 calc for M+H).

35. ImPyPy-β-PyPyPy-G-Dp:

Polyamide was prepared by automated solid phase methods as a white powder upon cleavage of 240 mg resin with N-methyl-bis(aminopropyl)amine (2 ml, 55° C.) (23.0 mg, 53% recovery). HPLC, r.t. 20.6; $^1$H NMR (DMSO-$d_6$) δ 10.45 (s, 1 H), 9.95 (s, 1 H), 9.92 (m, 3 H), 9.6 (br s, 1 H), 8.27 (t, 1 H, J=4.7 Hz), 8.11 (m, 2 H), 7.9 (s, 3 H), 7.38 (s, 1 H), 7.26 (d, 1 H, J=1.7 Hz), 7.21 (m, 2 H), 7.17 (m, 2 H), 7.13 (d, 1 H, J=1.8 Hz), 7.05 (m, 2 H), 6.93 (d, 1 H, J=1.6 Hz), 6.88 (d, 1 H, J=1.6 Hz), 6.83 (d, 1 H, J=1.7 Hz), 3.97 (s, 3 H), 3.82 (s, 9 H), 3.81 (s, 3 H), 3.79 (s, 3 H), 3.73 (m, 2 H), 3.44 (q, 2 H, J=5.5 Hz), 3.2 (m, 6 H), 2.85 (q, 2 H, J=5.8 Hz), 2.73 (d, 3 H, J=4.5 Hz), 1.89 (quintet, 2 H, J=6.4 Hz), 1.77 (quintet, 2 H, J=6.9 Hz) MALDI-TOF-MS, 992.9 (993.1 calc for M+H).

36. ImPyPy-G-PyPyPy-G-Dp-EDTA:

EDTA-dianhydride (50 mg) was dissolved in 1 mL DMSO/NMP solution and 1 mL DIEA by heating at 55° C. for 5 min. The dianhydride solution was added to ImPyPy-G-PyPyPy-G-Bp (12.0 mg, 11 μmol) dissolved in 750 μL DMSO. The mixture was heated at 55° C. for 25 minutes, and treated with 3 mL 0.1M NaOH, and heated at 55° C. for 10 minutes. 0.1% TFA was added to adjust the total volume to 8 mL and the solution purified directly by preparatory HPLC chromatography to provide ImPyPy-G-PyPyPy-G-Bp-EDTA as a white powder. (4.7 mg, 31% recovery after HPLC purification); HPLC, r.t. 28.8; $^1$H NMR (DMSO-$d_6$) δ 10.49 (s, 1 H), 9.97 (s, 1 H), 9.91 (s, 1 H), 9.89 (m, 2 H), 9.4 (br s, 1 H), 8.42 (t, 1 H, J=5.0 Hz), 8.31 (t, 1 H, J=5.5 Hz), 8.00 (m, 2 H), 7.38 (s, 1 H), 7.26 (d, 1 H, J=1.5 Hz), 7.22 (d, 1 H, J=1.4 Hz), 7.20 (d, 1 H, J=1.4 Hz), 7.14 (m, 3 H), 7.03 (m, 2 H), 6.92 (d, 1 H, J=1.5 Hz), 3.95 (s, 3 H), 3.85 (m, 4 H), 3.84 (s, 3 H), 3.80 (m, 6 H), 3.78 (s, 3 H), 3.76 (s, 3 H), 3.69 (m, 6 H), 3.55 (q, 2 H, J=5.7 Hz), 3.3–3.0 (m, 12 H), 2.69 (d, 3 H, J=3.9 Hz), 2.31 (t, 2 H, J=6.8 Hz), 1.73 (m, 4 H); MALDI-TOF-MS, 1254.8 (1254.3 calc for M+H).

37. ImPyPy-G-PyPyPy-β-Bp-EDTA:

Polyamide was prepared from ImPyPy-G-PyPyPy-β-Bp (20 mg) as described for ImPyPy-G-PyPyPy-G-Bp-EDTA. (13.0 mg, 55% recovery after HPLC purification). HPLC, r.t. 27.3; $^1$H NMR (DMSO-$d_6$) δ 10.49 (s, 1 H), 9.97 (s, 1 H), 9.91 (s, 1 H), 9.89 (m, 2 H), 9.4 (br s, 1 H), 8.42 (t, 1 H, J=5.0 Hz), 8.31 (t, 1 H, J=5.5 Hz), 8.00 (m, 2 H), 7.38 (s, 1 H), 7.26 (d, 1 H, J=1.5 Hz), 7.22 (d, 1 H, J=1.4 Hz), 7.20 (d, 1 H, J=1.4 Hz), 7.14 (m, 3 H), 7.03 (m, 2 H), 6.92 (d, 1 H, J=1.5 Hz), 3.95 (s, 3 H), 3.85 (m, 4 H), 3.84 (s, 3 H), 3.80 (m, 6 H), 3.78 (s, 3 H), 3.76 (s, 3 H), 3.69 (m, 6 H), 3.55 (q, 2 H, J=5.7 Hz), 3.3–3.0 (m, 12 H), 2.69 (d, 3 H, J=3.9 Hz), 2.31 (t, 2 H, J=6.8 Hz), 1.73 (m, 4 H); MALDI-TOF-MS, 1268.5 (1268.3 calc for M+H).

38. ImPyPy-β-PyPyPy-G-Bp-EDTA:

Polyamide was prepared from ImPyPy-β-PyPyPy-G-Bp (12 mg) as described for ImPyPy-G-PyPyPy-G-Bp-EDTA. (6 mg, 42% recovery after HPLC purification). HPLC, r.t. 28.0; $^1$H NMR (DMSO-$d_6$) δ 10.46 (s, 1 H), 9.95 (s, 1 H), 9.93 (m, 3 H), 9.9 (br s, 1 H), 8.43 (t, 1 H, J=5.1 Hz), 8.28 (t, 1 H, J=5.3 Hz), 8.03 (m, 2 H), 7.38 (s, 1 H), 7.26 (m, 2 H), 7.21 (d, 1 H, J=1.6 Hz), 7.17 (d, 1 H, J=1.8 Hz), 7.12 (d, 1 H, J=1.8 Hz), 7.10 (s, 1 H), 7.04 (d, 1 H, J=1.6 Hz), 6.93 (m, 2 H), 6.88 (d, 1 H, J=1.6 Hz), 6.84 (d, 1 H, J=1.4 Hz), 3.97 (s, 3 H), 3.87 (m, 4 H), 3.82 (m, 9 H), 3.79 (s, 3 H), 3.78 (s, 3 H), 3.68 (m, 6 H), 3.3–2.9 (m, 16 H), 2.71 (d, 3 H, J=4.1 Hz), 1.78 (m, 4 H); MALDI-TOF-MS, 1268.9 (1268.3 calc for M+H).

39. ImPyPy-γ-ImPyPy-β-PyPyPy-G-Dp:

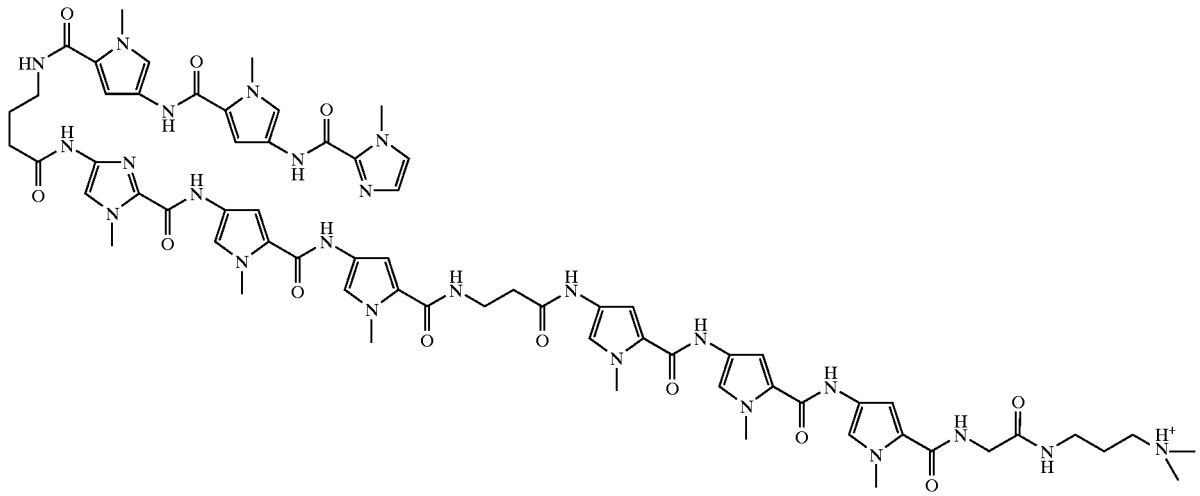

The polyamide was prepared by machine-assisted solid phase methods as a white powder. (12 mg 19% recovery). HPLC r.t. 29.5, UV $\lambda_{max}$ (ε), 238 (53,900), 312 (71,100) nm; $^1$H NMR (DMSO-$d_6$); d 10.46 (s, 1 H), 10.24 (s, 1 H), 9.96 (s, 1 H), 9.90 (m, 5 H), 9.2 (br s, 1 H), 8.25 (m, 1 H), 8.00 (m, 3 H), 7.44 (s, 1 H), 7.39 (s, 1 H), 7.26 (d, 1 H, J=1.3 Hz), 7.24 (d, 1 H, J=1.5 Hz), 7.20 (m, 2 H), 7.16 (m, 2 H), 7.13 (m, 2 H), 7.11 (d, 1 H, J=1.4 Hz), 7.05 (d, 1 H, J=1.4 Hz), 7.03 (d, 1 H, J=1.5 Hz), 6.93 (d, 1 H, J=1.3 Hz), 6.87 (m, 2 H), 6.84 (d, 1 H, J=1.5 Hz), 3.97 (s, 3 H), 3.92 (s, 3 H), 3.82 (m, 9 H), 3.79 (m, 6 H), 3.76 (m, 6 H), 3.73 (m, 2 H), 3.44 (q, 2 H, J=5.0 Hz), 3.17 (m, 4 H), 3.03 (m, 2 H), 2.74 (d, 6 H, J=4.8 Hz), 2.50 (m, 2 H), 2.33 (t, 2 H, J=6.7 Hz), 1.77 (m, 4 H). MALDI-TOF MS 1402.2 (1402.5 calc for M+H).

40. ImPyPy-γ-ImPyPy-β-PyPyPy-G-Dp-NH$_3$

The polyamide was prepared by machine-assisted solid phase methods as a white powder. (29 mg 59% recovery). HPLC r.t. 21.5, $^1$H NMR (DMSO-$d_6$); δ 10.50 (s, 1 H), 10.27 (s, 1 H), 9.96 (s, 1 H), 9.93 (m, 5 H), 9.2 (br s, 1 H), 8.27 (t, 1 H, J=5.1 Hz), 8.03 (m, 3 H), 7.90 (s, 3 H), 7.45 (s, 1 H), 7.40 (s, 1 H), 7.27 (d, 1 H, J=1.3 Hz), 7.25 (d, 1 H, J=1.4 Hz), 7.22 (m, 2 H), 7.18 (m, 2 H), 7.17 (d, 1 H, J=1.4 Hz), 7.14 (d, 1 H, J=1.3 Hz), 7.11 (m, 2 H), 7.06 (d, 1 H, J=1.5 Hz), 6.94 (d, 1 H, J=1.3 Hz), 6.88 (m, 2 H), 6.84 (d, 1 H, J=1.4 Hz), 3.97 (s, 3 H), 3.93 (s, 3 H), 3.83 (m, 9 H), 3.80 (m, 6 H), 3.76 (m, 6 H), 3.72 (d, 2 H, J=5.2 Hz), 3.43 (q, 2 H, J=5.0 Hz), 3.17 (m, 6 H), 3.11 (q, 2 H, J=5.3 Hz), 2.85 (q, 2 H, J=5.2 Hz), 2.73 (d, 3 H, J=3.9 Hz), 2.51 (t, 2 H, J=6.5 Hz), 2.35 (t, 2 H, J=6.7 Hz), 1.92 (quintet, 2 H, J=6.8 Hz), 1.78 (m, 4 H). MALDI-TOF MS 1445.6 (1445.6 calc for M+H).

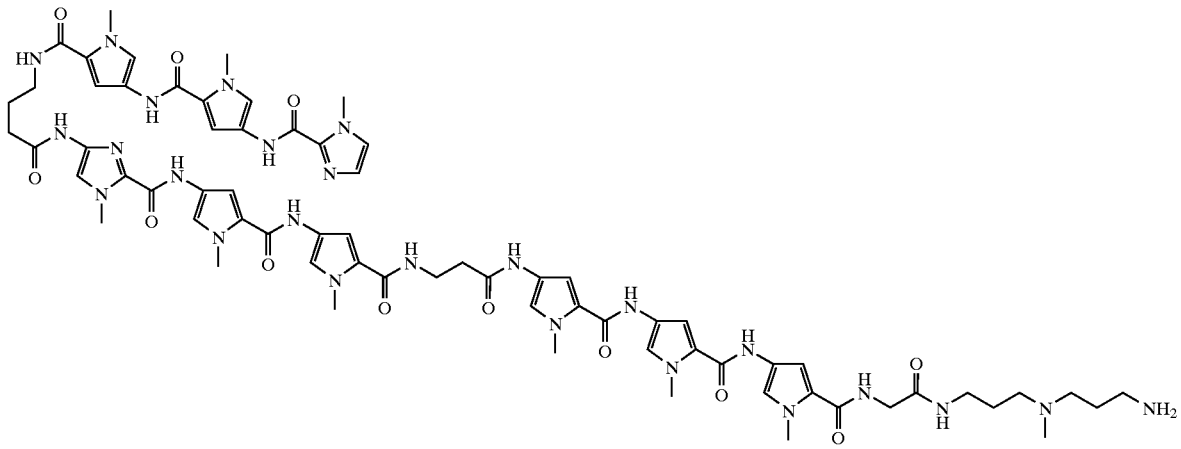

41. ImPyPy-γ-ImPyPy-β-PyPyPy-G-Dp-EDTA:

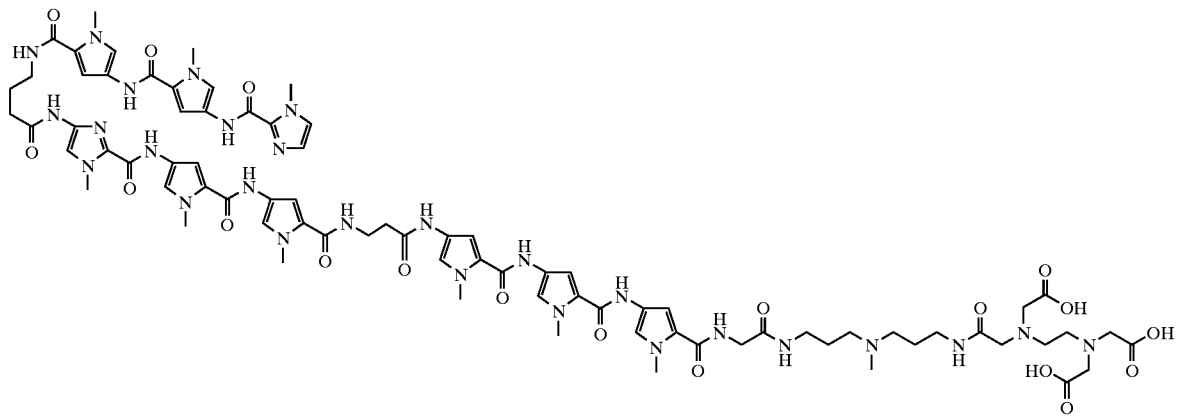

EDTA-dianhydride (50 mg) was dissolved in 1 mL DMSO/NMP solution and 1 mL DIEA by heating at 55° C. for 5 min. The dianhydride solution was added to ImPyPy-γ-ImPyPy-β-PyPyPy-G-Dp-NH$_2$ (9.0 mg, 5 μmol) dissolved in 750 μL DMSO. The mixture was heated at 55° C. for 25 minutes, and treated with 3 mL 0.1M NaOH, and heated at 55° C. for 10 minutes. 0.1% TFA was added to adjust the total volume to 8 mL and the solution purified directly by reversed-phase HPLC to provide ImPyPy-γ-ImPyPy-β-PyPyPy-G-Dp-EDTA as a white powder. (3 mg, 30% recovery after HPLC purification); MALDI-TOF MS 1720.1 (1719.8 calc for M+H).

42. Ac-PyImPy-γ-ImPyPy-β-PyPyPy-β-Dp:

3 H), 9.90 (s, 1 H), 9.85 (s, 1 H), 8.6 (br s, 1 H), 8.08 (m, 4 H), 7.52 (s, 1 H); 7.43 (s, 1 H); 7.24 (m, 2 H), 7.22 (d, 1 H, J=1.7 Hz), 7.20 (d, 1 H, J=1.6 Hz), 7.19 (d, 1 H, J=1.6 Hz), 7.14 (d, 1 H, J=1.5 Hz), 7.11 (d, 1 H, J=1.6 Hz), 7.07 (m, 2 H), 7.02 (d, 1 H, J=1.4 Hz), 6.96 (d, 1 H, J=1.7 Hz), 6.90 (m, 2 H), 6.88 (d, 1 H, J=1.8 Hz), 6.83 (d, 1 H, J=1.6 Hz), 3.94 (s, 3 H), 3.92 (s, 3 H), 3.81 (m, 12 H), 3.79 (s, 3 H), 3.78 (s, 3 H), 3.78 (s, 3 H), 3.52 (m, 4 H), 3.33 (m, 6 H), 2.95 (m, 2 H), 2.71 (d, 6 H, J=4.7 Hz), 2.32 (m, 4 H), 1.94 (s, 3 H), 1.73 (m, 4 H). MALDI-TOF MS; 1472.1 (1472.5 calc for M+H).

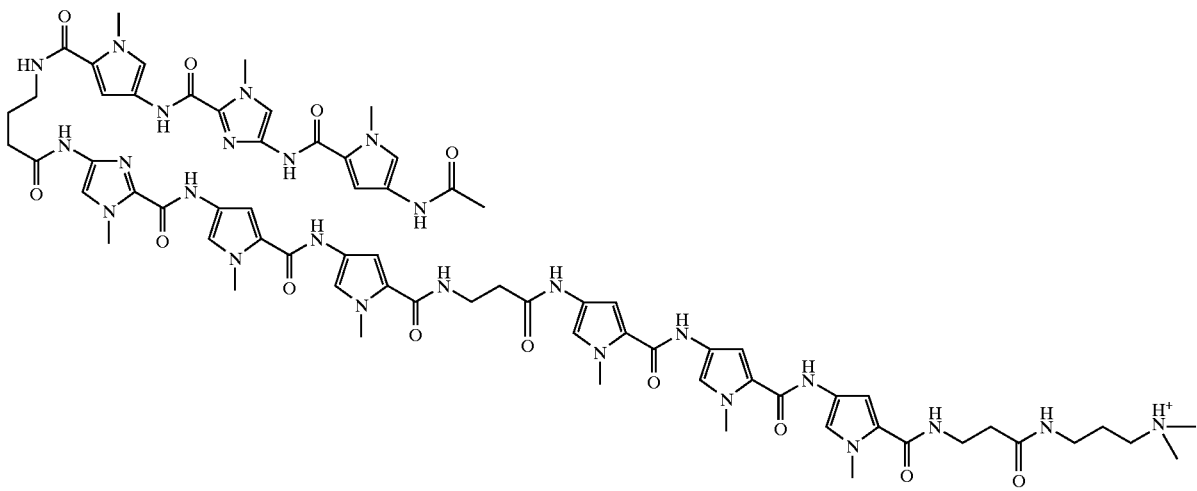

43. DM-γ-PyImPy-γ-ImPyPy-β-PyPyPy-β-Dp:

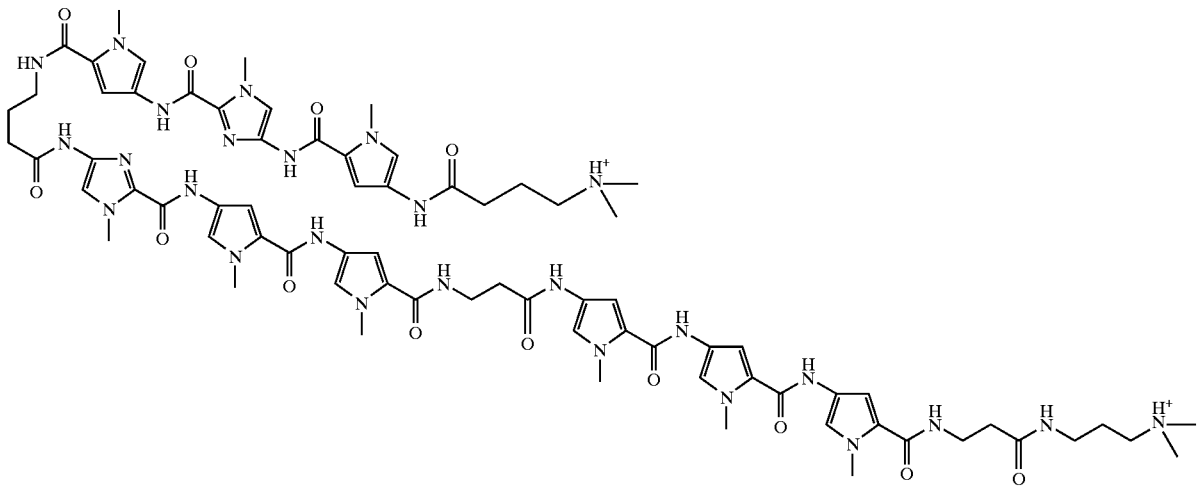

The polyamide was prepared by machine assisted solid phase methods (29) as a white powder (5 mg, 20% recovery). UV (H2O) λ$_{max}$ 242 nm, 310 nm (ε=75,000, calculated based on ε=8333/ring (30)); $^1$H NMR (DMSO-d$_6$): δ 10.27 (m, 2 H); 10.02 (s, 1 H); 9.99 (s, 1 H), 9.92 (m, The polyamide was prepared by machine assisted solid phase methods as a white powder (13 mg, 52% recovery). UV (H2O) λ$_{max}$ 242 nm, 310 nm (ε=75,000, calculated based on ε=8333/ring(30)); $^1$H NMR (DMSO-d$_6$): δ 10.28 (s, 1 H); 10.26 (s, 1 H), 9.99 (s, 1 H), 9.96 (s, 1 H), 9.94 (s, 1 H), 9.90 (m, 3 H), 9.88 (s, 1 H), 9.3 (br s, 1 H), 9.2 (br s, 1 H), 8.05 (m, 4 H), 7.52 (s, 1 H); 7.43 (s, 1 H); 7.27 (d, 1 H, J=1.6 Hz), 7.24 (d, 1 H, J=1.7 Hz), 7.20 (d, 1 H, J=1.6 Hz), 7.17 (m, 4 H), 7.14 (d, 1 H, J=1.6 Hz), 7.12 (d, 1 H, J=1.5 Hz), 7.03 (d, 1 H, J=1.6 Hz), 6.96 (d, 1 H, J=1.6 Hz), 6.90 (d, 1 H, J=1.5 Hz), 6.86 (m, 2 H), 3.94 (s, 3 H), 3.92 (s, 3 H), 3.81 (m, 12 H), 3.78 (m, 9 H), 3.56 (m, 4 H), 3.39 (m, 6 H), 2.95 (m, 4 H), 2.76 (d, 6 H, J=4.6 Hz), 2.71 (d, 6 H, J=4.6 Hz), 2.30 (m, 4 H), 1.88 (m, 2 H), 1.73 (m, 4 H). MALDI-TOF MS; 1543.3 (1543.6 calc for M+H).

44. DM-γ-ImPyPy-γ-ImPyPy-β-PyPyPy-β-PyPyPy-β-Dp:

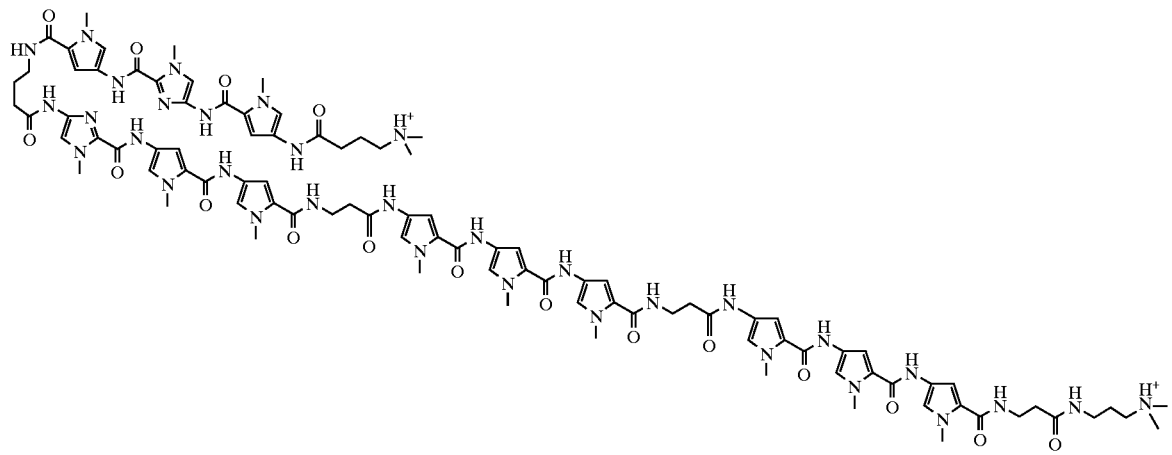

The polyamide was prepared by machine assisted solid phase methods as a white powder (3 mg, 10% recovery). UV (H2O) λ$_{max}$ 239 nm, 308 nm (ε=100,000, calculated based on ε=8333/ring); MALDI-TOF MS; 1981.3 (1981.1 calc for M+H).

45. ImPyPyPy-γ-ImPyPyPy-β-Dp:

Polyamide ImPyPyPy-γ-ImPyPyPy-β-Dp was prepared by machine-assisted solid phase methods as a white powder (17 mg, 56% recovery). HPLC, r.t.: 26.1 min; UV, λ$_{max}$ (ε): 234 nm (39,300), 312 nm (53,200); $^1$H NMR (DMSO-d$_6$): δ10.53 (s, 1H), 10.27 (s, 1H), 10.04 (s, 1H), 9.96 (s, 1H), 9.94 (s, 1H), 9.2 (br s, 1H), 8.08 (m, 3H), 7.49 (s, 2H), 7.44 (s, 1H), 7.31 (d, 1H, J=1.0 Hz), 7.23 (d, 1 H, J=1.1 Hz), 7.19 (m, 3H), 7.10 (s, 1H), 6.92 (d, 1 H, J=1.1 Hz), 6.90 (d, 1 H, J=1.1 Hz. 4.01 (s, 3H), 3 .97 (s, 3H), 3.86 (m, 6H), 3.82 (m, 6H), 3.41 (q, 2 H, J=6.0 Hz), 3.22 (q, 2 H, J=5.9 Hz), 3 .13 (q, 2 H, J=5.9 Hz), 3.0 (q, 2 H, J=5.6 Hz), 2.76 (d, 6 H, J=4.8 Hz), 2.37 (m, 4H), 1.78 (m, 4H); MALDI-TOF MS: 1223.4 (1223.3 calc. for M+H).

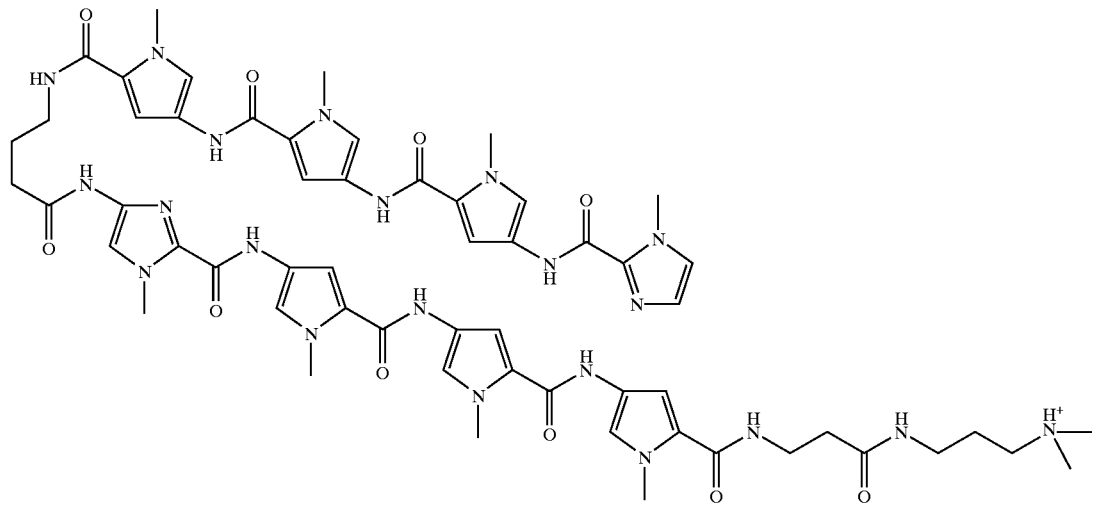

46. ImPyPyPy-γ-PyPyPyPy-β-Dp:

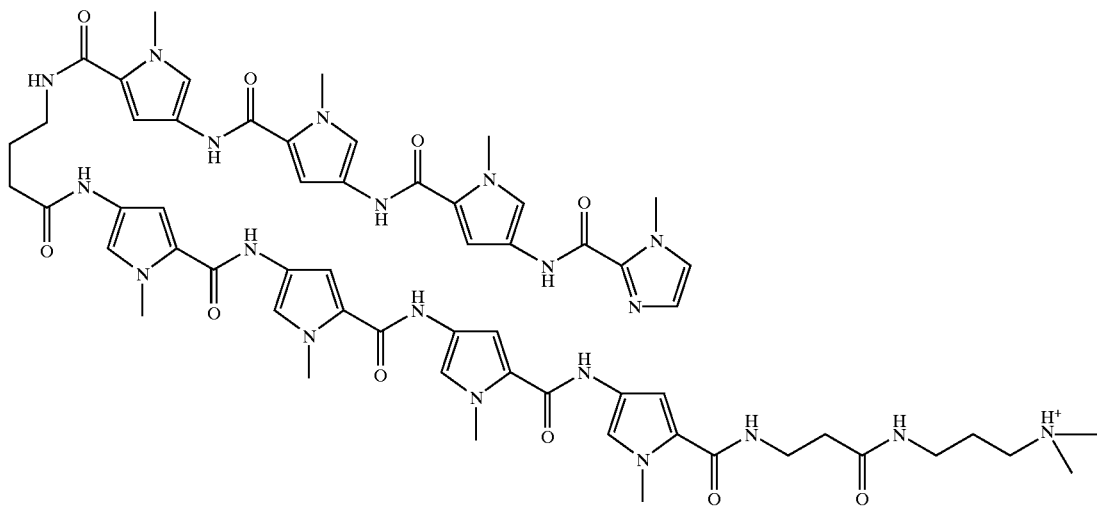

The polyamide ImPyPyPy-γ-PyPyPyPy-β-Dp was prepared by machine-assisted solid phase methods as a white powder (12 mg, 19% recovery). HPLC, r.t.: 29.5 min; UV, $\lambda_{max}$ (ε): 238 nm (53,900), 312 nm (71,100); $^1$H NMR (DMSO-d$_6$): δ10.46 (s, 1H), 10.24 (s, 1H), 9.96 (s, 1H), 9.90 (m, 5H), 9.2 (br s, 1H), 8.25 (m, 1H), 8.00 (m, 3H), 7.44 (s, 1H), 7.39 (s, 1H), 7.26 (d, 1 H, J=1.3 Hz), 7.24 (d, 1 H, J=1.5 Hz), 7.20 (m, 2H), 7.16 (m, 2H), 7.13 (m, 2 H), 7.11 (d, 1 H, J=1.4 Hz), 7.05 (d, 1 H, J=1.4 Hz), 7.03 (d, 1 H, J=1.5 HZ), 6.93 (d, 1 H, J=1.3 Hz), 6.87 (m, 2H), 6.84 (d, 1 H, J=1.5 Hz), 3.97 (s, 3H), 3.92 (s, 3H), 3.82 (m, 9H), 3.79 (m, 6H), 3.76 (m, 6H), 3.73 (m, 2 H), 3.44 (q, 2 H, J=5.0 Hz), 3.17 (m, 4H), 3.03 (m, 2H), 2.74 (d, 6 H, J=4.8 Hz), 2.50 (m, 2H) 2.33 (t, 2 H, J=6.7 Hz), 1.77 (m, 4H); MALDI-TOF MS: 1222.3 (1222.3 calc for M+H).

47. ImImImPy-γ-PyPyPyPy-β-Dp:

The product was synthesized by manual solid phase protocols and recovered as a white powder (7.6 mg, 11% recovery). UV $\lambda_{mix}$, $_{248}$ (42,000), 312 (48,500); $^1$H NMR (DMSO-d$_6$) d 10.32 (s, 1H), 10.13 (s, 1H) 9.93 (s, 1H), 9.90 (s, 1H), 9.89 (s, 1H), 9.84 (s, 1H), 9.59 (s, 1H), 9.23 (br s, 1H), 8.09 (t, 1 H, J=5.3 Hz), 8.04 (m, 2H), 7.65 (s, 1H), 7.57 (s, 1H), 7.46 (d, 1 H, J=0.6 Hz) 7.22 (m, 3H), 7.16 (s, 2H), 7.09 (d, 1 H, J=0.8 Hz), 7.06 (d, 2 H, J=1.1 Hz), 7.00 (d, 1 H, J=1.7), 6.88 (d, 1 H, J=1.8), 6.87 (d, 1 H, J=1.8 Hz), 4.02 (s, 3H), 4.00 (s, 3H), 3.99 (s, 3H), 3.84 (s, 3H), 3.83 (s, 3H), 3.83 (s, 3H), 3.80 (s, 3H), 3.79 (s, 3H), 3.37 (q, 2 H, J=6.2 Hz), 3.21 (q, 2 H, J=6.4 Hz), 3.10 (q, 2 H, J=6.2 Hz), 3.00 (m, 2H), 2.73 (d, 6 H, J=4.9 Hz), 2.34 (t, 2 H, J=7.2 Hz), 2.28 (t, 2 H, J=7.0 Hz), 1.76 (m, 4H); MALDI-TOF-MS, 1225.9 (1224.3 calc. for M+H).

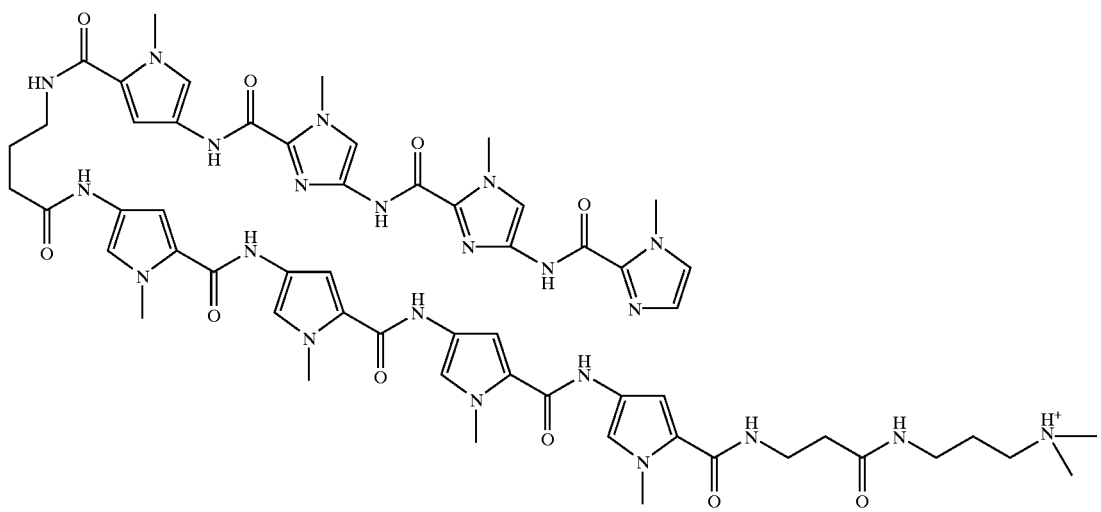

48. ImImImPy-γ-PyPyPyPy-β-Dp-NH₂:

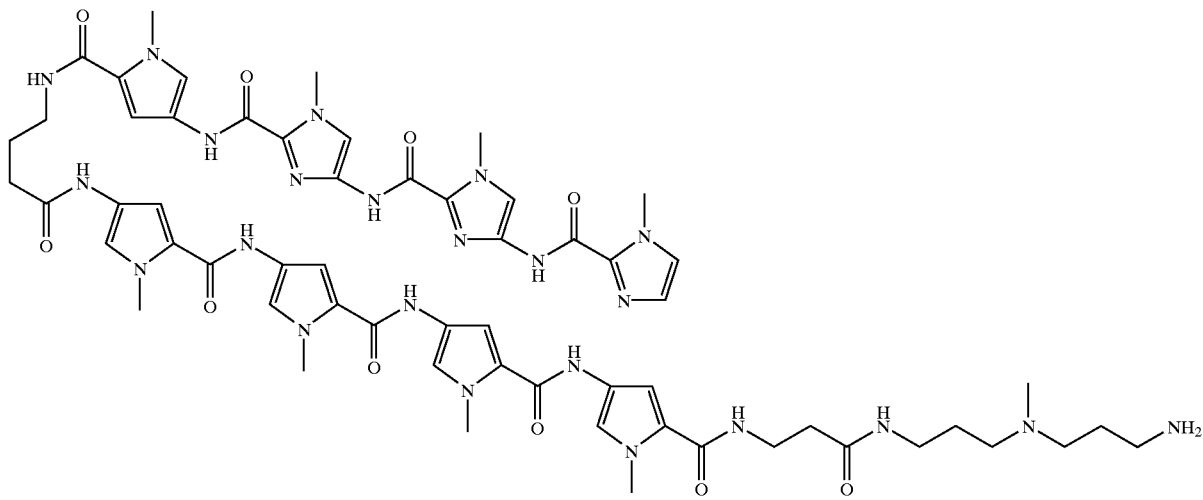

A sample of polyimide machine-synthesized on resin (350 mg, 0.16 mmol/gram) was placed in a 20 mL glass scintillation vial, and treated with 2 mL 3,3'-diamino-N-methyldipropylamine at 55° C. for 18 hours. The resin was removed by filtration through a disposable propylene filter, and the resulting solution dissolved with water to a total volume of 8 mL, and purified directly by preparatory reversed phase HPLC to provide ImImImPy-γ-PyPyPyPy-β-Dp-NH₂ (31 mg, 40% recovery) as a white powder. ¹H NMR (DMSO-d₆) δ10.37 (s, 1H), 10.16 (s, 1H), 9.95 (s, 1H), 9.93 (s, 1H), 9.91 (s, 1H), 9.86 (s, 1H), 9.49 (br s, 1H), 9.47 (s, 1H), 8.12 (m, 3H), 8.0 (br s , 3H), 7.65 (s, 1H), 7.57 (s, 1H), 7.46 (s, 1H), 7.20 (m, 3H), 7 .16 (m, 2H), 7.09 (d, 1 H, J=1.5 Hz), 7.05 (m, 2H), 7.00 (d, 1 H, J=1.6 Hz), 6.88 (m, 2H), 4.01 (s, 3H), 3.99 (s, 3H), 3.98 (s, 3H), 3.83 (s, 3H), 3.82 (s, 3H), 3.81 (s, 3H), 3.79 (s, 3H), 3.78 (s, 3H), 3.36 (q, 2 H, J=5.3 Hz), 3.21–3.05 (m, 8H), 2.85 (q, 2 H, J=4.9 Hz), 2.71 (d, 3 H, J=4.4 Hz), 2.34 (t, 2 H, J=5.9 Hz), 2.26 (t, 2 H, J=5.9 Hz), 1.85 (quintet, J=5.7 Hz), 1.72 (m, 4H). MALDI-TOF-MS, 1267.1 (1267.4 calc. For M+H).

49. ImImImPy-γ-PyPyPyPy-β-DP-EDTA:

Compound was prepared as described for ImImIm-γ-PyPyPy-(β-Dp-EDTA. (3.8 mg, 40%). ¹H NMR (DMSO-d₆) δ10.34 (s, 1H), 10.11 (s, 1H), 9.92 (s, 1H), 9.90 (s, 1H), 9.89 (s, 1H), 9.84 (s, 1H), 9.57 (s, 1H), 8.42 (m, 1H), 8.03 (m, 3H), 7.64 (s, 1H), 7.56 (s, 1H), 7.44 (s, 1H), 7.20 (m, 3H), 7.15 (m, 2H), 7.07 (d, 1 H, J=1,6 Hz), 7.05 (m, 2H), 6.99 (d, 1 H, J=1.6 Hz), 6.87 (m, 2H), 4.00 (s, 3H), 3.98 (s, 3H), 3.97 (s, 3H), 3.83 (m, 4H), 3.82 (s, 6 H), 3.79 (s, 3H), 3.78 (s, 6H), 3.67 (m, 4H), 3.4–3.0 (m, 16H), 2.71 (d, 3 H, J=4.2 Hz), 2.34 (t, 2 H, J=5.4 Hz), 2.25 (t, 2 H, J=5.9 Hz), 1.72 (m, 6H). MALDI-TOF-MS, 1542.2 (1542.6 calc. for M+H). The polyimide was loaded with Fe (II) by standard methods.

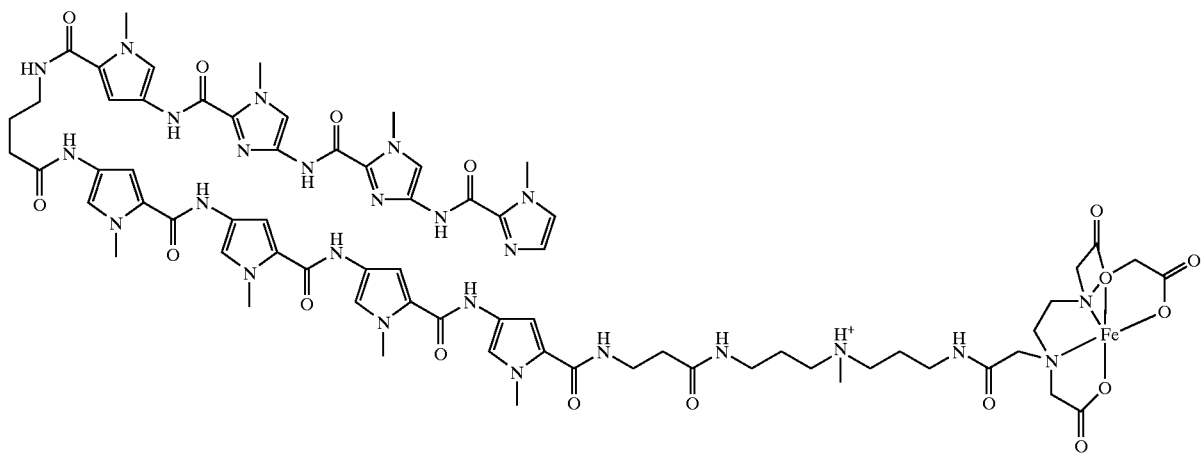

50. ImImPyPy-γ-ImImPyPy-β-Dp:

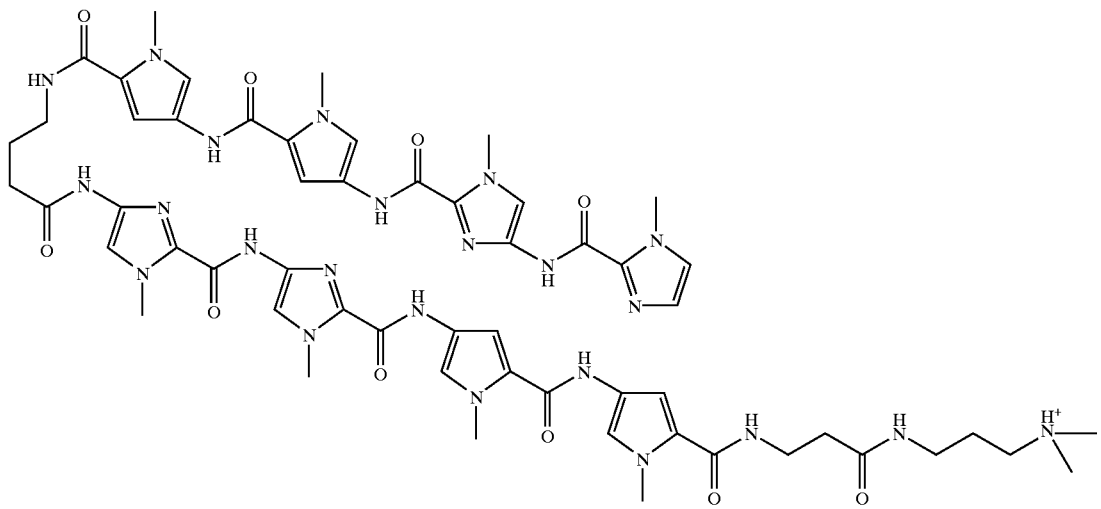

The polyimide ImImPyPy-γ-ImImPyPy-β-PAM-Resin was assembled on 0.2 mmol/gram Box-β-PAM-resin by machine assisted synthesis. The γ-Im step was assembled using Boc-γ-Im, acid (HBTU, DIEA), all other residues was added as appropriate activated Boc protected monomer units. A sample of resin (250 mg, 0.16 mmol/gram[21]) was placed in a 20 mL glass scintillation vial, 2 mL dimethylaminopropylamine added and the mixture allowed to stand at 55° C. for 18 hours. Resin was removed by filtration through a disposable propylene filter, and the resulting solution diluted with water to a total volume of e mL, and purified directly by preparatory reversed phase HPLC to provide ImImPyPy-γImImPyPy-β-Dp (26 mg, 45% recovery) as a white powder. UV $\lambda_{max}(H_2O)$ 248, 312 (66,000); $^1$H NMR (DMSO-$d_6$) d 10.34 (m, 2 H); 10:32 (m, 2H); 9.73 (m, 2H); 9.5 (br s, 1H), 9.32 (s, 1H); 8.10 (m, 3H); 7.55 (m, 2H); 7.52 (s, 1H); 7.44 (s, 1H); 7.23 (m, 2H), 7.14 (m, 4H); 7.06 (d, 1 H, J=1.4 Hz); 6.86 (m, 2H); 3.98 (m, 9H); 3.95 (s, 3H); 3.81 (m, 6H); 3.77 (m, 6H); 3.31 (m, 2H); 3.17 (t, 2 H, J=5.5 Hz) 3.06 (m, 2 H, J=5.7 Hz); 2.93 (m, 2 H, J=4.7 Hz); 2.74 (d, 6 H, J=4.4 Hz); 2.30 (m, 4H); 1.74 (m, 4H); MALDI-TOF-MS, 1224.9 (1225.3 calc. for M+H).

51. ImPyImPy-γ-ImPyImPy-β-Dp:

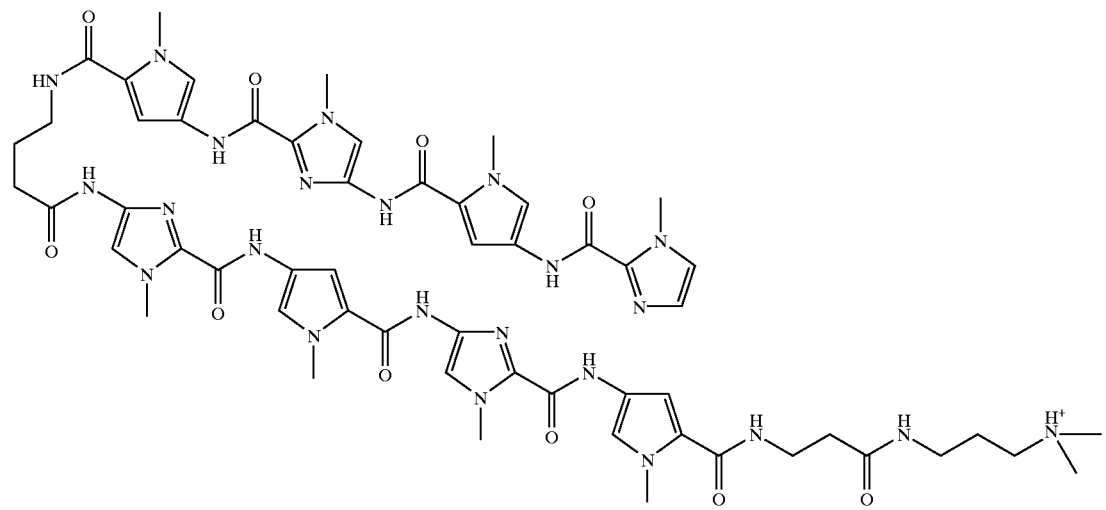

The polyamide ImPyImPy-γ-ImPyImPy-β-PAM-Resin was assembled on 0.2 mmol/gram Boc-β-PAM-resin by manual polyamide synthesis. The Py-Im and γ-Im steps were addedusing Boc-λ-Im acid and Boc-Py-Im acid (HBTU, DIEA), all other residues were added as appropriate activated Boc protected monomer units. A sample of resin (250 mg, 0.16 mmol/gram[21]) was placed in a 20 mL glass scintillation vial, 2 mL dimethylaminopropylamine added and the mixture allowed to stand at 55° C. for 18 hours. Resin was removed by filtration through a disposable propylene filter, and the resulting solution diluted with water to a total volume of 8 mL, and purified directly by preparatory reversed phase HPLC to provide ImPyImPy-γ-ImPyImPy-β-Dp (19 mg, 32% recovery) as a white powder. UV $\lambda_{max}(H_2O)$ 246, 312 (66,000); $^1$H NMR (DMSO-$d_6$) d 10.33 (m, 2H); 10.25 (m, 2H); 10.04 (m, 2H) ; 9.95 (s, 1H); 9.5 (br s, 1H), 8.10 (m, 3H); 7.57 (m, 2H); 7.48 (s, 1H); 7.42 (s, 1H); 7,40 (s, 1H); 7.23 (m, 2H), 7.17 (d, 1 H; J=1.5 Hz); 7.03

(d, 1 H, J=1.5 Hz); 6.98 (m, 3H); 4.02 (s, 3H); 3.99 (m, 6H); 3.81 (m, 6H); 3.97 (s, 3H); 3.88 (m, 6H); 3.83 (m, 6H); 3.42 (m, 2H); 3.18 (t, 2 H, J=5.2 Hz) 3.06 (m, 2 H, J=5.5 Hz); 2.80 (m, 2 H, J=4.7 Hz); 2.76 (d, 6 H, J=4.4 Hz), 2.38 (m, 4H); 1.93 (m, 4H); MALDI-TOF-MS, 1225.2. (1225.3 calc. for M+H).

d 9.91 (m, 2 H); 9.89 (m, 4H); 9.83 (s, 1H); 9.60 (s, 1H); 9.5 (br s, 1H); 8.34 (m, 1H); 8.10 (m, 2H); 7.63 (m, 2H); 7.50 (s, 1H); 7.42 (s, 1H); 7.19 (m, 2H); 7.13 (m, 2H); 7.04 (m, 2H); 6.86 (m, 2H); 1.98 (m, 6H); 3.96 (s, 3H); 3.93 (s, 3H); 3.81 (m, 6H); 3.77 (s, 3H); 3.73 (s, 3H); 3.30 (m, 2H); 3.10 (t, 2 H, J=5.7 Hz), 3.09 (m, 2 H, J=5.5 Hz), 2.91 (m, 2 H, J=4.6 Hz), 2.71 (d, 6 H, J=4.2 Hz), 2.32 (m, 4H); 1.70 (m, 4H); MALDI-TOF-MS, 1225.6 (1225.3 calc. for M+H).

52. ImImImIm-γ-PyPyPyPy-β-Dp:

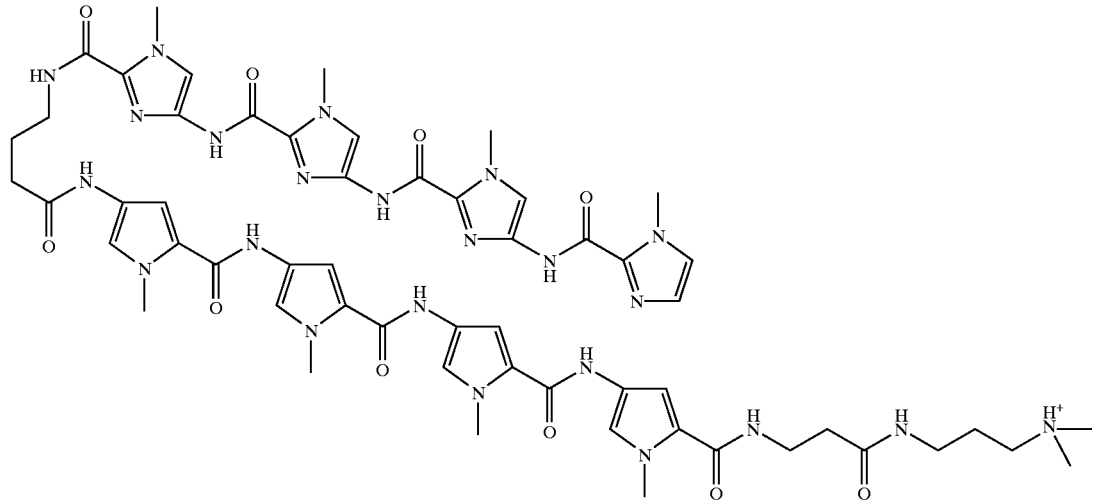

53. ImImImPy-β-PyPyPyPy-β-DP:

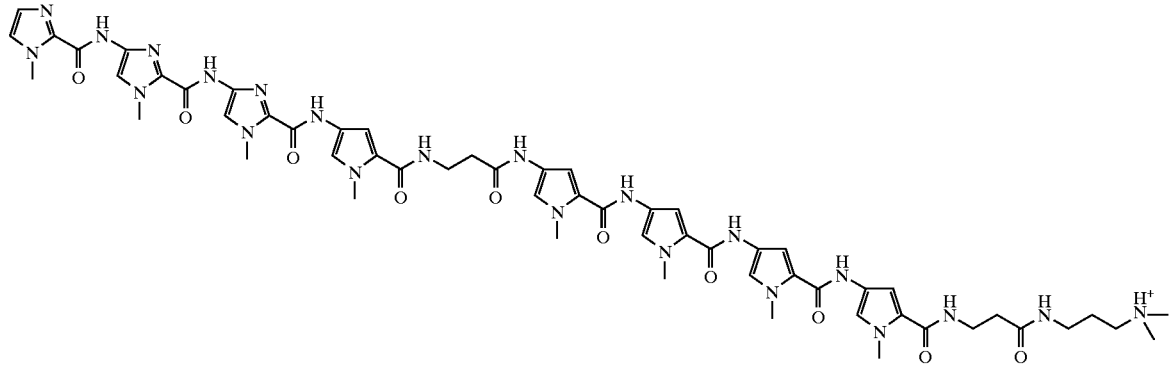

The polyamide ImImImIm-γ-PyPyPyPy-β-PAM-Resin was assembled on 0.2 mmol/gram Boc-b-PAM-resin by manual polyamide synthesis. The γ-Im step was added using Boc-γ-Im acid (HBTU, DIEA), all other residues were added as appropriate activated Boc protected monomer units. A sample of resin (150 mg, 0.16 mmol/gram[21]) was placed in a 20 mL glass scintillation vial, 2 mL dimethylaminopropylamine added and the mixture allowed to stand at 55° C. for 18 hours. Resin was removed by filtration through a disposable propylene filter, and the resulting solution diluted with water to a total volume of e mL, and purified directly by preparatory reversed phase HPLC to provide ImImImIm-γ-PyPyPyPy-β-Dp (12 mg, 21% recovery) as a white powder. UV $\lambda_{max}$(H$_2$O) 246, 314 (66,000); $^1$H NMR (DMSO-d$_6$)

A sample of ImImImPy-β-PyPyPyPy-β-resin prepared by machine-assisted solid phase synthesis 1240 mg, 0.16 mmol/gram) was placed in a 20 mL glass scintillation vial, and treated with dimethylaminopropylamine (2 mL) at 55° C. for 18 hours. Resin was removed by filtration, and the filtrate diluted to a total volume of 8 mL with 0.1% (wt/v) aqueous TFA. The resulting crude polyamide/amine solution was purified directly by reversed phase HPLC to provide the trifluoroacetate salt of ImImImPy-β-PyPyPyPy-β-Dp (31 mg, 40% recovery) as a white powder. $^1$H NMR (300 MHz, [D$_6$] DMSO, 20° C.): d=10.37 (s, 1H; NH), 10.12 (s, 1H; NH), 9.95 (s, 1H; NH), 9.94 (s, 1H; NH), 9.93 (s, $^1$H; NH), 9.92 (s, 1H; NH), 9.59 (s, 1H; NH), 9.4 (br s, 1H; CF$_3$COOH), 8.09 (m 3H; NH), 7.65 (s, 1H; CH), 7,56 (s, 1H; CH), 7,45 (s, 1H; CH), 7.27 (d, $^2$J(H,H)=1.3 Hz, 1H; CH), 7.22 (m, 2H; CH), 7.18 (d, $^2$J(H,H)=1.3 Hz, 1H; CH), 7.16 (d, $^2$J(H,H)=1.0 Hz, 1H; CH), 7.07 (m, 2H; CH;, 6.95 (d, $^2$J(H,H)=1.1 Hz, 1H; CH), 6.88 (d, $^2$J(H, H)=1.4 Hz, 1H; CH), 6.86 (d, $^2$J(H, H)=1.3 Hz, 1H; CH), 4.01 (s, 3H; NCH$_3$), 3.98 (m, 2H; NCH$_3$), 3.83 (s, 3H; NCH$_3$), 3.82 (m, 6H; NCH $_3$), 3.80 (s, 3H; NCH$_3$), 3.78 (s, 3H; NCH$_3$), 3.4 (m, 6H; CH$_2$), 3.11 (q, $^4$J(H,H)=5.2 Hz, 2H; CH$_2$), 2.94 (q, $^4$J (H, H). 5.3 Hz, 2H; CH$_2$), 2.69 (d, $^2$J(H,H)=4.4 Hz, 6H; N(CH$_3$)$_2$), 2.33 (t, $^3$J (H,H)=5.4 Hz, 2H; CH$_2$), 1.75 (q, $^5$J(H,H)=7.1 Hz, 2H; CH$_2$); UV/VIS (H$_2$O) $\lambda_{max}$ (q)=304 (66,600, calculated from $\epsilon$=8,333/ring$^{(14c)}$), 241 nm; MALDI-TOF-MS [M$^+$–H] 1210.4: calc. 1210.3.

54. ImImPyPy-β-PyPyPypy-β-Dp:

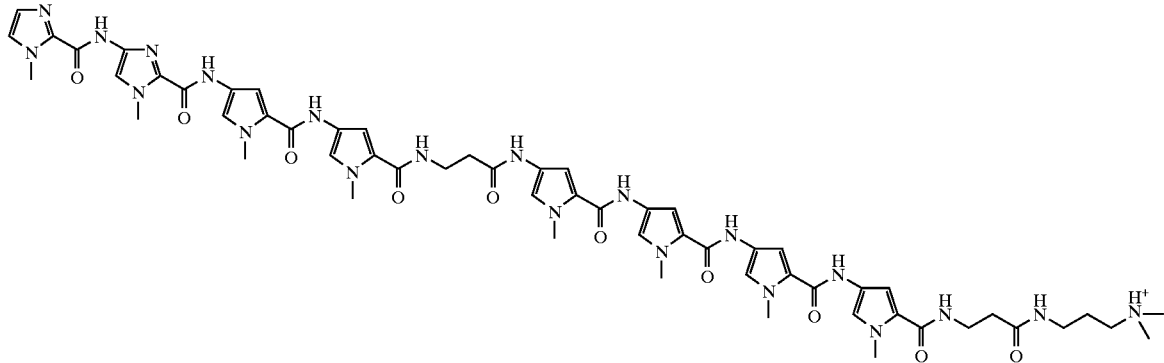

A sample of ImImPyPy-β-PyPyPyPy-β-resin prepared by machine-assisted solid phase synthesis (240 mg, 0.16 mmol/gram$^{15}$) was placed in a 20 mL glass scintillation vial, and treated with dimethylaminopropylamine (2 mL) at 55° C. for 18 hours, Resin was removed by filtration, and the filtrate diluted to a total volume of 8 mL with 0.1% (wt/v) aqueous TFA. The resulting crude polyamide/amine solution was purified directly by reversed phase HPLC to provide the trifluoroacetate salt of ImImPyPy-β-PyPyPyPy-β-Dp (31 mg, 40% recovery) as a white powder. $^1$H NMR (300 MHz, [D$_6$] $_{DMSO,}$ 20° C. δ=10.38 (s, 1H; NH), 9.95 (s, 1H; NH), 9.93 (s, 1H; NH), 9.91 (s, 1H; NH), 9.90 (m, 2H; NH), 9.76 (s, 1H; NH), 9.4 (br s, 1H; CF$_3$COOH), 8.09 (m, )H; NH), 7.56 (s, 1H; CH), 7,46 (s, 1H; CH), 7.27 (d, $^2$J(H,H)=1.8 Hz, 1H; CH), 7,21 (d, $^2$J(H,H)=1.7 Hz, 1H; CH), 7.20 (d, $^2$J(H,H)=1.9 Hz, 1H; CH), 7.19 (d, $^2$J(H,H)=1.9 Hz, 1H; CH), 7.16 (d, $^2$J(H,H)=1.9 Hz, 1H; CH), 7.15 (d, $^2$J(H,H)=1.6 Hz, 1H; CH), 7,14 (d, $^2$J(H,H)=1.9 Hz, 1H; CH), 7.12 (d, $^2$J(H,H)=1.6 Hz, 1H; CH), 7.07 (s, 1H; CH), 7.05 (d, $^2$J(H,H)=1.5 Hz, 1H; CH), 6.87 (d, $^2$J(H,H)=1.9 Hz, 1H; CH), 6.86 (d, $^3$J(H,H)=1.6 Hz, 1H: CH), 6.84 (d, $^2$J(H,H)=1.6 Hz, 1H; CH), 3.99 (m, 6H; NCH$_3$), 3.82 (m, 12H; NCH$_3$), 3.80 (s, 3H; NCH$_3$), 3.78 (s, 3H; NCH$_3$), 3.4 (m, 6H; CH$_2$), 3.09 (q, $^4$J(H,H)=5.6 Hz, 2H; CH$_2$), 2.97 (q, $^4$J(H, H)=5.2 Hz, 2H; CH$_2$), 2.71 (d, $^2$J(H,H)=4.2 Hz, 6H; N(CH$_3$)$_2$), 2:32 (t, $^3$J(H,H)=5.1 Hz, 2H; CH$_2$), 1.71 (q, $^5$J(H, H)=7.4 Hz, 2H; CH$_2$); UV/VIS (H$_2$O) $\lambda_{max}$ ($\epsilon$)=306 (66,600, calculated from e=8,333/ring), 243 nm; MALDI-TOF-MS (M$^+$–H) 1209.1; calc. 1209.3.

55. ImPyPyPy-βPyPyPyPy-βDp:

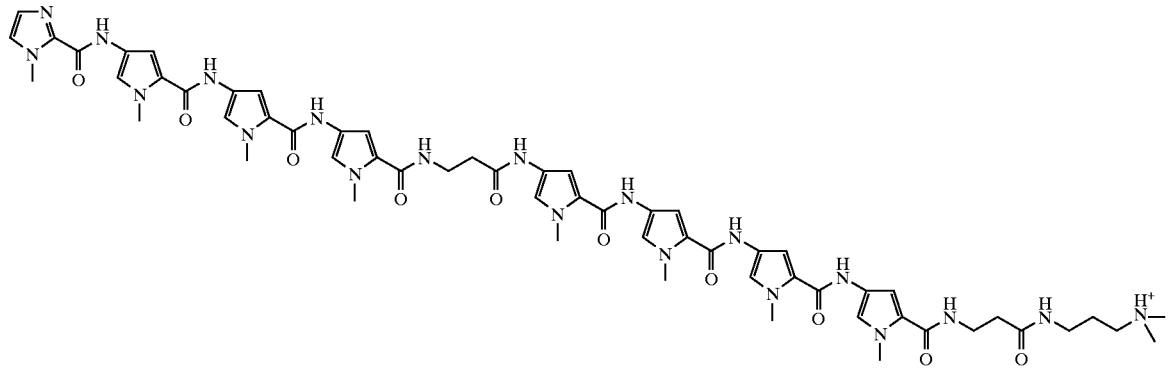

A sample of ImPyPyPy-β-PyPyPyPy-β-resin prepared by machine-assisted solid phase synthesis 1240 mg, 0.16 mmol/gram) was placed in a 20 mL glass scintillation vial, and treated with dimethylaminopropylamine (2 mL) ac 55° C. for 18 hours. Resin was removed by filtration, and the filtrate diluted to a total volume of 8 mL with ).1% (wt/v) aqueous TFA, The resulting crude polyamide/amine solution was purified directly by reversed phase HPLC to provide the trifluoroacetate salt of ImPyPyPy-β-PyPyPyPy-β-Dp (31 mg, 40% recovery) as a white powder. $^1$H NMR (300 MHz, [D$_6$] DMSO, 20° C. δ=10.49 (s, 1H; NH), 9.97 (s, 1H; NH), 9.95 (s, 1H; NH), 9.94 (s, 1H; NH), 9.93 (m, 2H; NH), 9.91 (s, 1H; NH), 9.4 (br s, 1H; CF$_3$COOH), 8.10 (m, 3H; NH), 7.38 (s, 1H; CH), 7.28 (d, $^2$J (H, H)=1.6 Hz, 1H; CH), 7.22

(m, 3H; CH), 7.19 (m, 2H; CH), 7.16 (m, 2H; CH), 7.09 (m, 2H; CH), 7.04 (m, 2H; CH), 6.87 (d, $^2J(H,H)$=1.6 Hz, 1H; CH), 6.86 (d, $^2J(H,H)$=1.6 Hz, 1H; CH), 6.84 (d, $^2J(H,H)$=1.5 Hz, 1H; CH), 3.97 (s, 3H; NCH$_3$), 3.82 (m, 15H; NCH$_3$), 3.80 (s, 3H; NCH$_3$), 3.78 (s, 3H; NCH$_3$), 3.4 (m, 6H; CH$_2$), 3.10 (q, $^4J(H;H)$=5.4 Hz, 2H; CH$_2$), 2.98 (q, $^4J(H,H)$=5.3 Hz, 2H; CH$_2$), 2.72 (d, $^2J(H,H)$=4.7 Hz, 6H; N(CH$_3$)$_2$), 2.33 (t, $^3J(H,H)$=7.0 Hz, 2H; CH$_2$), 1.71 (q, $^5J(H,H)$=6.4 Hz, 2H; CH$_2$), UV/VIS (H$_2$O) $\lambda_{max}$ (υ)=312 (66,600, calculated from ε=8,333/ring), 244 nm; MALDI-TOF-MS [M$^+$−H] 1208.2: calc. 1208.3.

56. ImPyPyPyPy-γ-ImPyPyPyPy-β-Dp:

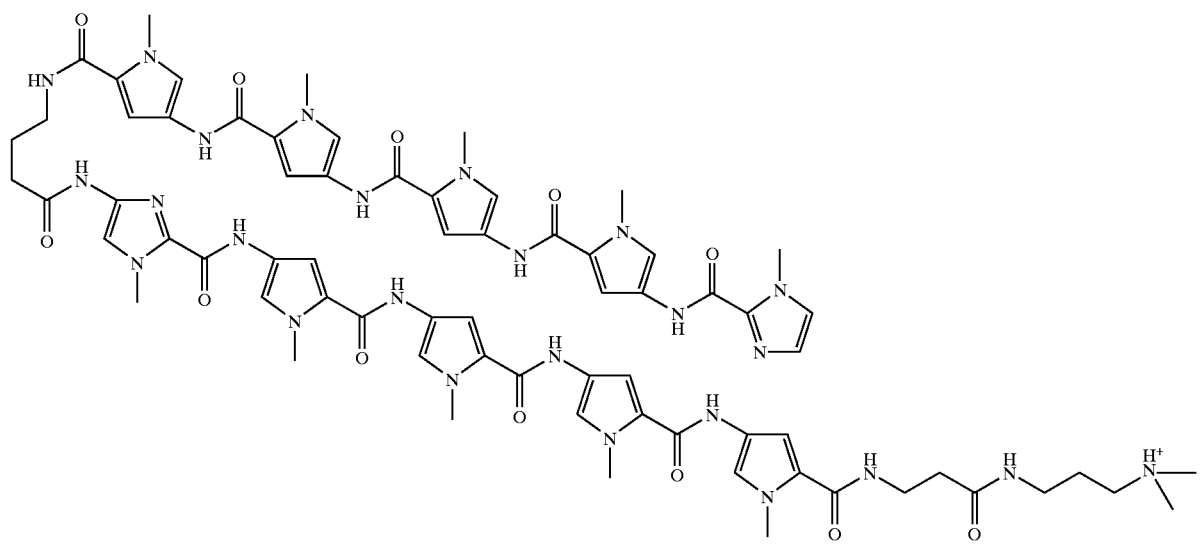

A sample of ImPyPyPyPy-γ-ImPyPyPyPy-β-resin prepared by machine-assisted solid phase synthesis (240 mg, 0.16 mmol/gram) was placed in a 20 mL glass scintillation vial, and treated with dimethylaminopropylamine (2 mL) at 55° C. for 18 hours. Resin was removed by filtration, and the filtrate diluted to a total volume of e mL with 0.1% (wt/v) aqueous TFA. The resulting crude polyamide/amine solution was purified directly by reversed phase HPLC to provide the trifluoroacetate salt of ImPyPyPyPy-γ-ImPyPyPyPy-β-Dp (13 mg, 18% recovery) as a white powder. UV (H$_2$O) $\lambda_{max}$ 241, 316 (ε) 83300 (calculated based on ε=8,333/ring); $^1$H NMR (DMSO-d$_6$) δ 10.52 (s, 1H), 10.29 (s, 1 H), 10.04 (s, 1H), 10.00 (s, 1H), 9.97 (m, 3H), 9.92 (m, 3H), 9.22 (br s, 1H), 8.06 (m, 3H), 8.03 (m, 2H), 7.46 (s, 1H), 7.41 (s, 1H), 7.29 (d, 1 H, J=1.0 Hz), 7.23 (m, 1H), 7.17 (m, 1H), 7.07 (m, 1H), 6.90 (d, 1 H, J=6.9 Hz), 3.99 (s, 3H), 3.94 (s, 3H), 3.85 (m, 6H), 3.79 (s, 3H), 3.38 (q, 2 H, J=3.2 Hz), 3.20 (q, 2 H, J=2,7 Hz), 3.11 (q, 2 H, J=1.8 Hz), 3.00 (q, 2 H, J=2 .1 Hz), 2.72 (d, 6 H, J+4.8 Hz), 2.35 (m, 4H), 1.75 (m, 4H); MALDI-TOF-MS, 1466.1 (1467.6 calc. for M+H).

57. ImImPyPyPy-γ-ImPyPyPyPy-β-Dp:

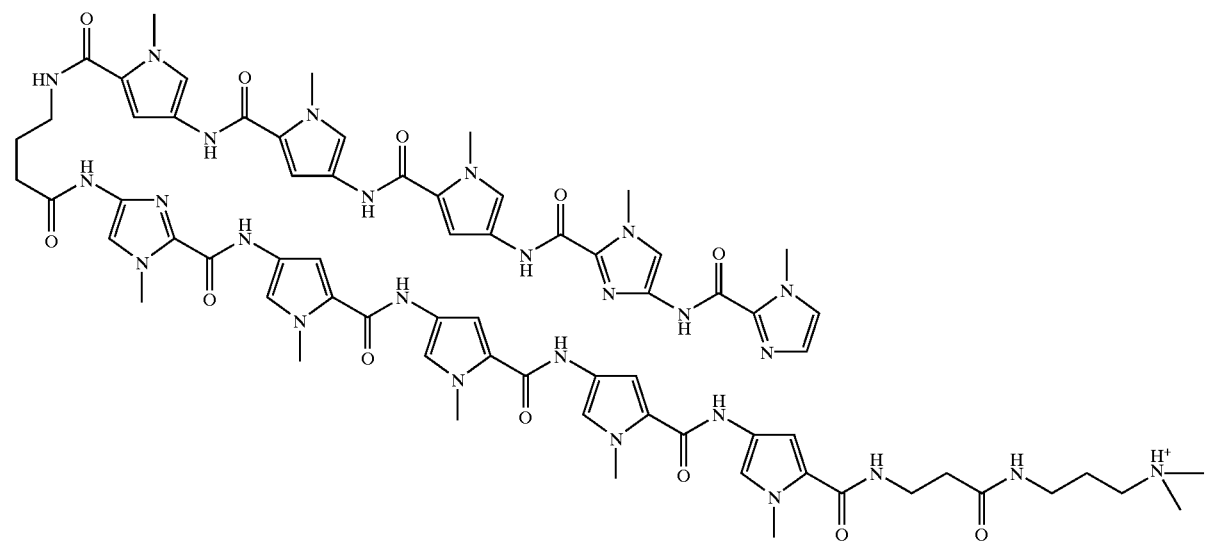

The polyamide was prepared as described for ImPyPyPyPy-γ-ImPyPyPyPy-β-Dp as a white powder (28 mg, 34% recovery). UV λ$_{max}$ 310 (83,300); $^1$H; NMR (DMSO-d$_6$) d 10.39 (s, 1H), 10.28 (s, 1H), 10.02 (s, 1H), 9.99 (s, 1H), 9.96 (m, 2H), 9.91 (s, 2H), 9,76 (s, 1H), 9.18 (br s, 1H), 8.05 (m, 3H), 7.57 (s, 1H), 7.46 (s, 2H), 7.25 (dd, 2 H, J=5.6), 7.23 (m, 4H), 7.16 (m, 4H), 7.07 (m, 4H), 6.88 (d, 1 H, J=5.1), 4.00 (s, 3H), 3.94 (s, 3H), 3.85 (m, 6H), 3.79 (s, 3H), 2.99 (q, 2 H, J=5.1), 2.73 (d, 6 H, J=4.8 Hz), 2.34 (m, 4H), 1.75 (m, 4H); MALDI-TOF-MS, 1468.2 (1468.6 calc. fox M+H).

58. ImPyPyPyPy-γ-ImPyPyPyPy-β-Dp-NH$_2$:

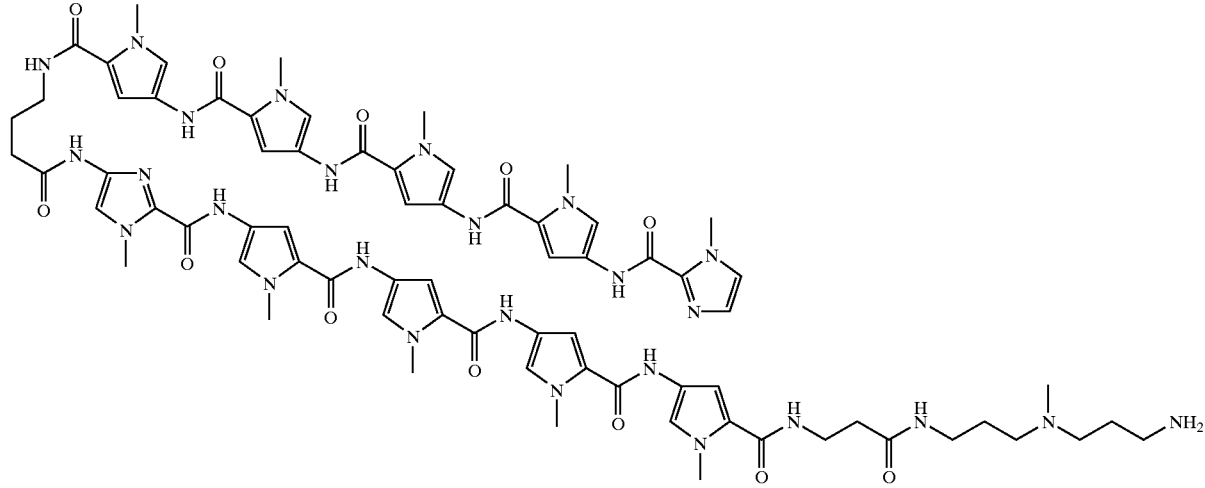

A sample of ImPyPyPyPy-γ-ImPyPyPyPy-β-resin prepared by machine-assisted solid phase synthesis (240 mg, 0.16 mmol/gram) was placed in a 20 mL glass scintillation vial, and treated with 3,3-diamino-N-methyldipropylamine (2 mL) at 55° C. for 18 hours. Resin was removed by filtration, and the filtrate diluted to a total volume of 8 mL with 0.1% (wt/v) aqueous TFA. The resulting crude polyamide/amine solution was purified directly by reversed phase HPLC to provide the trifluoroacetate salt of ImPyPyPyPy-γ-ImPyPyPyPy-β-NH$_2$ (31 mg, 40% recovery) as a white powder. UV λ$_{max}$ 241, 316 (ε) 83300 (calculated based on ε=8,333/ring[5]); $^1$H NMR (DMSO-d$_6$) δ10.53 (a, 1H), 10.26 (s, 1 H), 10.03 (s, 1H), 10.00 (s, 1H), 9.96 (m, 2H), 9.92 (m, 2H), 9.6 (br s, 1H), 8.07 (m, 4H), 7.89 (s, 3H), 7 .45 (s, 1H), 7.41 (s, 1H), 7.27 (d, 2 H, J=8.5 Hz), 7.23 (m, 4H), 7.16 (m, 4H), 7.06 (m, 4H), 6.87 (m, 2H), 3.98, (s, 3H); 3.94 (s, 3H), 3.84, (m, 6H), 3.79 (s, 3H), 3.35 (q, 2 H, J=5.7 Hz), 3.16 (m, 8H), 2.85 (q, 2 H, J=5.6 Hz), 2.72 (d, 2 H, J=4.2 Hz), 2.34 (m, 2H), 1.91 (m, 4H), 1.78 (m, 4H). MALDI-TOF MS, 1510.4 (1510.7 calc. for M+H).

59. ImImPyPyPy-γ-ImPyPyPyPy-β-Dp-NH$_2$:

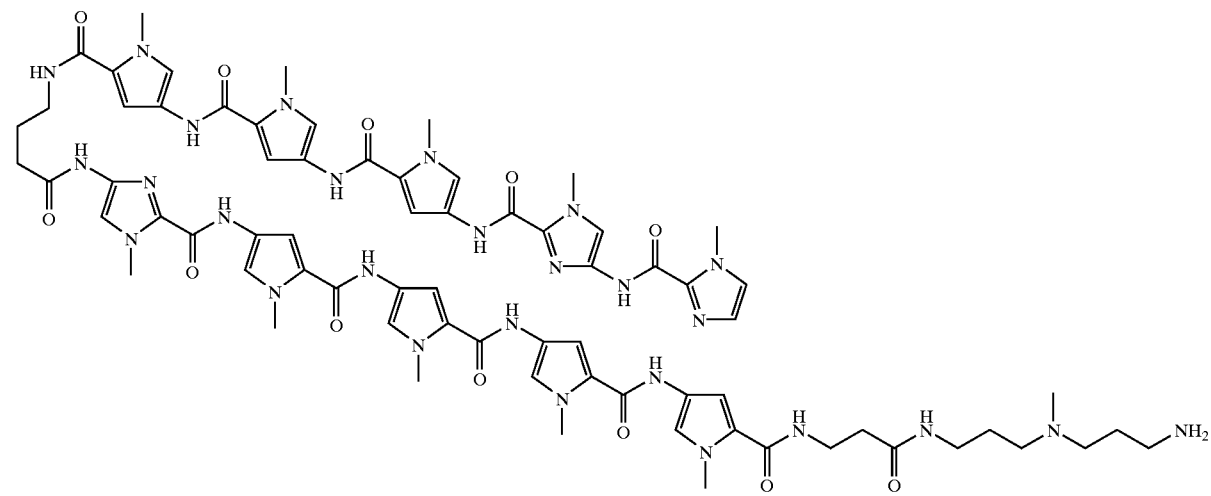

The polymide was prepared as a white powder as described for ImPyPyPyPy-γ-ImPyPyPyPy-β-NH$_2$. $^1$H NMR (DMSO-d$_6$) δ10.39 (s, 1H), 10.28 (s, 1H), 10.03 (s, 1H), 10.03 (s, 1H), 9.92 (m, 2H), 9.82 (s, 1H), 9.66 (br s, 1H), 8.11 (m, 4H), 7.89 (s, 3H), 7.57 (s, 1H), 7.46 (d, 2 H, J=2.4 Hz), 7.27 (dd, 2 H, J=1.0 Hz), 7.23 (m, 4H), 7.16 (m, 4H), 7.08 (m, 4H), 6.88 (m, 1H), 4,00 (s, 3H), 3.94 (s, 3H), 3.78 (s, 3H), 3.19 (q, 2 H, J=5.1 Hz), 3.05 (m, 8H), 2.86 (q, 2 H, J=4.8 Hz), 2.72 (d, 2 H, J=4.4 Hz), 2.34 (m, 4H), 1.90 (m, 4H), 1.78 (m, 4H), MALDI-TOF-MS, 1510.4 (1511.7 calc. for M+H).

60. ImPyPyPy-γ-ImPyPyPyPy-β-Dp-EDTA:

EDTA-dianhydride (50 mg) was dissolved by heating at 55° C. for 5 min. in a solution of DMSO/NMP (1 ml) and DIEA (1 mL). The dianhydride solution was added to ImPyPyPyPy-γ-ImPyPyPyPy-β-Dp-NH$_2$ (8.1 mg) dissolved in DMSO (750 μL) The mixture was heated at 55° C. for 25 minutes, and treated with 0.1M NaOH (3 mL), and heated at 55° C. for 10 minutes. Aqueous 0.1% (wt/v) TFA was added to adjust the total volume to 8 mL and the solution purified directly by preparatory HPLC chromatography to provide ImPypypypy-γ-ImPyPyPyPy-β-Dp-EDTA as a white powder. (2.4 mg, 22% recovery) MALDI-TOF-MS, 1766.4 (1766.7 calc. for M+H).

E. Plasmids, Footprinting, Affinity Cleavage

1. Construction of plasmid DNA

The experimental target plasmid pSES9hp was constructed by hybridization of the inserts: 5'-GATCCTATGTCAGTCATGCGGATGACTGTCAGT CATGGCCATGACTGTCAGTCATGCGCATGACTGT CAGTCTTAAGC-3' and 5-GATACAGTCAG TAC-CCCTACTGACAGTCAGTACCGGTACTGACAG CAGTACGCGTACTGACAGTCAGAATTCGTCGA-3'.

The hybridized insert was ligated into linearized pUC19 BamHI/HindIII plasmid using T4 DNA ligase. The resultant constructs were used to transform Top10F' OneShot competent cells from Invitrogen. Ampicillin-resistant white colonies were selected from 25 mL Luria-Bertani medium agar plates containing 50 μg/mL ampicillin and treated with XGAL and IPTG solutions. Large-scale plasmid purification was performed with Qiagen Maxi purification kits. Dideoxy sequencing was used to verify the presence of the desired insert. Concentration of the prepared plasmid was determined at 260 nm using the relationship of 1 OD unit=50 μg/mL duplex DNA.

2. Preparation of 3'-and 5'-End-Labeled Restriction Fragments

The plasmid pSES9hp was linearized with EcoRI and PvuII and then treated with Klenow fragment, deoxyadenosine 5'[α-$^{32}$P] triphosphate and thymidine 5'-[α-$^{32}$P] triphosphate for 3' labeling. Alternatively, pSES9hp was linearized with EcoRI, treated with calf alkaline phosphatase, and then 5' labeled with T4 polynucleotide kinase and deoxyadenosine 5'-[γ-$^{32}$P]triphosphate. The 5'labeled fragment was then digested with PvuII. The labeled fragment (3' or 5') was loaded onto a 5% non-denaturing polyacrylamide gel, and the desired 282 base pair band was visualized by autoradiography and isolated. Chemical sequencing reactions were performed according to published methods. (Maxam, A. M. & Gilbert, W. S. (1980). Sequencing End-Labeled DNA with Base-Specific Chemical Cleavages. *Methods Enzymol.* 65, 499–560; Iverson, H. L. & Dervan, P. B. (1987). Adenine-specific DNA chemical sequencing reaction. *Methods Enzymol.* 15, 7823–7830.)

3. MPE•Fe(II) Footprinting

All reactions were carried out in a volume of 40 μL. A polyamide stock solution or water (for reference lanes) was added to an assay buffer where the final concentrations were: 25 mM Tris-acetate buffer (pH 7.0), 10 mM NaCl, 100 μM/base pair calf thymus DNA, and 30 kcpm 3'- or 5'-radiolabeled DNA. The solutions were allowed to equilibrate for 4 hours. A fresh 50 μm MPE•Fe(II) solution was made from 100 μL of a 100 μm MPE solution and 100 μL of a 100 μM ferrous ammonium sulfate (Fe (NH$_4$)$_2$(S0$_4$)$_2$•6H$_2$O) solution. MPE•Fe(II) solution (5 μM) was added to the equilibrated DNA, and the reactions were allowed to equilibrate for 5 minutes. Cleavage was initiated by the addition of dithiothreitol (5 mM) and allowed to proceed for 14 min. Reactions were stopped by ethanol precipitation, resuspended in 100 mM tris-Borate-EDTA/ 80% formamide loading buffer, denatured at 85° C. for 5 min, placed on ice, and half of each tube (~15 kcpm) was immediately loaded onto an 8% denaturing polyacrylamide gel (5% crosslink, 7 M urea) at 2000 V.

4. Affinity Cleaving.

All reactions were carried out in a volume of 40 μL. A polyamide stock solution or water (for reference lanes) was added to an assay buffer where the final concentrations were: 25 mM Tris-acetate buffer (pH 7.0), 10 mM NaCl, 100 μM/base pair calf thymus DNA, and 20 kcpm 3'- or 5'-radiolabeled DNA. The solutions were allowed to equilibrate for 4 hours. A fresh solution of ferrous ammonium sulfate (Fe(NH$_4$)$_2$(SO$_4$)$_2$.6H$_2$O) (10 μM) was added to the equilibrated DNA, and the reactions were allowed to equilibrate for 15 minutes. Cleavage was initiated by the addition of dithiothreitol (10 mM) and allowed to proceed for 30 min. Reactions were stopped by ethanol precipitation, resuspended in 100 mM tris-borate-EDTA/80% formamide loading buffer, denatured at 85° C. for 5 min, placed on ice, and the entire sample was immediately loaded onto an 8% denaturing polyacrylamide gel (5% crosslink, 7 M urea) at 2000 V.

5. Identification of Binding Orientation by Affinity Cleaving.

Affinity cleavage assays (25 mM Tris-acetate, 10 mM NaCl, 100 μM/base pair calf thymus DNA, pH 7.0 and 22° C.) were performed in order to identify the binding orientations of the EDTA analogues of the three hairpin polyamides: ImImPyPy-γ-ImImPyPy-β-Dp-EDTA, ImPyImPy-γ-ImPyImPy-β-Dp-EDTA, and ImImImIm-γ-PyPyPyPy-β-Dp-EDTA The polyamides ImImPyPy-γ-ImImPyPy-β-Dp-EDTA, ImPyImPy-γ-ImPyImPy-β-Dp-EDTA recognize their respective palindromic match sequences, 5'-TGGCCA-3' and 5'-TGCGCA-3', in two equivalent orientations, consistent with hairpin formation. In contrast, the polyamide ImImImIm-γ-PyPyPyPy-β-Dp-EDTA recognizes a non-palindromic sequence, 5'-TGGGGA-3', in a single orientation with cleavage visible only on the 5'-side of the site, as predicted by the hairpin model.

Figure 17:
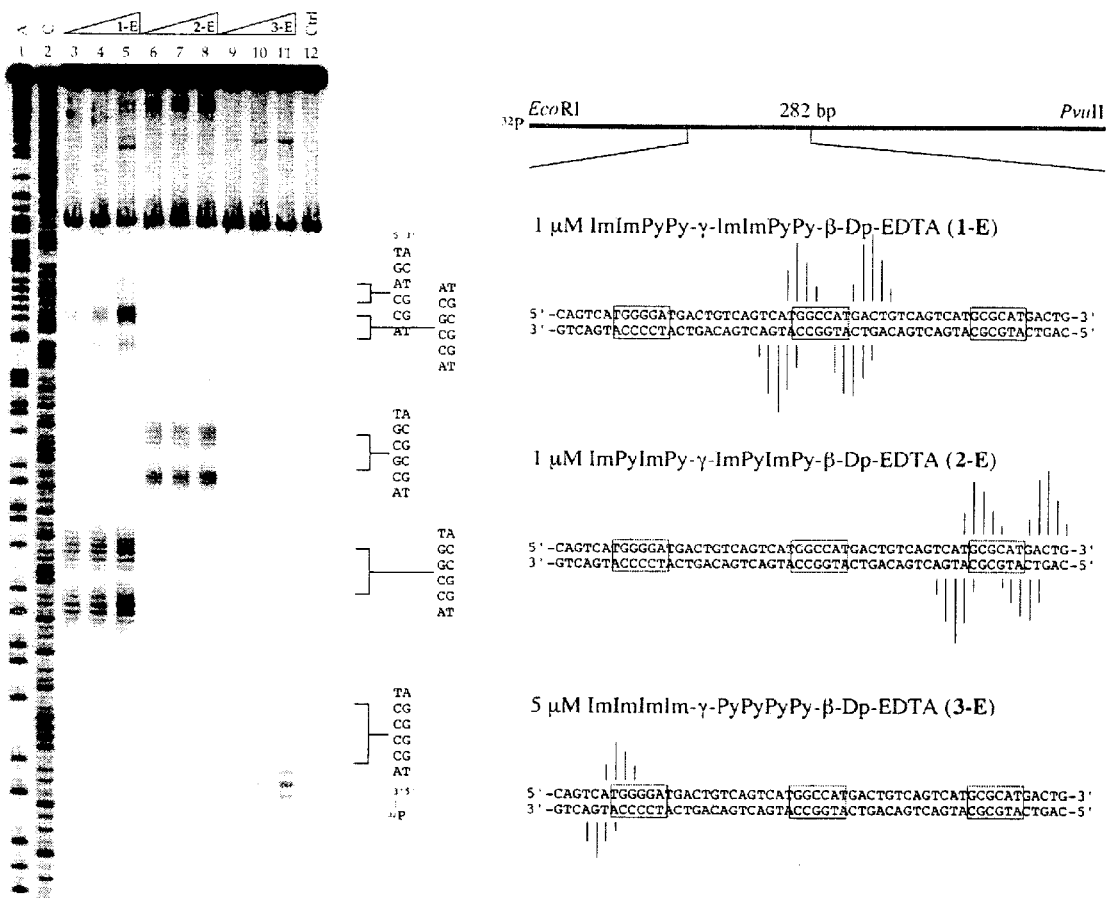
FIG. 17. Dnase I footprint titration.

Depicted in FIG. 17 is a representative affinity cleaving experiment on a 3'-$^{32}$P-labeled 282 bp EcoRI/PvuII restriction fragment from plasmid pSES9hp. The 5'-TGGCCA-3', 5'-TGCGCA-3 and 5'-TGGGGA-3' sites are shown on the right side of the autoradiogram. Lane 1, A reaction; lane 2, C reaction; lanes 3–5, 1 μM, 2 μM and 5 μM ImImPyPy-γ-ImImPyPy-β-Dp-EDTA (1-E); lanes 6–8, 1 μM, 2 μM and 5 μM ImPyImPy-γ-ImPyImPy-β-Dp-EDTA (2-E); lanes 9–11, 1 μM, 2 μM and 5 μM ImImImIm-γ-PyPyPyPy-β-Dp-EDTA (3-E); lane 12, intact DNA. All lanes contain 15 kcpm 3'-radiolabeled DNA, 25 mM Tris-acetate buffer (pH 7.0), 10 mM NaCl, and 100 μM/base pair calf thymus DNA. (Right) Affinity cleavage patterns for ImImPyPy-γ-ImImPyPy-β-Dp-EDTA and ImPyImPy-γ-ImPyImPy-β-Dp-EDTA at 1 μM concentration, and ImImImIm-γ-PyPyPyPy-β-Dp-EDTA at 5 μM concentration. Illustration of the 282 bp restriction fragment with the position of the sequence indicated. Bar heights are proportional to the relative protection from cleavage at each band. Boxes represent equilibrium binding sites determined by the published model, and only sites that were quantitated by DNase I footprint titrations are boxed.

6. DNase I Footprinting

All reactions were carried out in a volume of 400 μL. We note explicitly that no carrier DNA was used in these reactions. A polyamide stock solution or water (for reference lanes) was added to an assay buffer where the final concentrations were: 10 mM $CaCl_2$, and 20 kcpm 3'-radiolabeled. DNA. The solutions were allowed to equilibrate for a minimum of 12 hours at 22° C. Cleavage was initiated by the addition of 10 μL of a DNase I stock solution (diluted with 1 mM DTT to give a stock concentration of 0.28 u/mL) and was allowed to proceed for 5 min at 22° C. The reactions were stopped by adding 50 mL of a solution containing 2.25 M NaCl, 150 mM EDTA, 0.6 mg/mL glycogen, and 30 mM base-pair calf thymus DNA, and then ethanol precipitated. The cleavage products were resuspended in 100 mM tris-borate-EDTA/80% formamide loading buffer, denatured at 85° C. for 5 min, placed on ice, and immediately loaded onto an 8% denaturing polyacrylamide gel (5% crosslink, 7 M urea) at 2000 V for 1 hour. The gels were dried under vacuum at 80° C., then quantitated using storage phosphor technology.

The data were analyzed by performing volume integrations of the 5'-TGGCCA-3', 5'-TGCGCA-3', and 5'-TGGGGA-3' sites and a reference site. The apparent DNA target site saturation $\theta_{app}$, was calculated for each concentration of polyamide using the following equation:

$$\theta_{app} = 1 - \frac{I_{tot}/I_{ref}}{I_{tot}°/I_{ref}°} \quad (1)$$

where $I_{tot}$ and $I_{ref}$ are the integrated volumes of the target and reference sites, respectively, and $I_{tot}°$ and $I_{ref}°$ correspond to those values for a DNase I control lane to which no polyamide has been added. The ($[L]_{tot}$, $\theta_{app}$) data points were fit to a Langmuir binding isotherm (eq 2, n=1 or n=2) by minimizing the difference between $\theta_{app}$ and $\theta_{fit}$, using the modified Hill equation:

$$\theta_{fit} = \theta_{min} + (\theta_{max} - \theta_{min})\frac{K_a^n[L]_{tot}^n}{1 + K_a^n[L]_{tot}^n} \quad (2)$$

where $[L]_{tot}$ corresponds to the total polyamide concentration, $K_a$ corresponds to the equilibrium association constant, and $\theta_{min}$ and $\theta_{max}$ represent the experimentally determined site saturation values when the site is unoccupied or saturated, respectively. Data were fit using a non-linear least-squares fitting procedure of KaleidaGraph software (version 2.1, Abelbeck software) with $K_a$, $\theta_{max}$, and $\theta_{min}$ as the adjustable parameters. All acceptable fits had a correlation coefficient of R>0.97. At least three sets of acceptable data were used in determining each association constant. All lanes from each gel were used unless visual inspection revealed a data point to be obviously flawed relative to neighboring points. The data were normalized using the following equation:

$$\theta_{norm} = \frac{\theta_{app} - \theta_{min}}{\theta_{max} - \theta_{min}} \quad (3)$$

7. Quantitation by Storage Phosphor Technology Autoradiography

Photostimulable storage phosphorimaging plates (Kodak Storage Phosphor Screen S0230 obtained from Molecular Dynamics) were pressed flat against gel samples and exposed in the dark at 22° C. for 12–20 h. A Molecular Dynamics 400S PhosphorImager was used to obtain all data from the storage screens. The data were analyzed by performing volume integrations of all bands using the ImageQuant v. 3.2.

Example 2

Synthesis and Oxidative Cleavage of Double-Helical Dna By Polyamides Modified With A Polyamide-Ni(Ii) Tripeptide Conjugate Many anticancer drugs act through their ability to modify DNA. Novel polyamide conjugates have been designed which modify double-helical DNA in a sequence specific manner. More specifically the metalopeptide Ni(II)•Gly-Gly-His has been shown to promote the efficient oxidative cleavage of DNA in the presence of monoperoxyphthalic acid. (Mack and Dervan, *J. Am. Chem. Soc.*, 112, 4604 (1990); Mack and Dervan, *Biochemistry*, 31, 9399 (1992)).

Figure 18:
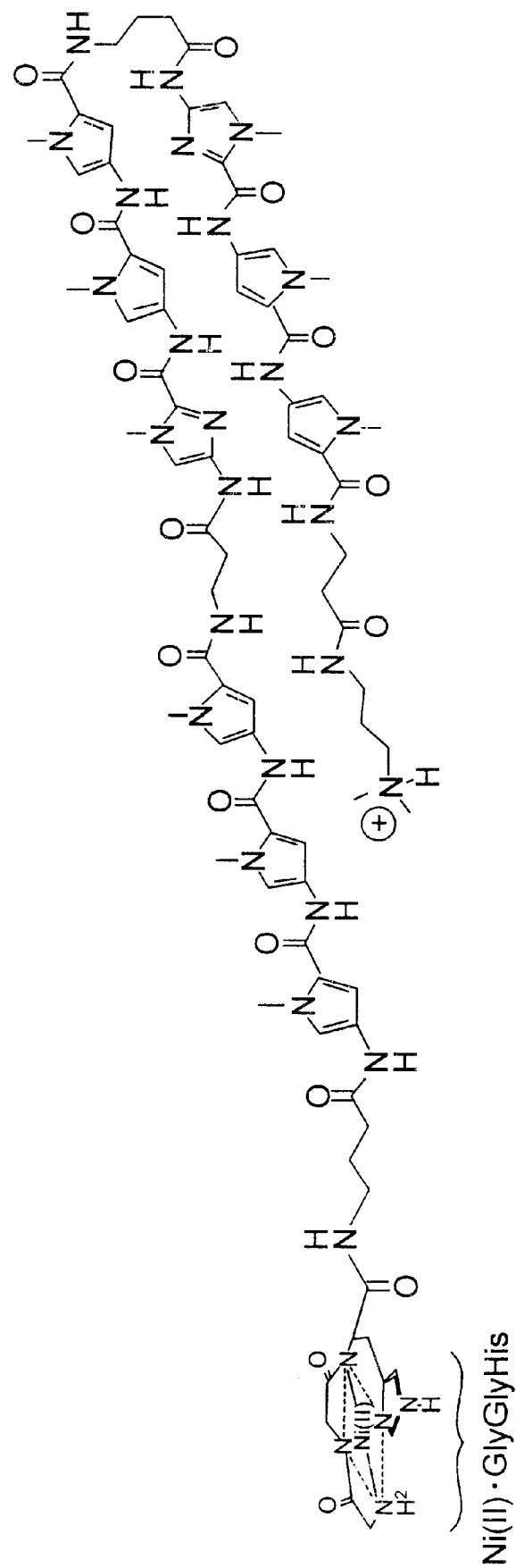
FIG. 18. Ni(II)-Gly-Gly-His modified polyamide.

The reaction is thought to proceed through a mechanism that involves abstraction of hydrogen atom(s) from the deoxyribose backbone of DNA by a nondiffusable high valent nickel bound oxygen. Bifunctional conjugates were designed in order to combine the ability of polyamides to recognize any predetermined DNA sequence with the Ni(II) •Gly-Gly-His chemistry. The symmetric anhydride of the amino acid His and the activated ester of Gly were coupled to the extended hairpin polyamide directly on the β-alanine-Pam resin employing solid phase chemistry protocols. Denaturing polyacrylamide gel electrophoresis of 32P end-labeled DNA treated with the Ni(II)•Gly-Gly-His modified polyamide at pH 7.5 demonstrated the ability of the conjugate to cleave the double helical DNA is a sequence selective manner in 77% and 72% yields on the 3'-end-labeled DNA (at 10 nM polyamide). The chemical structure of the Ni(II) •Gly-Gly-His modified polyamide is shown in FIG. 18.

Example 3

Sequence Specific Alkylation of Dna By Pyrrole-Imidazole Polyamides Modified With Dna Reactive Agents The design of sequence specific DNA binding-modifying molecules requires the integration of two separate entities: recognition and functional reactivity. The present inventor has discovered ligands which combine pyrrole-imidazole polyamide DNA binding motifs with mechanism based reactive functionalities capable of electrophilic modification of bases in the minor groove.

The design of sequence specific molecules for alkylation of double helical DNA requires both a specific DNA binding molecule and an atom specific DNA cleaving moiety. Hairpin polyamides are sequence specific molecules that can bind to any predetermined DNA sequence. Bromoacetyl and the prodrug analogue of the cyclopropyl electrophile of CC-1065 react in an atom specific manner with double helical DNA. By tethering a bromoacetyl moiety or the prodrug analogue of the cyclopropyl electrophile of CC-1065 to a hairpin polyamide the present inventor has discovered a sequence specific DNA alkylating agent which can be targeted to any predetermined DNA sequence at subnanomolar concentration.

The two criteria for successful bifunctional molecule design are sequence specific reactions at designated single atoms within the bound complex, and cleavage yields that are quantitative under physiological conditions (i.e. neutral pH, 37° C., 100–200 nM KCl/NaCl). In order to maximize stoichiometric reaction on the DNA, the 'cleaving functionality' must be sufficiently reactive with DNA at 37° C., be inert in aqueous media, and not react with buffer components, and not suffer unimolecular decomposition in competition with desired reactions on DNA. In order to design such bifunctional molecules, hairpin polyamides equipped with either an N-terminal bromoacetyl group or a prodrug analogue of the cyclopropyl electrophile of CC-1065 have been prepared.

A. Bromoacetylated polyamides

The polyamide $NH_2$PyPyPyPy-g-ImPyPyPy-b-Dp was designed to target the sequence 5'-AgTTT*A-3'. T* indicates the thymine opposite the alkylated adenine. The polyamide was synthesized by solid phase protocols, cleaved from the solid support with dimethyl amino propylamine, and purified by reverse phase HPLC chromatography. The terminal pyrrole residue was deprotected and left unacetylated, leaving a free primary amine on the N-terminus.

Figure 19:
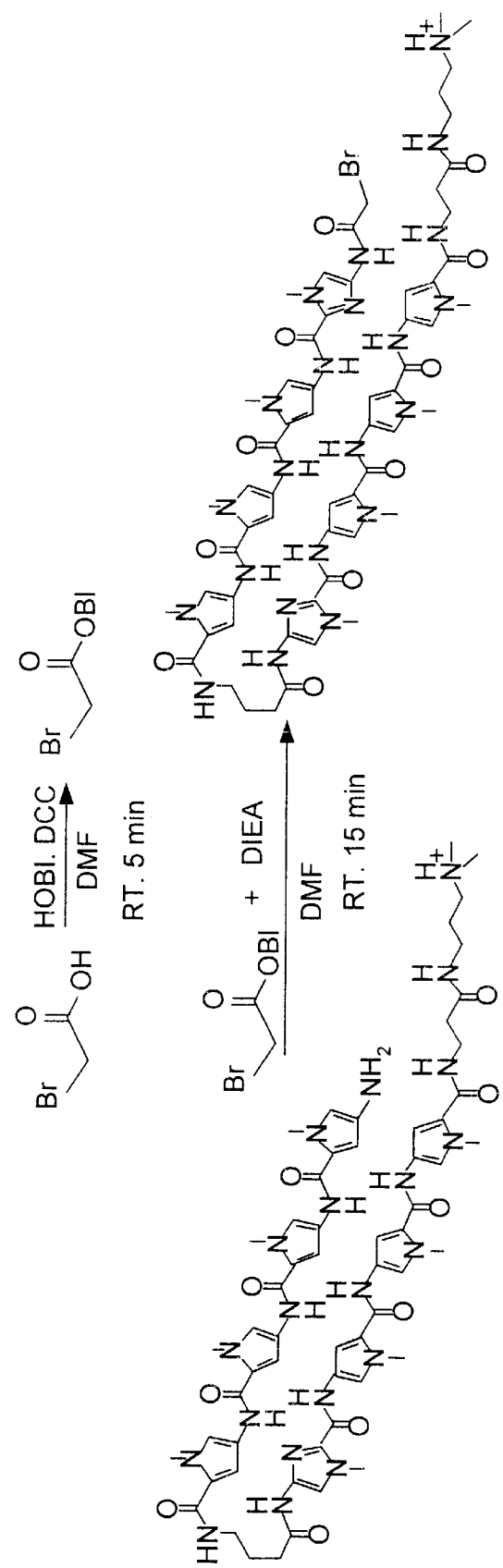
FIG. 19. Bromoacetylated hairpin polyamide.

In order to bromoacetylate the polyamide, bromoacetic acid was activated with HOBt and DCC in 1 ml DMF. After 5 minutes, the DCU was filtered off and the solution added to the polyamide with DIEA. After 15 minutes, the reaction mixture was purified directly by reversed phase HPLC to isolate the bromoacetylated polyamide. Short reaction times were used to avoid alkylation of the unprotected imidazole ring nitrogen. The purified N-bromoacetyl hairpin polyamide was characterized by mass spectrometry. The synthesis of a bromoacetylated hairpin polyamide is described in FIG. 19.

Another set of polyamides was synthesized, based on an extended hairpin motif. This motif combines the γ-turn of the hairpin motif with the β-alanine spacer of the extended motif, combining the 2:1 binding mode with the 1:1 binding mode. The following compounds were synthesized: PyPy-β-PyPyPy-γ-ImPyPy-β-Dp, PyPyPy-β-PyPyPy-γ-ImPyPy-β-Dp, PyPy-β-PyPyPy-γ-PyPyIm-β-Dp, and PyPyPyPyPyPy-γ-PyPyIm-β-Dp. The syntheses of the bromoacetylated extended hairpins were successful, and were prepared as described for the bromoacetylated hairpin polyamide. As controls, all four of the acetylated compounds were made as well.

B. Typical manual solid phase polyamide synthesis of PyPyPyPy-γ-ImPyPyPy-β-Dp.

Boc-β-alanine-Pam resin (1.25 g, 0.25 mmol) was placed in a 20 ml glass reaction vessel and shaken in DMF for 5 minutes and drained. The resin was washed with DCM (2 volumes) and deprotected with 80% TFA/DCM/0.5 M PhSH (1 wash, 1×20 minutes). Following deprotection, the resin was washed 3 time with DCM and 1 time with DMF. Boc-pyrrole-OBt ester (357 mg, 1 mmol) was added in 2 ml of DMF followed by 1 ml DIEA. The coupling reaction was shaken vigorously for 45 minutes. Resin samples (5 mg) were taken periodically to monitor the synthesis by HPLC. Successive cycles of the remaining monomers, Boc-Py-OBt (2×), Boc-γ-Im-COOH, Boc-Py-OBt (4×). Boc-γ-Im-COOH was activated by addition of HBTU (378 mg, 1 mmol) in 2 ml of DMF. DIEA (1 ml) was added and the solution was allowed to stand for 5 minutes until clear. After completion of the synthesis, the resin was washed with DMF, DCM, methanol, and ethyl ether. The resin was then lyophilized to remove solvent. The polyamide was cleaved off the resin with (N,N)-dimethylamino propylamine (2 ml) in a glass scintillation vial at 55° C. for 12 hours. The polyamide was filtered and HPLC purified in 0.1% TFA with a 0.25% $CH_3CN$ $min^{-1}$ gradient.

C. Synthesis of bromoacetylated polyamides

Bromoacetic acid (65 mg, 0.5 mmol) and hydroxybenzotriazole (65 mg, 0.5 mmol) were dissolved in 1 ml DMF. DCC (102 mg, 0.5 mmol) was added. After 5 minutes, the DCU was filtered off, and the solution added to the polyamide (10 mg, 0.1 mmol). The filter was washed with 1 ml DMF, and 100 µl DIEA which was added to the reaction. The reaction was allowed to sit at room temperature for 15 minutes. HPLC purification in 0.1% (w/v) TFA with gradient elution of 0.25% $CH_3CN$ $min^{-1}$ Bromoacetylated polyamide was recovered, (0.184 mg, 135.6 µmol). UV $\lambda_{max}(\epsilon)$: 312 nm (66,600). MALDI-TOF MS: 1358.3 (1357.29 calculated for M+1).

E. AcPyPyPyPy-γ-ImPyPyPy-Dp

Synthesized as above. UV $\lambda_{max}(\epsilon)$: 318 nm (66,600). MALDI-TOF MS: 1279.5 (1279.4 calculated for M+1).

F. $NH_2$PyPy-β-PyPyPy-γ-ImPyPy-β-Dp

Synthesized as above. UV $\lambda_{max}(\epsilon)$: 310 nm (66,600). $^1$H NMR (DMSO-$d_6$) δ 10.25 (s, 1H), 9.98 (m, 2H), 9.9 (m, 3H), 9.72 (m, 3H), 9.3 (1H, br s), 8.04–8.02 (m, 4H), 7.44 (s, 1H), 7.23 (d, 1H), 7.20 (d, 1H), 7.18 (s, 1H), 7.17 (d, 1H), 7.167 (s, 1H), 7.145 (s, 1H), 7.119 (s, 1H), 7.08 (s, 1H), 7.025 (s, 1H), 6.9 (s, 1H), 6.85 (s, 1H), 6.80 (d, 1H), 6.79 (s, 1H), 3.90 (s, 3H), 3.85 (s, 3H), 3.81 (s, 3H), 3.80 (s, 3H), 3.77 (s, 3H), 3.66 (br, 12H), 3.43–3.34 (m, 8H), 3.17 (m, 2H), 3.08 (m, 2H), 2.98 (m, 2H), 2.32 (m, 6H), 1.74 (m, 4H).

G. AcPyPy-β-PyPyPy-γ-ImPyPy-β-Dp

To a solution of $NH_2$PyPy-β-PyPyPy-γ-ImPyPy-β-Dp in DMSO/NMP (500 µl) and DIEA (500 µl) was added acetic anhydride (400 µl). The reaction was heated at 55° C. for 15 minutes and HPLC purified as above. UV $\lambda_{max}(\epsilon)$: 310 nm (66,600). MALDI-TOF MS: 1351.0 (1350.5 calculated for M+1).

H. BrAcPyPy-β-PyPyPy-γ-ImPyPy-β-Dp

Synthesized as bromoacetylated polyamide above. UV $\lambda_{max}(\epsilon)$: 314 nm (66,600). MALDI-TOF MS: 1429.3 (1429.4 calculated for M+1).

I. $NH_2$PyPyPy-β-PyPyPy-γ-ImPyPy-β-Dp

Synthesized as above. UV $\lambda_{max}(\epsilon)$: 314 nm (74,925). $^1$H NMR (DMSO-$d_6$) δ 10.25 (s, 1H), 10.02 (s, 1H), 9.99 (s, 1H), 9.90 (m, 3H), 9.72 (m, 2H), 8.03–8.06 (m, 4H), 7.44 (s, 1H), 7.23–7.21 (m, 3H), 7.17–7.12 (m, 4H), 7.09 (d, 1H), 6.98–6.83 (m, 6H), 3.92 (s, 3H), 3.87 (s, 3H), 3.82 (s, 3H), 3.79 (s, 3H), 3.77 (s, 3H), 3.51 (m, 12H), 2.72 (m, 4H), 2.48 (m, 4H), 2.32 (m, 6H) 1.78 (m, 4H).

J. AcPyPyPy-β-PyPyPy-γ-ImPyPy-β-Dp

Acetylated as above. UV $\lambda_{max}(\epsilon)$: 314 nm (74,295). MALDI-TOF MS: 1472.0 (1472.6 calculated for M+1) $NH_2$PyPy-β-PyPyPy-γ-PyPyIm-β-Dp. Synthesized as above. UV $\lambda_{max}(\epsilon)$: 310 nm (66,600). $^1$H NMR (DMSO-$d_6$) δ 10.31 (s, 1H), 9.98 (s, 1H), 9.91 (s, 1H), 9.89 (s, 1H), 9.84 (s, 1H), 9.71 (br, 2H), 8.06–8.08 (m, 3H), 7.95 (s, 1H), 7.48 (s, 1H), 7.28–7.15 (m, H), 7.08 (s, 1H), 7.02 (m, 2H), 6.91–6.86 (m, 3H), 6.80 (s, 1H), 3.91 (s, 3H), 3.86 (s, 3H), 3.82–3.78 (m, 12H), 3.56–3.43 (m, 12H), 3.22 (m, 2H), 3.10 (m, 2H), 3.0 (m, 2H), 2.4 (m, 2H), 2.3 (m, 6H), 1.7 (m, 4H)

K. AcPyPy-β-PyPyPy-γ-PyPyIm-β-Dp

Acetylated as above. UV $\lambda_{max}(\epsilon)$: 310 nm (66,600). MALDI-TOF MS: 1350.0 (1350.5 calculated for M+1) $NH_2$PyPyPyPyPyPy-γ-PyPyIm-β-Dp. Synthesized as above. UV $\lambda_{max}(\epsilon)$: 310 nm (74,925). $^1$H NMR (DMSO-$d_6$) δ 10.31 (s, 1H), 10.04 (s, 1H), 9.95 (d, 3H), 9.90 (s, 1H), 9.84 (d, 2H), 8.08–8.06 (m, 3H), 7.48 (s, 1H), 7.28 (s, 1H), 7.23–7.21 (m, 2H), 7.15 (s, 1H), 7.10–7.07 (m, 8H), 6.94–6.87 (m, 4H), 3.95–3.78 (m, ), 3.58 (m, 2H), 3.43 (m, 2H), 3.19 (m, 2H), 3.07 (m, 2H), 2.36 (m, 2H), 2.32 (m, 6H), 2.25 (m, (2H), 1.74 (m, 4H).

L. AcPyPyPyPyPyPy-γ-PyPyIm-β-Dp

Acetylated as above. UV $\lambda_{max}(\epsilon)$: 310 nm (74,295). MALDI-TOF MS: 1401.0 (1401.5 calculated for M+1). BrAcPyPyPyPyPyPy-γ-PyPyIm-β-Dp. Bromoacetylated as above. UV $\lambda_{max}(\epsilon)$: 310 nm (74.295). MALDI-TOF MS: 1480.7 (1480.4 calculated for M+1).

M. Alkylation reactions

Alkylation was examined on a 262 bp restriction fragment (EcoRI/FspI) of pBR322, radiolabeled on the 3' end (10,000 cpm/reaction). Polyamide or bromodistamycin were added at appropriate concentrations. Final reaction concentrations were 10 mM sodium phosphate (pH 7.0), 100 μM sonicated calf thymus DNA. The reactions were incubated at 37° C. for 0, 1, 5, 10, 20, and 40 hours. Following incubation, the reactions were ethanol precipitated and dissolved in 10 μl 10 mM sodium phosphate buffer and heated at 90° C. for 15 minutes. Piperidine (40 μl, 1.4 M) was added and the reaction heated again for 15 minutes at 90° C. Piperidine was lyophilized off and the reactions were resuspended in 7 μl 1× TBE/80% formamide loading buffer, denatured by heating at 85° C. for 10 minutes and placed on ice. Reactions were electrophoresed on 8% polyacrylamide gels (5% cross link, 7 M urea) in 1× TBE at 2000 V. Gels were dried and exposed to a storage phosphor screen (Molecular Dynamics).

N. NH$_2$PyPyPyPy-γ-ImPyPyPy-NH(CH$_2$)$_2$OH

Polyamide was synthesized as above on glycine linked Pam resin. For cleavage, resin (500 mg) was weighed out into a 50 ml flask in 5 ml 100% EtOH. An equal weight of LiBH$_4$ (500 mg, 23 mmol) was slowly added. Resin was incubated at 55° C. for 2 hours, adding more ethanol as needed. Polyamide was HPLC purified as above. UV $\lambda_{max}$ (ε): 314 nm (66,600). MALDI-TOF MS: 1124.0 (1124.2 calculated). $^1$H NMR (DMSO-d$_6$) δ 10.26 (s, 1H), 10.02 (s, 1H), 9.99 (s, 1H), 9.94 (d, 2H), 9.89 (d, 2H), 8.02 (m, 1H), 7.91 (m, 1H), 7.43 (s, 1H), 7.24–7.20 (m, 2H), 7.16–7.12 (m, 2H), 7.09–7.02 (m, 4H), 6.92–6.84 (m, 4H), 3.92–3.87 (m, 6H), 3.83–3.77 (m, 18H).

Example 4

Polyamide CBI Unit (+)CC-1065 is a natural product isolated from *Streptomyces zelensis*. It binds in the minor groove and shows antitumor activity due to a reactive cyclopropyl moiety which alkylates preferentially at N3 of adenine (Boger and Johnson. *Angew. Chem. Int. Ed. Eng.* 1996, 35, 1438–1474).

Figure 20:
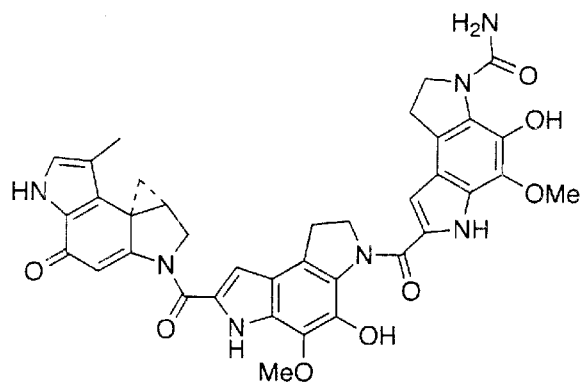
FIG. 20. Structure of (+) CC-1065 and duocarmycins.
Figure 20:
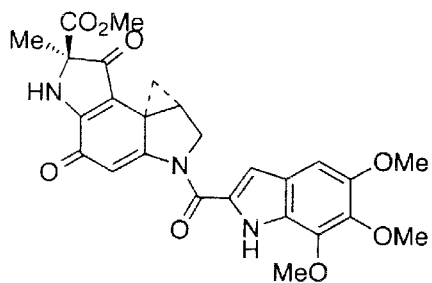
Figure 20:
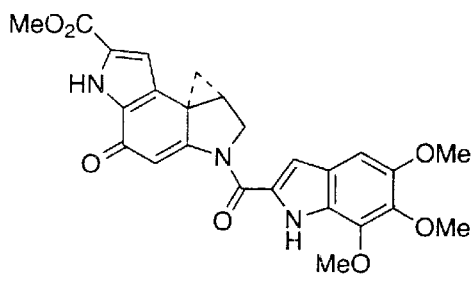

Also in this class of antitumor antibiotics are the duocarmycins. They are structurally very similar to CC-1065, having the reactive cyclopropyl ring, but lacking the third conjugated ring system. These compounds bind in AT tracts, and display strong sequence selectivity for alkylation at adenines. Alkylation will occur at N3 of guanine as well, but only when other AT bp are protected in the minor groove. The flanking sequence preferences for alkylation by CC-1065 are 5'-AAA-3'>5'-TTA-3'>5'-TAA-3'>5'-ATA-3'. The alkylation reaction is reversible for the two duocarmycin compounds but irreversible for CC-1065. This discrepancy is explained by the more extensive non-covalent interactions of CC-1065 with the DNA minor groove. (+)CC-1065 is the natural enantiomer. The unnatural enantiomer has been synthesized by Boger and coworkers and shown to alkylate DNA as well. Interestingly, where the natural enantiomer binds 3' to 5' from the site of alkylation, the unnatural enantiomer binds 5' to 3'. Structures of (+) CC-1065 and the duocarmycins are shown in FIG. 20.

Figure 21:
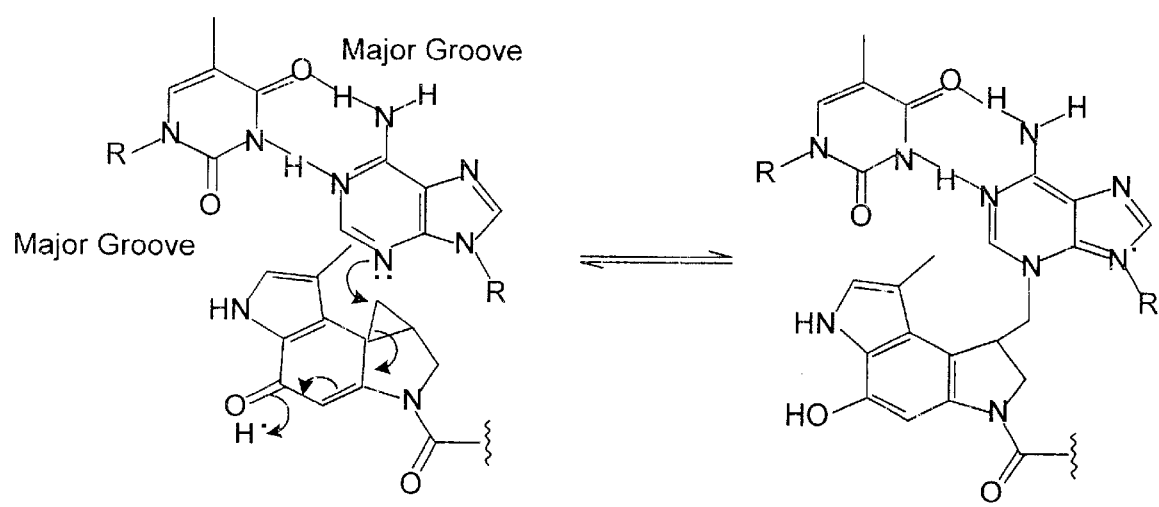
FIG. 21. Alkylation mechanism of CC-1065.

When compared to N-Bromoacetyldistamycin, CC-I065 shows very different reactivity. For reaction times of 1 hour at 37° C., N-Bromoacetyldistamycin shows almost no visible cleavage, while (+)CC-1065 shows intense cleavage at 13 adenines. After 10 hours at 37°, N-Bromoacetyldistamycin shows a comparable amount of cleavage to (+) CC-1065 at 1 hour, but at only one adenine. Despite the apparent similarities between these two molecules, being crescent-shaped with an electrophile that covalently binds DNA, the cyclopropyl electrophile of CC-1065 alkylation shows faster kinetics than that of N-Bromoacetyldistamycin. The alkylation mechanism for CC-1065 is shown in FIG. 21.

Figure 22:
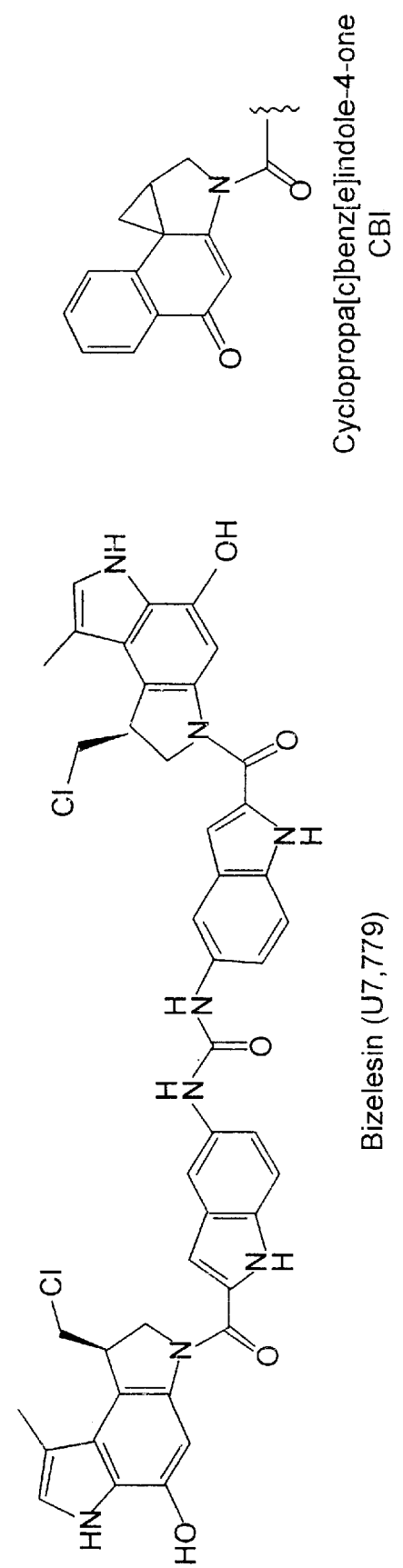
FIG. 22. Structure of Bizlesin and CBI.

Several pro-drug analogues of CC-1065 have also been made. One of the most popular is bizelesin, a bifunctional interstrand DNA crosslinker synthesized by Upjohn. It is believed to go through the same cyclopropyl intermediate as CC-1065, but is more stable than the cyclopropyl analogues. The structures of Bizelesin and CBI are shown in FIG. 22.

Boger et al have synthesized many modified versions of the A ring of (+)CC-1065 to examine the effects of steric changes on the alkylation potency of these drugs. In his work with CC-1065 derivatives, it has been shown that there is a direct linear correlation between drug stability and cytotoxicity. The more solvolytically stable compounds also show the highest degree of cytotoxicity. The most successful modification thus far, is the synthesis of 1,2,9,9a-tetrahydrocyclopropa[c]benz[e]indol-4-one (CBI) which replaces the fused pyrrole with a fused benzene ring, releasing ring strain in the system. (Boger, D. L., Yun, W., and Han, N. *Bioorganic and Medicinal Chemistry* 1995, 3, 1429–1453.) When coupled to the B and C rings of CC-1065, CBI showed greater stability, reactivity, and selectivity than (+)CC-1065 itself. Boger has also shown that a Boc protected CBI unit is sufficient for DNA alkylation. Its fast kinetics and efficient alkylation make CBI an ideal candidate to tether to a hairpin to generate a powerful sequence specific alkylator.

The CBI subunit was synthesized as described by Boger. (Boger, D. L. a McKie., J. A. *J. Org. Chem.* 1995, 60, 1271–1275.) Briefly, N-Boc-4-hydroxy-2-napthylamine was synthesized by the condensation of ammonia and 1,3 dihydroxynaphthalene with immediate Boc protection by Boc anhydride. After protection of the alcohol with benzyl bromide, treatment with NIS provided the iodonaphthylamine. Alkylation with allyl bromide provided a substrate for a favorable 5-exo-trig aryl radical-alkene cyclization to occur, using Bu$_3$SnH and TEMPO radical trap. Cleavage of the TEMPO trap intermediate occurred upon heating with activated Zn powder. Treatment with PPh$_3$/CCl$_4$, followed by hydrolysis of the benzyl ether gave the desired product.

Figure 23:
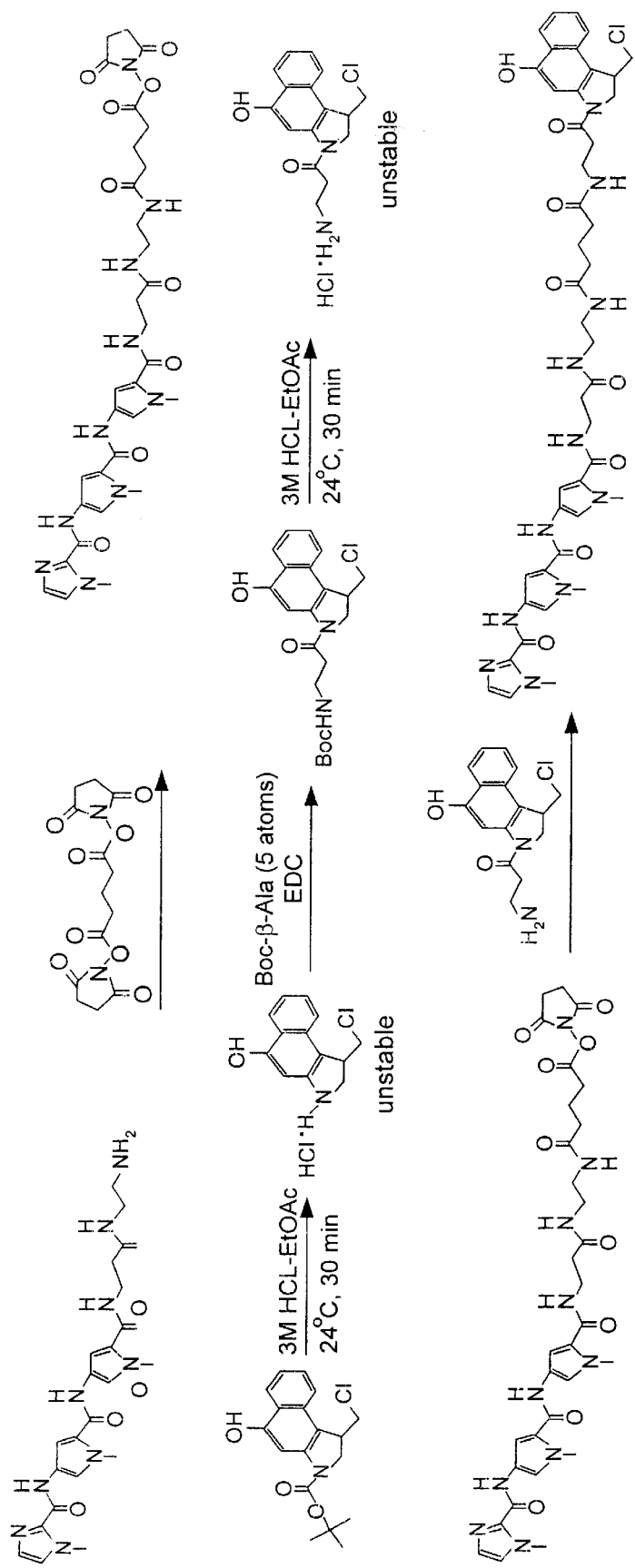
FIG. 23. Synthesis of CBI-polyamide conjugate.

In order to work out the coupling conditions of the polyamide-CBI unit, a simple three ring compound, ImPyPy-β-NH(CH$_2$)$_2$NH$_2$ was made. A new activation strategy used disuccinimidyl glutarate (DSG), a diacid activated with NHS esters. A β-alanine linker was added to the CBI unit to facilitate completion of the reaction, according to the procedure by Lukhtanov, E. A. and coworkers. (Lukhtanov, et al. *Nucleic Acids Research* 1996, 24, 683–687.) After HPLC purification, one major peak was isolated. This fraction was analyzed by mass spectrometry and NMR and could be identified as the polyamide-CBI (chloro) conjugate. The synthesis of a CBI-polyamide conjugate is shown in FIG. 23.

A. ImPyPy-β-ED

Polyamide was synthesized as above, and cleaved with ethylene diamine. HPLC purification as above. UV $\lambda_{max}(\epsilon)$: 300 nm (24,975). $^1$H NMR (DMSO-d$_6$) δ 10.47 (s, 1H), 9.91 (s, 1H), 8.06 (m, 1H), 7.67 (m, 1H), 7.38 (s, 1H), 7.25 (s, 1H), 7.15 (s, 1H), 7.12 (s, 1H), 7.02 (s, 1H), 6.84 (s, 1H), 3.96 (s, 3H), 3.80 (s, 3H), 3.76 (s, 3H), 3.37 (m, 2H), 3.35 (m, 2H), 2.83 (m, 2H), 2.46 (m, 2H).

B. ImPyPy-β-ED-succinimide-NHS

ImPyPy-β-ED (10 mg) was dissolved in 2 ml DMF added 100 µl at a time to a solution of disuccinimidyl glutarate (100 mg) and DIEA (10 µl) in 1 ml DMF at room temperature. The reaction was monitored by analytical HPLC and was complete within an hour after final addition of polyamide. Preparative HPLC gave a white powder. MS (FAB): 695.2 (calculated 694.3). $^1$H NMR (DMSO-d$_6$) δ 10.49 (s, 1H), 9.91 (s, 1H), 8.01 (m, 1H), 7.92 (m, 1H), 7.87 (m, 1H), 7.38 (s, 1H), 7.25 (s, 1H), 7.17 (s, 1H), 7.11 (s, 1H), 7.04 (s, 1H), 6.78 (s, 1H), 3.96 (s, 3H), 3.80 (s, 3H), 3.76 (s, 3H), 3.33 (m, 2H), 3.05 (m, 2H), 2.77 (m, 2H), 2.65 (m, 2H), 2.55 (m, 2H), 2.30 (m, 2H), 2.28 (m, 2H), 2.16 (m, 2H), 2.13 (m, 2H), 1.78 (m, 2H).

C. Boc-β-alanine-CBI

Deprotect alcohol (217 mg, 0.65 mmol) as above. After removing ethyl acetate, dissolve in dry DMF (10 ml). Add to Boc-β-alanine (245.98 mg, 1.3 mmol) and EDC (767 mg, 4 mmol). Reaction was stirred under argon overnight. Solvent was removed in vacuo and precipitated in 20 ml of water. The precipitate was centrifuged, washed, with water, and lyophilized. Flash chromatography gave a yellow powder. $^1$H NMR (DMSO-d$_6$) δ 9.43 (br s, 1H), 8.31 (s, 1H), 8.29 (s, 1H), 7.65 (d, 1H), 7.53 (t, 1H), 7.40 (t, 1H), 5.56 (m, 1H).

D. CBI conjugated polyamide

Boc-β-alanine CBI was deprotected as above. A solution of ImPyPy-β-ED-succinimide-NHS (20 mg) in 100 µl DMF was added with 10 µl DIEA. Reaction was stirred at room temperature under argon overnight. HPLC purification gave a white powder. MS(FAB): 884.1 (calculated 884.4) $^1$H NMR (DMSO-d$_6$) δ 10.50 (s, 1H), 10.36 (br s, 1H), 9.91 (s, 1H), 8.04 (m, 2H), 7.92 (m, 2H), 7.87 (m, 1H), 7.81 (m, 1H), 7.73 (m, 2H), 7.44 (t, 2H), 7.41 (s, 1H), 7.27–7.25 (m, 3H), 7.16 (s, 1H), 7.10 (s, 1H), 7.06 (s, 1H).

Example 5

Polyamide-Intercalator Conjugates

The artificial regulation of protein:DNA interactions is a potentially powerful therapeutic tool. Protein recognition of DNA, both specific and non-specific, is based heavily on the nearby DNA structure. (Luisi, B. (1995) in *DNA-Protein: Structural Interactions*, ed. Lilley, D. M. J. (IRL Press, Oxford), p. 23.) For example, a bent sequence of DNA may recruit a non-specific protein, as in HMG-I, or prevent a protein from making the appropriate contacts for high-affinity binding. Small molecules designed to bind predetermined sequences of DNA and modulate the local DNA topology may be a general approach for regulation of the function of DNA binding proteins.

Intercalators are a class of molecules which are potent antibiotic and antitumor drugs. (Neidle and Abraham, (1984) *CRC Crit. Rev. Biochem.* 17, 73–121. Wang, A. H-J. (1992) *Curr. Opin. Struct. Biol.* 2, 361–368.) Lerman first described intercalation as the insertion of a flat, aromatic chromophore between adjacent base pairs of the double helix. (Lerman, L. S. (1961) *J. Mol. Biol.* 3, 18–30.) The rise of B-form DNA is usually 3.4 A/base pair. The stacking of the intercalator separates the adjacent base pairs by another 3.4 A and extends the length of the helix and equivalent amount per bound intercalator. The base pairs neighboring the intercalation site are also unwound 10–26° with respect to one another. Generally, it is these structural distortions introduced by intercalation which are considered to be the basis for their therapeutic activity. However, it is important to note that in most cases the DNA helix returns to its B-form structure within a few base pairs of the intercalation site.

Due to their nature of stacking between the base pairs, intercalators generally exhibit little or no sequence specificity. A few natural products, such as actinomycin D and the anthracycline and pluramycin families of intercalators, have added functionalitites which impart preference for certain dinucleotide steps. (Hansen and Hurley (1996) *Acc. Chem. Res.* 29, 249-\.) Actinomycin D, consists of an aromatic phenoxazone core coupled to two identical cyclic pentapeptides that make contacts to the exocyclic amine of guanine, granting specificity for intercalation at 5'-GC-3' steps. Similarly, carbohydrate moieties attached to the chromophore of the anthracycline and pluramycin intercalators interact with the DNA bases in both the major and minor grooves and grant these molecules their sequence preferences. In almost all cases, the sequence specificity of these natural products is limited to the two base pairs adjacent to the intercalation site.

Netropsin and distamycin A are pyrrole carboxamide natural products which bind in the minor groove of DNA at sites of 4–5 contiguous A,T base pairs. (Krylov, et al. (1979) *Nucleic Acids Res.* 6, 289–304; Zasedatelev, et al. (1974) *Mol. Biol. Rep.* 1, 337–342; Zasedatelev, et al. (1976) *Dokl. Akad. Nauk SSSR* (1976) 231, 1006–1009; Zimmer, and Wanhert (1986) *Prog. Biophys. Mol. Biol.* 47, 31–112; Van Dyke, et al. (1982) *Proc. Natl. Acad. Sci., USA* 79, 5470–5474; Van Dyke and Dervan (1982) Cold Spring Harbor *Symp. Quant. Biol.* 47, 347–353; Van Dyke and Dervan, (1983) *Biochemistry* 47, 2373–2377; Harshman and Dervan (1985) *Nucleic Acids Res.* 13, 4825–4835; Fox and Waring, (1984) *Nucleic Acids Res.* 12, 9271–9285; Lane et al. (1983) *Proc. Natl. Acad. Sci., USA* 80, 3260–3264). In an attempt to create an intercalator with designed sequence specificity, a number of researchers have linked analogs of distamycin or netropsin to a non-specific intercalator. (Bailly and Henichart, (1991) *Bioconj. Chem.* 2, 379–393; Bourdouxhe-Housiaux, et al. (1996) *Biochemistry* 35, 4251–4264; Bailly, et al. (1994) *Biochemistry* 33, 15348–15364; Subra, et al. (1991) *Biochemistry* 30, 1642–1650; Eliadis, et al. (1988) *J. Chem. Soc. Chem. Comm.* 1049–1052; Wang, et al. (1994) *Gene* 149, 63–67; Arcamone, F. (1994) *Gene* 149, 57–61.) Although these efforts have met with some success, these compounds target mixed sequences of A•T and G•C base pairs. More specifically none of these compounds can bind a broad range of predetermined DNA sequences. Even more specifically, none of these compounds can bind a predetermined sequence with subnanomolar affinity.

Linking a non-specific intercalator moiety to a polyamide may produce the sequence specific distortions of DNA structure required to regulate protein:DNA interactions. Ethidium bromide is a common intercalator which has been shown to bind DNA with a Ka of approximately $10^5$ M$^{-1}$ and unwind the DNA helix by 26°. (LePecq and Paoletti (1967) *J. Mol. Biol.* 27, 87–106; Waring, M. (1970) *J. Mol. Biol.* 54, 247–279; Wang, J. C. (1974) *J. Mol. Biol.* 89, 783–801; Bresloff and Crothers (1975) *J. Mol. Biol.* 95, 103–123). A derivative of ethidium, methidium, has been used previously in the preparation of designed intercalators and serves as the basis of methidium-propyl-Fe•EDTA (MPE) footprinting. (Dervan and Becker (1978) *J. Am. Chem. Soc.* 100, 1968–1970; Hertzberg and Dervan (1982) *J. Am. Chem. Soc.* 104, 313–315.) The synthesis and DNA-binding properties of a series of methidium-polyamide conjugates have been discovered by the present inventor.

Methidium-polyamide conjugates are designed to sequence specifically induce helical unwinding and extension which may be sufficient to inhibit DNA binding by a wide variety of DNA binding proteins, such as the transcription factor, GCN-4, SP1, and NF-κB.

A. Design and Synthesis of Methidium-Polyamide Intercalators

Figure 24:
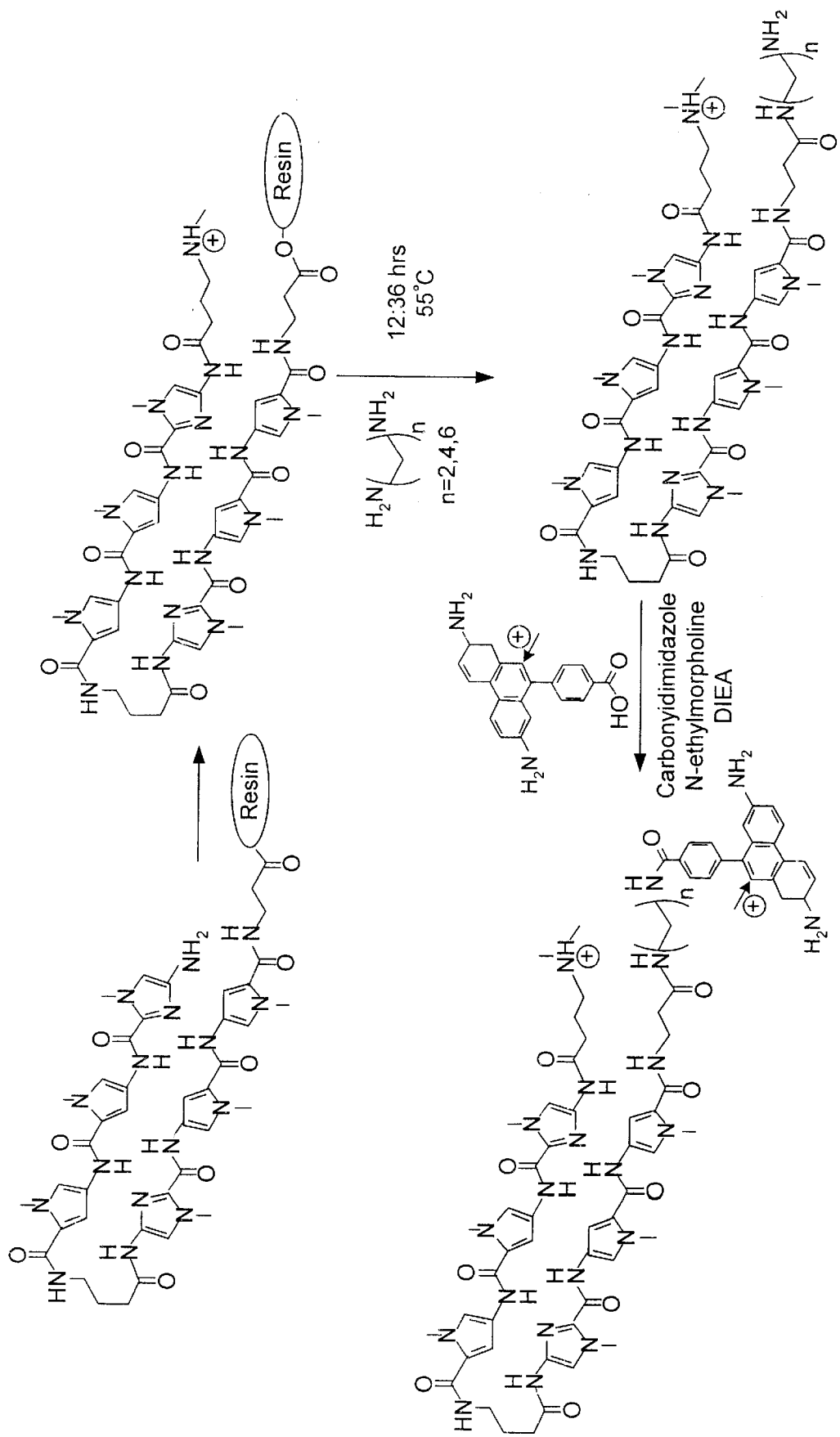
FIG. 24. Synthesis of bifunctional methidium-polyamide conjugates.

A series of methidium-polyamide conjugates of the general design DMγ-ImPyPy-γ-ImPyPy-β-$C_n$-Mdm (DMγ=N, N-dimethyl-γ-aminobutyric acid, $C_n$=diamine linker of n carbons, Mdm=p-carboxymethidium) were synthesized. Polyamides generally contain a C-terminal positively charged dimethylaminopropyl amide. In this case, since the C-terminus is conjugated to the methidium, DMγ was placed on the N-terminus to retain the net positive charge. This alteration has no significant effect on polyamide binding. Boc-chemistry solid phase polyamide synthesis allows for the rapid preparation of milligram quantities of purified polyamide suitable for methidium conjugation in solution. DMγ-ImPyPy-γ-ImPyPy-β-Pam-resin was prepared from Boc-Py-OBt ester and Boc-Im acid monomers. Aminolysis with various diamines ($NH_2(CH_2)_nNH_2$, n=2, 4, 6) followed by preparatory HPLC purification afforded free polyamide with a C-terminal primary amine suitable for coupling to methidium. Reaction of the polyamide amine with the acylimidazole ester ofp-carboxy methidium and HPLC purification produced a series of methidium-polyamide conjugates with various linker lengths. The polyamide/methidium coupling reaction was quantitative by analytical HPLC. An average recovery of purified conjugate of 14.5% from DMγ-ImPyPy-γ-ImPyPy-β-$C_n$-$NH_2$ was acheived. The $^1$H NMR spectrum of each conjugate has resonances consistent with polyamide and methidium protons, as well as an additional broad triplet at 8.75 ppm resulting from the amide bond formed in the polyamide/methidium coupling reaction. MALDI-TOF mass spectrometry analysis of each conjugate reveals the presence of compounds consistent with the mass of the conjugated species, with no free polyamide or methidium observed. The synthesis of bifunctional methidium-polyamide conjugates is described in FIG. 24.

DMγ-ImPyPy-γ-ImPyPy-β-$C_n$-Mdm conjugates are targeted to the 5'-TGACT-3' portion of the ARE and GCRE binding sites of GCN4. By CPK modeling, intercalation is expected to occur between the two base pairs at the 3' end of the GCN4 biding site, AT for ARE (5'-CTGACTAAT-3') and TT GCRE (5'-ATGACTCTT-3') (intercalation site bolded). Coupling of the methidium ($K_a$ $10^5$ $M^{-1}$) and polyamide ($K_a$ $10^5$ $M^{-1}$) moieties is also expected to produce a significant increase in binding affinity. Binding of a methidium-polyamide conjugate to a 5'-AGTGTA-3' site is depicted below. The methidium is represented as a grey rectangle and is placed between the base pairs where intercalation is predicted based on molecular modeling studies.

$^1$H NMR were recorded on a GE 300 instrument operating at 300 MHz. Spectra were recorded in DMSO-$d_6$ with chemical shifts reported in parts per million relative to residual DMSO-$d_5$. UV spectra were measured on a Hewlett-Packard Model 8452A diode array spectrophotometer. Matrix-assisted, laser desorption/ionization time of flight mass spectrometry was carried out at the Protein and Peptide Microanalytical Facility at the California Institute of Technology. HPLC analysis was performed either on a HP 1090 M analytical HPLC or a Beckman Gold system using a Rainen C18, Microsorb MV, 5 μm, 300×4.6 mm reversed phase column in 0.1% (wt/v) TFA with acetonitrile as eluent and a flow rate of 1.0 ml/min, gradient elution 1.25% acetonitrile/min. Preparatory HPLC was carried out on a Beckman instrument using a Waters DeltaPak 25×100 mm 100 μm $C_{18}$ column in 0.1% (wt/v) TFA, gradient elution 0.25%/min. $CH_3CN$. Wafer was obtained from a Millipore Milli-Q water purification system. Reagent-grade chemicals were used unless otherwise stated. Restriction endonucleases were purchased from either New England Biolabs or Boeringher-Mannheim and used according to the manufacturer's protocol. Sequenase (version 2.0) was obtained from United States Biochemical, And DNase I (FPLCpure) was obtained from Boeringher-Mannheim. [α-$^{32}$P]-Thymidine-5'-triphosphate (3000 $C_i$/mmol), and [α-$^{32}$P]-deoxyadenosine-5'-triphosphate (6000 $C_i$/mmol), were purchased from Du Pont/NEN.

B. Synthesis of Polyamide-Methidium Conjugates

Boc-Im acid and Boc-Py-OBt were synthesized in 5 and 6 steps, respectively. DMγ-ImPyPy-γ-ImPyPy-β-Pam-resin was prepared using Boc-chemistry manual solid phase synthesis protocols. Polyamide was cleaved from the resin (400 mg) by aminolysis in neat diamine (2 mL, 24–48 hours, 60° C.) and purified by preparative HPLC. p-Carboxy methidium acid (50 mg) in DMSO (1 mL) was activated by reaction with carbonyl diimidazole (22 mg) and N-ethylmorpholine (15 μL) in DMSO (200 μL) (25° C., 1 hour). Aliquots of this solution (375 μL) and DIEA (150 μL) were added to DMγ-ImPyPy-γ-ImPyPy-β-$C_n$-$NH_2$ (n=2, 4, 6) polyamides, each in DMSO (150 μL). After 12–24 hours the reaction was diluted with 0.1% (wt.v) TFA (5 mL) and purified by HPLC.

C. Dmγ-ImPyPy-γ-ImPyPy-β-$C_2$-Mdm

Coupling of p-carboxy methidium acid acid to DMγ-ImPyPy-γ-ImPyPy-β-$C_2$-$NH_2$ (20 mg, 19 μmol) afforded DMγ-ImPyPy-γ-ImPyPy-β-$C_2$-Mdm as a purpose powder. (3.0 mg, 2 μmol, 10.5% recovery). HPLC r.t. 28.9, UV $\lambda_{max}$ (ε), 290 (93,000); $^1$H NMR (DMSO-$d_6$); d 10.38 (s, 1 H), 10.25 (s, 1 H), 9.99 (s, 1 H), 9.95 (s, 1 H), 9.89 (s, 2 H), 9.4

5'-G C A  T A A G T G T A A A G C C-3'

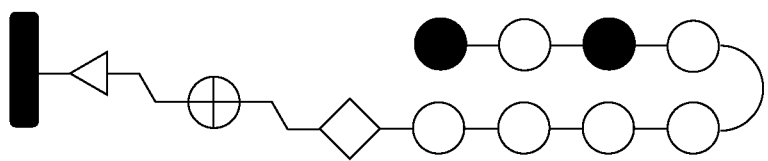

32p 3'-C G T  A T T C A C A T T T C G G-5'

(br s, 1 H), 8.80 (t, 1 H), 8.65 (t, 2 H), 8.18 (d, 2 H), 8.08 (m, 3 H), 7.73 (d, 2 H), 7.48 (d, 1 H), 7.42 (s, 1 H), 7.41 (s, 1 H), 7.30 (d, 2 H), 7.23 (s, 2 H), 7.15 (m, 2 H), 6.86 (s, 1 H), 6.82 (s, 1 H), 6.30 (d, 1 H), 3.93 (s, 9 H), 3.82 (s, 3 H), 3.80 (s, 3 H), 3.78 (s, 6 H), 3.38 (m, 2 H), 3.18 (m, 2 H), 3.08 (m, 4 H), 2.76 (d, 6 H), 2.35 (m, 9 H), 1.92 (m, 2 H), 1.76 (m, 2 H). MALDI-TOF MS 1390.8 (1390.6 calc. for M+H).

D. DMγ-ImPyPy-γ-ImPyPy-β-C$_4$-Mdm

Coupling of p-carboxy methidium acid acid to DMγ-ImPyPy-γ-ImPyPy-β-C$_4$-NH$_2$ (35 mg, 32 μmol) afforded DMγ-ImPyPy-γ-ImPyPy-β-C$_4$-Mdm as a purpose powder. (8.7 mg, 6 μmol, 19% recovery). HPLC r.t. 29.7, UV $\lambda_{max}$ (ε), 290 (93,000); $^1$H NMR (DMSO-d$_6$); d 10.38 (s, 1 H), 10.25 (s, 1 H), 9.97 (s, 1 H), 9.95 (s, 1 H), 9.90 (s, 2 H), 9.4 (br s, 1 H), 8.74 (t, 1 H), 8.61 (t, 2 H), 8.17 (d, 2 H), 8.02 (m, 2 H), 7.95 (t, 1 H), 7.73 (d, 2 H), 7.48 (d, 1 H), 7.43 (s, 1 H), 7.42 (s, 1 H), 7.30 (d, 2 h), 7.23 (s, 2 H), 7.15 (m, 2 H), 6.87 (s, 1 H), 6.82 (s, 1 H), 6.30 (d, 1 H), 3.93 (m, 6 H), 3.92 (s, 3 H), 3.82 (s, 3 H), 3.81 (s, 3 H), 3.77 (s, 6 H), 3.38 (m, 2 H), 3.18 (m, 2 H), 3.08 (m, 4 H), 2.76 (d, 6 H), 2.40 (m, 9 H), 1.92 (m, 2 H), 1.78 (m, 2 H), 1.50 (m, 4 H). MALDI-TOF MS 1418.7 (1418.6 calc. for M+H).

E. DMγ-ImPyPy-γ-ImPyPy-β-C$_6$-Mdm

Coupling of p-carboxy methidium acid acid to DMγ-ImPyPy-γ-ImPyPy-β-C$_6$-NH$_2$ (30 mg, 27 μmol) afforded DMγ-ImPyPy-γ-ImPyPy-β-C$_6$-Mdm as a purple powder. (5.3 mg, 3.7 μmol, 14% recovery). HPLC r.t. 30.6, UV $\lambda_{max}$ (ε), 290 (93,000); $^1$H NMR (DMSO-d$_6$); d 10.38 (s, 1 H), 10.26 (s, 1 H), 9.98 (s, 1 H), 9.95 (s, 1 H), 9.90 (s, 2 H), 9.4 (br s, 1 H), 8.73 (t, 1 H), 8.61 (t, 2 H), 8.17 (d, 2 H), 8.02 (m, 2 H), 7.89 (t, 1 H), 7.73 (d, 2 H), 7.48 (d, 1 H), 7.44 (s, 1 H), 7.43 (s, 1 H), 7.30 (d, 2 H), 7.24 (s, 2 H), 7.14 (m, 2 H), 6.88 (s, 1 H), 6.83 (s, 1 H), 6.31 (d, 1 H), 3.93 (m, 9 H), 3.83 (m, 6 H), 3.78 (s, 6 H), 3.31 (m, 2 H), 3.18 (m, 2 H), 3.03 (m, 4 H), 2.76 (d, 6 H), 2.35 (m, 9 H), 1.92 (m, 2 H), 1.78 (m, 2 H), 1.50 (m, 6 H). MALDI-TOF MS 1446.7 (1446.9 calc. for M+H).

Example 6

Polyamide Dye Conjugates

Solution methods for the sequence-specific detection of nucleic acids offer several advantages in terms of sample preparation and of time resolution of measurements. Currently most efforts in this direction focus on hybridization methods of single stranded targets. The targeting of double helical DNA allow for the direct detection of biological DNA samples including plasmid, cosmid, or genomic DNA. DNA-binding pyrrole-imidazole polyamide will sequence-specifically deliver environmentally sensitive fluorochromes to the DNA. Several dyes show a markedly increased fluorescence upon binding to DNA, among these are Hoechst 33258, ethidium bromide, and most notably thiazole orange. More generally, dyes such as dansyl and mansyl show tremendous sensitivity to environment.

Conjugates have been prepared with a number of such dyes in order to develop sequence-specific, high affinity DNA fluorochromes. The polyamide portion of each dye was prepared using solid phase synthetic methodology and reacted with an amine reactive fluorochrome. A number of dyes and 'linker diamines' are being investigated. These conjugates are unique, in that they combine the ability to recognize any predetermined DNA sequence with the ability to signal binding events directly.

Figure 25:
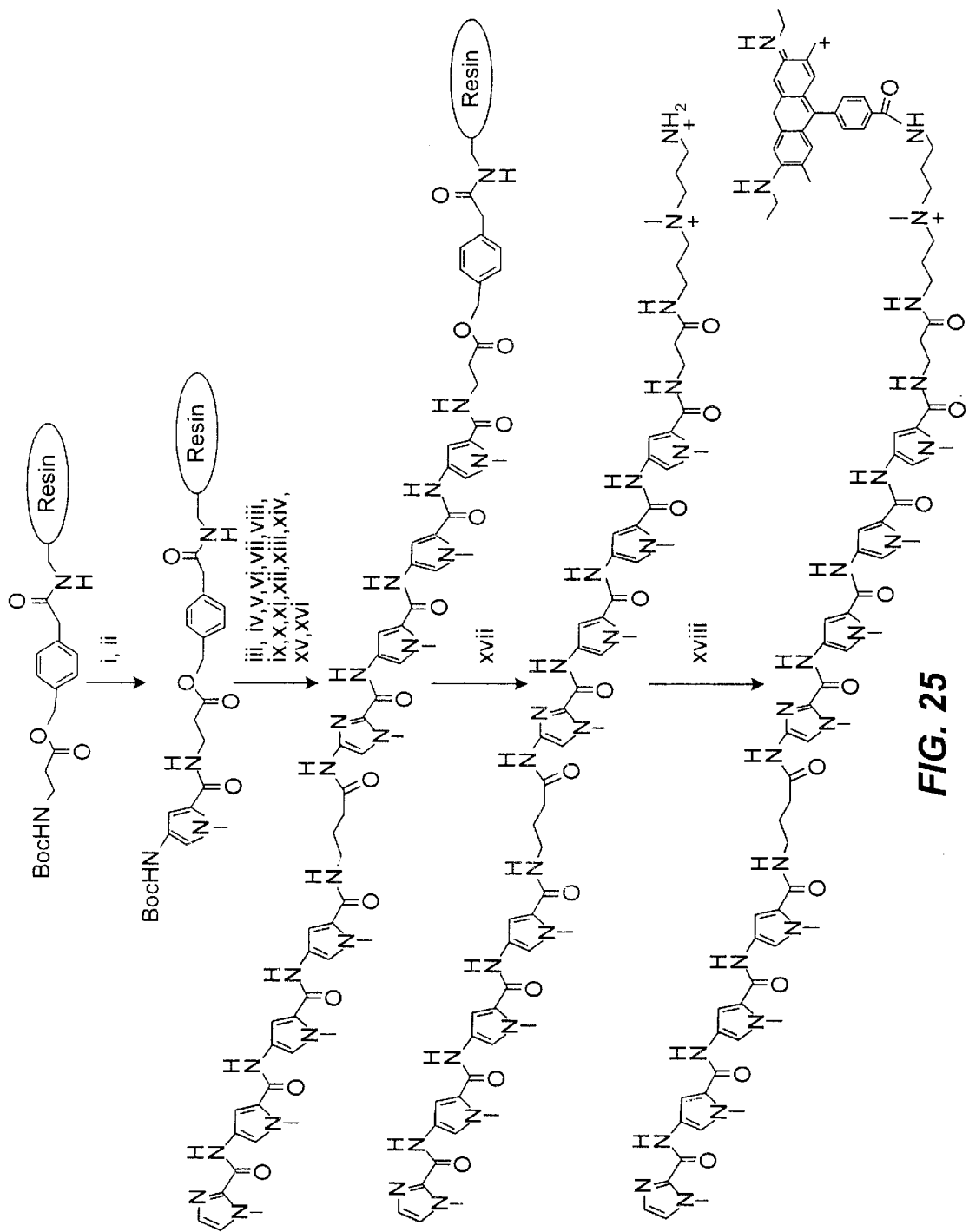
FIG. 25. Synthesis of polyamide-rhodamine conjugate.
Figure 26A:
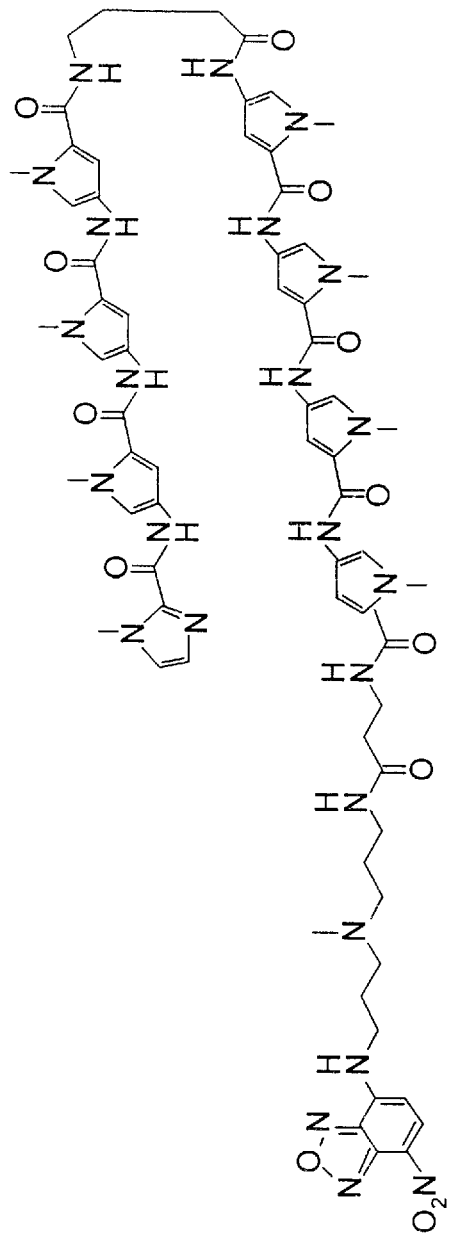
FIG. 26. Structure of polyamide-DYE conjugates.
Figure 26B:
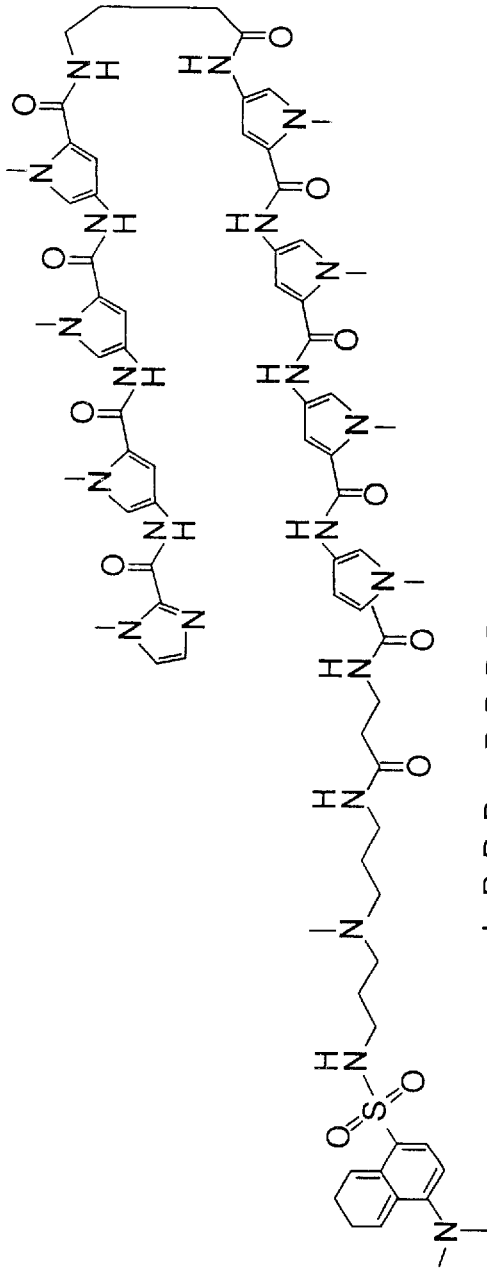
Figure 26C:
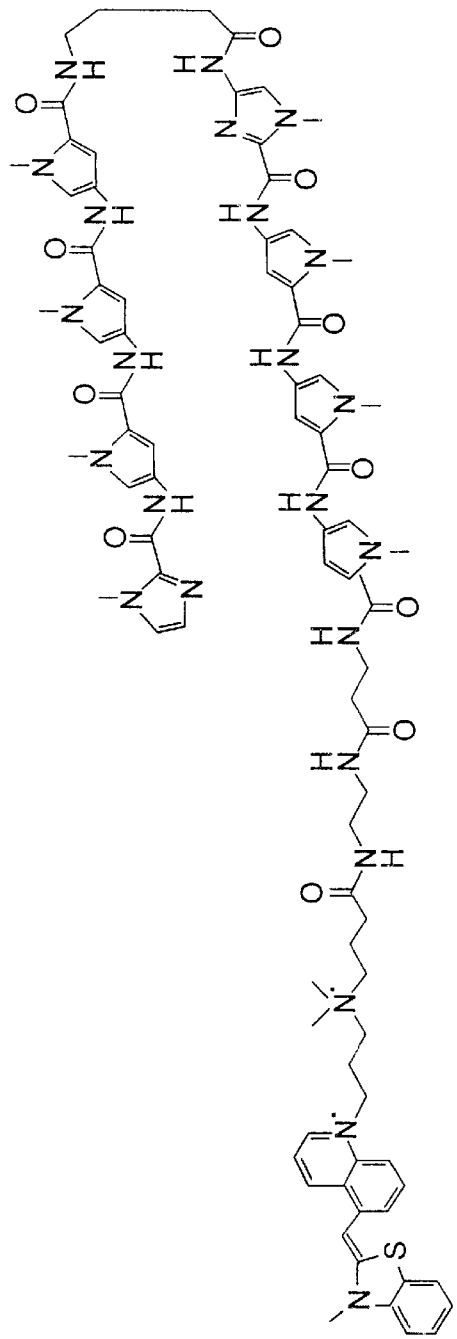
Figure 26D:
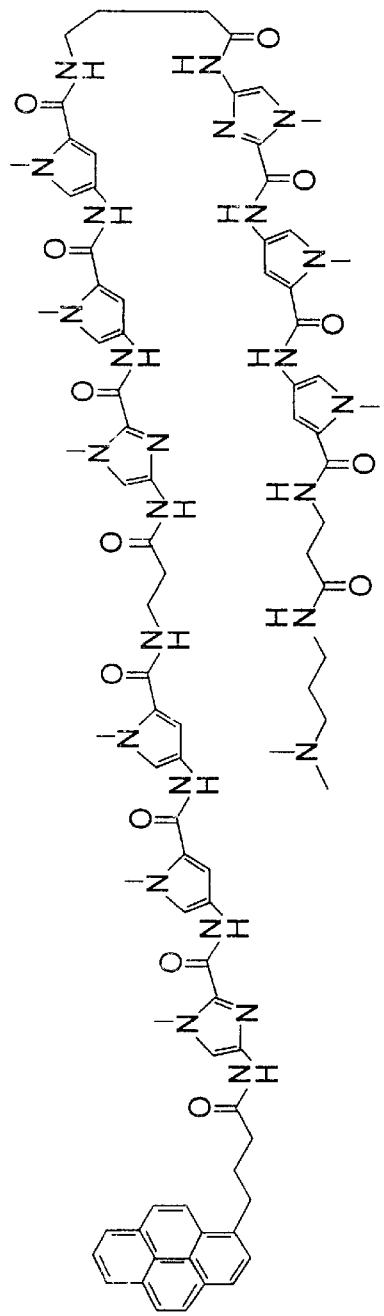

The synthesis of a polyamide-rhodamine conjugate is outlined below. [(i) 80% TFA/DCM 0.4M PhSH; (ii) BocPy-OBt, DIEA, DMF; (iii) 80% TFA/DCM, 0.4M PhSH; (iv) BocPy-OBt, DIEA, DMF; (v) 80% TFA/DCM, 0.4M PhSH; (vi) BocPy-OBt, DIEA, DMF; (vii) 80% TFA/DCM, 0.4M PhSH; (viii) Boc-γ-aminobutyric acid-Im-OBt, HBTU, DIEA, DMF; (ix) 80% TFA/DCM, 0.4M PhSH; (x) BocPy-OBt, DIEA, DMF; (xi) 80% TFA/DCM, 0.4M PhSH; (xii) BocPy-OBt, DIEA, DMF; (xiii) 80% TFA/DCM, 0.4M PhSH; (xiv) BocPy-OBt, DIEA, DMF; (xv) 80% TFA/DCM, 0.4M PhSH; (xvi) Imidazole-2-carboxylic acid (HBTU/DIEA); (xvii) diamino-N-methyldipropylamine, 55° C.; (xviii) 5-carboxyrhodamine 6G succinimidyl ester, 20 mM HEPES, pH 7.5, 25° C.] (FIG. 25). The chemical structures of a number of polyamide-DYE conjugates are shown in FIGS. 26A–D.

Example 7

DNA Detection Through Energy Transfer

Systems which show enhanced or specific fluorescence upon binding to a specific DNA sequence could be useful reagents for genomic analysis. Energy transfer between Dyes provides a means of detecting simultaneous binding of sequence-specific imidazole-pyrrole polyamides to proximal DNA binding sites. (Ju, et al. *Proc. Natl. Acad. Sci.* 92, 4347–4351; Nie et al., *Science* 266, 1018–1021). Two DNA binding polyamides will be prepared to target adjacent DNA binding site, one conjugated to a donor dye, the other conjugated to an acceptor dye. Dye pairs will be chosen such that the donor dye can be excited without exciting the acceptor. With excitation at this energy, fluorescence of the acceptor fluorochrome will only occur while proximal to the donor fluorochrome thorugh energy transfer from the donor. The required binding of the two polyamides will lengthen the effective recognition sequence to the levels appropriate for genomic level analysis and will improve the specificity of the technique.

Using dye conjugation chemistry developed by the present inventor, conjugates will be prepared purified, and characterized. Donor-acceptor pairs such as fluorescein-rhodamine or thiazole-orange/rhodamine will be analyzed for their computability in this system. This energy transfer system increases the currently accessible recognition sequence for polyamides and provides for a unique binding-dependent signal, applicable for both homogenous and heterogenous detection systems.

Pyrene and similar systems for excimers (excited state dimers) provide two or more molecules are close in three dimensional space. DNA-binding polyamides deliver pyrene to proximal positions on DNA. Binding is then monitored by the formation of the excimer.

The structures of a pyrene conjugate is shown below:

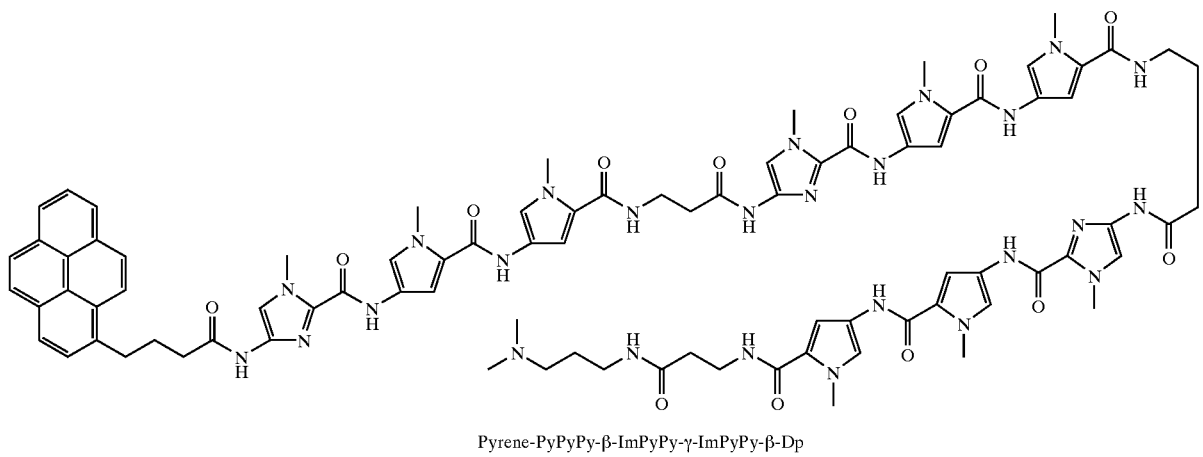

Pyrene-PyPyPy-β-ImPyPy-γ-ImPyPy-β-Dp

Example 8

Polyamide Biotin Conjugates

Conjugates prepared between sequence specific DNA binding polyamides and biotin are useful for a variety of applications. First, such compounds can be readily attached to a variety of matrices through the strong interaction of biotin with the protein streptavidin. (Weber. P. C., Ohlendorf, D. H., Wendoloski, J. J., Salemme, F. R. *Science* 243, 85–88) Readily available strepdavidin-derivatized matrices include magnetic beads for separations as well as resins for chromatography. (Ito, T., Smith, C. L., Cantor, C. R. *Proc. Natl. Acad. Sci.* 89, 495–498; Tagle, D. A., Swaroop, M., Lovett, M., Collins, F. S. *Nature* 361, 751–753)

Figure 27:
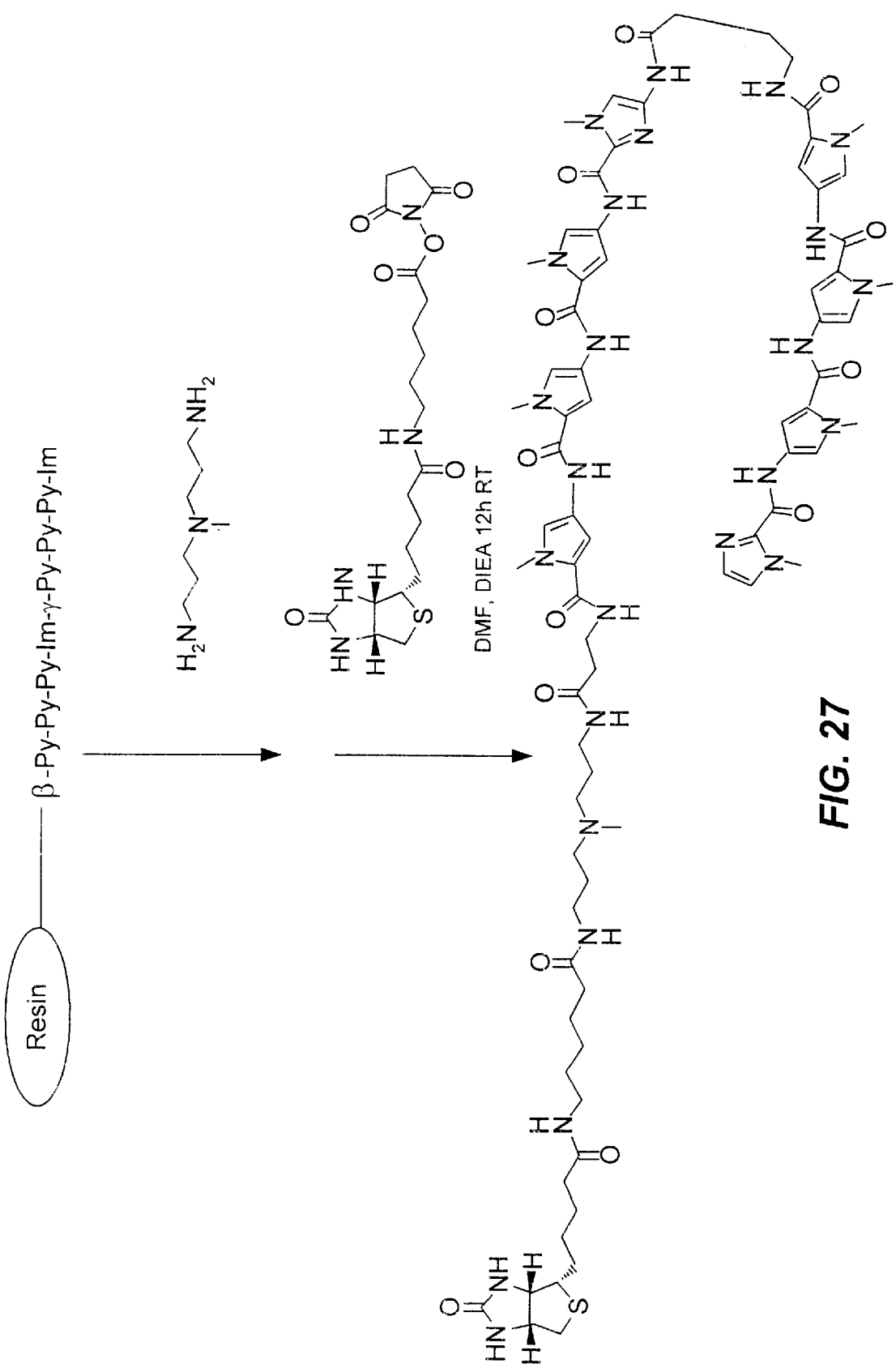
FIG. 27. Synthesis of biotin-polyamide conjugates.
Figure 28C:
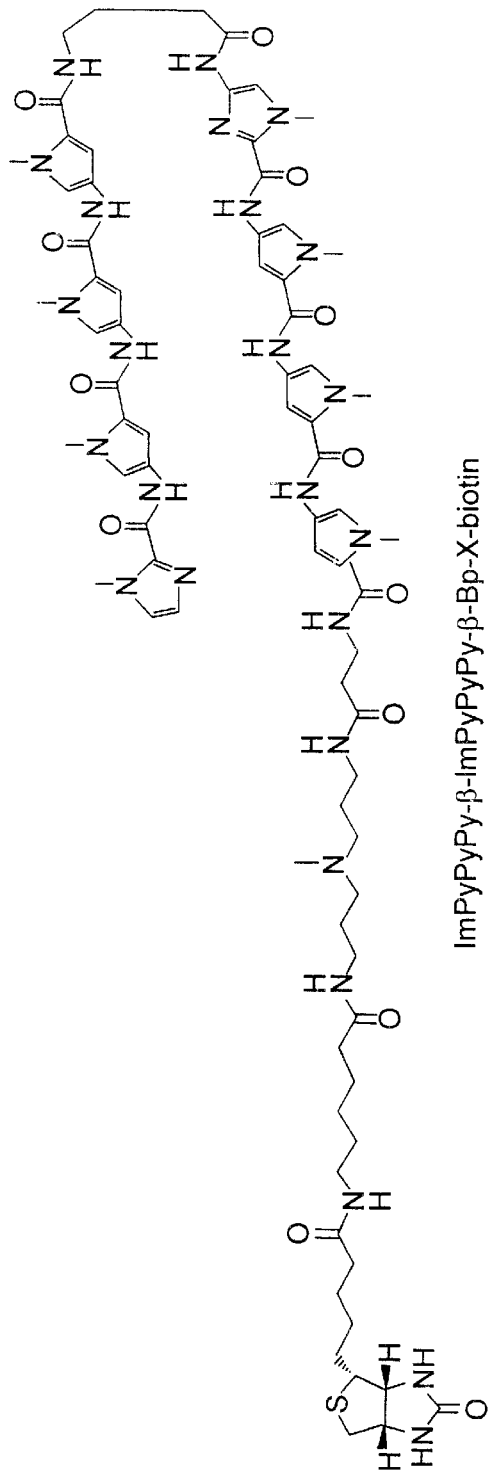
FIG. 28. Bifunctional biotin-polyamide conjugates.
Figure 28D:
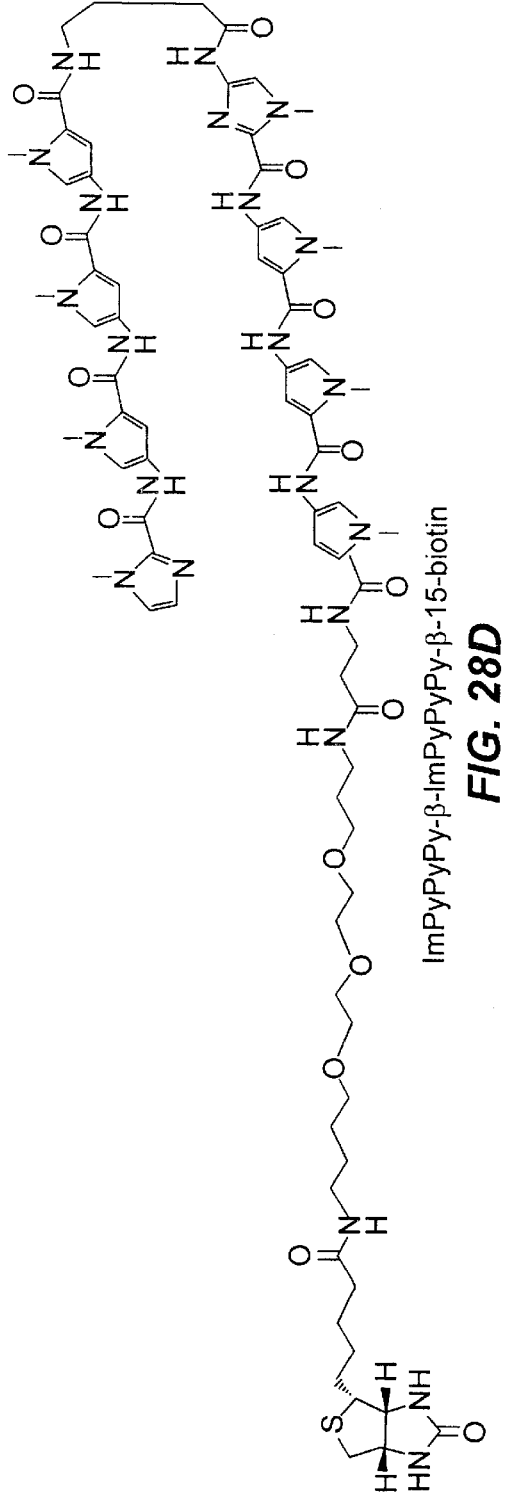
Figure 29:
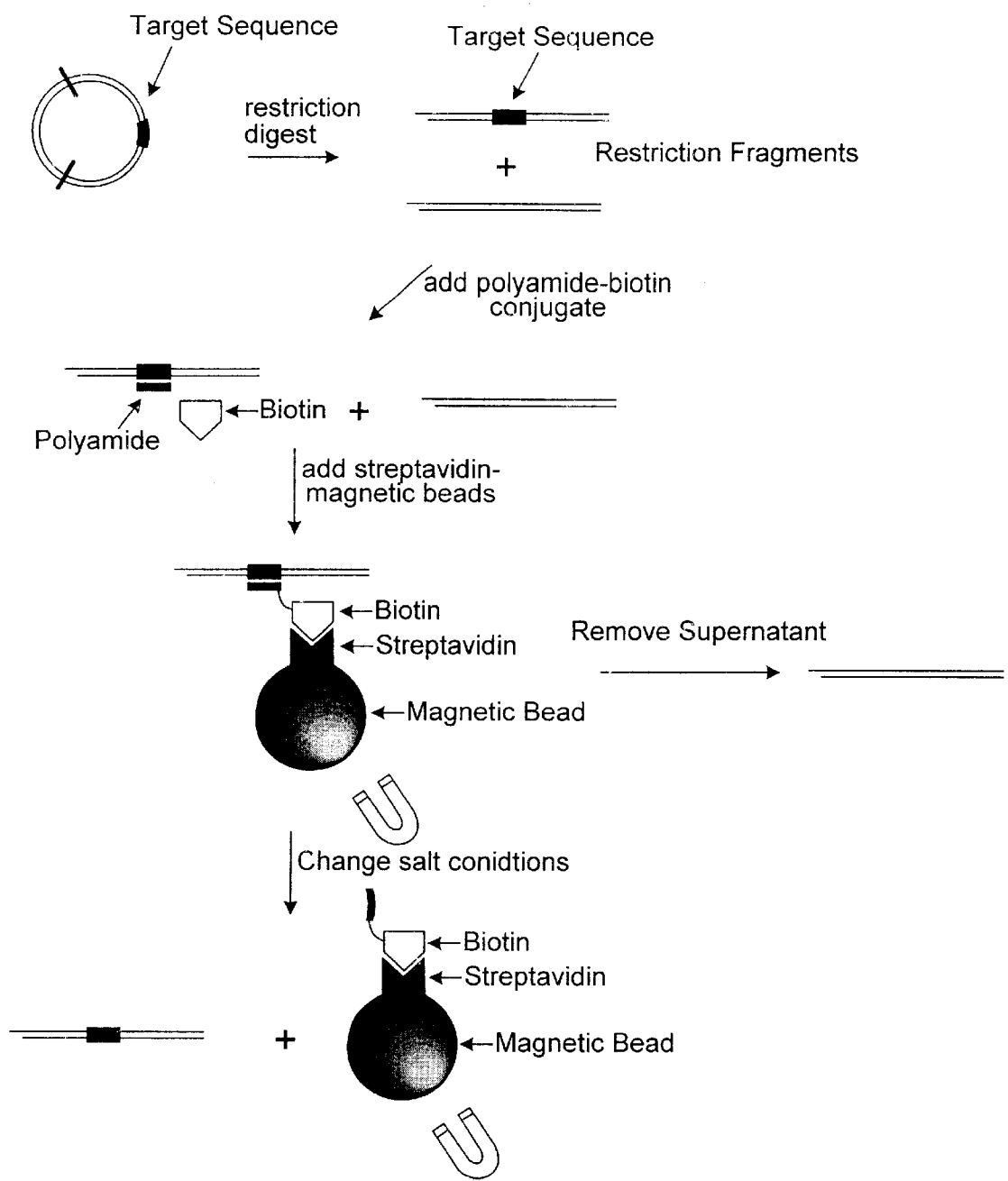
FIG. 29. Affinity capture using bifunctional biotin-polyamide conjugates.

A number of such polyamide-biotin conjugates have been synthesized by solid phase synthetic methods. Following resin cleavage with a variety of diamines, the polyamides were reacted with carious biotin carboxylic acid derivatives to yield conjugates. The conjugates were purified by HPLC and characterized by MALDI-TOF mass spectroscopy and 1H NMR. The synthesis of biotin-polyamide conjugate is shown in FIG. 27. The chemical structure of a number of bifunctional biotin-polyamide conjugates prepared by the present invention are shown in FIGS. 28A–D. A scheme for sequence specific affinity capture by a bifunctional polyamide-biotin conjugates is outlined in FIG. 29.

Example 9

Photoactivated Modification of DNA By A Polyamide-Psoralen Conjugate

Figure 30:
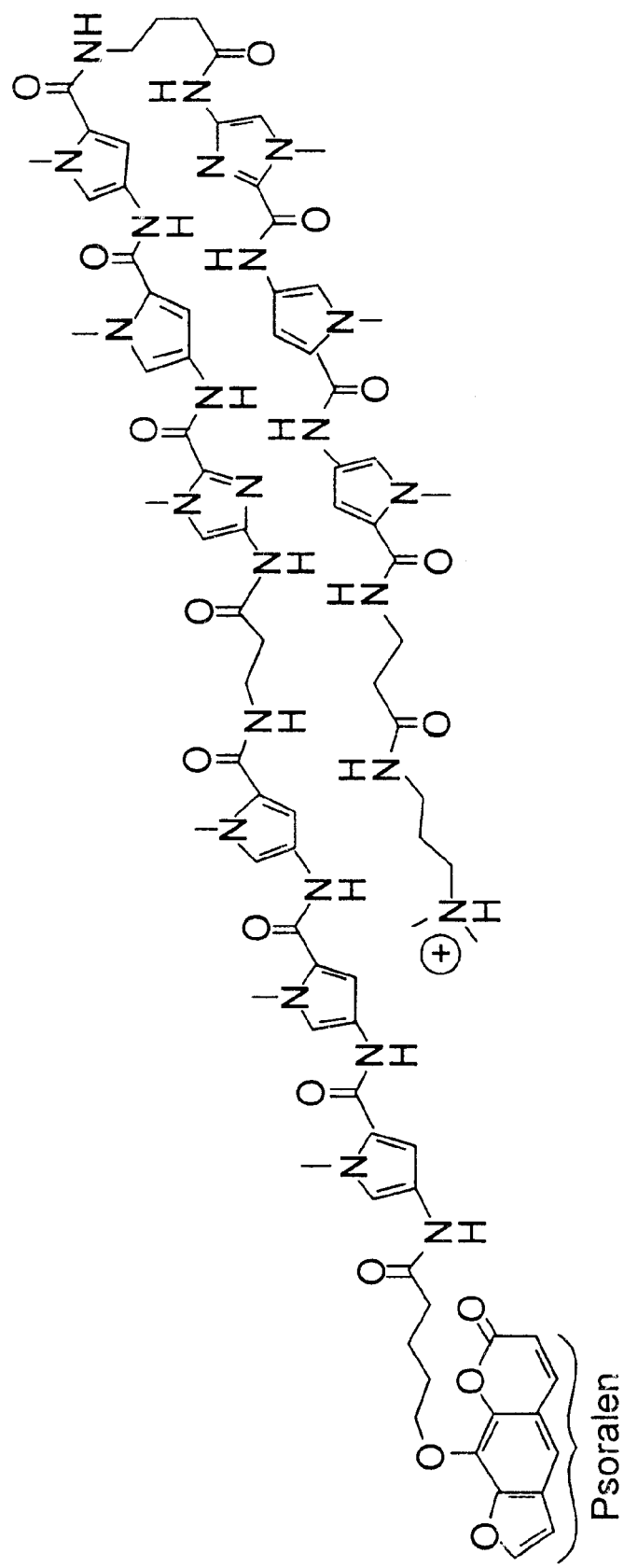
FIG. 30. Psoralen-polyamide conjugate.

Photoactivated modification of DNA by a polyamide-psoralen conjugate. Psoralen and psoralen derivatives have been used as photoactive drugs in the treatement of cancer. (Edelson, et al. *N. Engl. J. Med.* 316, 297 (1987)) These molecules intercalate into double-helical DNA and upon irradiation with UVA undergo a [2+2] cycloaddition reaction with the 5,6 double bond of thymine residues to form both monoadducts and interstrand DNA cross-links. (*Psoralen DNA Photobiology*, Volumes 1 and 2; Gesparro, F. P., Ed. CRC Press, Inc., Boca Raton, Fla. 1988.) Our recent interests have focused on the synthesis and in vitro analysis of photoactive polyamide-psoralen conjugate B which is desinged to form covalent attachments to DNA in a sequence-specific manner. The use of light as a trigger for the permanent covalent modification of DNA may prove to be attractive tool for potential in vivo applications such as the specific inhibition of transcription by minor groove binding polyamides. The extended hairpin polyamide-psoralen conjugate B was synthesized by coupling the OBt ester of S-(8-psoralenyloxy)pentanoic acid. (Lee, et al., *J. Med. Chem.* 1994, 37, 1208.) to the extended hairpin polyamide directly on the β-alanine-Pam resin. Upon equilibration of the psoralen-polyamide conjugate at pH 7.5 with a 247 bp restriction fragment followed by irradiation at 360 nm, the extent of intrastrand cross-link formation was shown to be between 15–20% and 54–57% at 10 nM and 100 nM concentrations of polyamide respectively. Our current work involves the use of a polymerase stop assay as a tool to map the sites of intrastrand covalent modification as well as sites of potential monoadduct formation on double-helical DNA. The structure of the psoralen-polyamide conjugate is shown in FIG. 30.

Example 10

In Vitro Assay for Polyamide Binding

An engineered, radiolabeled restriction fragment from pUC-19 was prepared in which a nine bp polyamide binding site overlaps by two base pairs with the cleavage site for the restriction endonucleases Pvu II. Clevage by Pvu II is prevented when the overlapping polyamide binding site is occupied by the polyamide. As a control, a second radiolabeled DNA fragment was prepared which contains a Pvu II site, but lacks the overlapping polyamide binding site.

Figure 6:
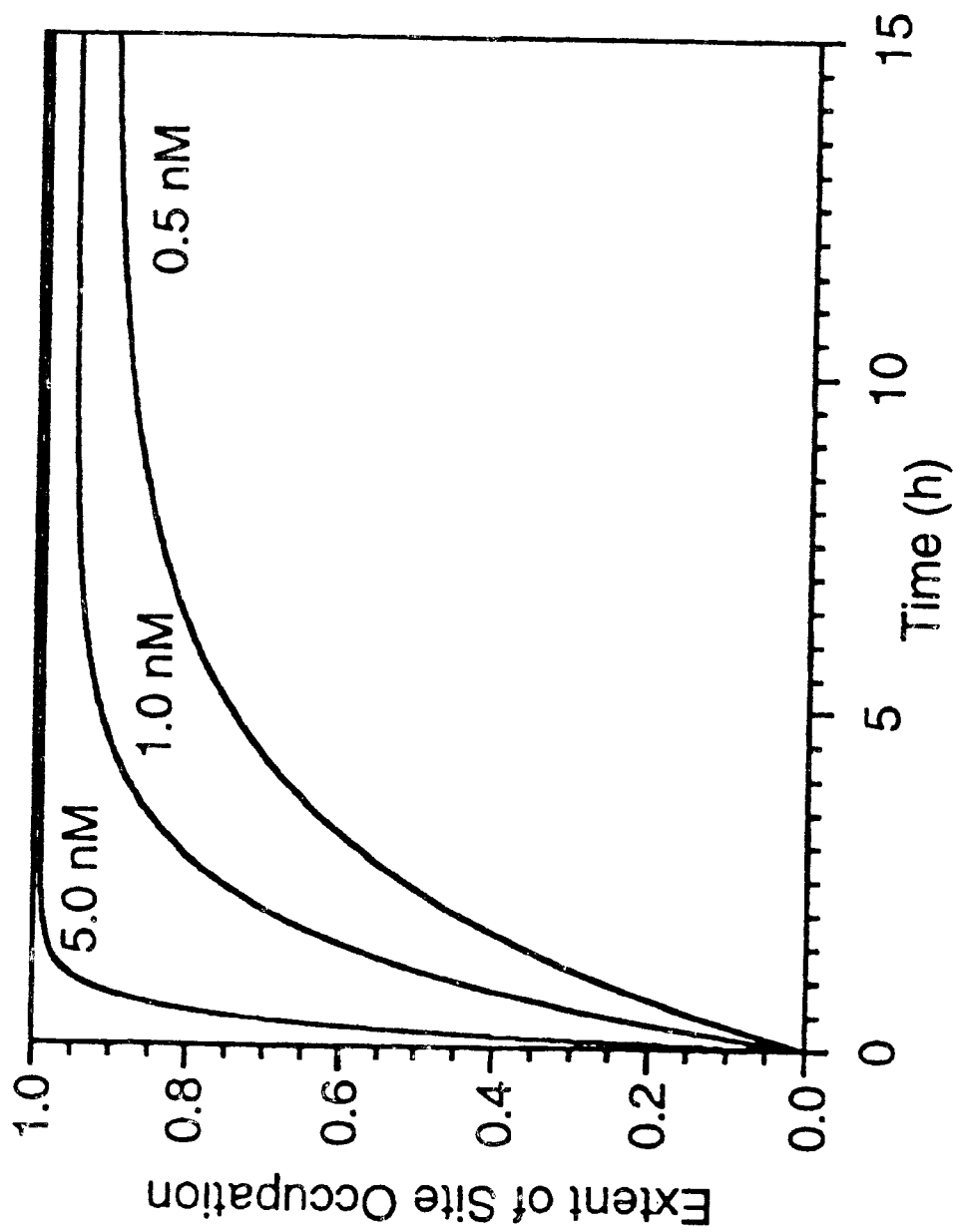
FIG. 6. Association profile of extended hairpin polyamides.

The rate of polyamide association with its target binding site was assessed by combining solutions of the polyamide with the radiolabeled target and reference fragments and allowing them to for 5 minutes to 5 hours before initiating a treatment (1–2 minutes) with the enzyme Pvu II. Under the experimental conditions, the reference site is nearly completely digested, but protection at the target site is observed and can be correlated with polyamide concentration and the time of equilibration. Similarly, the dissociation rate is analyzed by adding an excess of unlabeled competitor DNA to an equilibrated solution of the labeled DNA fragments and polyamide. Addition of the competitor reduces the concentration of free polyamide to zero. The rate at with polyamide dissociation occurs from the target site on the labeled fragment can be followed by the rate of loss of protection from Pvu II digestion as the re-equilibration time is increased. The association profile with respect to time for the 9-ring extended hairpin polyamide ImPyPy-γ-ImPyPy-β-PyPyPy-G-Dp binding its cognate 9 base pair match site is shown in FIG. 6.

The extended hairpin dissociation rate has been determined to be $k_d=3.1\pm0.2\times10^{-5}$ s$^{-1}$, this corresponds to a half-time of 6.2 h (10 mM Bis-Tris (pH 7.0), 50 mM NaCl, 5 mM MgCl$_2$, 1 mM mercaptoethanol at 37° C.). Wherein half-time is defined as the time required for 50% of a population of DNA and polyamide to dissociate or associate. The association rate has been determined at $k_a=1.3\pm0.8\times10^4$ M$^{-1}$s$^{-1}$, this corresponds to a half-time of 3.0 h at 5.0 nM. The determined value for the equilibrium association constant ($K_{eq}=6.3\pm0.8\times10^8$ M$^{-1}$) correlates well with the kinetically determined ratio ($k_a/k_d=4.2\pm2.6\times10^8$ M$^{-1}$).

These results demonstrate that polyamides bind to a designated target site within seconds to minutes, but that it may take hours for dissociation to occur at such a site. More specifically these results demonstrate that polyamides bind DNA with a combination of association and dissociation rates which provide effective modulation of the activity of DNA binding proteins.

Example 11

Cooperative Hairpin Dimers for Recognition of DNA by Py-Im Polyamides

Small molecules which permeate cells and bind predetermined DNA sequences have the potential to control the expressoin of specific genes. Trauger, et al. *Nature* 1996, 382, 559–561; Gottesfeld, et al. *Nature* 1997, 387, 202–205). Recently, an eight-ring polyamide which binds to a six base pair target site was shown to inhibit gene transcription in cell culture (Gottesfeld, et al. *Nature* 1997, 387, 202–205). Polyamides recognizing longer DNA sequences should provide more specific biological activity (P. B. Dervan, *Science* 1986, 232, 464) which could be achieved by synthesizing larger hairpins (Turner, et al. EJ. *Am. Chem. Soc.* 1997, 119, 7636–7644). However, the upper limit of polyamide size with regard to efficient cell permeation is not known.

Alternatively, a more biomimetic approach is to bind larger DNA sequences while maintaining the size of the polyamide. Nature's transcription factors often bind large DNA sequence by formation of cooperative protein dimers at adjacent half-sites (Ptashne, et al. *A Genetic Switch*, Blackwell Scientific Publications and Cell Press: Palo Alto, Calif. 1986; Pabo, et al. *Ann. Rev. Biochem.* 1992, 61, 1053–1095; Marmorstein, et al. *Nature* 1992, 356, 408–414; Klemm, et al. *Cell* 1994, 77, 21–32; Bellon, et al. *Nature Struct. Biol.* 1997, 4, 586–591). For cooperatively binding extended Py-Im polyamide dimers, the two ligands can slip sideways with respect to one another, allowing recognition of other sequences (Trauger, et al. *J. Am. Chem. Soc.* 1996, 118, 6160–6166; Swalley, et al. *Chem. Eur. J.* 1997, 3, 1600–1607). Hairpin polyamides utilizing the turn-specific γ-aminobutyric acid linker are constrained to be fully overlapped and preclude the "slipped motif" option (Mrksich, et al. *J. Am. Chem. Soc.* 1994, 116, 7983–7988; Parks, et al. ibid. 1996, 118, 6153–6159; Swalley, et al. ibid. 1996, 118, 8198–8206; Swalley, et al. ibid. 1997, 119, 6953–6961; Trauger, et al. *Chem. & Biol.* 1996, 3, 369–377; Declairac, et al., *J. Am. Chem. Soc.* 1997, 119, 7909–7916). Provided herein is a cooperative six-ring extended hairpin polyamide which dimerizes to specifically bind a predetermined ten base pair sequence.

Figure 31:
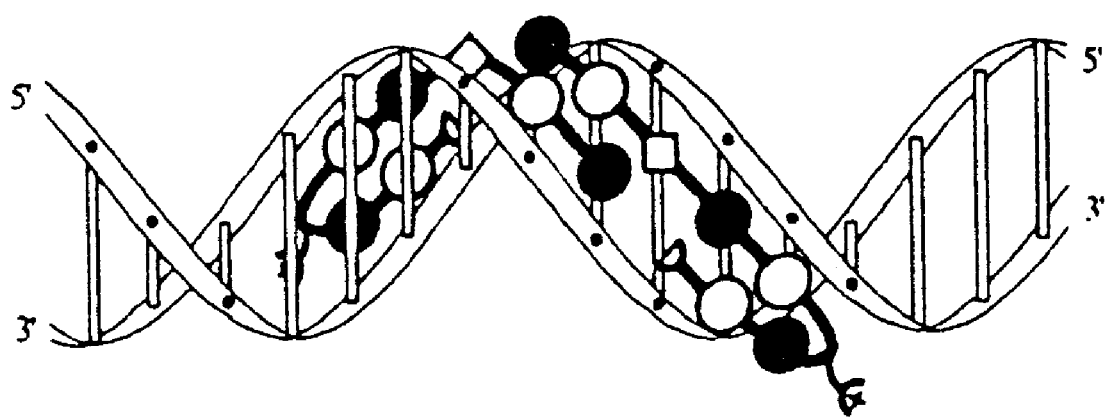
FIG. 31. Cooperative dimerization of polyamides.

A sequence contained in the regulatory region of the HIV-1 genome was selected as the target site (Jones, et al. *Ann. Rev. Biochem.* 1994, 63, 717–743; Frech, et al. *Virology* 1996, 224, 256–267). To design the ligand, the polyamide ring pairing rules provided herein, such as the inclusion of β-alanine (β) to relax ligand curvature, and the preference of γ-aminobutyric acid (γ) for a "hairpin turn" conformation within polyamide-DNA complexes were considered. This analysis suggested that the six-ring polyamide having the core sequence ImPy-β-ImPy-γ-ImPy might bind the target sequence 5'-AGCAGCTGCT-3' through formation of a cooperative hairpin dimer (FIG. 31). To avoid a collision between the N-terminal end of one ligand and the C-terminal end of the second within the complex, the positively-charged β-alanine-dimethylaminoproplyamide C-terminus used in standard polyamides has been replaced with the shorter, uncharged (CH$_2$)$_2$OH group (C$_2$-OH). The cationic "turn" residue (R)-2,4-diaminobutyric acid ((R)$^{H2N}$γ) maintains the overall +1 charge for optimal solubility in water.

Polyamide ImPy-β-ImPy-(R)$^{H2N}$γ-ImPy-C$_2$-OH was synthesized using solid-phase methods (E. E. Baird, P. B. Dervan, *J. Am. Chem. Soc.* 1996, 118, 6141–6146) on glycine-PAM resin (available in 0.3 mmol/g substitution from Peptides International, Louisville, Ky.), reductively cleaved from the solid support using LiBH$_4$ (Mitchell, et al., *J. Org. Chem.* 1978, 43, 2845; Stewart, et al. *Solid Phase Peptide Synthesis*, Pierce Chemical Company, Rockford, Ill., 1984) and purified by HPLC (reverse-phase). The identity and purity of the polyamides was confirmed by $^1$H NMR, analytical HPLC, and MALDI-TOF MS. MALDI-TOF MS (monoisotopic) (M+H): ImPy-β-ImPy-(R)$^{H2N}$γ-ImPy-C$_2$-OH, obsd 953.3, calcd (C$_{42}$H$_{53}$N$_{18}$O$_9$) 953.4; ImPy-β-ImPyPy-(R)$^{H2N}$γ-PyImPy-C$_2$-OH, obsd 1197.5, calcd (C$_{54}$H$_{65}$N$_{22}$O$_{11}$) 1197.5.

Figure 32:
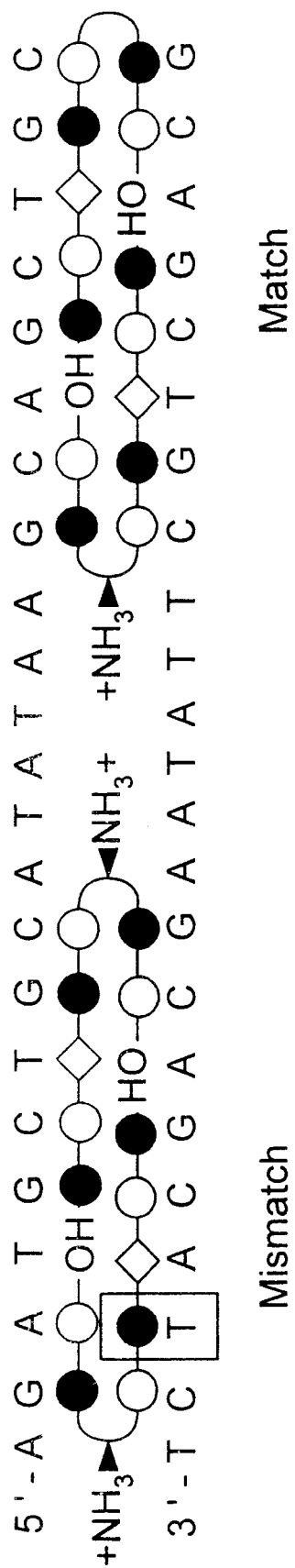
FIG. 32. Binding of polyamides to mismatched sites.
Figure 32:
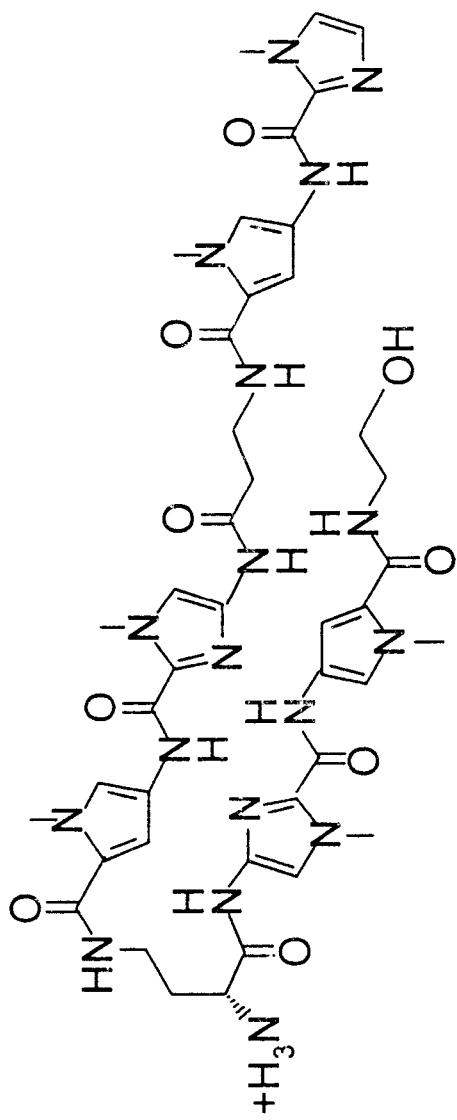

FIG. 32 illustrates the (ImPy-β-ImPy-(R)$^{H2N}$γ-ImPy-C$_2$-OH)$_2$•5'-AGCAGCTGCT-3' complex, demonstrating binding models for complexes of a 10 base pair match and single-base pair mismatch sites (the mismatched base pair is highlighted by shading). The shaded and open circles represent imidazole and pyrrole rings, respectively, diamonds represent β-alanine, half-circles represent (CH$_2$)$_2$OH groups, and curved lines represent (R)-2,4-diaminobutyric acid.

Figure 33A:
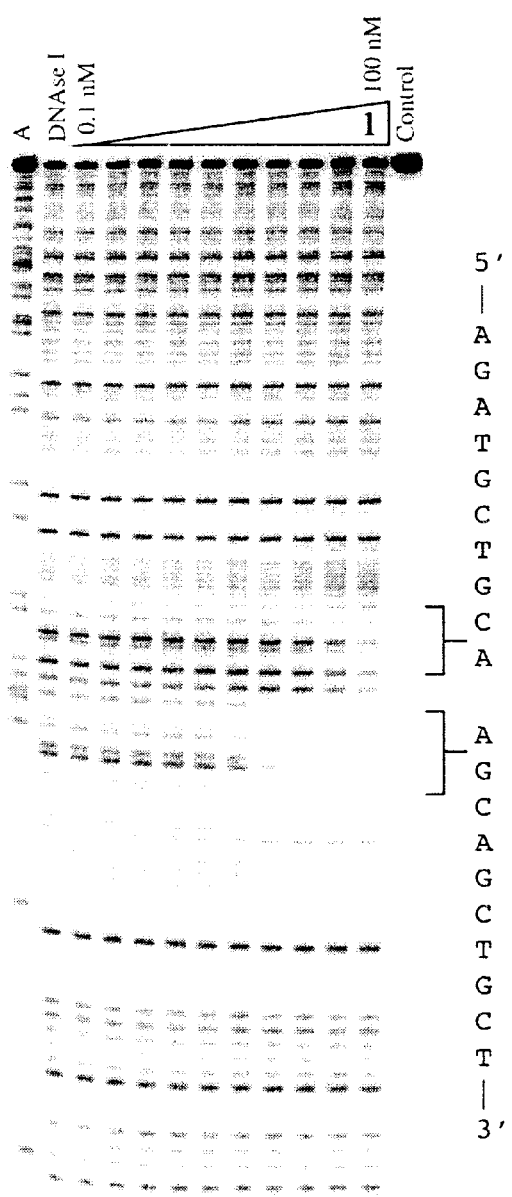
FIG. 33. Footprint titration of polyamides.

FIG. 33a represents a storage phosphor autoradiogram of the 8% denaturing polyacrylamide gel used to separate the fragments generated by DNase I digestion in a quantitative footprint titration experiment with polyamide ImPy-β-ImPy-(R)$^{H2N}$γ-ImPy-C$_2$-OH: lane 1, A lane; lane 2, DNase I digestion products obtained in the absence of polyamide; lanes 3–12, DNase I digestion products obtained in the presence of 0.1, 0.2, 0.5, 1, 2, 5, 10, 20, 50, and 100 nM polyamide ImPy-β-ImPy-(R)$^{H2N}$γ-ImPy-C$_2$-OH, respectively. All reactions contain pJT-LTR 3'-$^{32}$P-end-labeled EcoRi/HindIII restriction fragment (15 kcpm), 10 mM Tris•HCl, 10 mM KCl, 10 mM MgCl$_2$, and 5 mM CaCl$_2$ (pH 7.0, 24° C.). Plasmid pJT-LTR was prepared by ligating an insert having the sequence 5'-CCGGTAACC AGAGAGAC-CCAGTACAGGCAAAAAGCAGCTGCT-TATATGCAGCATCTGAGGGACGCCACTC-CCCAGTCCCGCCCAGGCCA CGCCTCCCTGGAAACTCCCCAGCG-GAAAGTCCCTTGTAGAAAGCTCGATGTCAGCAGTC TTTGTAGTACTCCGGATG-CAGCTCTCGGGCCACGTGATGAAAT-GCTAGGCGGCTGTCAA TCGA-3' to the large AvaI/SalI fragment of pUC19.

Figure 33B:
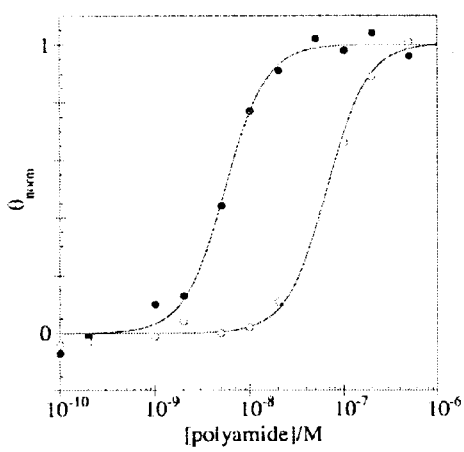

Quantitative DNase I footprinting on a 245 base pair 3'-$^{32}$P-end-labeled restriction fragment showed that ImPy-β-ImPy-(R)$^{H2N}$γ-ImPy-C$_2$-OH binds its match stie 5'-AGCAGCTGCT-3' at nanomolar concentrations (apparent monomeric association constant, K$_a$=1.9 (±0.3)× 10$^8$ M$^{-1}$), and also binds a single-base pair mismatch site 5'-AGATGCTGCA-3' with 9-fold lower affinity, K$_a$=2.2 (±0.5)×10$^7$ M$^{-1}$ (FIG. 33b).

The binding data for match and single-base pair mismatch sites were well-fit by cooperative binding isotherms, consistent with formation of cooperative 2:1 polyamide-DNA complexes.$^{(5)}$ A double-base pair mismatch site, 5'-AGCTGCATCC-3', is also bound with 65-fold lower affinity. The fact that this mismatch site, which contains the "half-site" 5'-AGCTGCA-3', is not effectively bound indicates that recognition of the match site occurs through cooperative dimerization, and not due to formation of 1:1 hairpin complexes.

Further study of the generality and sequence specificity of this motif is in progress and will be reported in due course. For example, we found that the eight-ring polyamide ImPy-β-ImPyPy-(R)$^{H2N}$γ-PyImPy-C$_2$-OH binds the twelve base pair match site 5'-AAGCAGCTGCTT-3' with 10-fold higher affinity than ImPy-β-ImPy-(R)$^{H2N}$γ-ImPy-C$_2$-OH, and is approximately 100-fold specific for this site versus the double-base pair mismatch site 5'-CAGATGCTGCAT-3'.

The DNA-binding affinity and specificity for the six-ring polyamide ImPy-β-ImPy-(R)$^{H2N}$γ-ImPy-C$_2$-OH for its ten base pair binding site are typical of standard six-ring hairpins which recognize five base pairs. Thus, use of a the cooperative hairpin dimer motif doubles the binding site size relative to the standard hairpin motif without sacrificing affinity or specificity, and without increasing the molecular weight of the ligand. As provided herein, a novel cooperative hairpin dimer motif, relatively low molecular weight pyrrole-imidazole polyamides (MW approximately 950–1, 200) can specifically recognize 10–12 base pairs of DNA.

Figure 34:
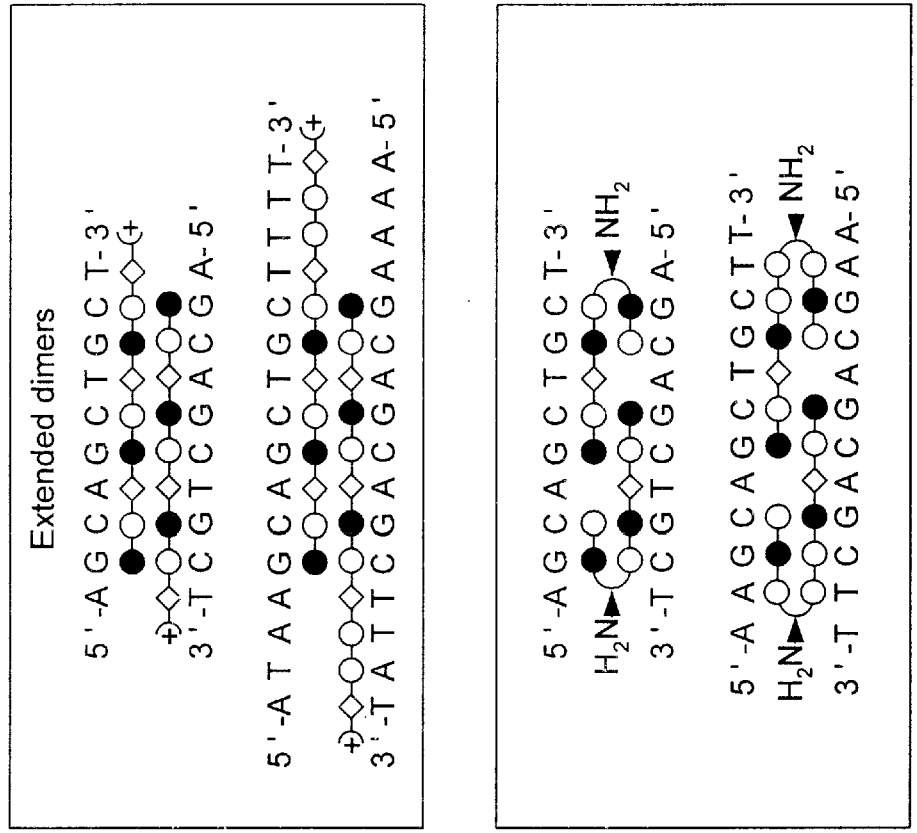
FIG. 34. Generalizable polyamide motifs.
Figure 34:
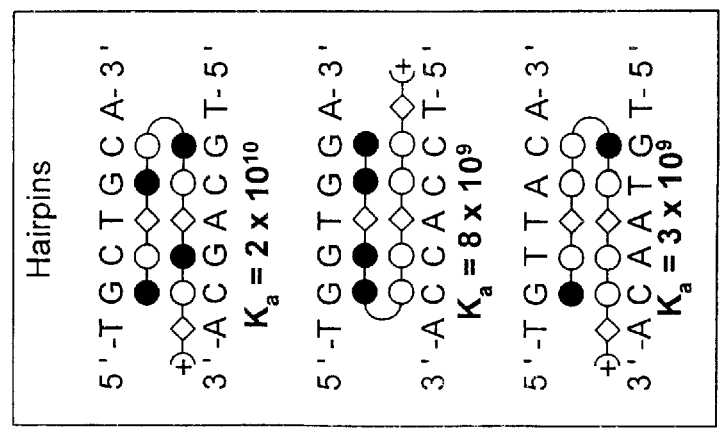
Figure 35A:
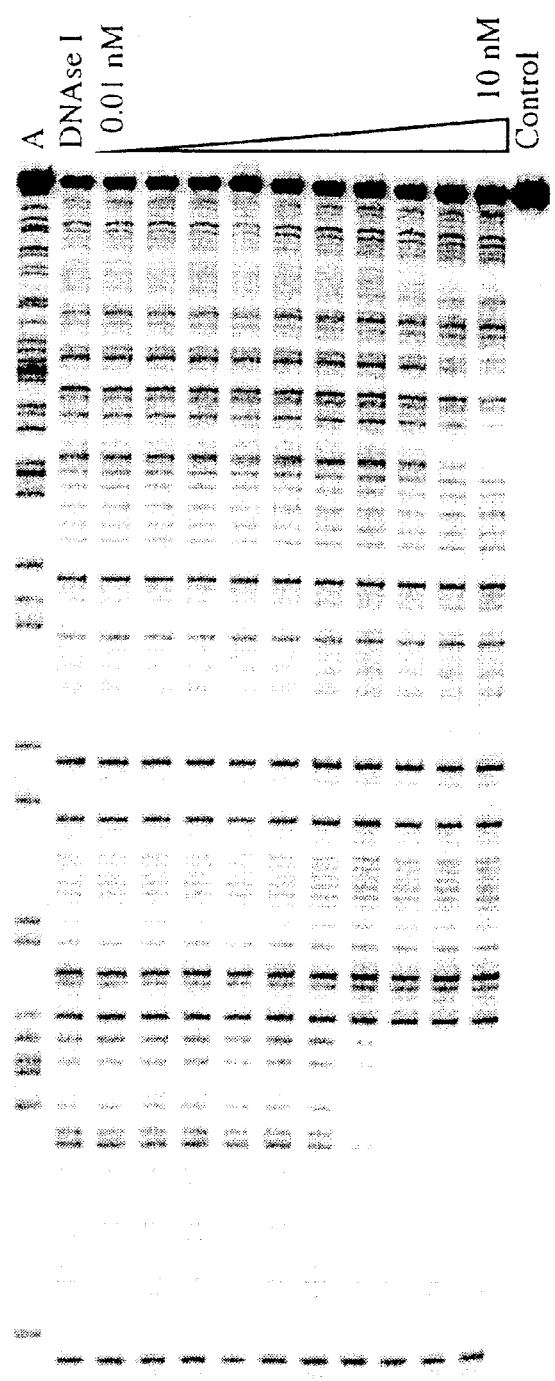
FIG. 35. Examples of polyamides.
Figure 35B:
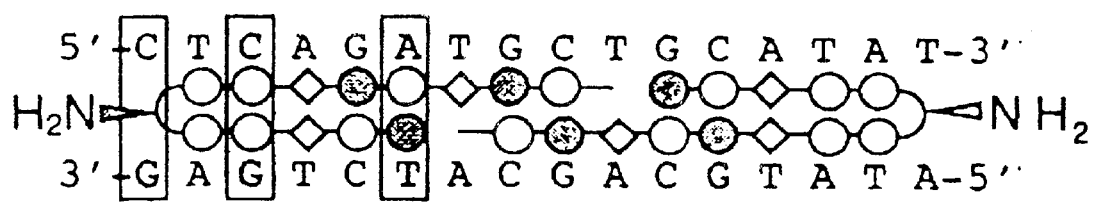
Figure 35B:
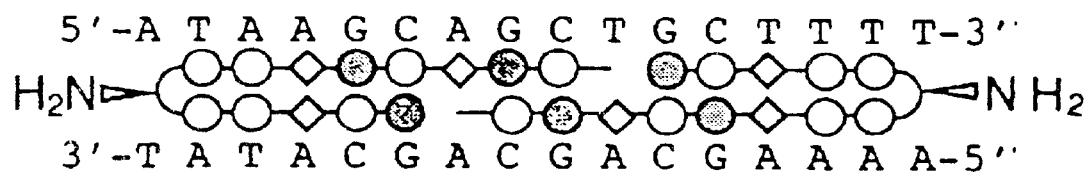
Figure 36:
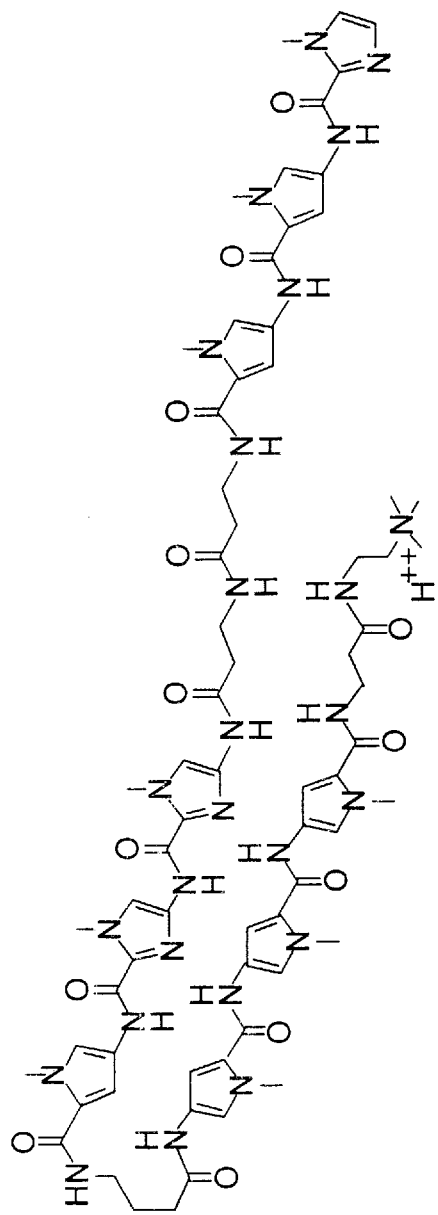
FIG. 36. Determination of polyamide affinity.
Figure 36:
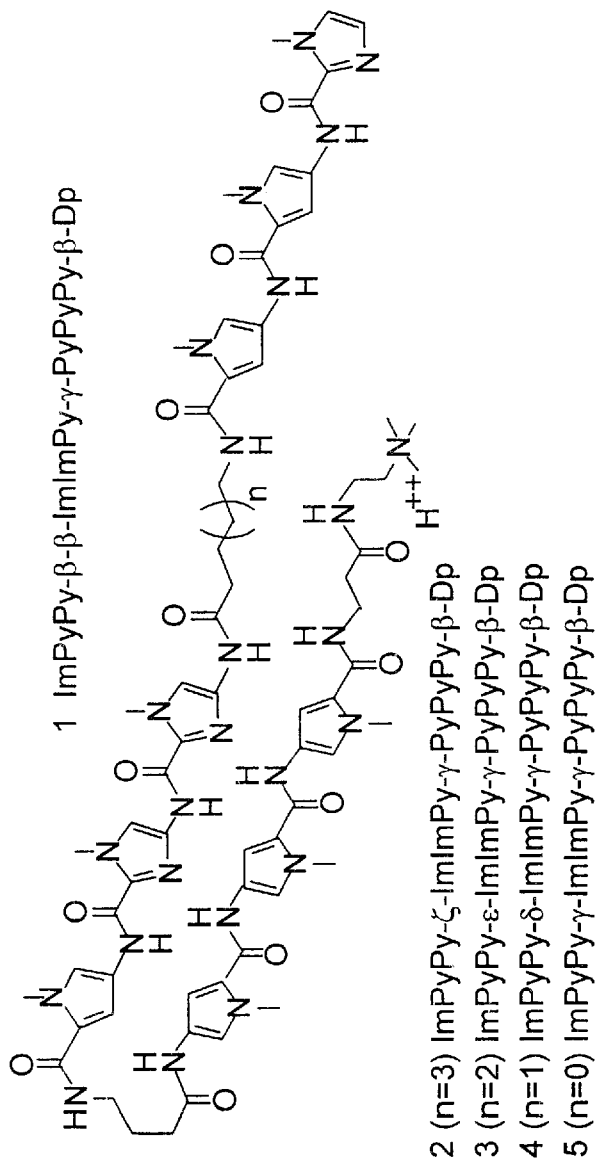
Figure 37:
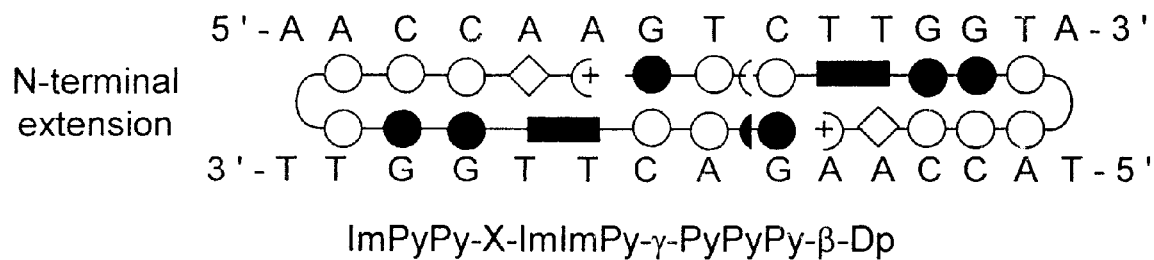
FIG. 37. N-terminally extended polyamides.

FIG. 34 provides general polyamide motifs for use in designing polyamides having improved binding and specificity. FIG. 35 provides five general formulas for polyamides of the present invention. FIG. 36 illustrates the DNA footprint analysis and affinities of additional cooperatively-bound polyamides. FIG. 37 demonstrates the N-terminal extension of the polyamide ImPyPy-X-ImImPy-γ-PyPyPy-β-Dp where X is γ, C5-8, β-β, or β-C5.

Table 5 illustrates recognition of 15 Base-Pairs by ImPyPy-X-ImImPy-γ-PyPyPy-β-Dp polyamides. Association constants (K$_a$) for the match site 5'-AACCAAGTCTTGGTA-3' and specificities for the match site versus center (5'-AACCAACTGTTGGTA-3') and edge (5'-AACCAAGTCTTGCGA-3') mismatch sites are also illustrated

TABLE 5

| X = | Length of X (# atoms) | K$_a$ (M$^{-1}$) Match | Specificity Center mismatch | Edge mismatch |
|---|---|---|---|---|
| γ | 5 | 1 × 10$^7$ | 1 | 1 |
| C5 | 6 | 4 × 10$^8$ | 11 | 19 |
| C6 | 7 | 2 × 10$^8$ | 12 | 15 |
| C7 | 8 | 2 × 10$^8$ | 2 | 2 |
| β—β | 8 | 3 × 10$^8$ | 2 | 2 |
| C8 | 9 | 2 × 10$^8$ | 10 | 10 |
| β-C5 | 10 | 1 × 10$^8$ | 2 | 2 |

Solution conditions: 10 mM Tris.HCl, 10 mM KCl, 10 mM MgCl$_2$, and 5 mM CaCl$_2$ at 24° C. and pH 7.0. The parent hairpin Ac-ImImPy-γ-PyPyPy-β-Dp binds both 5 base pair binding sites within the 15 base pair target site 5'-AACCAAGTCTTGGTA-3' with K$_a$ = 10$^7$ M$^{-1}$.

Table 6 illustrates recognition of 15 Base-Pairs by ImImPy-γ-PyPyPy-X-ImPyPy-β-Dp polyamides. Association constants (K$_1$) for the match site 5'-AACCAAGTCTTGGTA-3' and specificities for the match site versus center (5'-AACCAACTGTTGGTA-3') and edge (5'-AACCAAGTCTTGCGA-3') mismatch sites are shown.

TABLE 6

| X = | Length of X (# atoms) | K$_a$ (M$^{-1}$) Match | Specificity Center mismatch | Edge mismatch |
|---|---|---|---|---|
| C5 | 6 | 1 × 10$^9$ | 2 | 2 |
| C6 | 7 | 2 × 10$^8$ | 1 | 2 |
| C7 | 8 | 1 × 10$^9$ | 1 | 1 |
| β—β | 8 | 1 × 10$^{10}$ | 1 | 1 |

Solution conditions: 10 mM Tris.HCl, 10 mM KCl, 10 mM MgCl$_2$, and 5 mM CaCl$_2$ at 24° C. and pH 7.0. The parent hairpin ImImPy-γ-PyPyPy-β-Dp binds both 5 base pair binding sites within the 15 base pair target site 5'-AACCAAGTCTTGGTA-3' with K$_a$ = 10$^7$ M$^{-1}$.

Solution conditions: 10 mM Tris.HCl, 10 mM KCl, 10 mM MgCl$_2$, and 5 mM CaCl$_2$ at 24° C. and pH 7.0. The parent hairpin ImImPy-γ-PyPyPy-β-Dp binds both 5 base pair binding sites within the 15 base pair target site 5'-AACCAAGTCTTGGTA-3' with K$_a$=1×10$^8$ M$^{-1}$.

Table 7 illustrates recognition of 15 base pairs of ImPyPy-X-ImImPy-γ-PyPyPy-C3-OH. Association constants (K$_a$) for the match site 5'-AACCAAGTCTTGGTA-3' and specificities for the match site versus center (5'-AACCAACT GTTGGTA-3') and edge (5'-AACCAAGTCTTGCGA-3') mismatch sites.

TABLE 7

| Polyamide | $K_a$ | Specificity | |
|---|---|---|---|
| | 5'-AACCAAGTCTTGGTA-3' | 5'-AACCAACTGTTGGTA-3' | 5'-AACCAAGTCTTGCGA-3' |
| ImPyPy-C5-ImImPy-γ-PyPyPy-C3-OH | $3 \times 10^7$ | >3 | >3 |
| ImPyPy-C6-ImImPy-γ-PyPyPy-C3-OH | $3 \times 10^7$ | 2 | 2 |
| ImPyPy-β-β-ImImPy-γ-PyPyPy-C3-OH | $1 \times 10^8$ | 3 | 3 |
| Ac-ImImPy-γ-PyPyPy-C3-OH | $7 \times 10^6$ | — | — |

Table 8 illustrates recognition of 16 Base-Pairs by ImPyPyPy-X-ImImPy-γ-PyPyPy-β-Dp. Association constants ($K_a$) for the match site 5'-AACCAAGTACTTGGTA-3' and specificities for the match site versus center (5'-AACCAACTAGTTGGTA-3') and edge (5'-AACCAAGTACTTGCGA-3') mismatch sites.

Table 10 illustrates recognition of 16 Base-Pairs by a polyamide having the formula ImPyPyPy-X-ImImPy-γ-PyPyPy-C3-OH. Association constants ($K_a$) for the match site 5'-AACCAAGTACTTGGTA-3' and specificities for the match site versus center (5'-AACCAACTAGTTGGTA-3') and edge (5'-AACCAAGTACTTGCGA-3') mismatch sites.

TABLE 8

| Polyamide | $K_a$ | Specificity | |
|---|---|---|---|
| | 5'-AACCAAGTACTTGGTA | 5'-AACCAACTAGTTGGTA | 5'-AACCAAGTACTTGCGA |
| ImPyPyPy-C5-ImImPy-γ-PyPyPy-β-Dp | $7 \times 10^8$ | >3 | >3 |
| ImPyPyPy-C6-ImImPy-γ-PyPyPy-β-Dp | $1 \times 10^8$ | 1 | 1 |
| ImpyPyPy-β-β-ImImPy-γ-PyPyPy-β-Dp | $3 \times 10^8$ | 1 | 1 |
| Ac-ImImPy-γ-PyPyPy-β-Dp | $3 \times 10^7$ | — | — |

Table 9 illustrates recognition of recognition of 9–11 base pairs by ImPyPy-X-ImPyPy-β-Dp.

TABLE 9

| Polyamide | 5'-TGTCAGACA-3' | 5'-TGTCAAGACA-3' | 5'-TGTCAAAGACA-3' | 5'-gcggtTGTCAacccg-3' |
|---|---|---|---|---|
| ImPyPy-G-ImPyPy-β-Dp | $1 \times 10^8$ | $3 \times 10^7$ | $3 \times 10^7$ | $3 \times 10^7$ |
| ImPyPy-β-ImPyPy-β-Dp | $2 \times 10^8$ | $2 \times 10^8$ | $1 \times 10^9$ | $1 \times 10^9$ |
| ImPyPy-γ-ImPyPy-β-Dp | $5 \times 10^7$ | $1 \times 10^8$ | $1 \times 10^8$ | $2 \times 10^8$ |
| ImPyPy-C5-ImPyPy-β-Dp | $2 \times 10^8$ | $1 \times 10^9$ | $1 \times 10^9$ | $1 \times 10^9$ |
| ImPyPy-C6-ImPyPy-β-Dp | $1 \times 10^8$ | $2 \times 10^8$ | $5 \times 10^7$ | $5 \times 10^7$ |
| ImPyPy-C7-ImPyPy-β-Dp | $2 \times 10^7$ | $1 \times 10^8$ | $3 \times 10^7$ | $7 \times 10^7$ |
| ImPyPy-C8-ImPyPy-β-Dp | $1 \times 10^7$ | $3 \times 10^7$ | $1 \times 10^7$ | $1 \times 10^7$ |
| ImPyPy-C11-ImPyPy-β-Dp | $5 \times 10^6$ | $2 \times 10^7$ | $2 \times 10^7$ | $1 \times 10^7$ |
| ImPyPy-β-ImPyPy-β-Dp | $2 \times 10^8$ | $2 \times 10^8$ | $1 \times 10^9$ | $1 \times 10^9$ |
| ImPyPy-β-β-ImPyPy-β-Dp | $1 \times 10^7$ | $5 \times 10^7$ | $1 \times 10^7$ | $2 \times 10^7$ |
| ImPyPy-β-β-β-ImPyPy-β-Dp | $1 \times 10^7$ | $1 \times 10^7$ | $7 \times 10^7$ | $1 \times 10^7$ |
| ImPyPy-β-Py-β-ImPyPy-β-Dp | $3 \times 10^8$ | $2 \times 10^8$ | $1 \times 10^9$ | $<10^8$ |
| ImPyPy-β-ImPyPy-β-Dp | $2 \times 10^8$ | $2 \times 10^8$ | $1 \times 10^9$ | $1 \times 10^9$ |
| ImPyPy-β-PyPyPy-β-Dp | $2 \times 10^8$ | $5 \times 10^7$ | $5 \times 10^7$ | $3 \times 10^7$ |

Solution conditions: 10 mM Tris•HCl, 10 mM KCl, 10 mM MgCl$_2$, and 5 mM CaCl$_2$ and 5mM CaCl$_2$ at 22 °C and pH 7.0.

TABLE 10

| Polyamide | $K_a$ | Specificity | |
|---|---|---|---|
| | 5'-AACCAAGTACTTGGTA | 5'-AACCAACTAGTTGGTA | 5'-AACCAAGTACTTGCGA |
| ImpyPyPy-C6-ImImPy-γ-PyPyPy-C3-OH | $<10^8$ | — | — |
| Ac-ImImPy-γ-PyPyPy-C3-OH | $7 \times 10^6$ | — | — |

Table 11 illustrates recognition of 17 Base-Pairs by a polyamide of the formula ImPyPy-β-X-β-ImImPy-γ-PyPyPy-β-Dp, X=β or Py. Association constants ($K_a$) for the match site 5'-AACCATAGTCTATGGTA-3' and specificities for the match site versus center (5'-AACCATAG CGTATGGTA-3') and edge (5'-AACCAAGTCTTG CGA-3') mismatch sites.

1994, 63, 717–743; Frech, et al. *Virology* 1996, 224, 256–267). Consideration of the previously published polyamide ring pairing rules (Wade, et al. *J. Am. Chem. Soc.* 1992, 114, 8783–8794; Mrksich, et al. *Proc. Natl. Acad. Sci.* 1993, 32, 11385–11389; Geierstanger, et al. *J. Am. Chem. Soc.* 1993, 115, 4474–4482; White, et al. *Chem. & Biol.* 1997, 4, 569–578; Pelton, et al. *Proc. Natl. Acad. Sci. U.S.A.* 1989,

TABLE 11

| Polyamide | $K_a$ | | Specificity |
| --- | --- | --- | --- |
| | 5'-AACCATAGTCTATGGTA | 5'-AACCATAGCGTATGGTA | 5'-AACCATAGTCTATGCGA |
| ImPyPy-β-β-β-ImImPy-γ-PyPyPy-β-Dp | ? | ? | ? |
| ImPyPy-β-Py-β-ImImPy-γ-PyPyPy-β-Dp | ? | ? | ? |
| Ac-ImImPy-γ-PyPyPy-β-Dp | $3 \times 10^7$ | — | — |

Example 12

Recognition of 16 Base Pairs in the Minor Groove of DNA by an Im-Py Polyamide Dimer Cell-permeable small molecules which bind predetermined DNA sequences with affinity and specificity comparable to natural DNA-binding proteins have the potential to regulate the expression of specific genes. Recently, an 8-ring hairpin Py-Im polyamide which binds 6 base pairs of DNA was shown to inhibit transcription of a specific gene in cell culture (Gottesfeld, et al. *Nature* 1997, 387, 202–205). Polyamides recognizing longer DNA sequences should provide more specific biological activity. To specify a single site within the 3 billion base pair human genome, ligands which specifically recognize 15–16 base pairs are necessary. For this reason, recognition of 16 base pairs represents a milestone in the development of chemical approaches to DNA recognition (Dervan, P. B. *Science* 1986, 232, 464; Dervan, P. B. In *The Robert A. Welch Foundation Conference on Chemical Research XXXI. Design of Enzymes and Enzyme Models*; Houston, Tex., Nov. 2–4, 1987; pp 93–109; Dervan, P. B. In *Nucleic Acids and Molecular Biology*, Vol. 2; Springer-Verlag: Heidelberg, 1988; pp 49–64; Moser, et al. *Science* 1987, 238, 645–650; Le Doan, et al. *Nucleic Acids Res.* 1987, 15, 7749; Strobel, et al. *Science* 1991, 254, 1639–1642; Thuong, et al. *Angew. Chem. Int. Ed. Engl.* 1993, 32, 666–690). A Py-Im polyamide dimer which targets 16 contiguous base pairs in the minor groove of DNA is provided herein.

As the length of a polyamide dimer having the general sequence $ImPy_{2-6}$ increases beyond 5 rings (corresponding to a 7 base pair binding site), the DNA-binding affinity ceases to increase with polyamide length (Kelly, et al. *Proc. Natl. Acad. Sci. U.S.A.* 1996, 93, 6981–6985). A structural basis for this observation is provided by the recently determined X-ray crystal structure structure of a 4-ring homodimer in complex with DNA, which reveals a perfect match of polyamide rise-per-residue with the pitch of the DNA duplex, but overwound ligand curvature (Keilkopf, et al. *Nature Struct. Biol.* 1998, 5, 104–109). The curvature mismatch explains the observation that flexible β-alanine residues reset an optimum fit of polyamide dimers with the DNA helix at long binding sites (Trauger, et al. *J. Am. Chem. Soc.* 1996, 118, 6160–6166; Swalley, et al. *Chem. Eur. J.* 1997, 3, 1600–1607).

The 16 base pair sequence 5'-ATAAGCAGCTGCTTTT-3' present in the regulatory region of the HIV-1 genome was utilized as a binding site (Jones, et al. *Ann. Rev. Biochem.* 86, 5723–5727; Pelton, et al. *J. Am. Chem. Soc.* 1990, 112, 1393–1399; Chen, et al. *Nature Struct. Biol.* 1994, 1, 169–175; White, et al. *Biochemistry* 1996, 35, 12532–12537), the A, T specificity of β/β pairs, and the "slipped" dimer motif (Geierstanger, et al. *Nature Struct. Biol.* 1996, 3, 321–324; Trouger, et al. Chem & Biol. 1996, 3, 369–377) suggested that the 8-ring polyamide ImPy-β-ImPy-β-ImPy-β-PyPy-β-Dp (1) would specifically bind the target sequence as a cooperative antiparallel dimer (FIG. 38).

Figure 38:
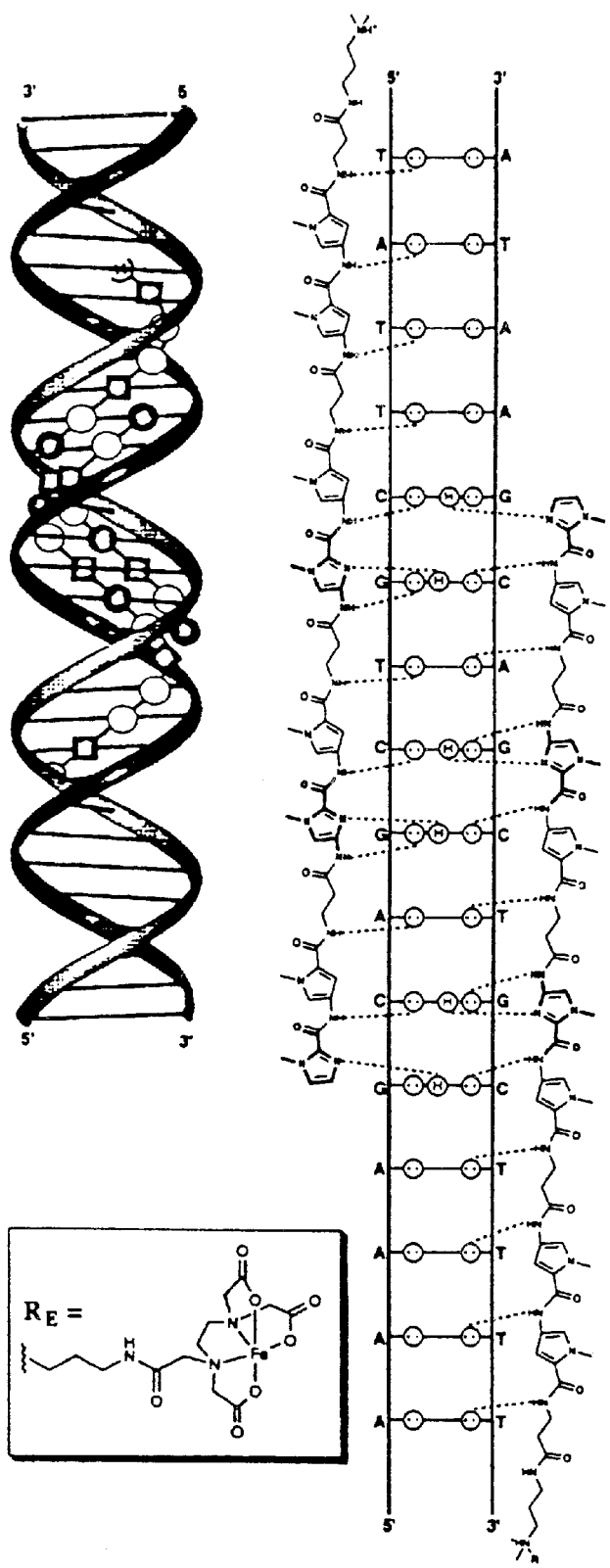
FIG. 38. Polyamides binding 16 base pair sequence.
Figure 40:
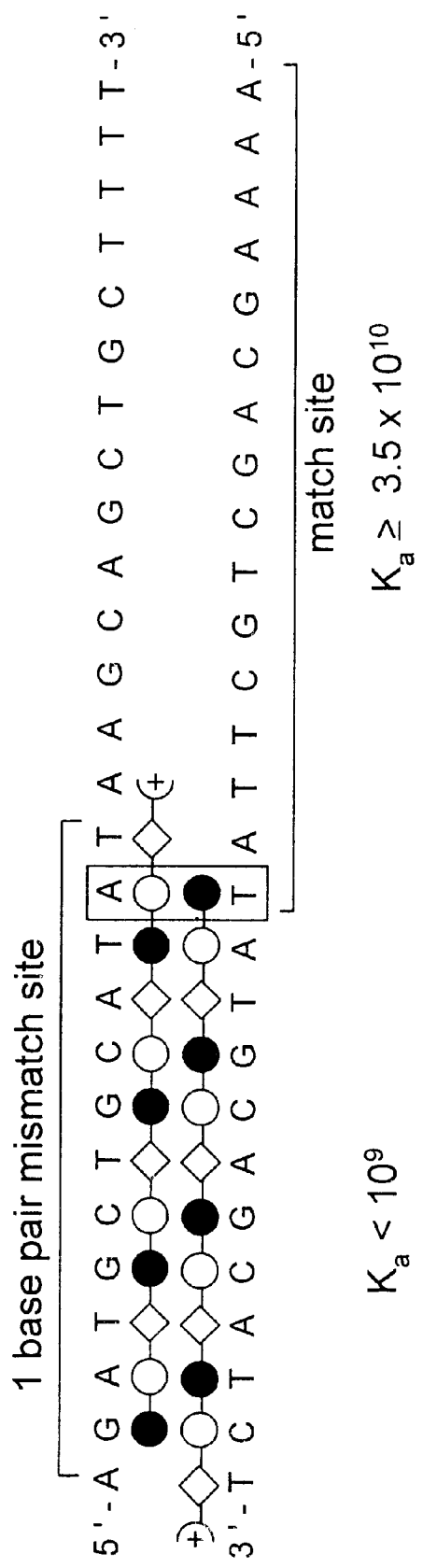
FIG. 40. Binding of polyamides to mismatched sites.
Figure 41:
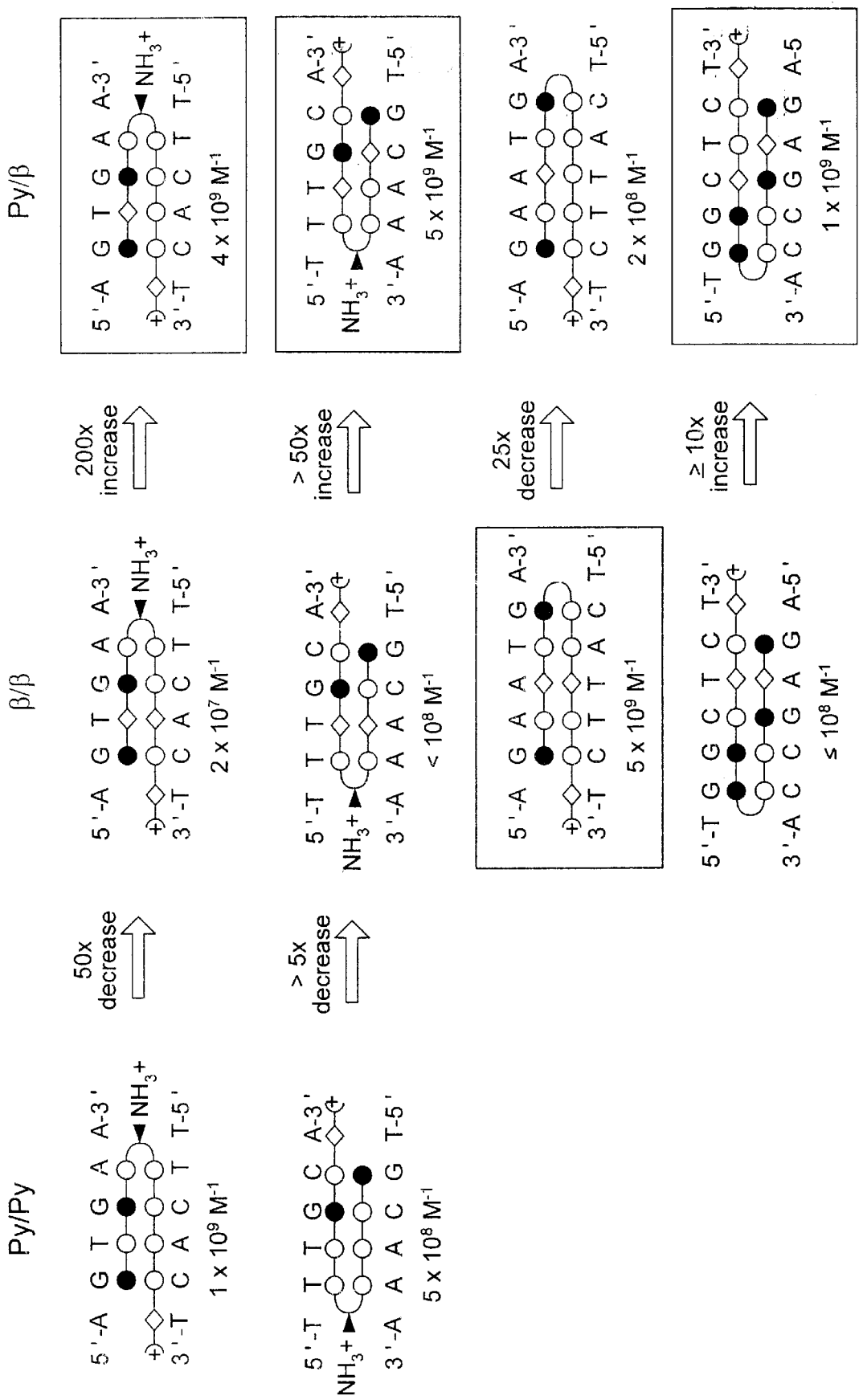
FIG. 41. β-substitution in polyamides.
Figure 42:
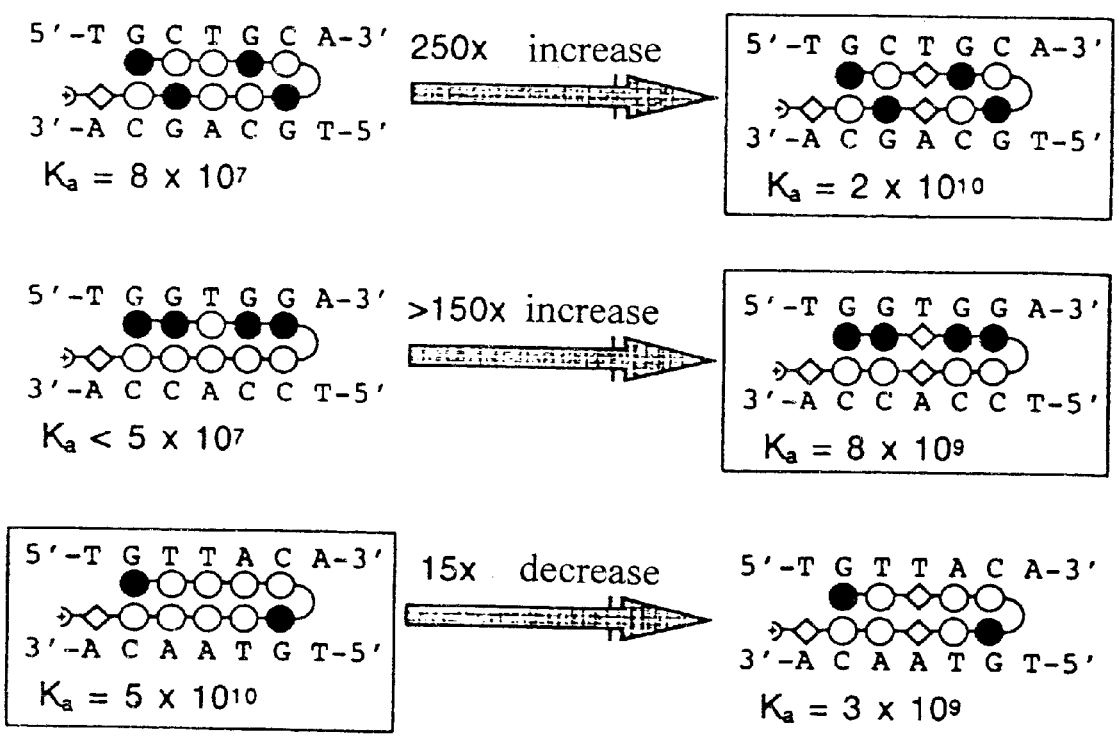
FIG. 42. Affinity determinations for β-substituted polyamides.
Figure 43:
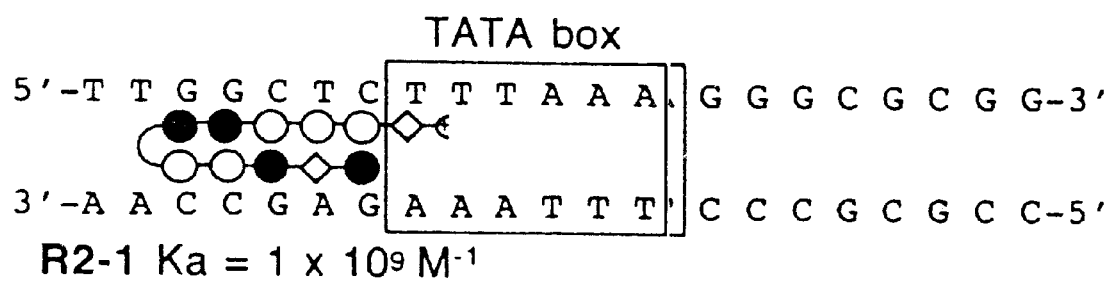
FIG. 43. Binding of polyamides to TATA box.
Figure 43:
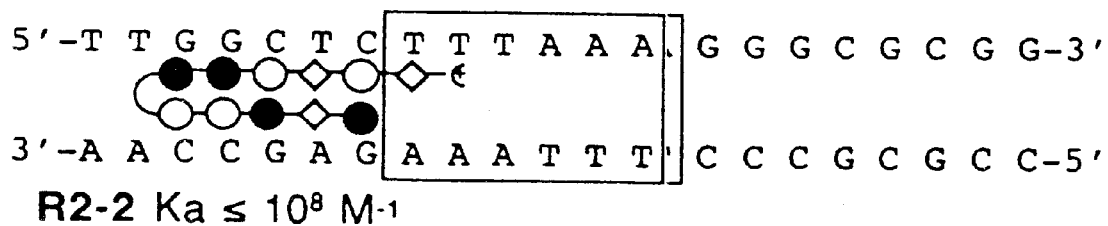

FIG. 38 illustrates a model of the complex of ImPy-β-ImPy-β-ImPy-β-PyPy-β-Dp (1, R=H) or ImPy-β-ImPy-β-ImPy-β-PyPy-β-Dp-EDTA.Fe(II) (1-E, R=$R_E$) Im=N-methylimidazole, Py=N-methylpyrrole, β=β-alanine, Dp =dimethylaminopropylamide) with 5'-ATAAGCAGCTGCTTTT-3'. The shaded and open circles represent imidazole and pyrrole rings, respectively, and the diamonds represents β-alanine. Circles with dots represent lone pairs on N3 of purines and O2 of pyrimidines, and circles containing an H represent the N2 hydrogen of guanine. Putative hydrogen bonds are illustrated by dashed lines. The polyamides were synthesized using solid-phase methods (Baird, et al. *J. Am. Chem. Soc.* 1996, 118, 6141–6146), purified by HPLC, and the identity and purity confirmed by $^1$H NMR, analytical HPLC and MALDI-TOF MS.

A quantitative DNase I footprinting experiment carried out on a 245 base pair 3'-$^{32}$P-end-labeled restriction fragment revealed that the polyamide specifically binds it target site at subnanomolar concentrations (apparent monomeric association constant, $K_a$ $3.5 \times 10^{10}$ M$^{-1}$) (FIG. 39) (Baird, et al. *J. Am. Chem. Soc.* 1996, 118, 6141–6146; Brenowitz, et al. *Methods Enzymol.* 1986, 130, 132–181; Cantor, C. R.; Schimmel, P. R., *Biophysical Chemistry, Part III: The Behavior of Biological Macromolecules*; W. H. Freeman, New York, N.Y., 1980, p 863).

FIG. 39 illustrates a storage phosphor autoradiogram of an 8% denaturing polyacrylamide gel used to separate the fragments generated by DNAse I digestions in a quantitative footprint titration experiment with polyamide ImPy-β-ImPy-β-ImPy-β-PyPy-β-Dp (1): lane 1, A lane; lane 2, DNase I digestion products obtained in the absence of polyamide; lanes 3–10, DNase I digestion products obtained in the presence of 0.01, 0.02, 0.05, 0.1, 0.2, 0.5, and 1 nM polyamide ImPy-β-ImPy-β-ImPy-β-PyPy-β-Dp, respectively; lane 11, intact DNA. All reactions contain 3'-$^{32}$P-end-labeled EcoRI/HindIII restriction fragment from plasmid pJT-LTR (15 kcpm), 10 mM Tris.HCl, 10 mM KCl, 10 mM MgCl$_2$, and 5 mM CaCl$_2$ (pH 7.0, 24° C.). b) Autoradiogram of a gel used to separate the fragments generated by an affinity cleavage reaction using polyamide ImPy-β-ImPy-β-ImPy-β-PyPy-β-Dp-EDTA.Fe (II) (1-E). Lanes 1 and 5: A sequencing lanes; lanes 2–4: cleavage products obtained in the presence of 0.03, 0.1, 0.3 and 1 nM ImPy-β-ImPy-β-ImPy-β-PyPy-β- Dp-EDTA.Fe (II), respectively; lane 6: intact DNA. All reactions contain labeled restriction fragment (7 kcpm), and 20 mM HEPES, 300 mM NaCl, 50 μg/mL glycogen, 1 μM Fe (II), and 5 mM DTT (pH 7.3, 24° C.). The sequence of the restriction fragment in the region of the 16 base pair target site and a model of the (ImPy-β-ImPy-β-ImPy-β-PyPy-β-Dp-EDTA.Fe (II))$_2$.DNA complex are shown along the right side of the autoradiogram. Line heights are proportional to the observed cleavage intensity at the indicated base.

The method used for determining association constants involves the assumption that $[L]_{tot} \sim [L]_{free}$, where $[L]_{free}$ is the concentration of polyamide free in solution (unbound). For very high association constants this assumption becomes invalid, resulting in underestimated association constants. In the experiments described here, the DNA concentration is estimated to be ~5 pM. As a consequence, apparent association constants greater than $1-2 \times 10^{10}$ M$^{-1}$ represent a lower limit of the true association constant. The binding data were well-fit by a cooperative binding isotherm, consistent with formation of a cooperative 2:1 complex. To provide further evidence that ImPy-β-ImPy-β-ImPy-β-PyPy-β-Dp binds as an extended dimer, an affinity cleavage experiment was carried out with the polyamide-EDTA.Fe (II) conjugate of ImPy-β-ImPy-β-ImPy-β-PyPy-β-Dp shown in FIG. 39b. Cleavage was observed at each end of the match sequence, consistent with a dimeric, antiparallel binding mode. With regard to sequence specificity, there is a proximal two-base pair mismatch site, 5'-cAGATGCTGCATATa-3', to the 5' side of the $^{32}$P-labeled strand which is bound with at least 35-fold lower affinity than the match site. However, other mismatch sites on the restriction fragment are bound with 10–20-fold lower affinity, revealing limitations of this first effort at 16 base pair recognition. Undoubtedly there is ample room for further optimization of sequence specificity.

The high binding affinity and the affinity cleavage pattern observed for the 16 base pair polyamide.DNA complex indicates that 8 pairs of amide residues form a fully overlapped core which properly positions the 6 Im/Py pairs for recognition of 6 G,C base pairs and 2 β/β pairs for recognition of 2 A,T base pairs. Polyamides composed of 2-ring subunits connected by β-alanine appear to be isohelical with B-DNA, and allow placement of Imidazole residues at any ring position, thus providing a generalizable motif for recognition of predetermined DNA sequences. The data presented herein allows for the design of polyamides capable of binding 16 base pairs of DNA at subnanomolar concentrations of suitable size for permeating cells (i.e., MW~1,200).

The references described throughout this specification are fully incorporated by reference. While a preferred form of the invention has been shown in the drawings and described, since variations in the preferred form will be apparent to those skilled in the art, the invention should not be construed as limited to the specific form shown and described, but instead is as set forth in the claims.

I claim:
1. A polyamide of the formula

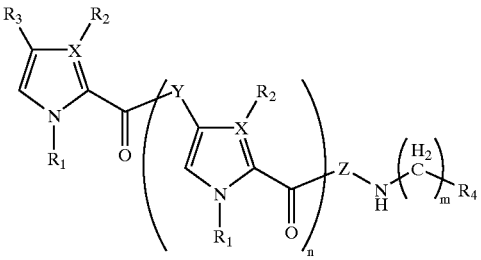

or a pharmaceutically acceptable salt thereof, wherein:
n is 5–11;
m is 0–6;
each Y is independently selected from the group consisting of

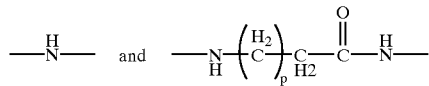

wherein
p is 0 to 5, provided that at least one Y is not —NH-;
Z is a covalent bond or

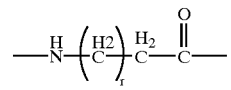

wherein
r is 1–3;
each X is independently selected from the group consisting C and N;
each R$_1$ is independently selected from the group consisting of H, C$_{1-6}$ alkylamine, C$_{1-6}$ alkyldiamine, C$_{1-6}$ alkylcarboxylate, C$_{1-6}$ alkyl, C$_{1-6}$ alkenyl, C$_{1-6}$ alkynyl and C$_{1-6}$ alkyl-L;
each R$_2$ independently selected from the group consisting of H and OH if X is C, and is not present if X is N;
R$_3$ is selected from the group consisting of H, Cl, NO, N-acetyl, benzyl, C$_{1-6}$ alkyl, C$_{1-6}$ alkenyl, and C$_{1-6}$ alkynyl; and
R$_4$ is —NR$^5$R$^6$ or —NH(CH$_2$)$_{0-6}$NR$_5$R$_6$, where R$_5$ and R$_6$ are independently chosen from the group consisting of H, Cl, NO, N-acetyl, benzyl, C$_{1-6}$ alkyl, C$_{1-6}$ alkylamine, C$_{1-6}$ alkyldiamine, C$_{1-6}$ alkylcarboxylate, C$_{1-6}$ alkenyl, C$_{1-6}$ alkyl, and C$_{1-6}$ alkyl-L;
wherein L is a detectable label, and wherein at least one R$_1$, R$_5$, of R$_6$ is C$_{1-6}$ alkyl-L.
2. The polyamide of claim 1, wherein one or more R$_2$ is H, one or more R$_1$ is CH$_3$, and one or more X is N.
3. The polyamide of claim 1 selected from the group consisting of
ImPyPyPy-γ-PyPyPyPy-β-Dp, PyPyImPy-γ-PyPyPyPy-β-Dp, ImPyPyPy-γ-ImPyPyPy-β-Dp, PyImPyPy-γ-PyImPyPy-β-Dp, ImPyImPy-γ-PyPyPyPy-β-Dp, ImImPyPy-γ-PyPyPyPyβ-Dp, ImImImPy-γ-PyPyPyPy-β-Dp, ImImPyPy-γ-ImPyPyPy-β-Dp, ImPyPyPy-γ-ImImPyPy-β-Dp, ImImPyPy-γ-ImImPyPy-β-Dp, ImPyImPy-γ-ImPyImPy-β-Dp, ImImImPy-γ-ImPyPyPyPy-β-Dp, and ImImImIm-γ-PyPyPyPy-β-Dp, bound to a detectable label, wherein Im is N-methyl-Imidazole, Py is methylpyrrole, β is β-alanine, Dp is dimethylaminopropylamide, and γ is γ-aminobutyric acid.

4. The polyamide of claim 1, wherein said polyamide binds to a double-stranded DNA molecule with an association constant of at least $10^8$ M$^{-1}$.

5. The polyamide of claim 4, wherein said polyamide binds to a double-stranded DNA molecule with an association constant of at least $10^9$ M$^{-1}$.

6. The polyamide of claim 1, wherein the detectable label is a fluorescent molecule.

7. The polyamide of claim 1, wherein the detectable label is biotin.

8. A polyamide selected from the group consisting of

ImPyPyPy-γ-PyPyPyPy-β-Dp, PyPyImPy-γ-PyPyPyPy-β-Dp, ImPyPyPy-γ-ImPyPyPy-β-Dp, PyImPyPy-γ-PyImPyPy-β-Dp, ImPyImPy-γ-PyPyPyPy-β-Dp, ImImPyPy-γ-PyPyPyPy-β-Dp, ImImImPy-γ-PyPyPyPy-β-Dp, ImImPyPy-γ-ImPyPyPy-β-Dp, ImPyPyPy-γ-ImImPyPy-β-Dp, ImImPyPy-γ-ImPyPyPy-β-Dp, ImPyImPy-γ-ImPyImPy-β-Dp, ImImImPy-γ-ImPyPyPyPy-β-Dp, ImImImIm-γ-PyPyPyPy-β-Dp, Im-β-PyPy-γ-Im-β-PyPy-β-Dp, Im-β-ImIm-γ-Py-β-PyPy-β-Dp, Im-β-ImPy-γ-Im-β-ImPy-β-Dp, ImPyPyPy-γ-ImPyPyPyPy-β-Dp, ImPyImPyPy-γ-ImPyPyPyPy-β-Dp, ImImPyImIm-γ-PyPyPyPyPy-β-Dp, ImPyPyImPy-γ-ImPyPyImPy-β-Dp, ImPy-β-PyPy-γ-ImPy-β-PyPy-β-Dp, ImIm-β-ImIm-γ-PyPy-β-PyPy-β-Dp, ImPy-β-ImPy-γ-ImPy-β-ImPy-β-Dp, ImPy-β-PyPyPy-γ-ImPyPy-β-PyPy-β-Dp, ImIm-β-PyPyPy-γ-PyPyPy-β-PyPy-β-Dp, ImPy-β-ImPyPy-γ-ImPyPy-β-PyPy-β-Dp, ImIm-β-PyPyPy-γ-ImImPy-β-PyPy-β-Dp, ImPy-β-PyPyPy-γ-PyPyPy-β-ImPy-β-Dp, ImPyPyPyPy-γ-ImPyPyPyPy-β-Dp, ImPyPy-β-PyPy-γ-ImPyPy-β-PyPy-β-Dp, ImPyPyPy-β-Py-γ-Im-β-PyPyPyPy-β-Dp, ImImPyPyPy-γ-ImPyPyPyPy-β-Dp, Im-β-PyPyPyPy-γ-Im-β-PyPyPyPy-β-Dp, ImPyPyPy-β-Py-γ-ImPyPyPy-β-Py-β-Dp, ImPyImPyPyPy-γ-ImPyPyPyPy-β-Dp, ImPyPy-β-PyPy-γ-ImPy-β-PyPyPy-β-Dp, ImPyPyPy-β-γ-ImPyPyPyPy-β-β-Dp, ImPy-β-ImPyPy-γ-ImPy-β-ImPyPy-β-Dp, Im-β-PyPyPyPy-γ-ImPyPyPy-β-Py-β-Dp, Im-β-ImPyPyPy-γ-ImPyPyPy-β-Py-β-Dp, ImPyPy-β-PyPyPy-β-Dp, ImImPy-β-PyPyPy-β-Dp, ImImIm-β-PyPyPy-β-Dp, ImPyPyPy-β-PyPyPy-β-Dp, ImPyPyPy-β-PyPyPy-β-Dp, ImPyPy-β-PyPyPyPy-β-Dp, ImPyPyPy-β-PyPyPy-β-Dp, ImImPyPy-β-PyPyPyPy-β-Dp, ImImImPy-β-PyPyPyPy-β-Dp, ImPyPyPy-β-ImPyPyPy-β-Dp, ImImPyPy-β-ImPyPyPy-β-Dp, ImImPyPyPy-β-PyPyPyPy-β-Dp, ImImImPyPy-β-PyPyPyPy-β-Dp, ImIm-β-PyPy-β-PyPy-β-PyPy-β-Dp, ImImPy-β-PyPyPy-β-PyPyPy-β-PyPyPy-β-Dp, PyImPy-γ-ImPyPy-β-PyPyPy-β-PyPyPy-β-Dp, PyImPy-γ-ImPyPy-β-PyPyPy-β0PyPyPy-β-Dp, ImImPy-γ-ImPyPy-β-PyPyPy-β-Dp, ImPyPy-γ-ImPyPy-G-PyPyPy-β-Dp, ImPyPyPy-γ-ImImImPy-β-PyPyPy-β-Dp, ImImPyPy-β-Dp, ImImPyPy-γ-ImImPyPy-β-PyPyPyPy-β-Dp, and ImImPyPy-γ-PyPyPyPy-β-PyPyPyPy-β-Dp, bound to a detectable label wherein Im is N-methyl-Imidazole, Py is methylpyrrole, β is β-alanine, Dp is dimethylaminopropylamide, and γ is γ-aminobutyric acid.

\* \* \* \* \*